(12) United States Patent
Bombard et al.

(10) Patent No.: US 8,475,474 B2
(45) Date of Patent: Jul. 2, 2013

(54) ANASTOMOSIS METHOD UTILIZING TOOL WITH FLUID-DRIVEN ACTUATOR

(75) Inventors: David L. Bombard, San Francisco, CA (US); Philipe R. Manoux, San Francisco, CA (US); Joshua M. O. Newth, Palo Alto, CA (US); James T. Nielsen, San Francisco, CA (US); Nathan H. White, Palo Alto, CA (US); Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 654 days.

(21) Appl. No.: 12/577,589

(22) Filed: Oct. 12, 2009

(65) Prior Publication Data
US 2010/0069934 A1 Mar. 18, 2010

Related U.S. Application Data

(60) Division of application No. 11/054,265, filed on Feb. 9, 2005, now Pat. No. 7,682,368, which is a continuation-in-part of application No. 10/750,712, filed on Dec. 31, 2003, now Pat. No. 7,371,243, which is a continuation-in-part of application No. 10/720,618, filed on Nov. 24, 2003, now Pat. No. 7,300,444, which is a continuation-in-part of application No. 10/607,524, filed on Jun. 26, 2003, now abandoned, which is a continuation-in-part of application No. 10/392,336, filed on Mar. 19, 2003, now Pat. No. 7,766,924, which is a continuation-in-part of application No. 10/151,441, filed on May 20, 2002, now Pat. No. 7,285,131, which is a continuation-in-part of application No. 09/363,255, filed on Jul. 28, 1999, now Pat. No. 6,391,038.

(51) Int. Cl.
*A61B 17/10* (2006.01)
*A61B 17/04* (2006.01)

(52) U.S. Cl.
USPC .............. 606/142; 227/178.1; 227/180.1

(58) Field of Classification Search
USPC ............ 606/139, 142, 143; 227/175.1–182.1
See application file for complete search history.

(56) References Cited

U.S. PATENT DOCUMENTS

| 3,254,650 A | 6/1966 | Collito |
| 3,254,651 A | 6/1966 | Collito |

(Continued)

FOREIGN PATENT DOCUMENTS

| DE | 69406845 | 4/1998 |
| DE | 19732234 | 1/1999 |

(Continued)

OTHER PUBLICATIONS

"Atlas of Surgical Stapling", *Ethicon Endo-Surgery*, (1999).

(Continued)

*Primary Examiner* — Gary Jackson
*Assistant Examiner* — Michael Mendoza
(74) *Attorney, Agent, or Firm* — Cardica, Inc.

(57) ABSTRACT

A method of performing anastomosis between a graft vessel and a target vessel, each having a circumferential wall and a lumen therethrough, may include providing an anastomosis tool including a tissue effector and a fluid-driven actuator operationally connected to that tissue effector; connecting the fluid-driven actuator to an energy source; placing an end of the graft vessel in proximity to the side of the target vessel; and actuating the fluid-driven actuator to connect the end of the graft vessel to the side of the target vessel.

15 Claims, 122 Drawing Sheets

U.S. PATENT DOCUMENTS

| | | |
|---|---|---|
| 3,519,187 A | 7/1970 | Kapitanov et al. |
| 3,618,842 A | 11/1971 | Bryan |
| 3,774,615 A | 11/1973 | Lim et al. |
| 3,795,034 A | 3/1974 | Strekopytov et al. |
| 3,949,924 A | 4/1976 | Green |
| 4,076,162 A | 2/1978 | Kapitanov et al. |
| 4,214,587 A | 7/1980 | Sakura, Jr. |
| 4,241,861 A | 12/1980 | Fleischer |
| 4,248,267 A | 2/1981 | Brandenberg |
| 4,318,313 A | 3/1982 | Tartaglia et al. |
| 4,331,277 A | 5/1982 | Green |
| 4,350,160 A | 9/1982 | Kolesov et al. |
| 4,352,358 A | 10/1982 | Angelchik |
| 4,354,628 A | 10/1982 | Green |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,553,542 A | 11/1985 | Schenck et al. |
| 4,593,693 A | 6/1986 | Schenck |
| 4,603,693 A | 8/1986 | Conta et al. |
| 4,605,001 A | 8/1986 | Rothfuss et al. |
| 4,607,637 A | 8/1986 | Berggren et al. |
| 4,617,928 A | 10/1986 | Alfranca |
| 4,624,255 A | 11/1986 | Schenck et al. |
| 4,624,257 A | 11/1986 | Berggren et al. |
| 4,633,874 A | 1/1987 | Chow et al. |
| 4,657,019 A | 4/1987 | Walsh et al. |
| 4,665,906 A | 5/1987 | Jervis |
| 4,747,407 A | 5/1988 | Liu et al. |
| 4,752,024 A | 6/1988 | Green et al. |
| 4,773,420 A | 9/1988 | Green |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,938,408 A | 7/1990 | Bedi |
| 4,951,861 A | 8/1990 | Schulze et al. |
| 5,005,749 A | 4/1991 | Aranyi |
| 5,018,657 A | 5/1991 | Pedlick et al. |
| 5,062,842 A | 11/1991 | Tiffany |
| 5,104,025 A | 4/1992 | Main et al. |
| 5,119,983 A | 6/1992 | Green et al. |
| 5,156,310 A | 10/1992 | Biedenharn |
| 5,156,613 A | 10/1992 | Sawyer |
| 5,156,619 A | 10/1992 | Ehrenfeld |
| 5,172,845 A | 12/1992 | Tejeiro |
| 5,178,634 A | 1/1993 | Ramos Martinez |
| 5,193,731 A | 3/1993 | Aranyi |
| 5,197,649 A * | 3/1993 | Bessler et al. ............. 227/179.1 |
| 5,205,459 A | 4/1993 | Brinkerhoff et al. |
| 5,211,683 A | 5/1993 | Maginot |
| 5,234,447 A | 8/1993 | Kaster et al. |
| 5,250,058 A | 10/1993 | Miller et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,300,065 A | 4/1994 | Anderson |
| 5,304,220 A | 4/1994 | Maginot |
| 5,314,435 A | 5/1994 | Green et al. |
| 5,314,468 A | 5/1994 | Ramos Martinez |
| 5,333,773 A | 8/1994 | Main et al. |
| 5,336,233 A | 8/1994 | Chen |
| 5,350,104 A | 9/1994 | Main et al. |
| 5,364,001 A | 11/1994 | Bryan |
| 5,364,389 A | 11/1994 | Anderson et al. |
| 5,366,462 A | 11/1994 | Kaster et al. |
| 5,376,095 A | 12/1994 | Ortiz |
| 5,392,979 A | 2/1995 | Green et al. |
| 5,395,030 A | 3/1995 | Kuramoto et al. |
| 5,417,361 A | 5/1995 | Williamson, IV |
| 5,431,322 A | 7/1995 | Green et al. |
| 5,443,497 A | 8/1995 | Venbrux |
| 5,447,514 A | 9/1995 | Gerry et al. |
| 5,452,836 A | 9/1995 | Huitema et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,465,896 A | 11/1995 | Allen et al. |
| 5,478,003 A | 12/1995 | Green et al. |
| 5,478,354 A | 12/1995 | Tovey et al. |
| 5,489,058 A | 2/1996 | Plyley et al. |
| 5,522,834 A | 6/1996 | Fonger et al. |
| 5,533,661 A | 7/1996 | Main et al. |
| 5,535,935 A | 7/1996 | Vidal et al. |
| 5,540,677 A | 7/1996 | Sinofsky |
| 5,558,667 A | 9/1996 | Yarborough et al. |
| 5,562,241 A | 10/1996 | Knodel et al. |
| 5,571,167 A | 11/1996 | Maginot |
| 5,580,067 A | 12/1996 | Hamblin et al. |
| 5,586,711 A | 12/1996 | Plyley et al. |
| 5,605,572 A | 2/1997 | Berger |
| 5,609,285 A | 3/1997 | Grant et al. |
| 5,611,794 A | 3/1997 | Sauer et al. |
| 5,620,452 A | 4/1997 | Yoon |
| 5,632,432 A | 5/1997 | Schulze et al. |
| 5,632,433 A | 5/1997 | Grant et al. |
| 5,636,780 A | 6/1997 | Green |
| 5,643,340 A | 7/1997 | Nunokawa |
| 5,653,373 A | 8/1997 | Green et al. |
| 5,655,698 A | 8/1997 | Yoon |
| 5,657,921 A | 8/1997 | Young et al. |
| 5,662,258 A | 9/1997 | Knodel et al. |
| 5,662,259 A | 9/1997 | Yoon |
| 5,669,544 A | 9/1997 | Schulze et al. |
| 5,669,918 A | 9/1997 | Balazs et al. |
| 5,669,934 A | 9/1997 | Sawyer |
| 5,673,840 A | 10/1997 | Schulze et al. |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,369 A | 1/1998 | Vaitekunas et al. |
| 5,707,380 A | 1/1998 | Hinchliffe et al. |
| 5,709,693 A | 1/1998 | Taylor |
| 5,711,472 A | 1/1998 | Bryan |
| 5,725,544 A | 3/1998 | Rygaard |
| 5,749,895 A | 5/1998 | Sawyer et al. |
| 5,752,965 A | 5/1998 | Francis et al. |
| 5,776,130 A | 7/1998 | Buysse et al. |
| 5,797,920 A | 8/1998 | Kim |
| 5,799,857 A | 9/1998 | Robertson et al. |
| 5,816,471 A | 10/1998 | Plyley et al. |
| 5,817,113 A | 10/1998 | Gifford, III et al. |
| 5,824,015 A | 10/1998 | Sawyer |
| 5,827,265 A | 10/1998 | Glinsky et al. |
| 5,827,271 A | 10/1998 | Buysse et al. |
| 5,833,690 A | 11/1998 | Yates et al. |
| 5,833,698 A | 11/1998 | Hinchliffe et al. |
| 5,862,972 A * | 1/1999 | Green et al. ................ 227/175.1 |
| 5,865,730 A | 2/1999 | Fox et al. |
| 5,878,938 A | 3/1999 | Bittner et al. |
| 5,879,371 A | 3/1999 | Gardiner et al. |
| 5,893,369 A | 4/1999 | Lemole |
| 5,904,697 A | 5/1999 | Gifford, III et al. |
| 5,913,866 A | 6/1999 | Ginn et al. |
| 5,915,616 A | 6/1999 | Viola et al. |
| 5,918,791 A | 7/1999 | Sorrentino et al. |
| 5,921,995 A | 7/1999 | Kleshinski |
| 5,944,730 A | 8/1999 | Nobles et al. |
| 5,976,159 A | 11/1999 | Bolduc |
| 5,993,464 A | 11/1999 | Knodel |
| 6,004,335 A | 12/1999 | Vaitekunas et al. |
| 6,015,416 A | 1/2000 | Stefanchik et al. |
| 6,024,748 A | 2/2000 | Manzo et al. |
| 6,036,700 A | 3/2000 | Stefanchik et al. |
| 6,039,733 A | 3/2000 | Buysse et al. |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |

| | | | |
|---|---|---|---|
| 6,071,289 A | 6/2000 | Stefanchik et al. | |
| 6,083,234 A | 7/2000 | Nicholas et al. | |
| 6,110,187 A | 8/2000 | Donlon | |
| 6,117,148 A | 9/2000 | Ravo et al. | |
| 6,176,413 B1 | 1/2001 | Heck et al. | |
| 6,183,486 B1 | 2/2001 | Snow et al. | |
| 6,187,019 B1 | 2/2001 | Stefanchik | |
| 6,193,129 B1 | 2/2001 | Bittner et al. | |
| 6,193,734 B1 | 2/2001 | Bolduc et al. | |
| 6,200,263 B1 | 3/2001 | Person | |
| 6,209,773 B1 | 4/2001 | Bolduc et al. | |
| 6,248,117 B1 | 6/2001 | Blatter | |
| 6,254,617 B1 | 7/2001 | Spence et al. | |
| 6,280,460 B1 | 8/2001 | Bolduc et al. | |
| 6,394,948 B1 | 5/2002 | Borst et al. | |
| 6,436,097 B1 | 8/2002 | Nardella | |
| 6,461,365 B2 | 10/2002 | Bolduc et al. | |
| 6,514,263 B1 | 2/2003 | Stefanchik et al. | |
| 6,520,973 B1 | 2/2003 | McGarry | |
| 6,530,932 B1 | 3/2003 | Swayze | |
| 6,551,334 B2 | 4/2003 | Blatter et al. | |
| 6,569,173 B1 | 5/2003 | Blatter et al. | |
| 6,623,494 B1 | 9/2003 | Blatter | |
| 6,626,921 B2 | 9/2003 | Blatter et al. | |
| 6,652,642 B2 | 11/2003 | Sare et al. | |
| 6,663,590 B2 | 12/2003 | Blatter | |
| 6,726,694 B2 | 4/2004 | Blatter et al. | |
| 6,736,825 B2 | 5/2004 | Blatter et al. | |
| 6,743,244 B2 | 6/2004 | Blatter et al. | |
| 6,821,286 B1 | 11/2004 | Carranza et al. | |
| 6,905,504 B1 | 6/2005 | Vargas | |
| 6,942,675 B1 | 9/2005 | Vargas | |
| 6,994,669 B1 | 2/2006 | Gannoe et al. | |
| 2001/0004698 A1 | 6/2001 | Blatter et al. | |
| 2001/0023353 A1 | 9/2001 | Vargas et al. | |
| 2001/0023354 A1 | 9/2001 | Blatter et al. | |
| 2002/0095166 A1 | 7/2002 | Vargas et al. | |
| 2003/0014064 A1 | 1/2003 | Blatter | |
| 2004/0068279 A1* | 4/2004 | Hindrichs et al. | 606/153 |
| 2004/0097994 A1 | 5/2004 | Blatter et al. | |
| 2004/0225306 A1 | 11/2004 | Blatter et al. | |
| 2005/0216043 A1 | 9/2005 | Blatter et al. | |
| 2005/0267496 A1 | 12/2005 | Loshakove et al. | |
| 2006/0167485 A1 | 7/2006 | Blatter | |

FOREIGN PATENT DOCUMENTS

| | | |
|---|---|---|
| EP | 1354559 | 5/1995 |
| EP | 1354559 A2 | 5/1995 |
| EP | 0625335 B1 | 11/1997 |
| EP | 0820724 | 1/1998 |
| EP | 0885595 | 12/1998 |
| EP | 0938870 | 9/1999 |
| EP | 0820725 | 1/2000 |
| EP | 0990420 | 4/2000 |
| FR | 2316910 | 7/1976 |
| SU | 1667844 | 8/1991 |
| WO | WO-98/19625 | 5/1998 |
| WO | WO-99/11178 | 3/1999 |
| WO | WO-99/21491 | 5/1999 |
| WO | WO-00/12013 | 3/2000 |
| WO | WO-00/59380 | 10/2000 |

OTHER PUBLICATIONS

"510(k) Notification for the Cardica C-Port Anastomosis System", Section 9, *"Substantial Equivalence,"* and Appendices B, C, E, (Unpublished).

* cited by examiner

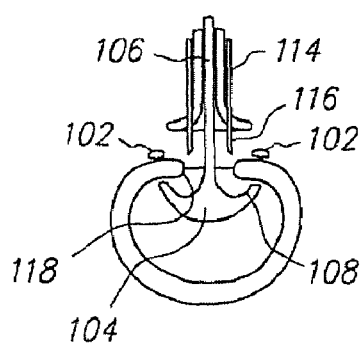 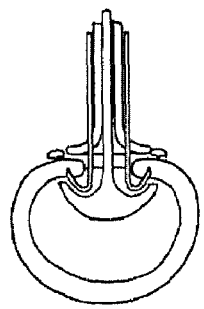 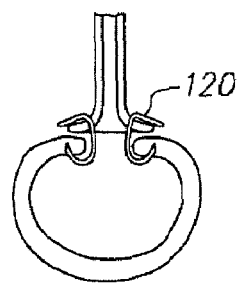
FIG. 20   FIG. 21   FIG. 22
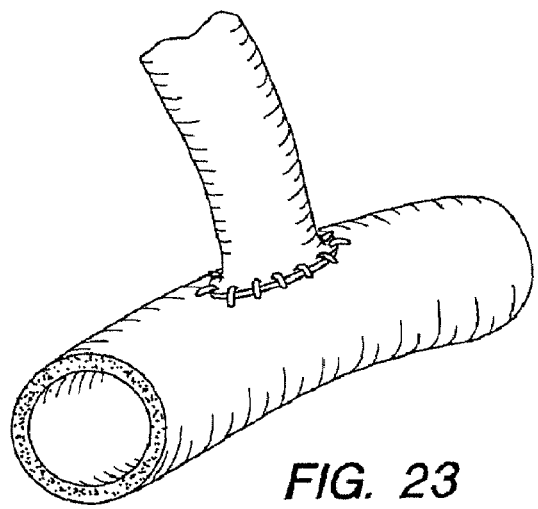
FIG. 23
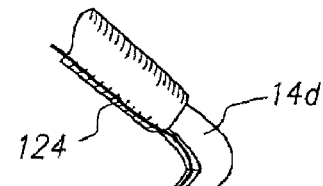
FIG. 24
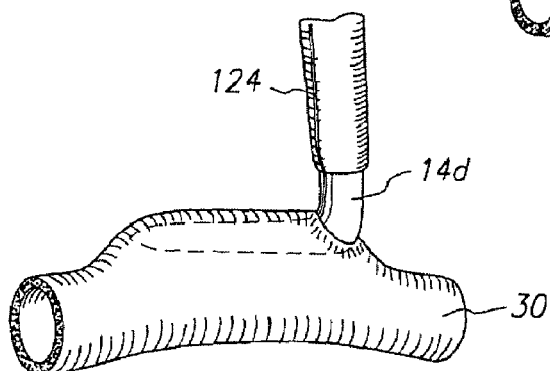
FIG. 25

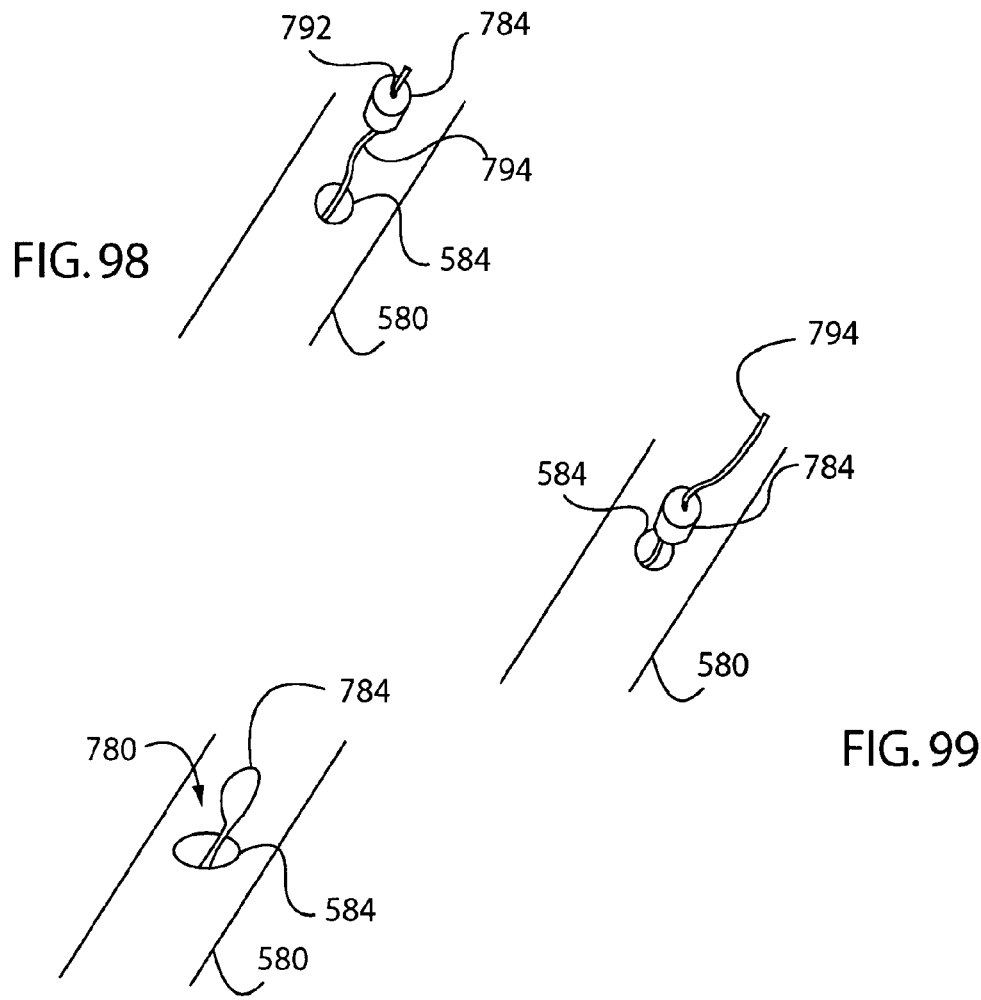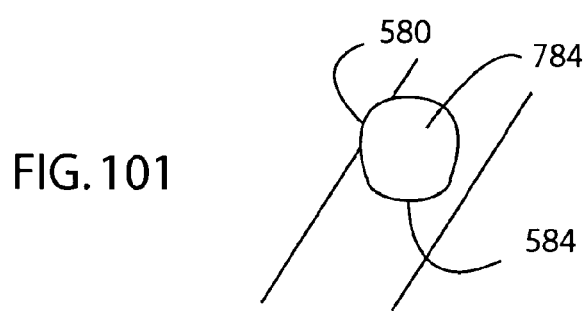

ANASTOMOSIS METHOD UTILIZING TOOL WITH FLUID-DRIVEN ACTUATOR

This application is a divisional of U.S. patent application Ser. No. 11/054,265, filed on Feb. 9, 2005, now U.S. Pat. No. 7,682,368; which in turn is continuation-in-part of U.S. patent application Ser. No. 10/750,712, filed on Dec. 31, 2003, now U.S. Pat. No. 7,371,243; which in turn is a continuation-in-part of U.S. patent application Ser. No. 10/720,618, filed on Nov. 24, 2003, now U.S. Pat. No. 7,300,444; which in turn is a continuation-in-part of U.S. patent application Ser. No. 10/607,524, filed on Jun. 26, 2003 now abandoned; which in turn is a continuation-in-part of U.S. patent application Ser. No. 10/392,336, filed on Mar. 19, 2003 now U.S. Pat. No. 7,766,924; which in turn is a continuation-in-part of U.S. patent application Ser. No. 10/151,441, filed on May 20, 2002, now U.S. Pat. No. 7,285,131; which in turn is a continuation-in-part of U.S. patent application Ser. No. 09/363,255, filed on Jul. 28, 1999, now U.S. Pat. No. 6,391,038; all of which are herein incorporated by reference in their entirety.

FIELD OF THE INVENTION

The invention relates to a surgical apparatus and method for performing anastomosis.

BACKGROUND

Anastomosis is a procedure by which two hollow tissue structures are joined together. More particularly, vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart-lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patient's chest with the aid of visualizing scopes. In both conventional and less invasive CABG procedures, the surgeon has to suture one end of the graft vessel to the coronary artery and the other end of the graft vessel to a blood-supplying artery, such as the aorta. The suturing process is a time consuming and difficult procedure requiring a high level of surgical skill. In order to perform the suturing of the graft to a target vessel such as the coronary artery or the blood supplying artery, a surgeon holds the edges of the incision in the target vessel with one hand and holds a needle in the other hand for suturing, or an assistant may hold the edges of the incision in the target vessel while a surgeon makes small stitches as close as possible to the edges of the incision. This suturing requires a high degree of precision and is quite time consuming. In addition, during conventional CABG procedures blood flow at the anastomosis site is stopped during suturing. This prevents bleeding from the incision site but also prevents blood from reaching a portion of the heart muscle served by the vessel. Further, during off-pump CABG procedures a side clamp or other device may be used to isolate a portion of the wall of the aorta to which a graft vessel is sutured. The use of a side clamp or similar device can cause emboli to detach from the wall of the aorta and enter the bloodstream, which is undesirable.

BRIEF DESCRIPTION OF THE DRAWINGS

FIGS. 20-22 are side cross sectional views of the steps of performing the anastomosis with the continuous anastomosis staple shown in FIG. 19.

FIG. 23 is a perspective view of the completed anastomosis performed as shown in FIGS. 19-22.

FIGS. 24-27 are perspective views of the steps of an alternative anvil and clamp system for controlling an anastomosis site and forming an incision through the clamped tissue of the target vessel.

FIG. 98 is a schematic view of another embodiment of a sealer prior to its deployment.

FIG. 99 is a schematic view of the sealer of FIG. 98 after deployment.

FIG. 100 is a schematic view of another embodiment of a sealer prior to its deployment.

FIG. 101 is a schematic view of the sealer of FIG. 100 after deployment.

FIG. 115 is a side cross-section view of an embodiment of the tissue effector including another embodiment of a cutter, where the cutter is in a first position.

FIG. 116 is a side cross-section view of the tissue effector of FIG. 115, where the cutter is in a second position.

FIG. 117 is a side cross-section view of the tissue effector of FIG. 115, where the cutter is in a third position.

FIG. 118 is a side cross-section view of the tissue effector of FIG. 115, where the cutter is in a fourth position.

FIG. 119 is a side cross-section view of an embodiment of the tissue effector including another embodiment of a cutter, where the cutter is in a first position.

FIG. 120 is a side cross-section view of the tissue effector of FIG. 119, where the cutter is in a second position.

FIG. 121 is a side cross-section view of the tissue effector of FIG. 119, where the cutter is in a third position.

FIG. 122 is a side cross-section view of the tissue effector of FIG. 119, where the cutter is in a fourth position.

FIG. 123 is a detail perspective view of a location near distal end of the tissue effector, where the bending features are located on an upper surface of the anvil arm, and where the bending features corresponding to the toe of the anastomosis are offset toward one another.

FIG. 124 is a different detail perspective view of the tissue effector of FIG. 123.

FIG. 125 is a side cross-section view of an embodiment of the tissue effector including another embodiment of a cutter, where the cutter is in a first position.

FIG. 126 is a side cross-section view of the tissue effector of FIG. 125, where the cutter is in a second position.

Figure 125:
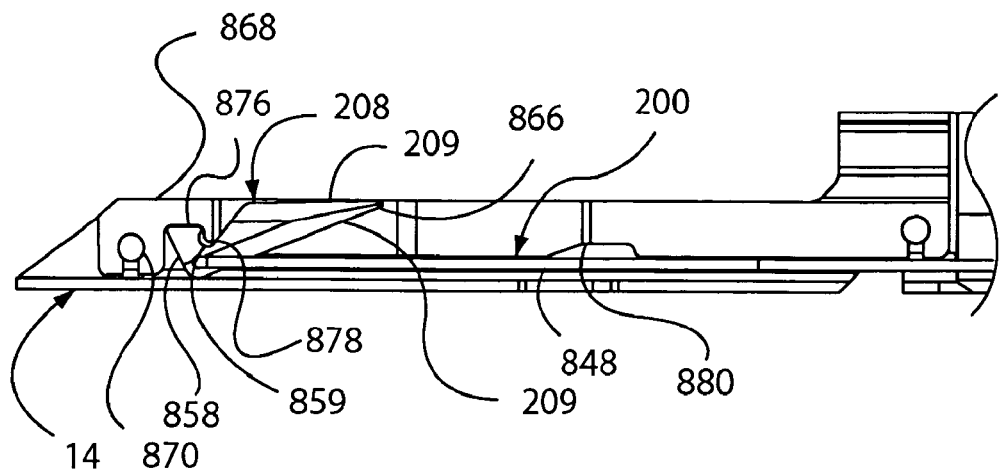
Figure 127:
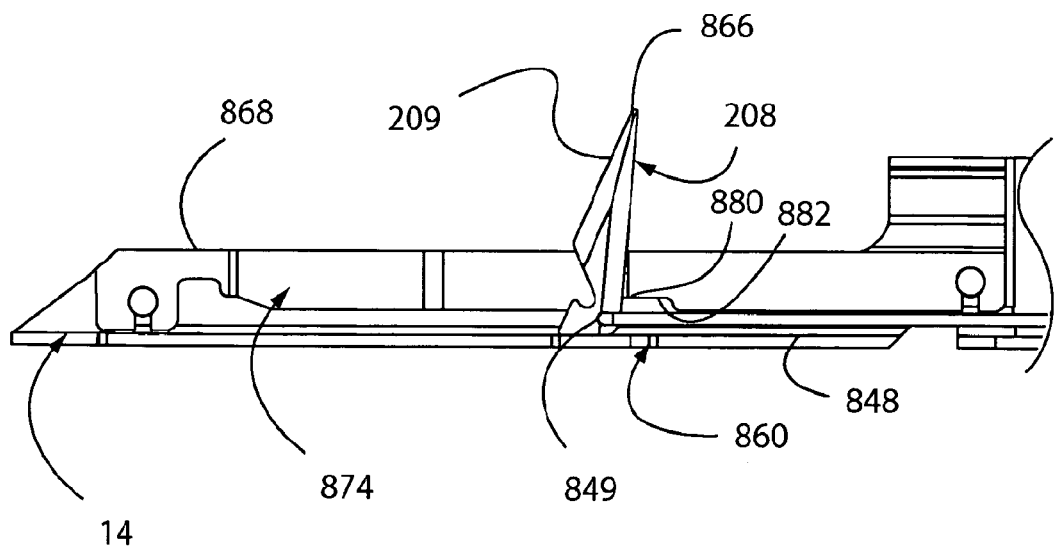

FIG. 127 is a side cross-section view of the tissue effector of FIG. 125, where the cutter is in a third position.

Figure 128:
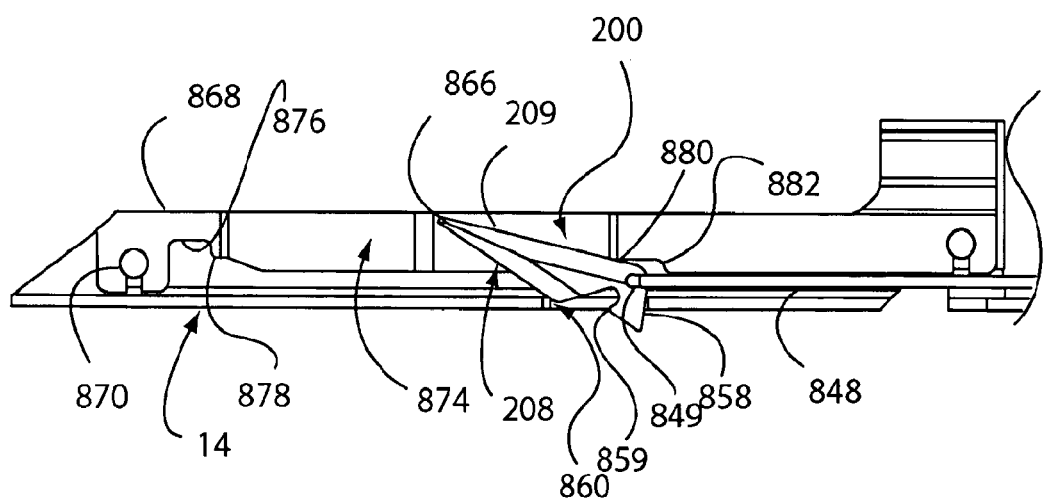

FIG. 128 is a side cross-section view of the tissue effector of FIG. 125, where the cutter is in a fourth position.

Figure 129:
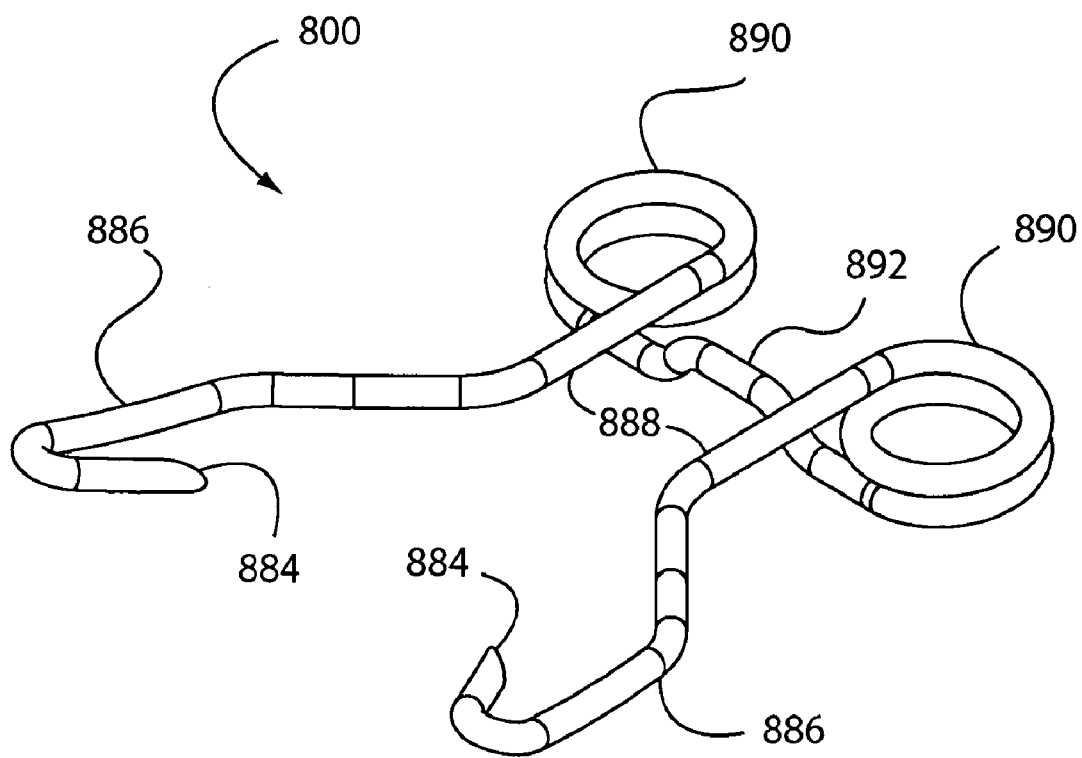

FIG. 129 is a perspective view of an embodiment of a sealer.

Figure 130:
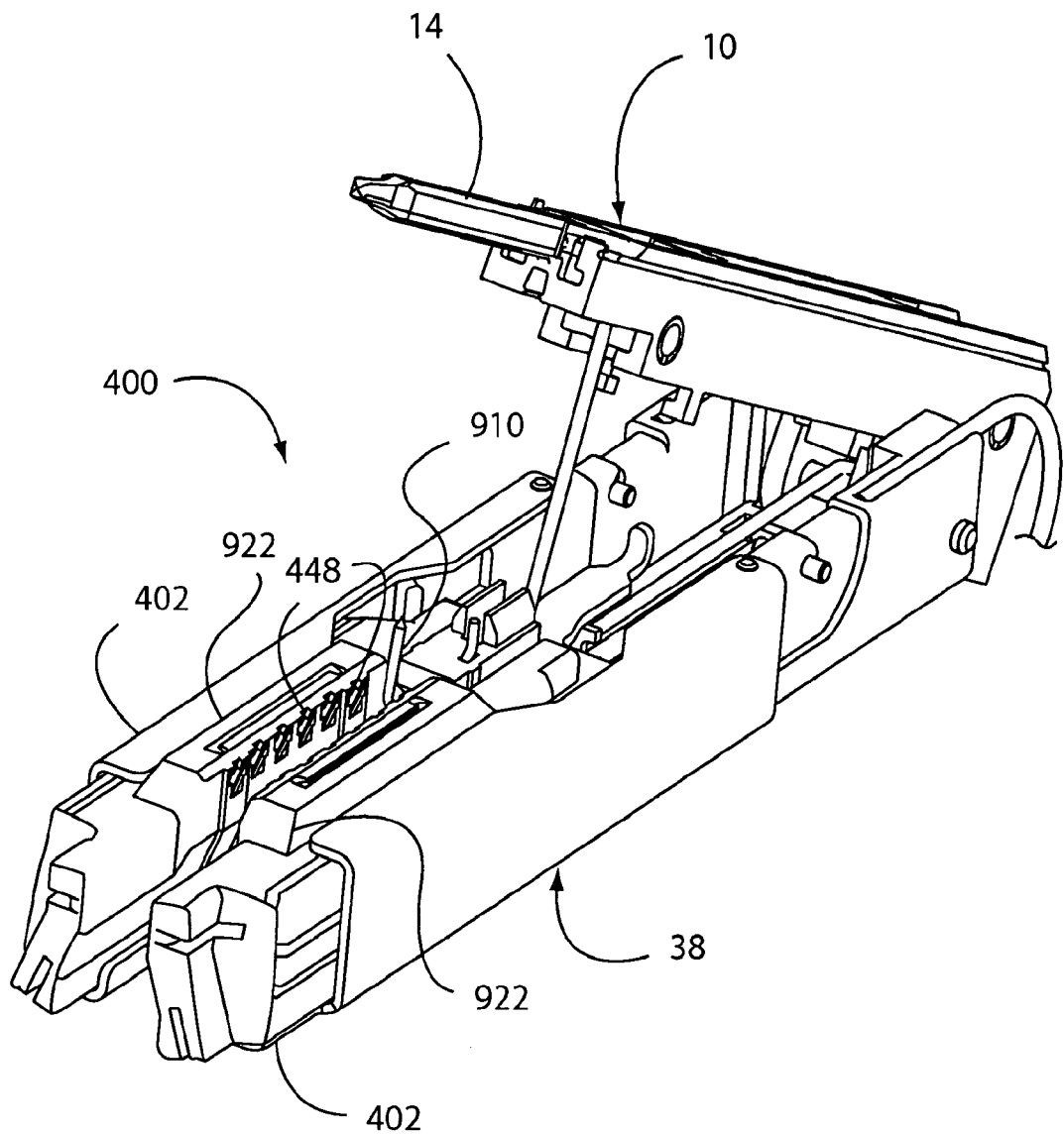

FIG. 130 is a perspective view of an embodiment of a tissue effector that includes a graft affixer connected to the staple holder.

Figure 131:
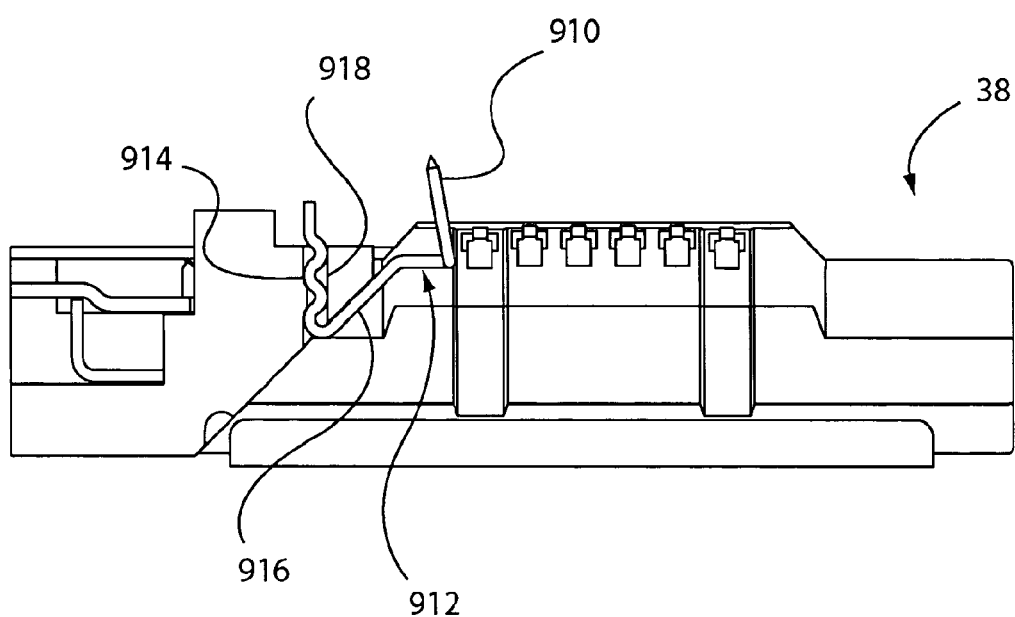

FIG. 131 is a side cross section view of the staple holder of FIG. 130, where the tissue effector is in the open position.

Figure 132:
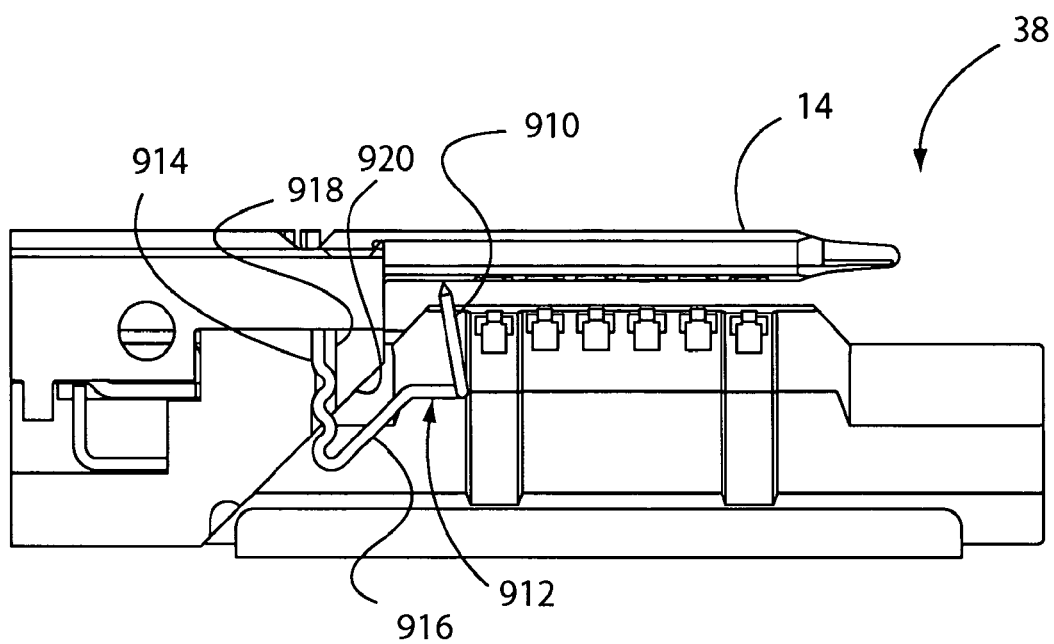

FIG. 132 is a side cross-section view of the staple holder of FIG. 130, where the tissue effector is in the closed position.

Figure 133:
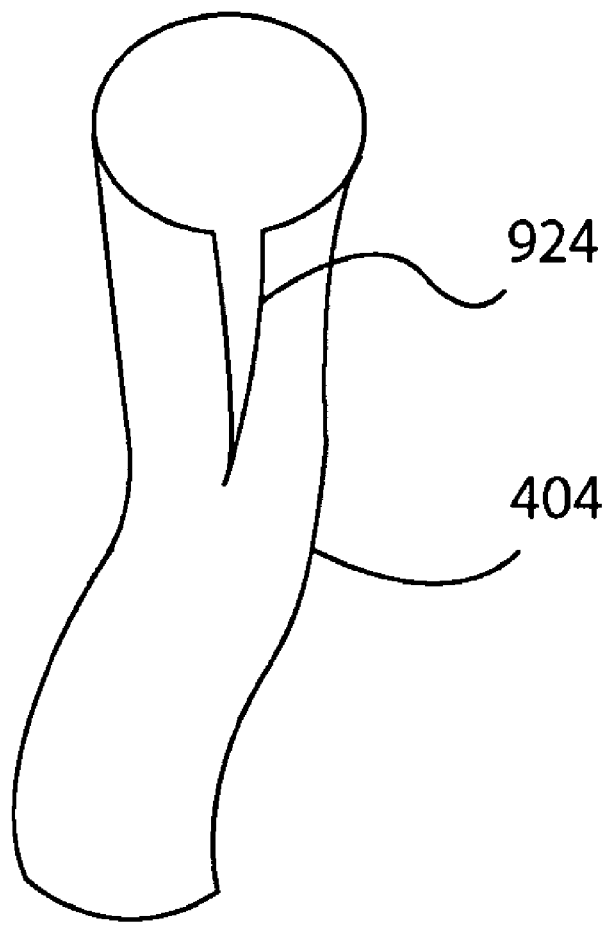

FIG. 133 is a perspective view of a graft vessel prepared for use with the tissue effector of FIG. 130.

Figure 134:
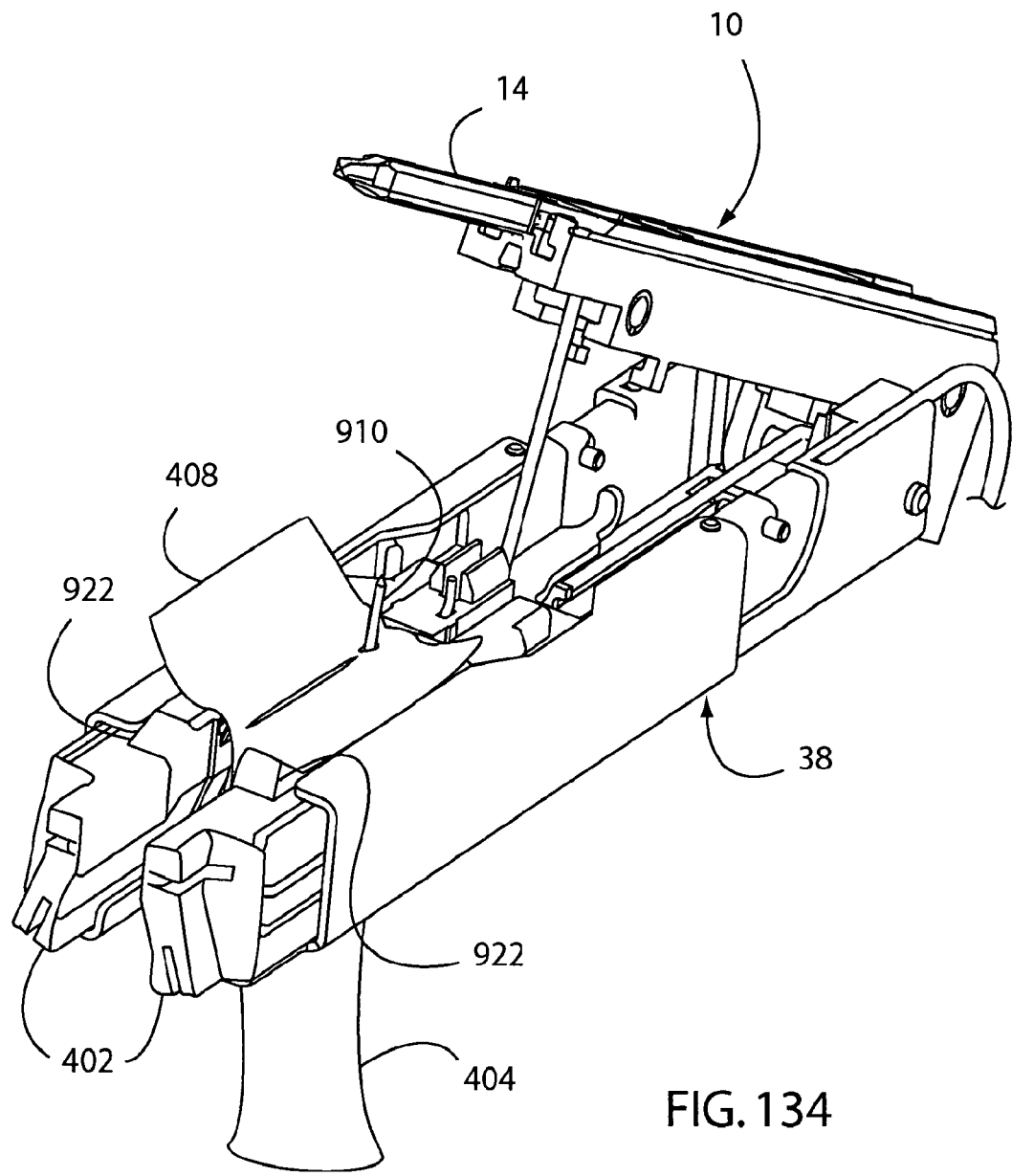

FIG. 134 is a perspective view of the tissue effector of FIG. 130, with a graft vessel affixed thereto.

Figure 135:
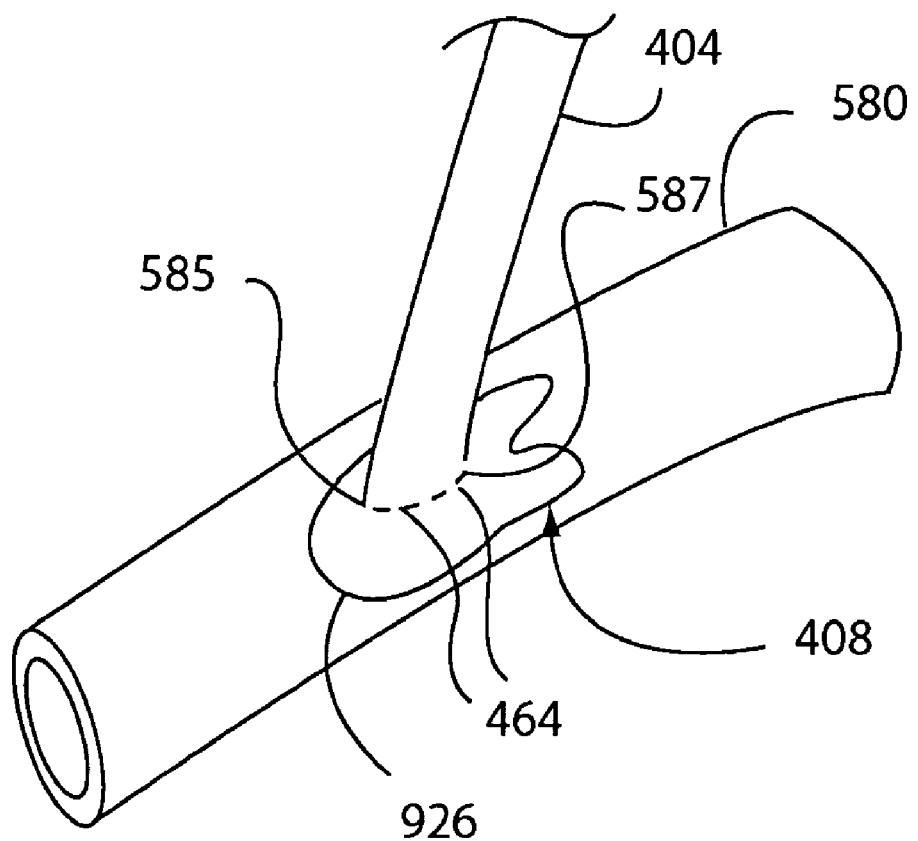

FIG. 135 is a perspective view of a completed anastomosis performed with the tissue effector of FIG. 130 and the graft vessel of FIG. 134.

Figure 136:
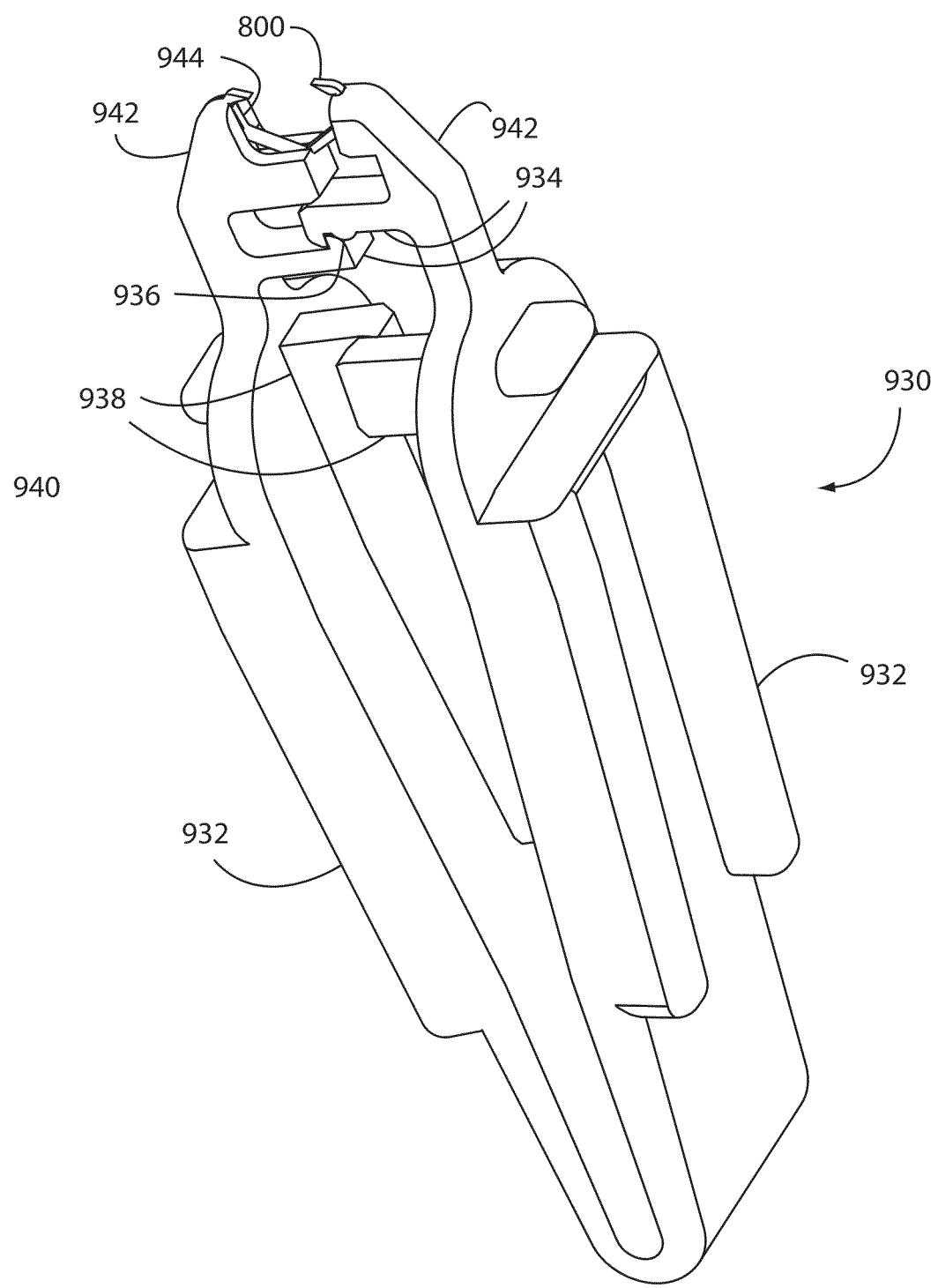

FIG. 136 is a perspective view of an exemplary applier that may be used to apply a clip to the anvil entry hole.

Figure 137:
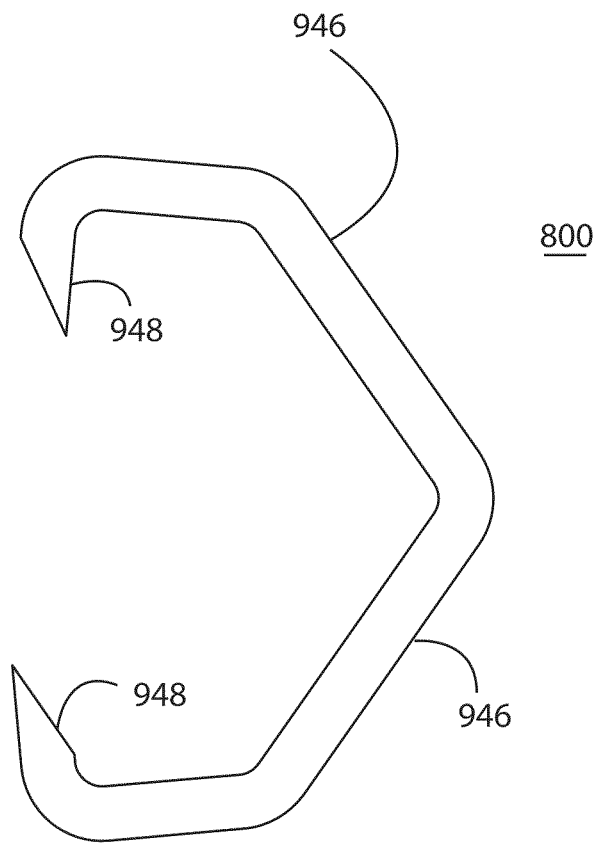

FIG. 137 is a top view of a clip that may be used with the applier of FIG. 136, where that clip in is an open position.

Figure 138:
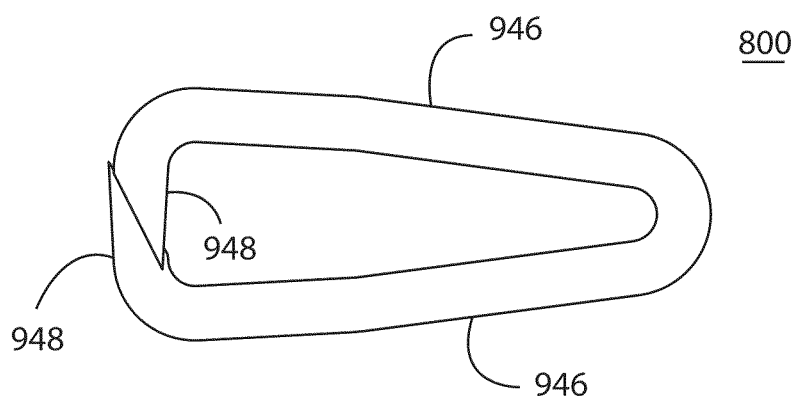

FIG. 138 is a top view of the clip of FIG. 137 in a closed position.

Figure 139:
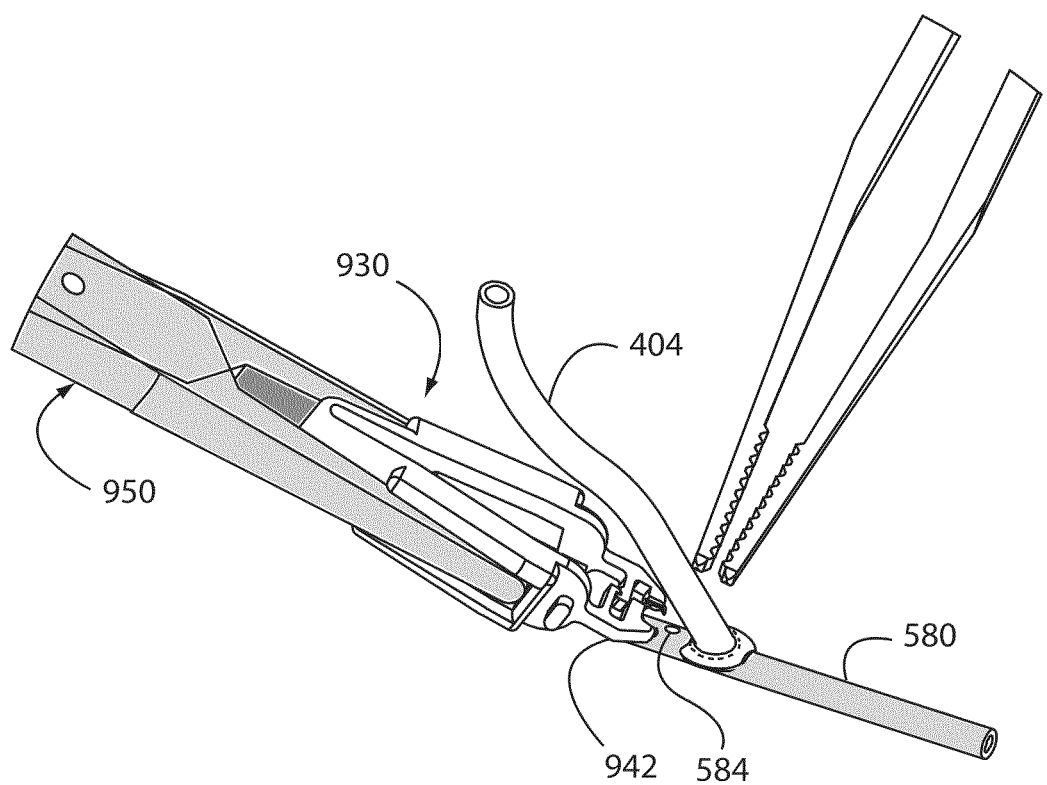

FIG. 139 is a perspective view of the applier of FIG. 136 in use.

Figure 140:
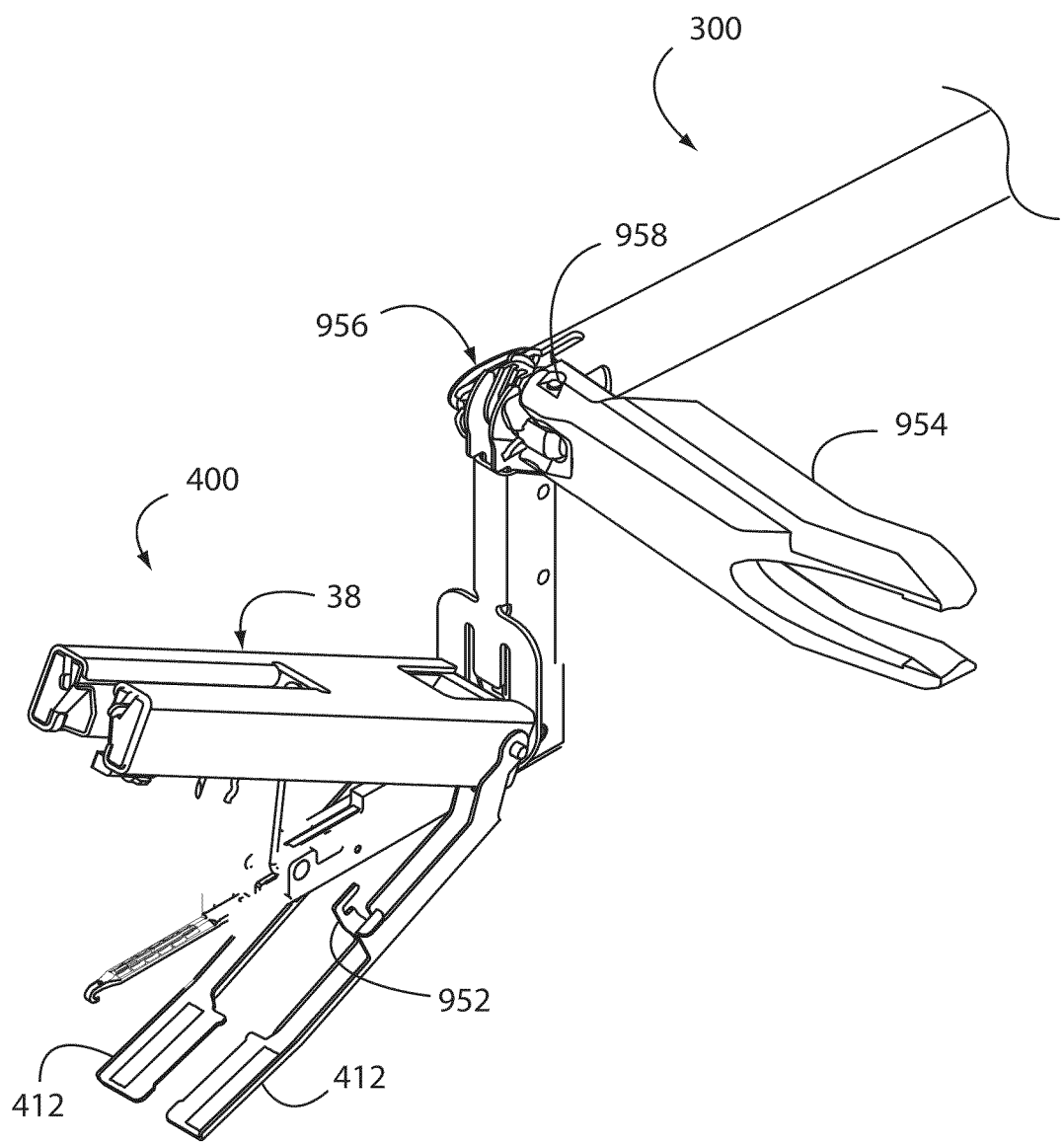

FIG. 140 is a perspective view of an exemplary anastomosis tool.

Figure 141:
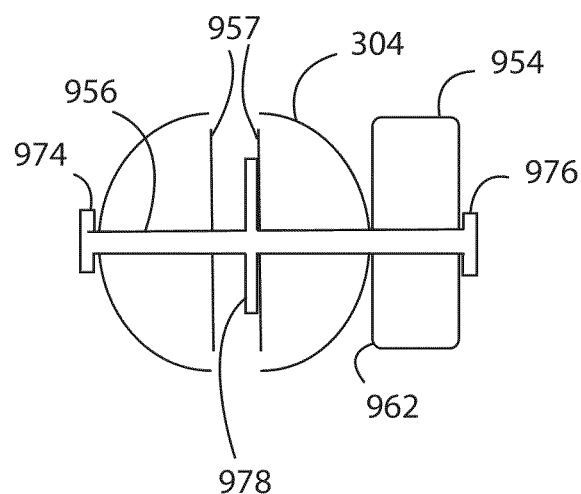

FIG. 141 is a detail view of an exemplary articulated shaft.

Figure 142:
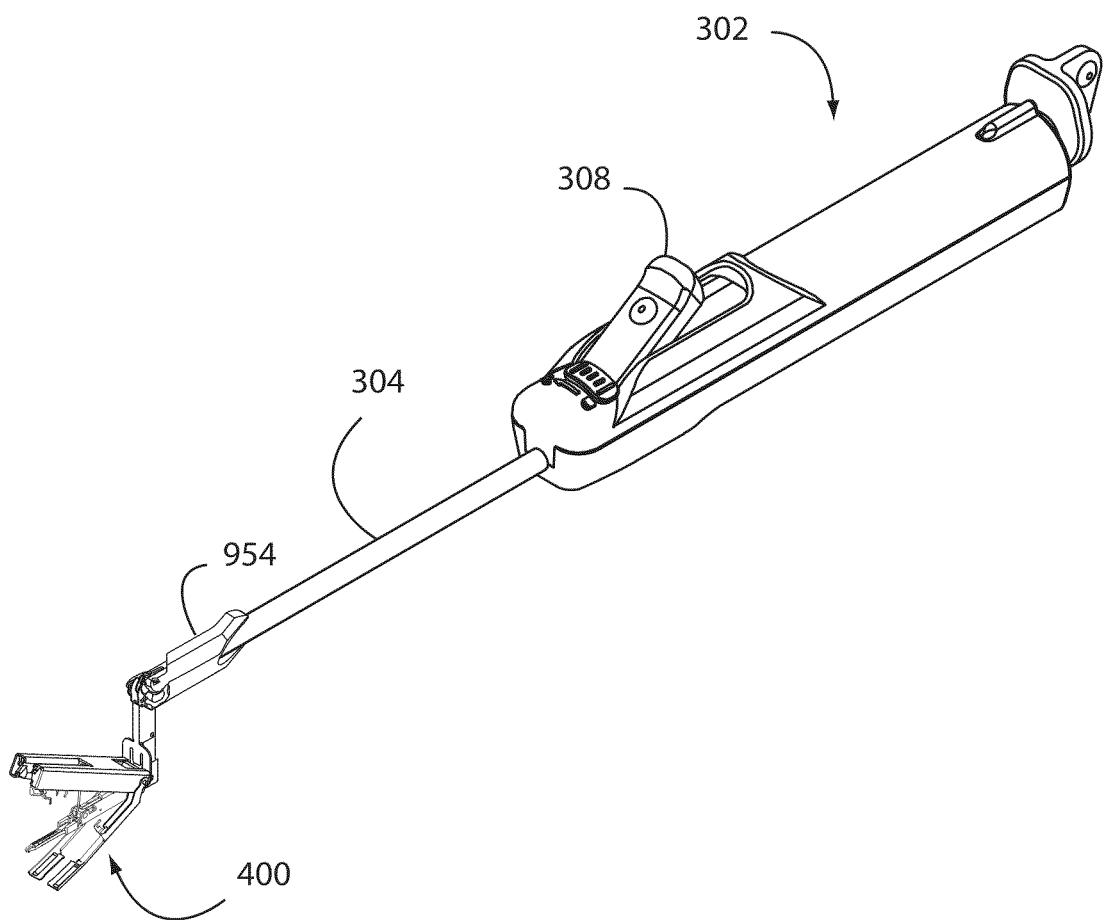

FIG. 142 is a perspective view of an exemplary anastomosis tool.

Figure 143:
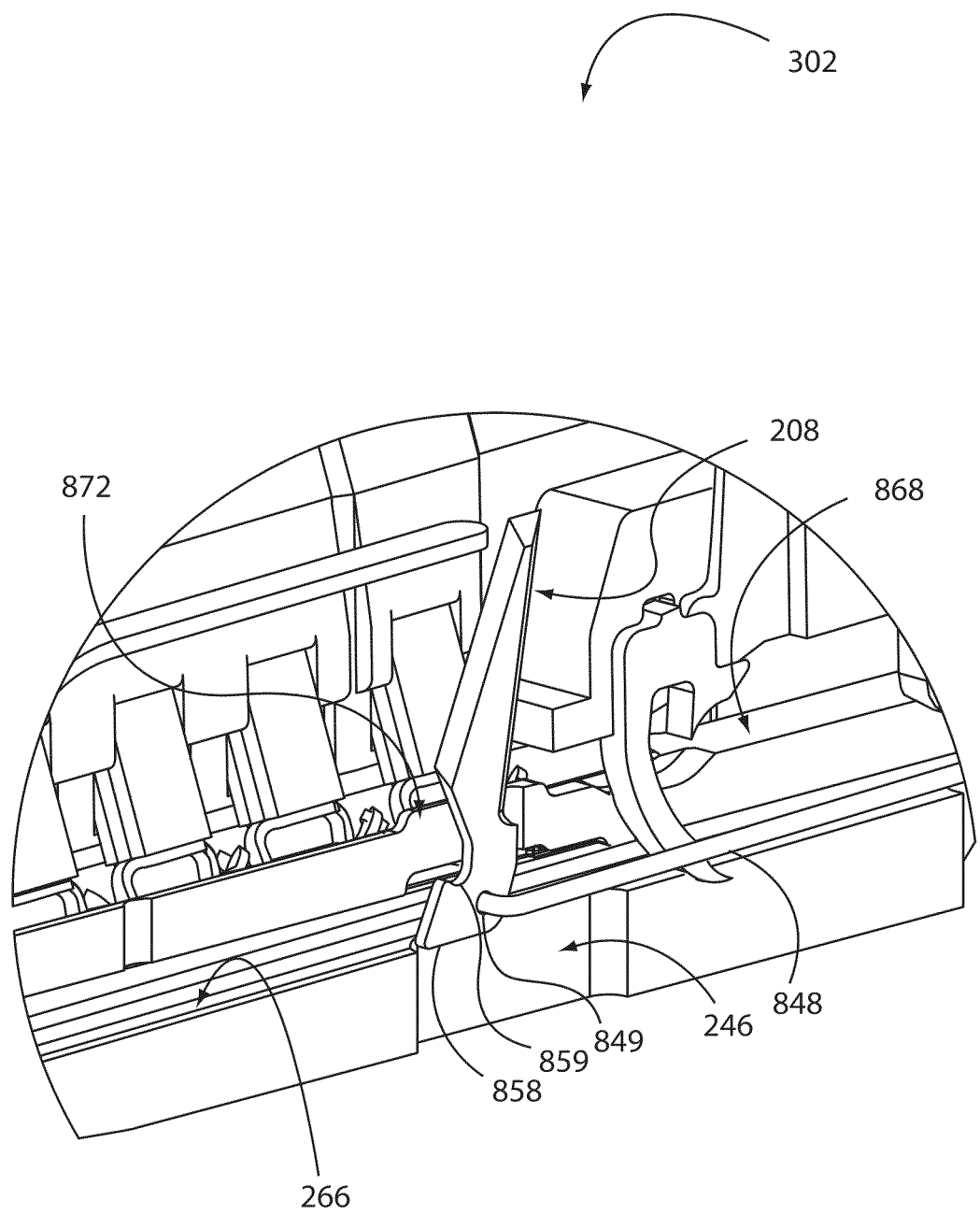

FIG. 143 is a detail cutaway view of an exemplary anvil and cutter of an anastomosis tool.

Figure 144:
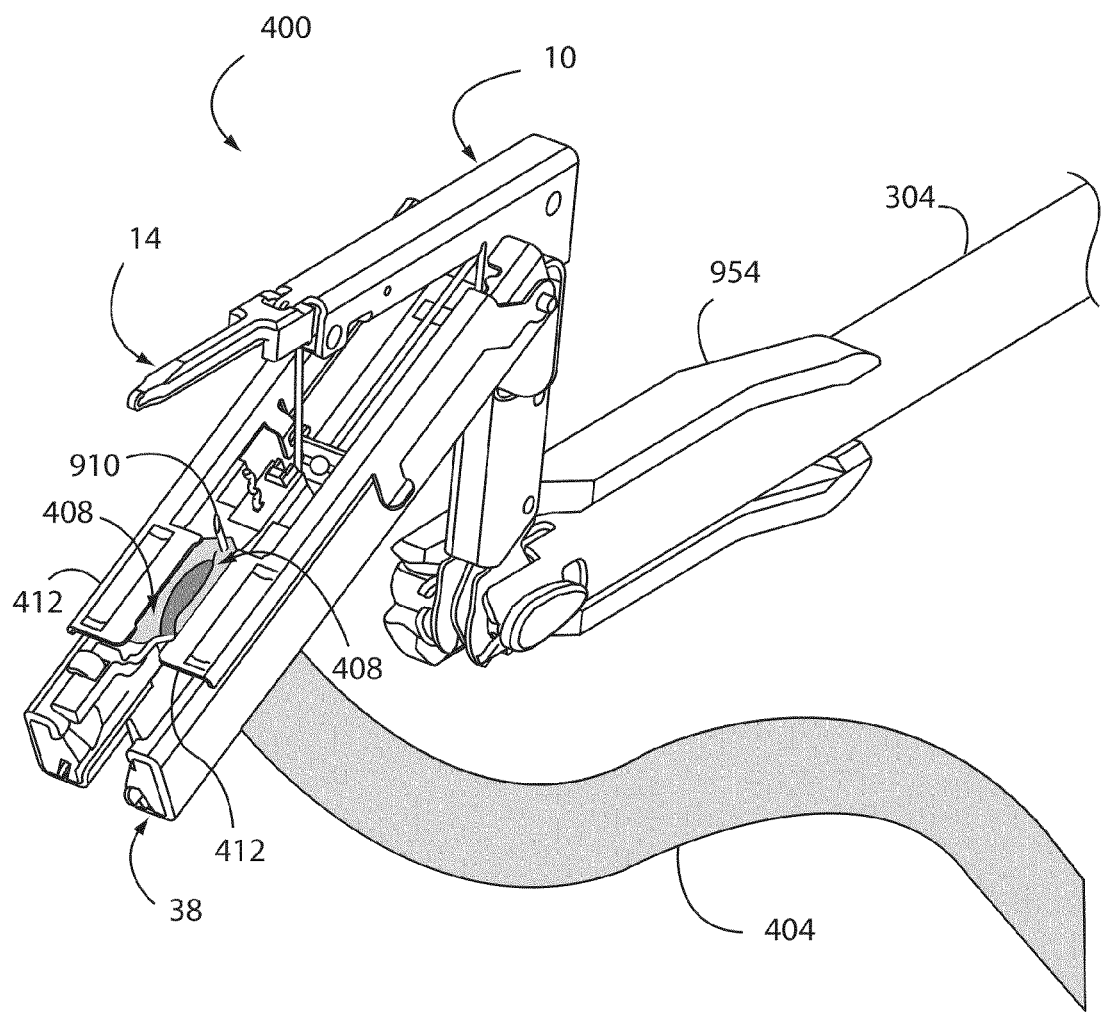

FIG. 144 is a perspective view of the distal end of an exemplary anastomosis tool, showing a graft vessel attached to the tissue effector of that tool.

Figure 145:
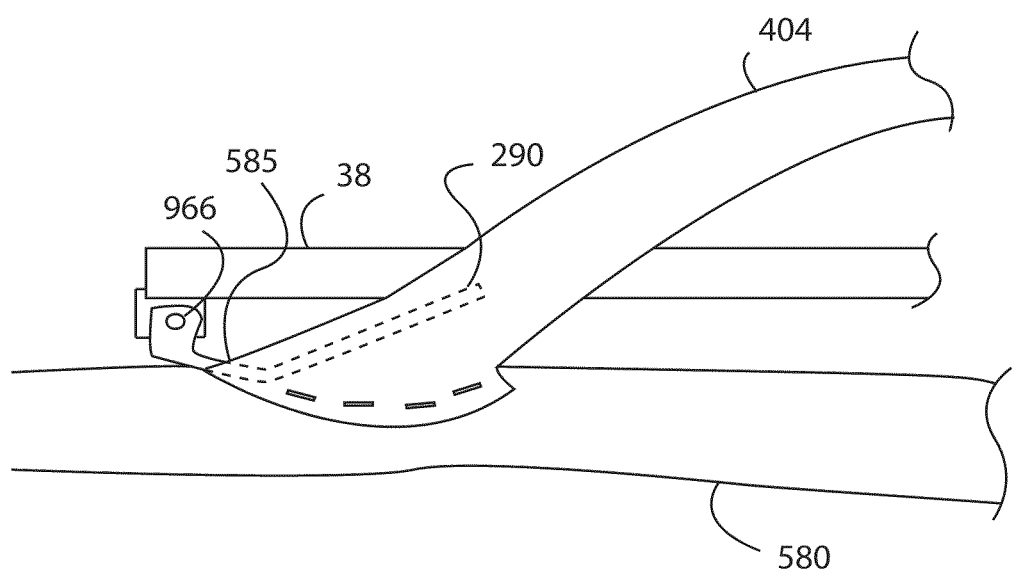

FIG. 145 is a cross-section of an exemplary staple holder of a tissue effector, showing the relationship between a shield connected to the staple holder and the graft vessel.

Figure 146:
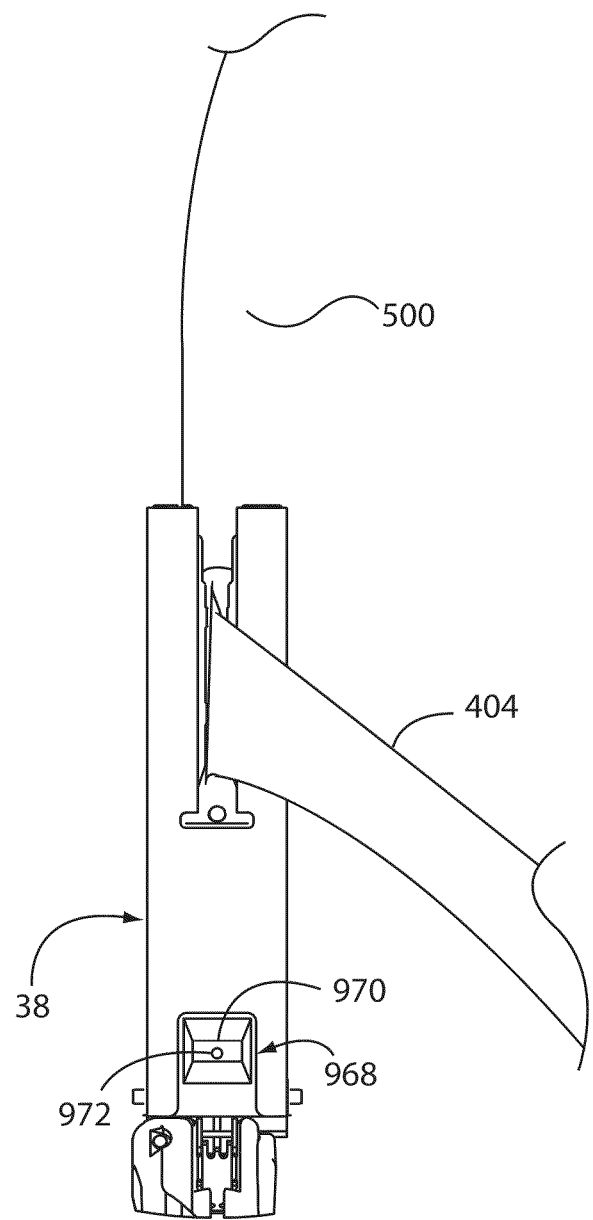

FIG. 146 is a top view of a tissue effector having a deployment indicator.

Figure 147:
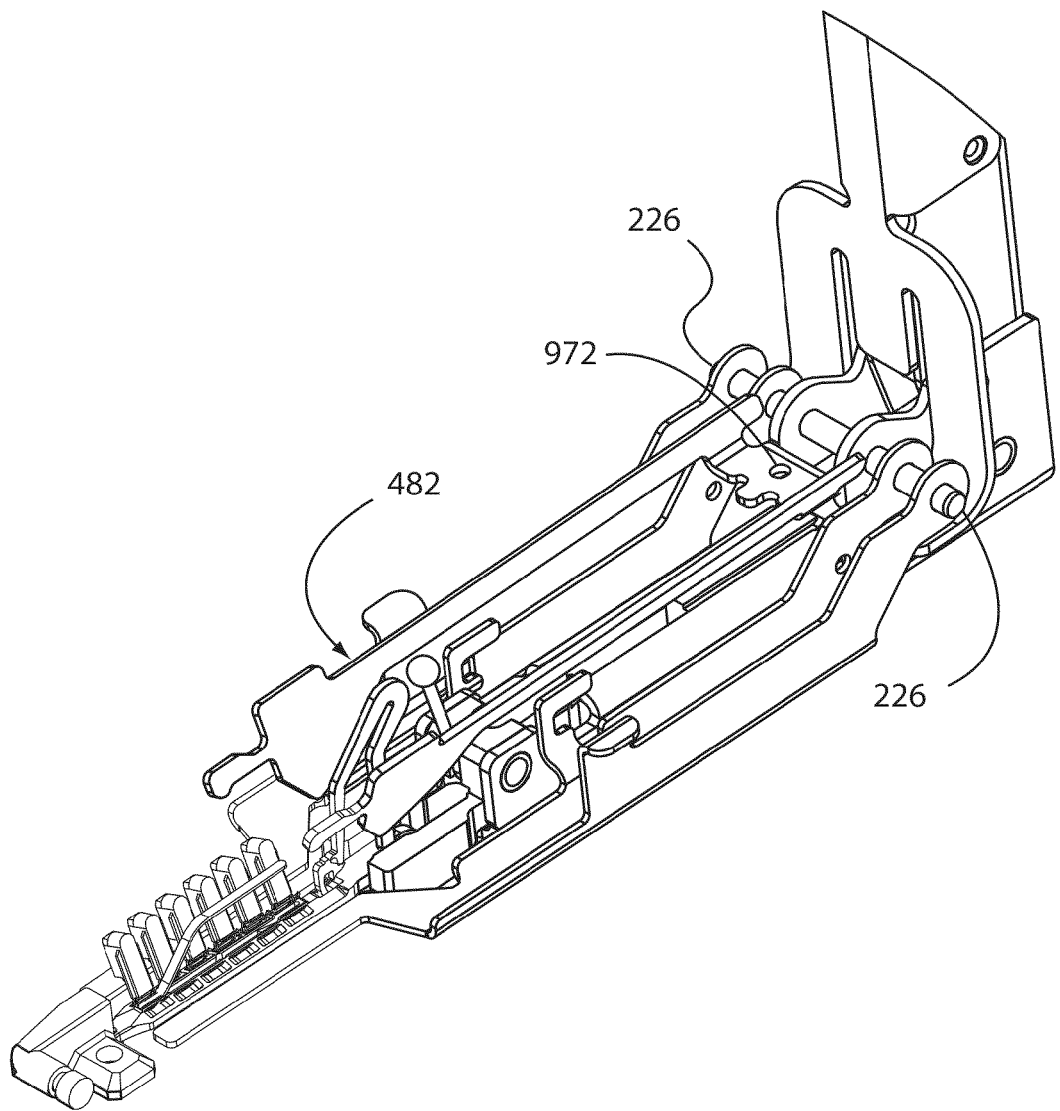

FIG. 147 is a perspective view of another exemplary embodiment of a sled 482.

Figure 148:
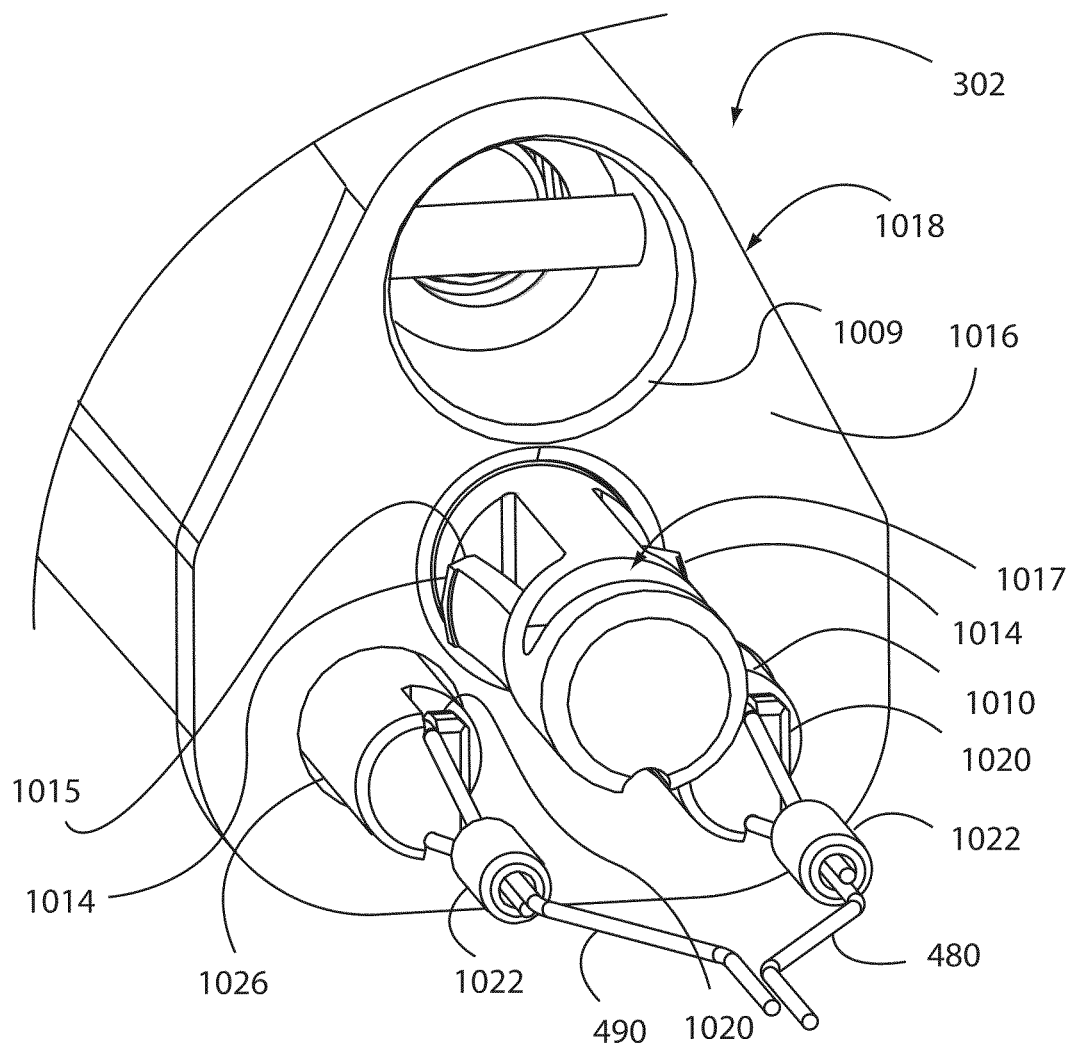

FIG. 148 is a perspective cutaway view of an exemplary fluid-driven actuator within the handle of an anastomosis tool.

Figure 149:
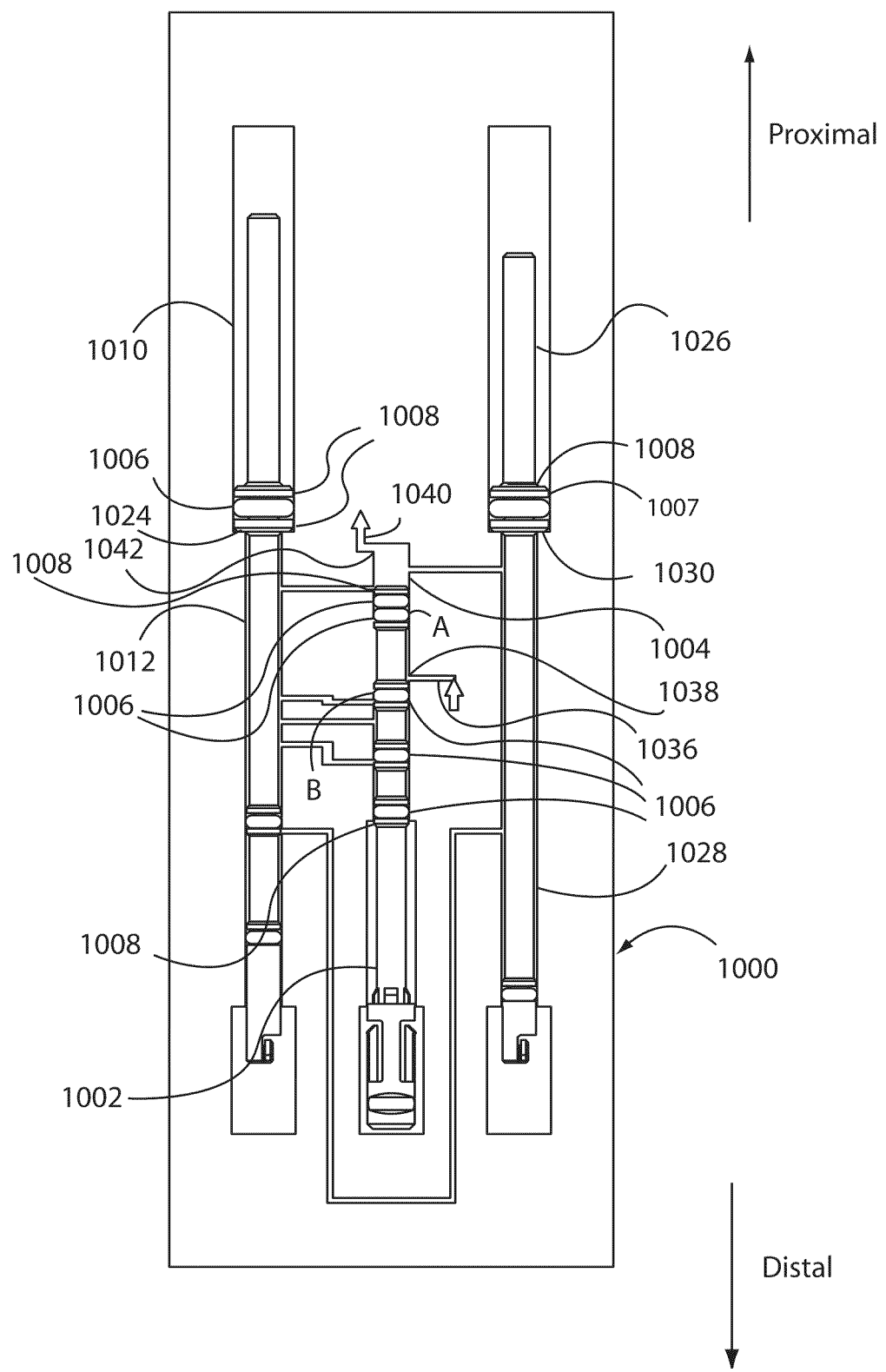

FIG. 149 is a schematic view of an exemplary fluid-driven actuator in a first, resting state.

Figure 150:
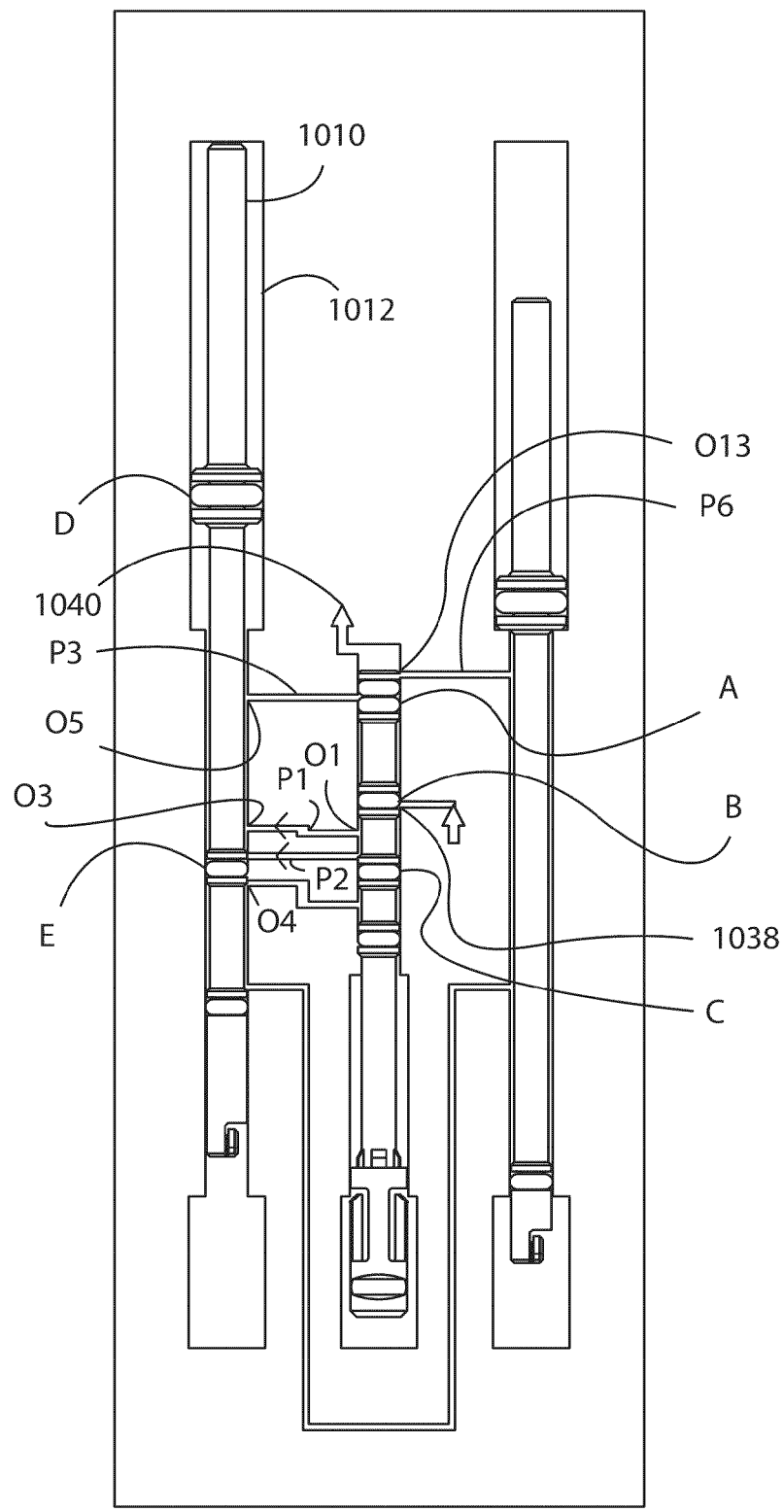

FIG. 150 is a schematic view of an exemplary fluid-driven actuator in a second, clamping state.

Figure 151:
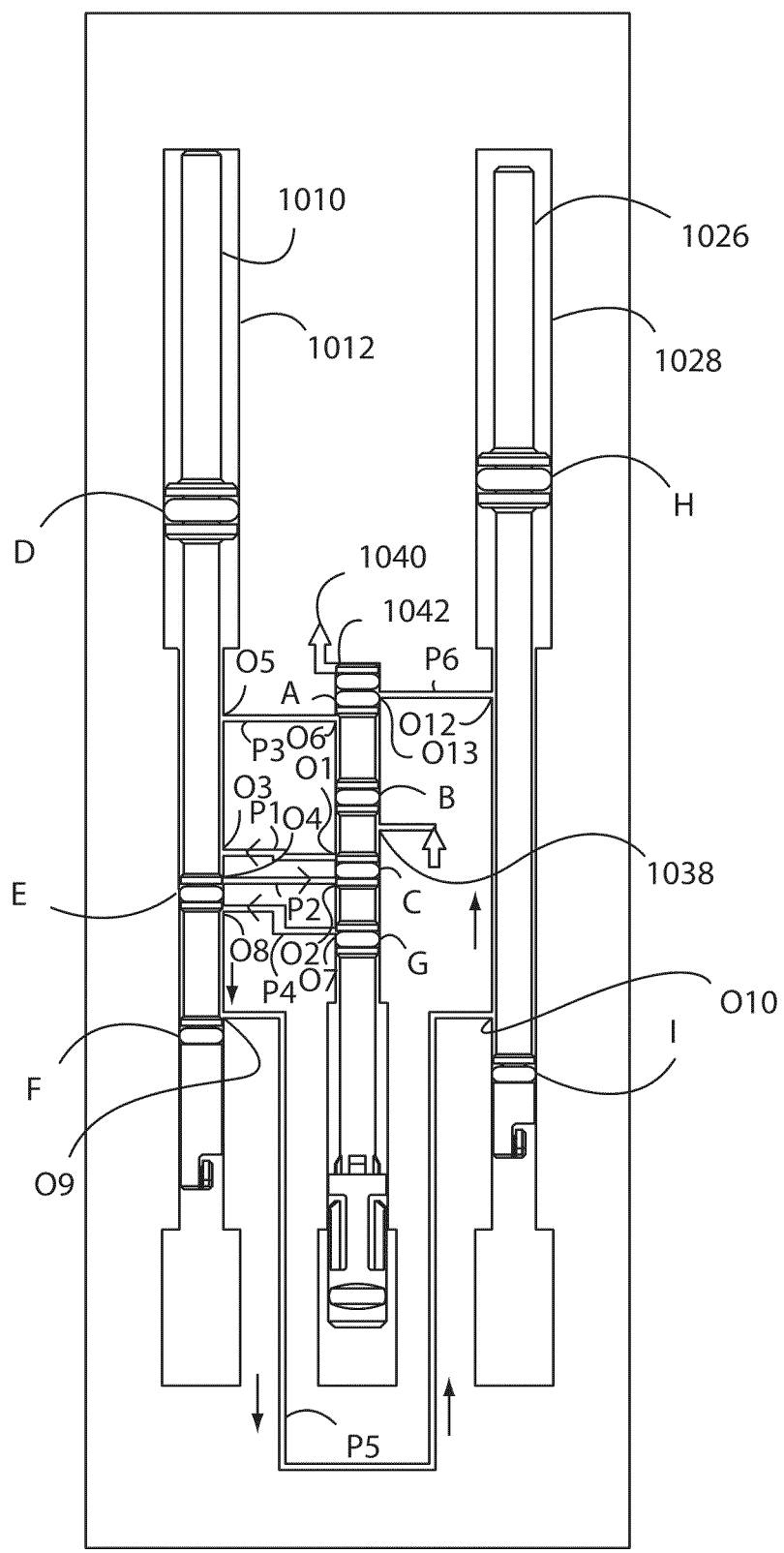

FIG. 151 is a schematic view of an exemplary fluid-driven actuator in a third, firing state.

Figure 152:
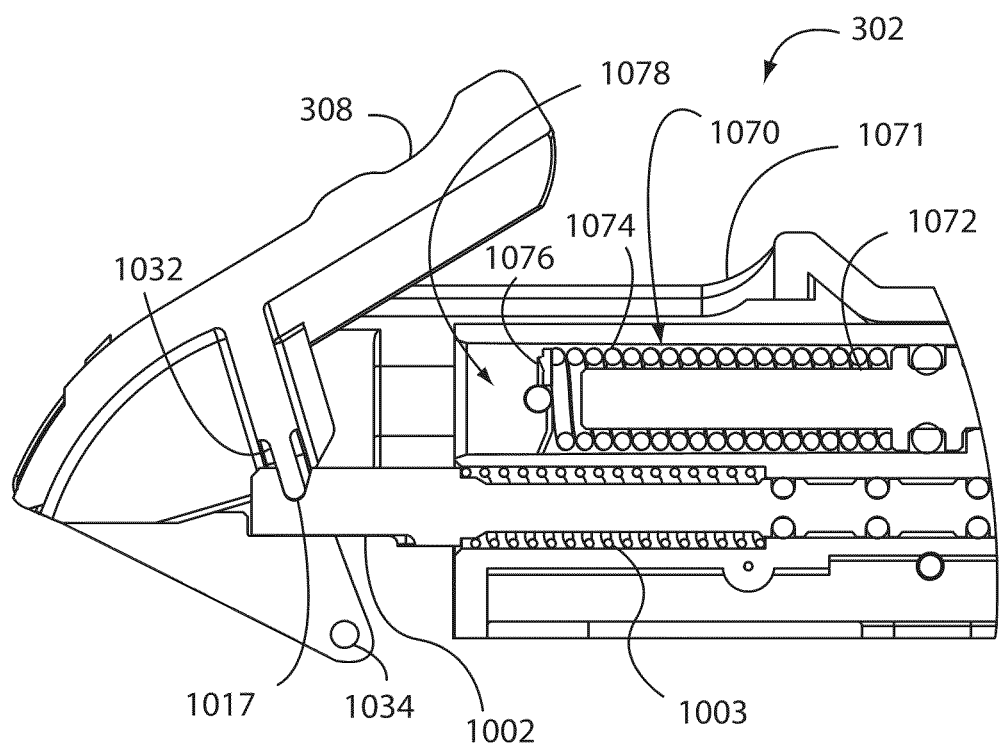

FIG. 152 is a cross-section view of a distal portion of an exemplary handle of an anastomosis tool.

Figure 153:
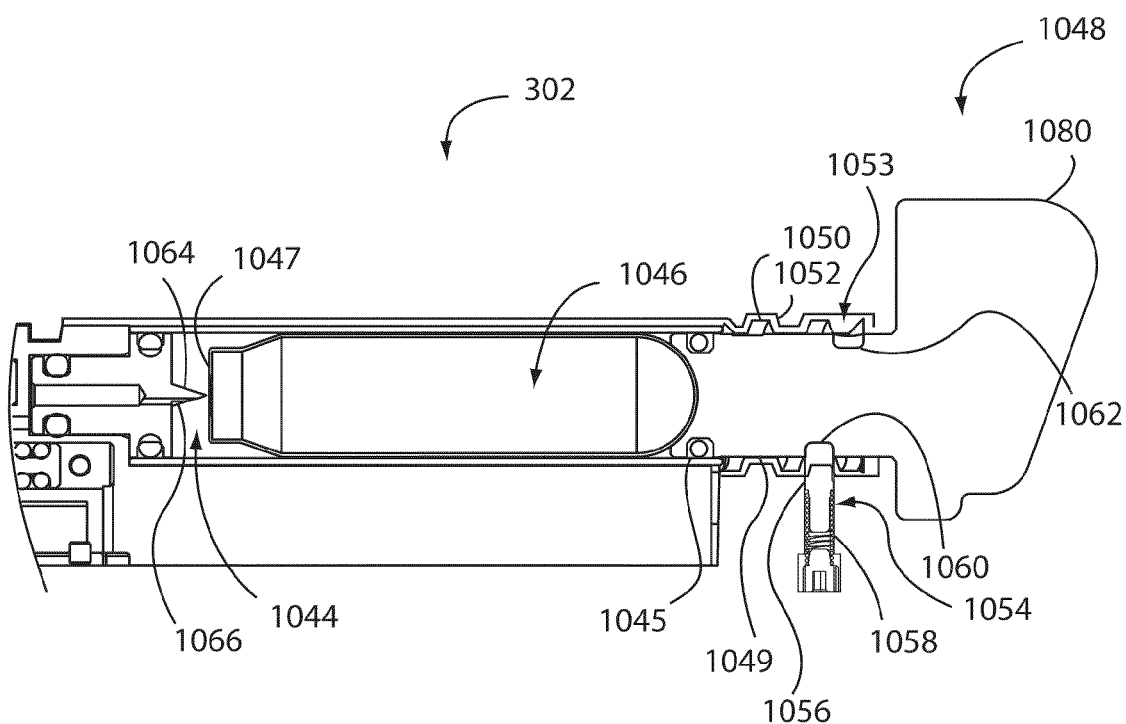

FIG. 153 is a cross-section view of a proximal portion of an exemplary handle of the anastomosis tool of FIG. 142.

Figure 154:
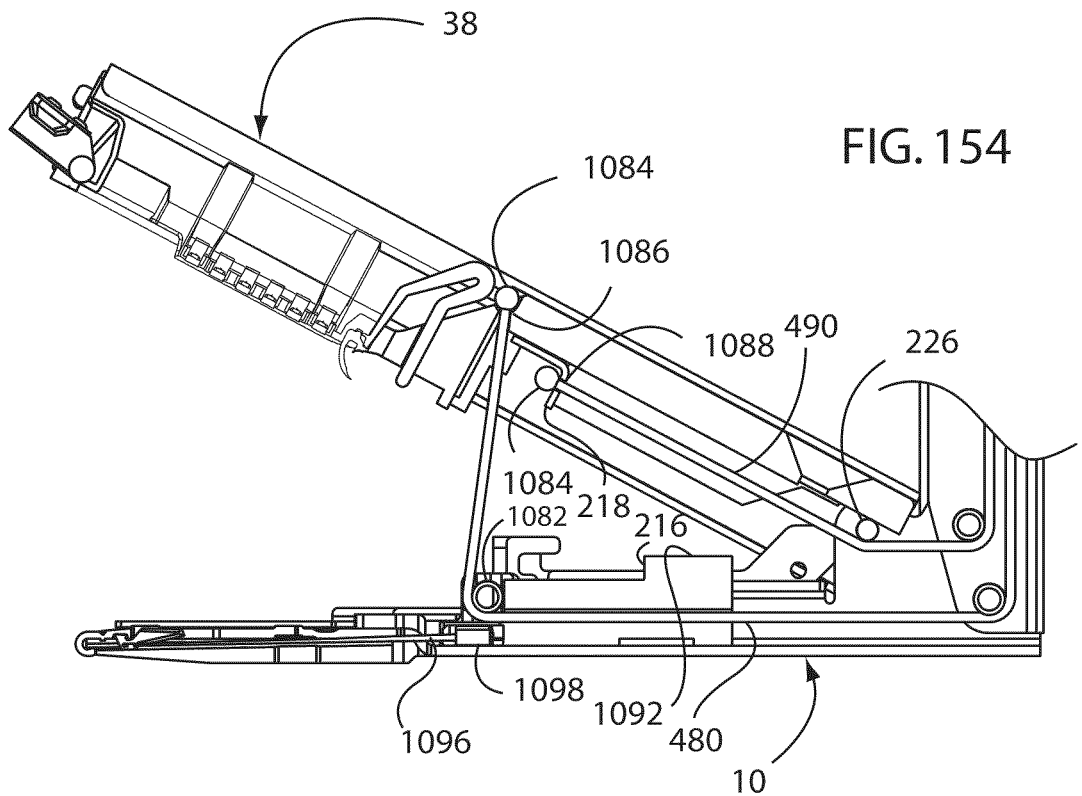

FIG. 154 is a cross-section view of an exemplary tissue effector of the anastomosis tool of FIG. 142.

Figure 155:
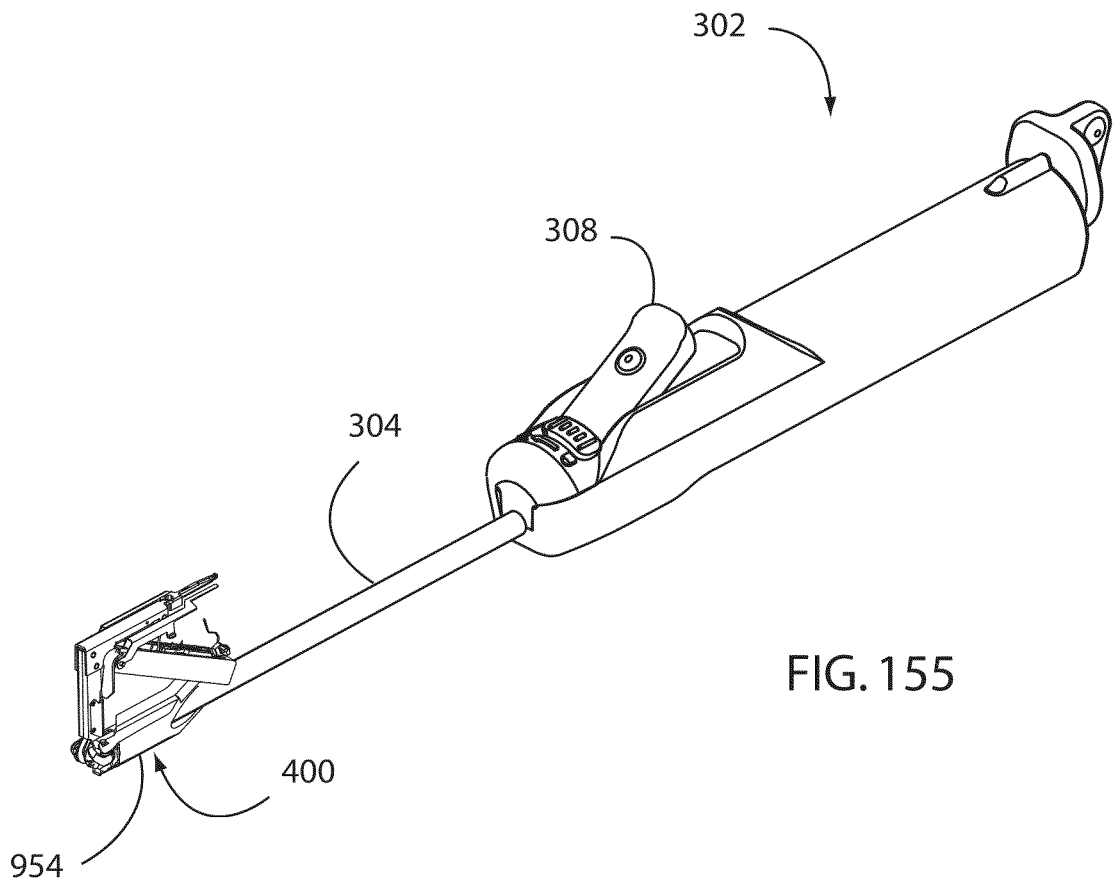

FIG. 155 is a perspective view of an exemplary tissue effector of the anastomosis tool of FIG. 142 in a graft preparation position.

Figure 156:
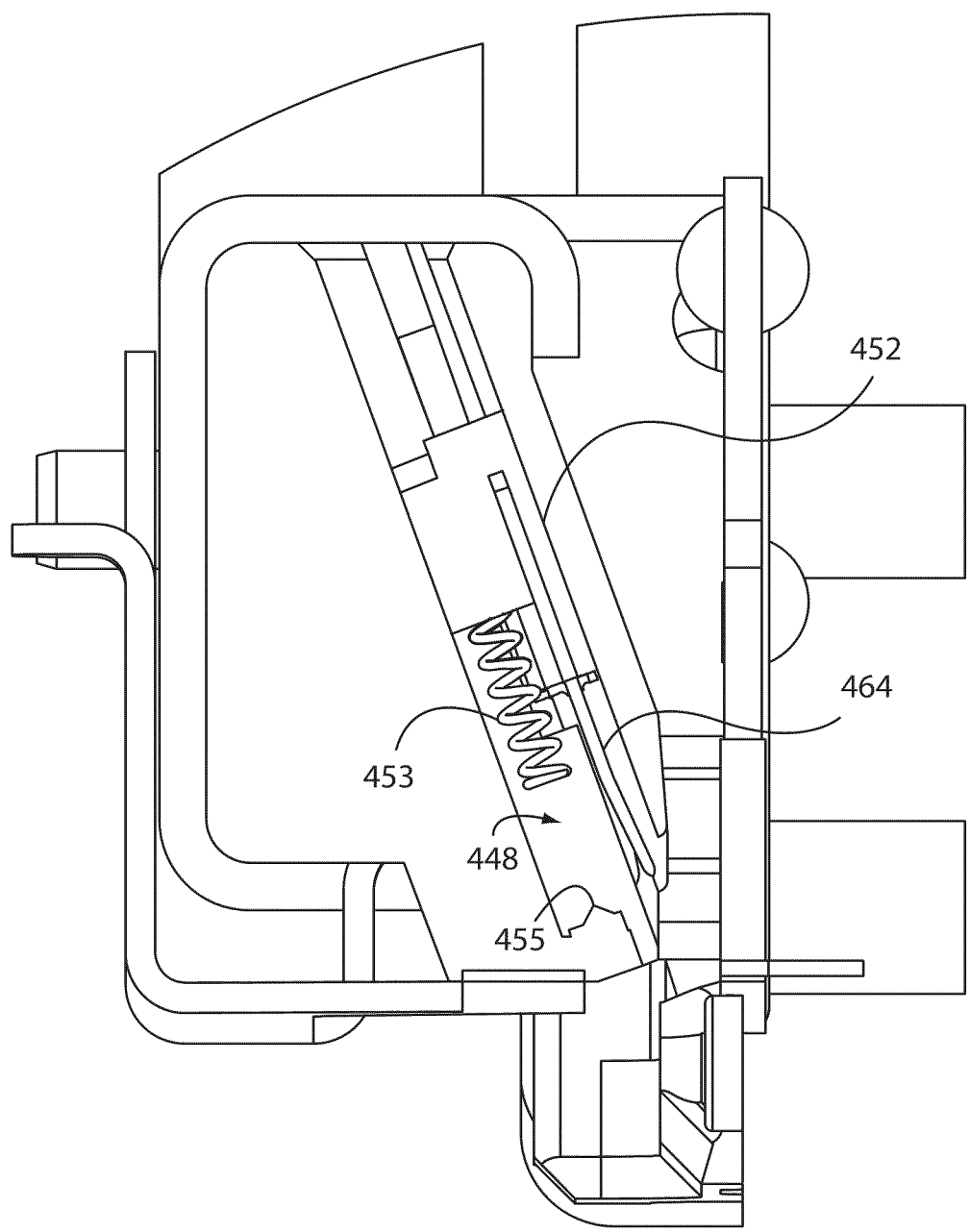

FIG. 156 is a cutaway view of a connector bay in the staple holder showing an exemplary connector deployer.

Figure 157:
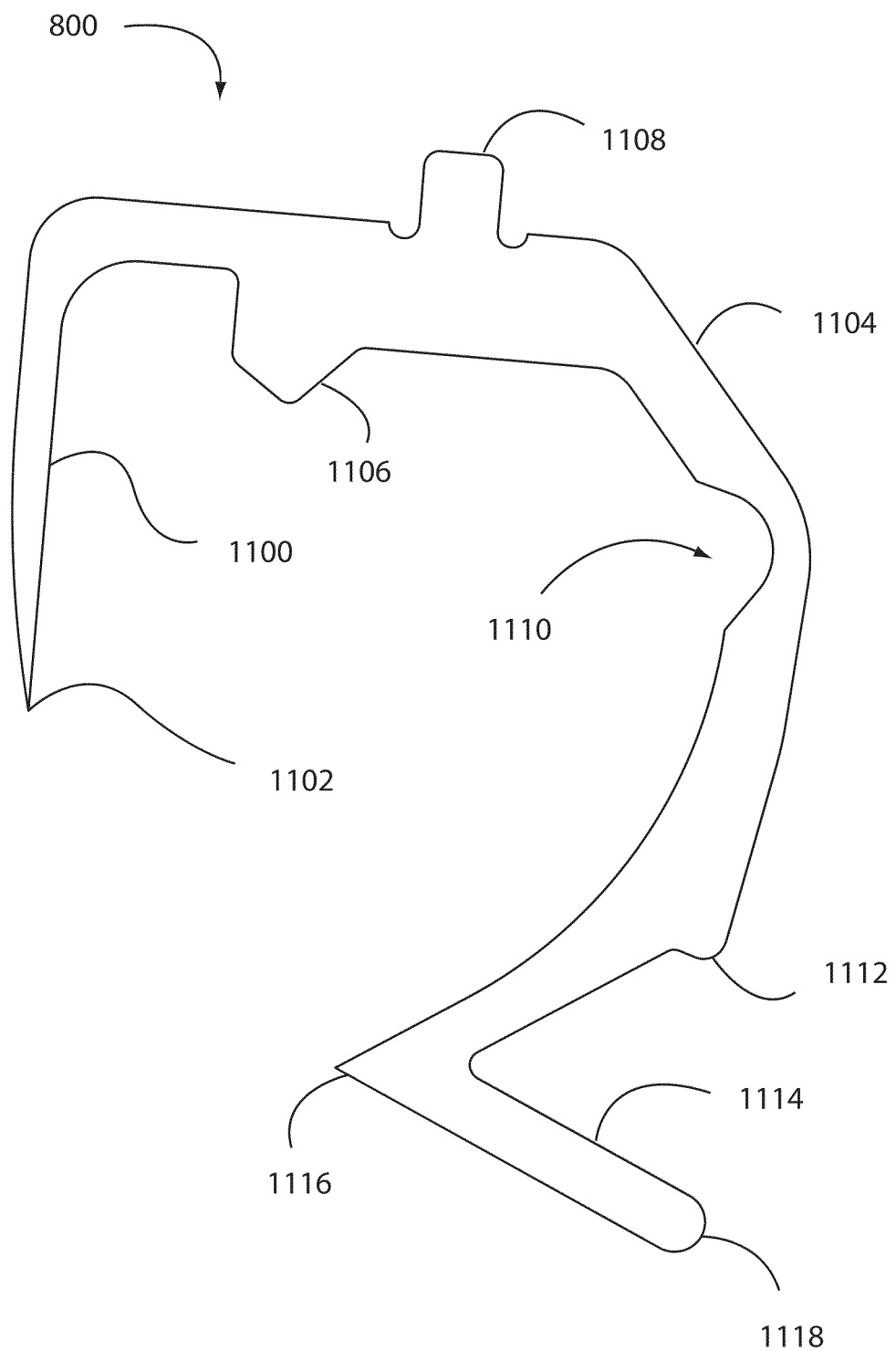

FIG. 157 is a top view of an exemplary clip used to seal the anvil entry hole adjacent to the anastomosis site, in an open configuration.

Figure 158:
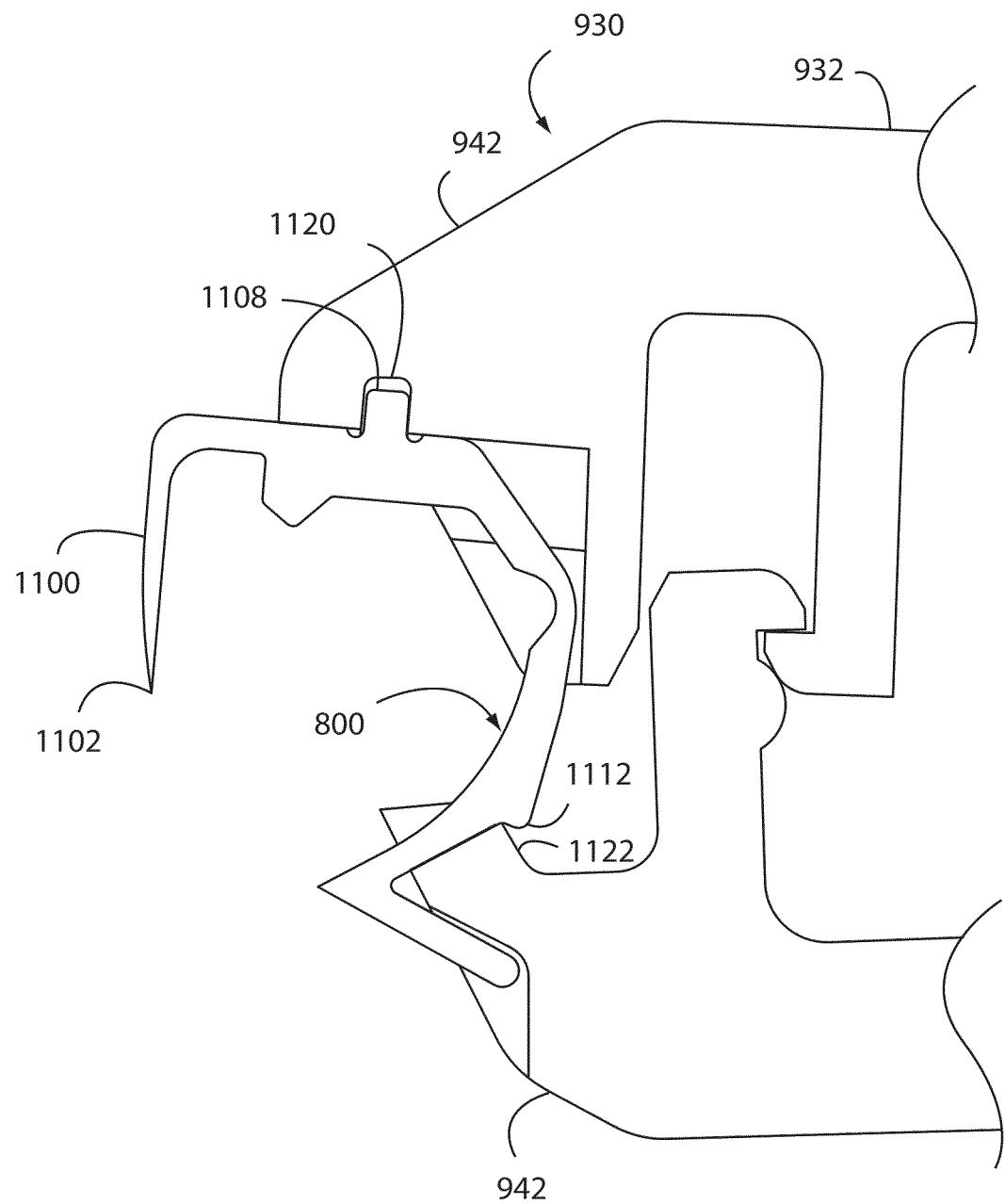

FIG. 158 is a side cross-section view of the clip of FIG. 157 held by an exemplary applier, where that applier is in a first position.

Figure 159:
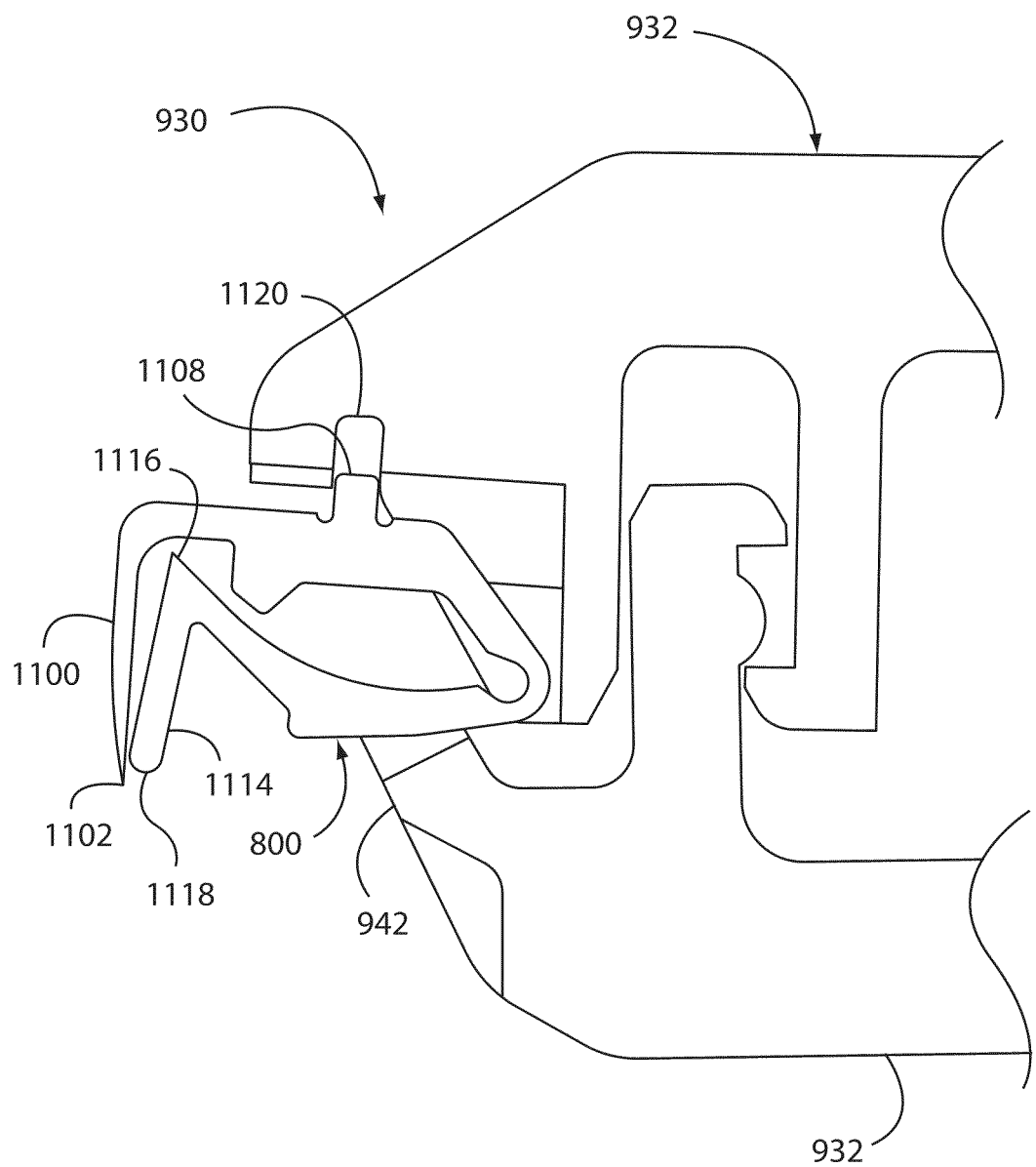

FIG. 159 is a side cross-section view of the clip of FIG. 157 held by the applier of FIG. 158, where that applier is in a second position.

Figure 160:
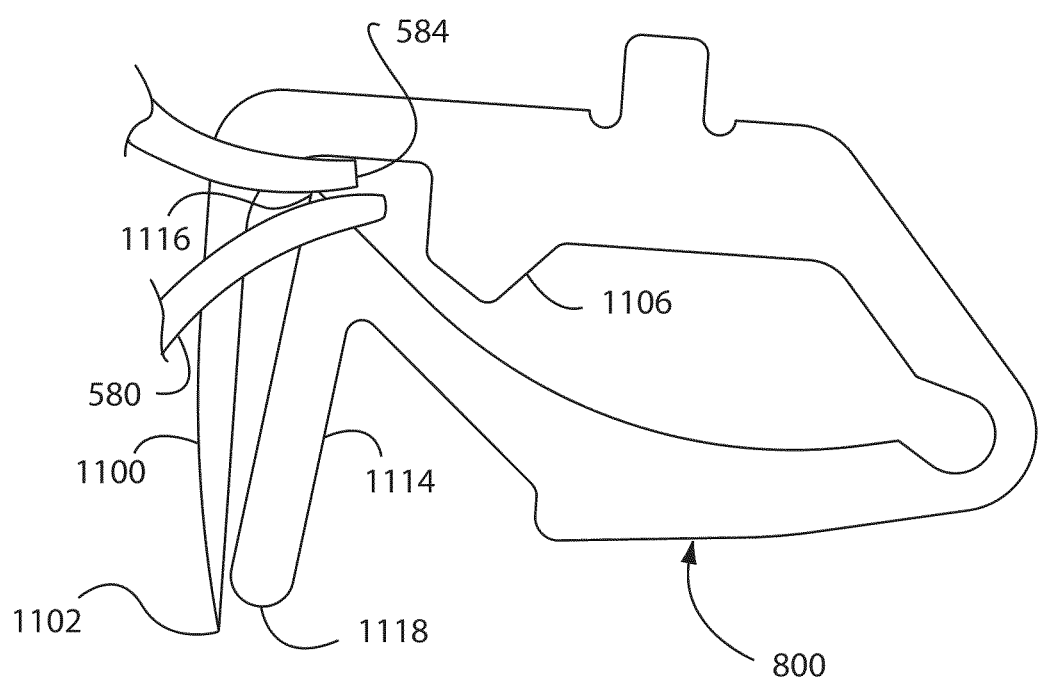

FIG. 160 is a side view of the clip of FIG. 157 in a closed configuration in the tissue of the target vessel.

Figure 161:
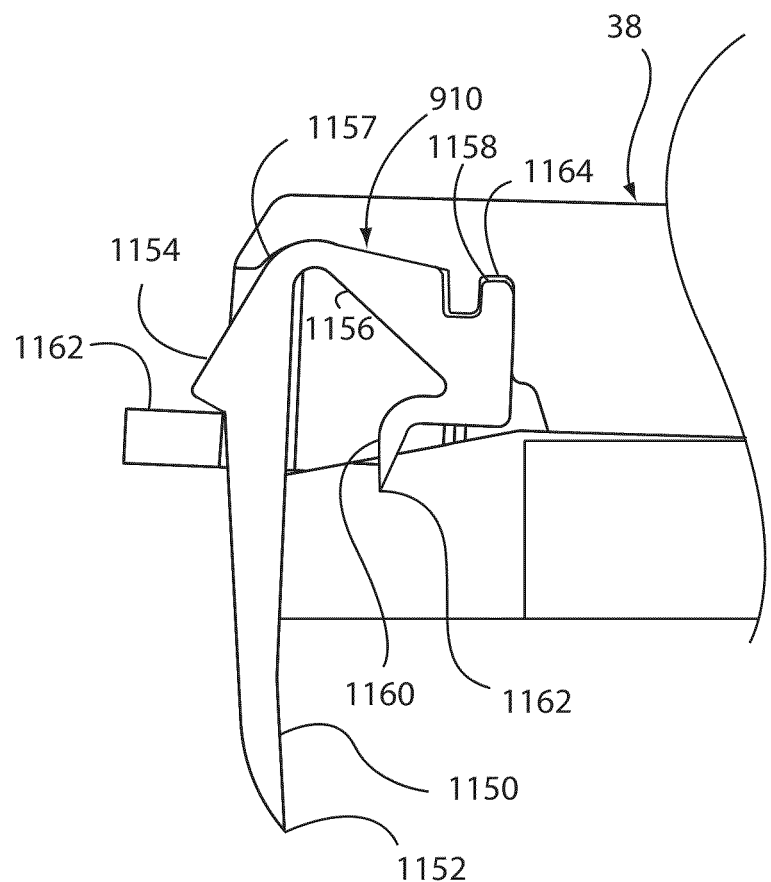

FIG. 161 is a side view of an exemplary heel clip detachably connected to the staple holder, in an open position.

Figure 162:
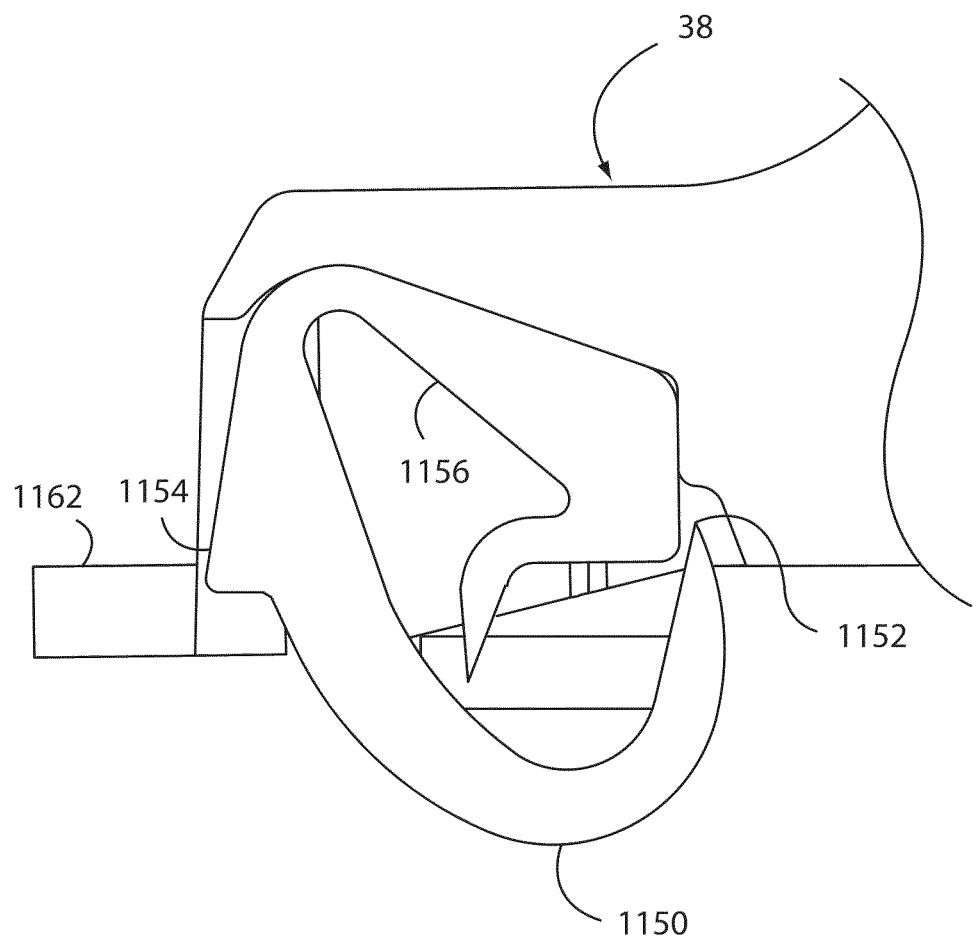

FIG. 162 is a side view of the exemplary heel clip of FIG. 161 detachably connected to the staple holder, after it has been deformed to a closed position.

Figure 163:
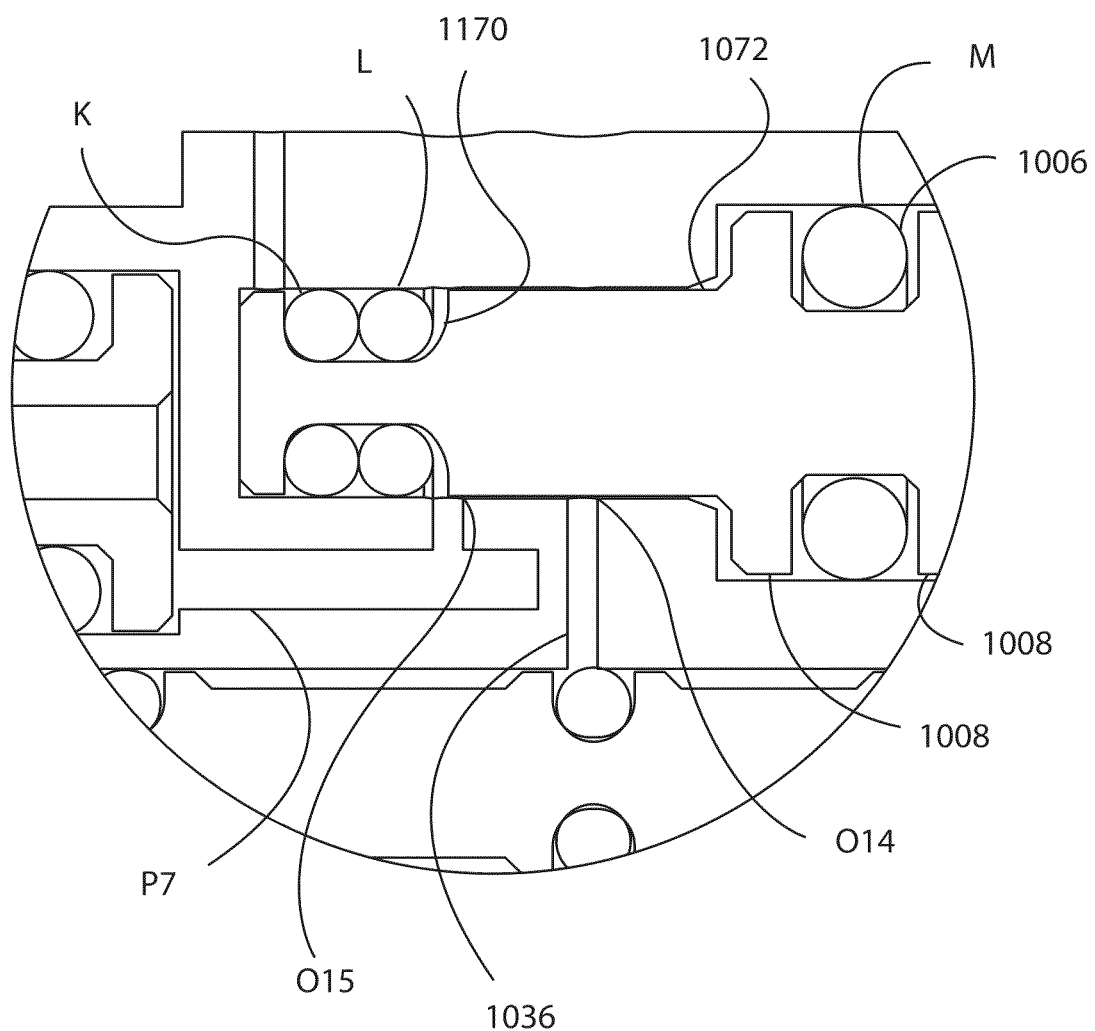

FIG. 163 is a schematic view of a pressure regulation assembly in a first state.

Figure 164:
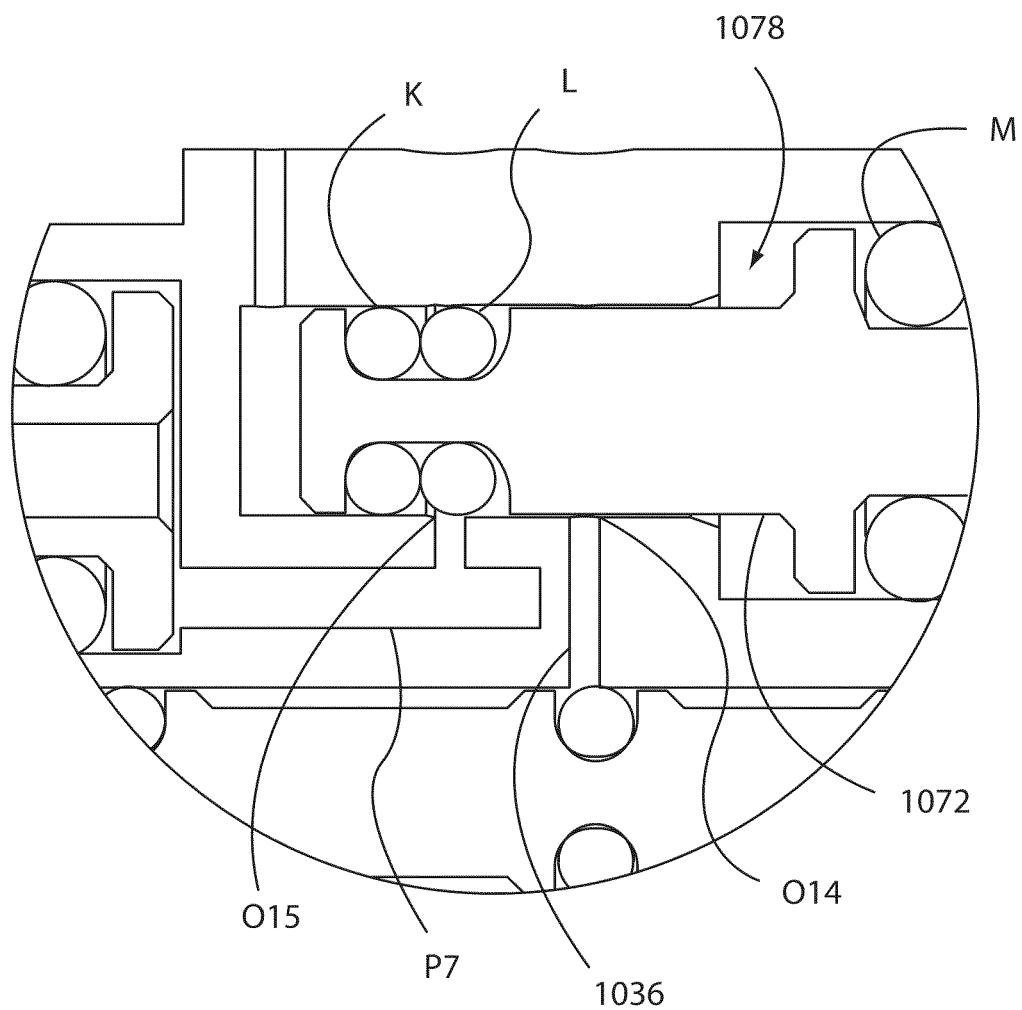

FIG. 164 is a schematic view of a pressure regulation assembly in a second state.

Figure 165:
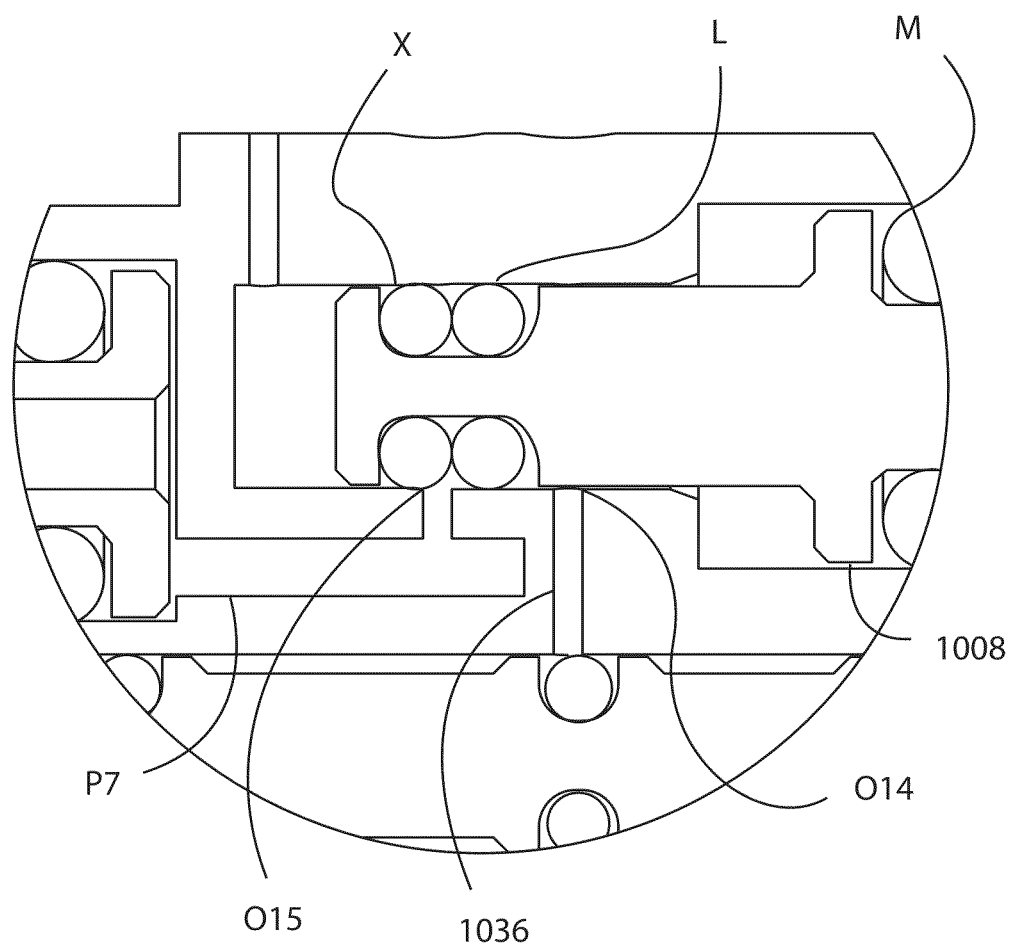

FIG. 165 is a schematic view of a pressure regulation assembly in a third state.

The use of the same reference symbols in different figures indicates similar or identical items.

DETAILED DESCRIPTION

Anvil

Figure 1:
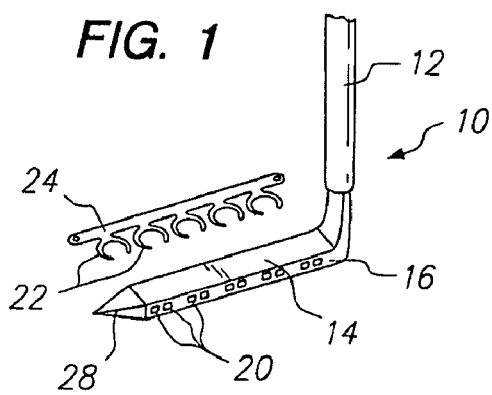
FIG. 1 is a perspective view of an anvil and a plurality of staples according to a first aspect of the present invention.

As shown in FIG. 1, one embodiment of an anvil 10 includes a handle 12 and an anvil arm 14 extending from the handle 12. The anvil arm 14 may be oriented substantially perpendicular to the handle 12, or oriented at a different angle. The anvil arm 14 may be provided with one or more staple bending features 16 on opposite sides of the anvil arm 14. In the anvil 10 shown in FIG. 1, the staple bending features 16 each include a plurality of recesses 20 which receive the ends of staples 22 and cause the staple ends to bend over. At least one of the staple bending features 16 may be configured differently or omitted, if desired. The staples 22 may be connected to a staple holding strip 24. The staples 22 are U-shaped and are arranged in a spaced apart parallel configuration such that the staples 22 all lie in a single plane. Alternately, the staples 22 may be shaped differently, and/or lie in one or more different planes. An exemplary anvil arm 14 has a height and a width of about 2 mm or less, advantageously about 1 mm or less, and a length of about 2 to 15 mm, advantageously 5 to 12 mm. The length of the anvil will vary depending on the diameter of the graft vessel selected. The length to width ratio of the anvil arm 14 is substantially between 2:1 and 15:1. A different length to width ratio may be used, if desired. As one example, the staples 22 have widths of about 0.2-3 mm. Advantageously, the staples 22 have widths of substantially 2 mm or less. The leg lengths of the staples 22 are substantially 0.2-3 mm. Alternately, other staple widths and/or leg lengths may be used.

Figure 2:
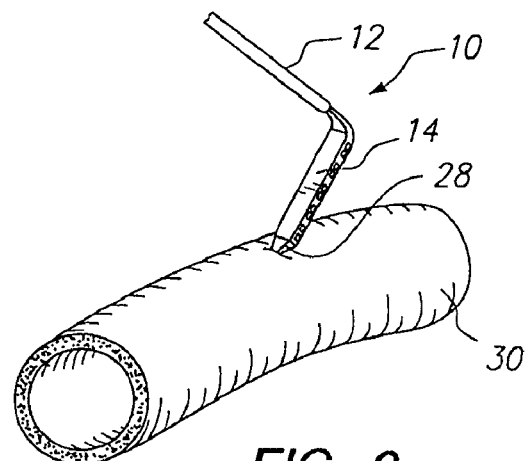
FIG. 2 is a perspective view of the anvil of FIG. 1 being inserted into a target vessel.

The anvil arm 14 has a sharp distal end 28 for puncturing the tissue of a target vessel to insert the anvil arm 14 into the target vessel. As illustrated in FIG. 2, the anvil arm 14 is inserted into a pressurized or unpressurized target vessel 30 by puncturing the target vessel with the distal end 28 of the anvil arm 14. The hole that is formed in the wall of the target vessel 30 by the anvil arm 14 is small enough to prevent significant bleeding through the puncture site. Alternately, the hole is closed by hand suturing. Alternately, the hole is closed with a biocompatible glue, adhesive or the like. Alternately, the hole is closed with a clip, clamp, or other implantable device that remains on the target vessel, as described in greater detail below. Such a device may be positioned on the outer surface and/or inner surface of the target vessel, and may extend into the hole. A device for closing the hole may be constructed from nitinol or other superelastic or pseudoelastic material, or from stainless steel or other material, where that device moves between a first configuration and a second configuration during deployment, and where the second configuration holds the hole closed. The hole is less than substantially 2 mm wide, and advantageously less than 1 mm wide. Alternately, the anvil arm 14 has a blunt distal end 28 that is inserted through a hole created with a separate instrument, by a different instrument connected to the anvil arm 14, or by a sharp member connected to the anvil arm 14 that can be retracted into the anvil arm 14 or otherwise blunted or concealed after puncturing or creating an incision in the wall of the target vessel.

Figure 3:
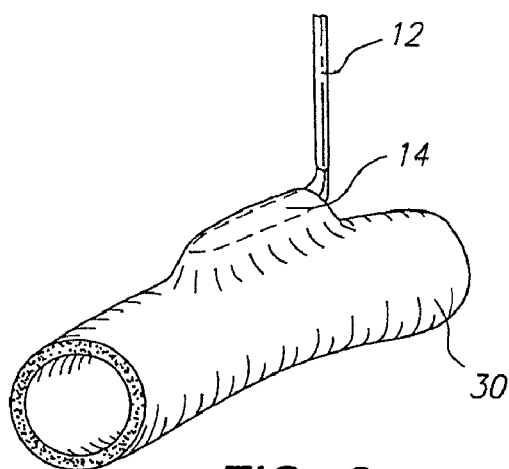
FIG. 3 is a perspective view of the anvil tenting a wall of a target vessel for an anastomosis procedure.

Once the anvil arm 14 has been inserted into the target vessel 30, the anvil arm 14 may be pulled against an inner wall of the target vessel 30, causing tenting of the thin tissue of the vessel wall as illustrated in FIG. 3. This tenting of the vessel wall provides control over the anastomosis site during an anastomosis procedure that is described with respect to FIGS. 4-6. However, the target vessel wall need not be tented in order to control the anastomosis site during the anastomosis procedure.

Staple Holder and Connectors

Figure 4:
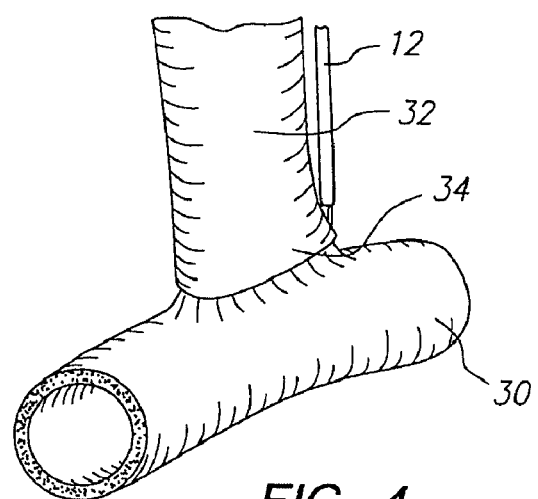
FIG. 4 is a perspective view of a graft vessel placed adjacent an exterior of the tented target vessel for the anastomosis procedure.
Figure 5:
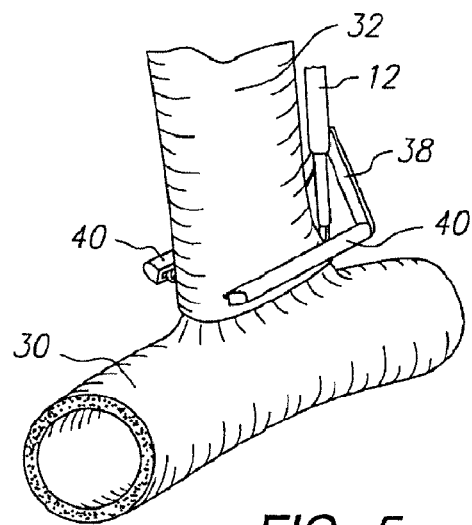
FIG. 5 is a perspective view of the staples being applied to the graft vessel and the target vessel during an anastomosis procedure.
Figure 29:
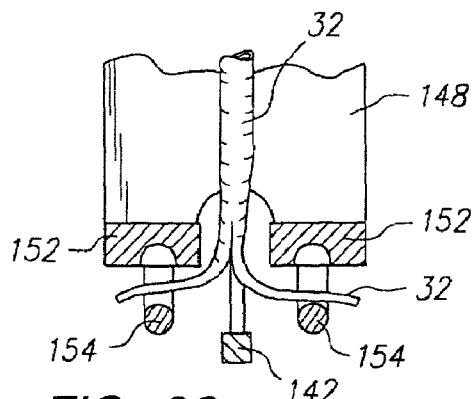
FIG. 29 is a cross sectional view taken along line C-C of FIG. 28, showing a first step of the anastomosis procedure.
Figure 30:
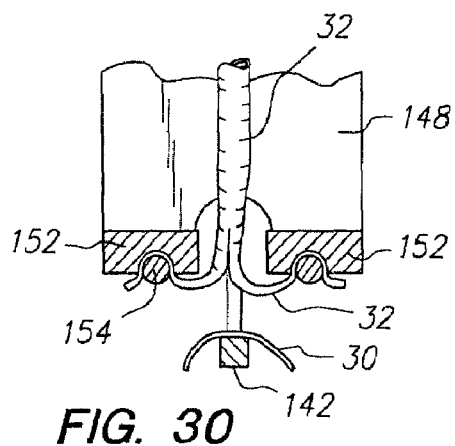
FIG. 30 is a cross sectional view taken along line C-C of FIG. 28, showing a second step of the anastomosis procedure.
Figure 31:
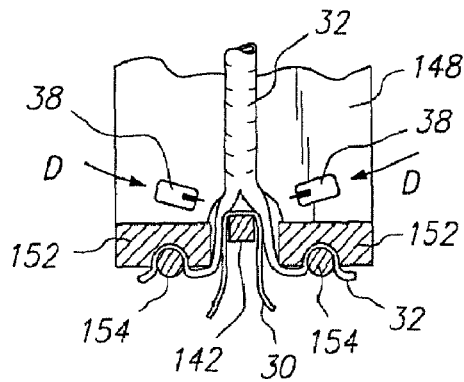
FIG. 31 is a cross sectional view taken along line C-C of FIG. 28, showing a third step of the anastomosis procedure.

As shown in FIG. 4, a graft vessel 32 is advanced to the anastomosis site and an end 34 of the graft vessel 32 is positioned adjacent an exterior surface of the target vessel 30 at the anastomosis site. At least part of the tented portion of the target vessel 30 is positioned within the perimeter of the end 34 of the graft vessel 32. As shown in FIG. 5, a staple holder 38 is provided having two arms 40 which are pivotally connected to the handle 12 of the anvil 10. Alternatively, the pivoting arms 40 of the staple holder 38 may be connected to the handle 12 in a different way, or may be connected to a separate or additional device. The arms 40 are spaced apart from one another across at least a part of their length. Thus, the graft vessel can be positioned between the arms 40. That is, the arms 40 are positioned on substantially opposite sides of the graft vessel. In this way, each arm 40 may be positioned against a flap at an end of the graft vessel, as illustrated in FIGS. 29-31. The arms 40 may be configured differently, if desired.

Figure 6:
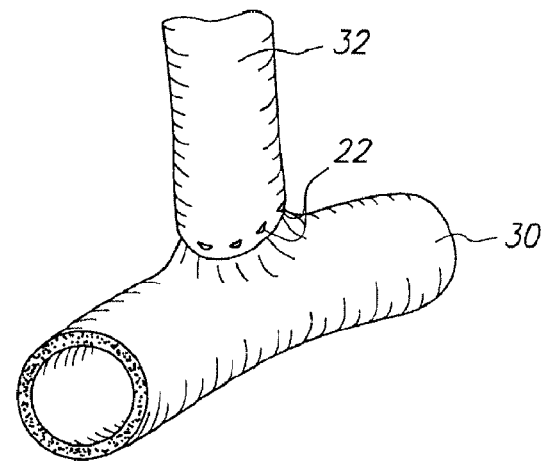
FIG. 6 is a perspective view of the completed anastomosis according to the first aspect of the present invention.

Referring also to FIG. 1, the staple holder 38 may be used to hold individual staples 22 and/or staple holding strips 24. In one embodiment, each arm 40 of the staple holder 38 carries one row of staples 22 or one staple holding strip 24, where the staples 22 are arranged in a substantially linear row. Alternately, staples 22 or staple strips 24 may be arranged in two or more rows, parallel or otherwise, on one or more arms 40. Alternately, the staples 22 may be staggered on one or more arms, such that at least one row of staples 22 does not fall along a straight line. Alternately, the staples 22 may be arranged in a nonlinear manner on at least one arm 40. The staples 22 or staple strips 24 may be arranged or aligned in any manner on each arm 40 that results in a secure anastomosis between the graft vessel and the target vessel. The staples 22 are inserted through the flaps at the end of the graft vessel 32, or another portion of the graft vessel, and into the target vessel 30 by pivoting the arms 40 of the staple holder 38 towards the anvil arm 14. The staple bending features 16 are positioned in a configuration corresponding to the configuration of the staples 22, such that each staple 22 engages a corresponding staple bending feature 16 during deployment. When the ends of the staples 22 engage the staple bending features 16 on the anvil arm 14, the ends of the staples 22 are bent over, securing the graft vessel 32 and target vessel 30 together. Once the staple ends are bent over, the staples 22 are released from the staple holding strip 24 or the staple holder 38, resulting in spaced apart staples 22 securing the graft vessel 32 and the target vessel 30 together as shown in FIG. 6. Alternately, the staple holder 38 is a mechanism that deploys connectors other than or in addition to staples 22 and/or staple holding strips 24.

After stapling is complete, an incision is formed in the wall of the target vessel 30 to allow blood flow between the target vessel and the graft vessel 32. Some examples of methods and devices for forming the incision will be described in further detail below. Alternately, the incision is formed in the wall of the target vessel 30 before, or while, stapling is performed. FIG. 6 illustrates a completed anastomosis between a target vessel 30 and a graft vessel 32 with a plurality of staples 22. The spacing between the staples 22 is approximately 1 to 4 mm. This spacing is similar to the spacing between sutures in a conventional sutured anastomosis. A different spacing between the staples 22 may be used if desired. After completion of the anastomosis, the anvil arm 14 is withdrawn from the target vessel 30 between adjacent staples 22. The withdrawal of the anvil arm 14 leaves a gap that is approximately the same as the spacing between adjacent staples. Accordingly, substantially no blood leakage occurs at the location where the anvil arm has been withdrawn.

Figure 7:
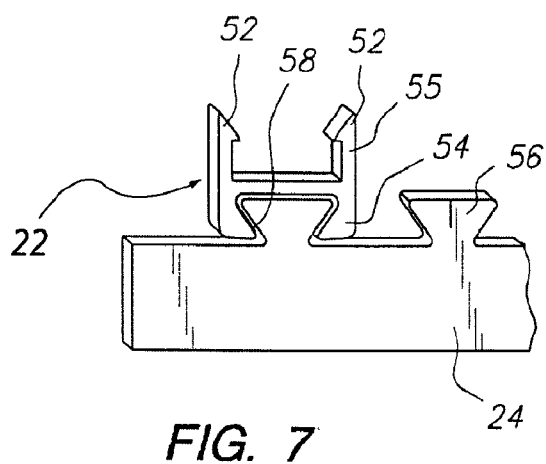
FIG. 7 is a perspective view of a staple supported on a staple holding strip.
Figure 8:
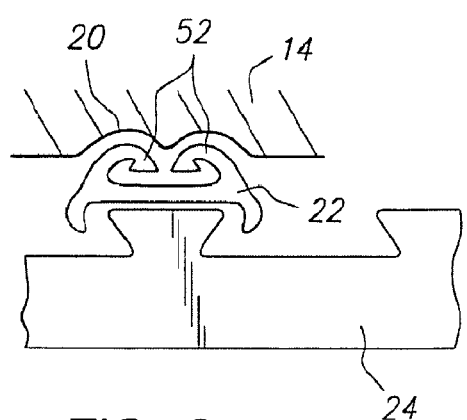
FIG. 8 is a side view of the staple and staple holding strip of FIG. 7 when the ends of the staple have been bent by contact with an anvil.

FIGS. 7 and 8 illustrate one example of a staple 22 connected to a staple holding strip 24. This staple 22 includes barbed staple ends 52 extending from the front portion of the staple 22 and a C-shaped portion 54 extending from a rear of the staple 22 for connecting the staple 22 to the staple holding strip 24. The staple holding strip 24 includes a plurality of protrusions 56 for receiving the staples 22. The C-shaped portion 54 of each staple 22 is received around one of the protrusions 56 and is secured in place at one or more locations, such as by welds 58 or by a frangible linkage or connection. Alternately, the C-shaped portion 54 of each staple 22 may be secured to the staple-holding strip 24 in a different way. As shown in FIG. 8, when the staple holding strip 24 is advanced toward the anvil arm 14, the barbed staple ends 52 are received in the recesses 20 in the anvil arm 14. Contact between each staple end 52 and the corresponding recess 20 generates a moment that causes the barbed staple ends 52 to bend towards one another. At the same time that the barbed staple ends 52 bend over, or after the bending of the staple ends 52, the staple 22 is detached from the staple holding strip 24. The staple 22 may be detached from the staple holding strip 24 by the action of bending the barbed staple ends 52 such that the C-shaped portion 54 of the staple 22 splays outward and breaks apart from the corresponding protrusion 56 on the staple holding strip 24, by bending a frangible connection between the staple holding strip and the staples to separate the staples, or any other known separation methods, such as melting of a connection between the staple and the staple holding strip.

Figure 9:
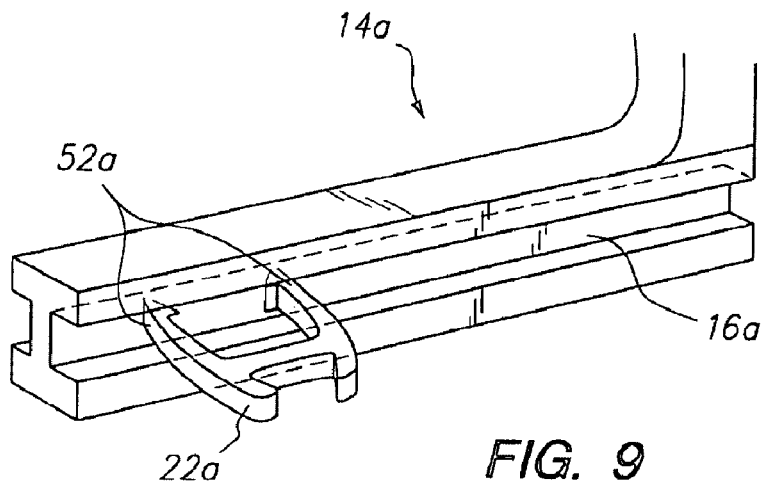
FIG. 9 is a perspective view of an anvil and staple according to another aspect of the present invention.

FIG. 9 illustrates an alternate staple 22a having inwardly curved barbed staple ends 52a. Because the staple ends 52a are themselves curved, the corresponding staple bending feature or features 16a need not be curved to bend the ends 52a of the staples 22a. As shown in FIG. 9, the staple bending features 16a on each side of the anvil arm 14a may be formed as a single longitudinal groove along the anvil arm 14a, where the staple bending feature 16a has a substantially flat surface. When the curved ends 52a of the staple 22a are received in the groove 16a of the anvil arm 14a, the ends bend inward to secure the tissue with the staple. Alternately, the staple may be configured differently. Alternately, two or more different kinds of staples are deployed by the staple holder 38 in order to form a single anastomosis.

Figure 10A:
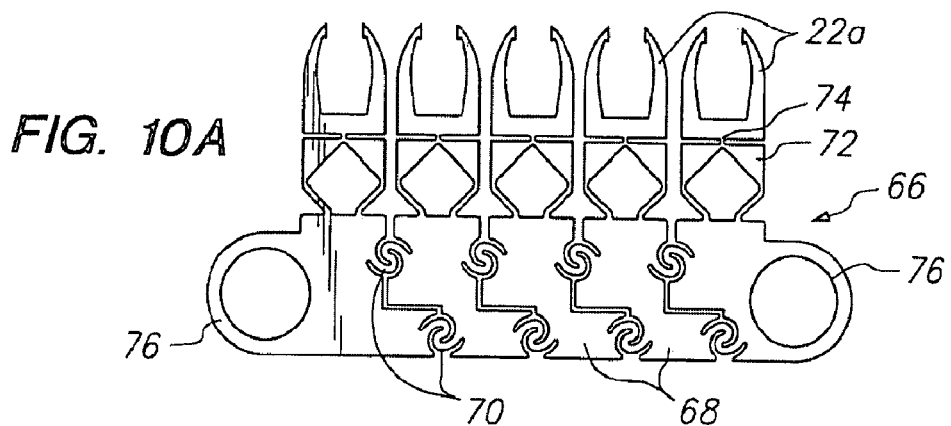
FIGS. 10A and 10B are side views of a plurality of staples supported on two examples of expandable staple holding strips.

Referring also to FIG. 10A, a plurality of staples 22a are positioned on an expandable staple holding strip called an expandable backbone 66. The expandable backbone 66 includes a plurality of elements 68 which are interconnected by one or more expanding members 70. Each of the backbone elements 68 is provided with a connecting diamond member 72 that is connected to one of the staples 22a. As shown in FIG. 10A, each staple 22a is connected to the corresponding diamond member 72 by a thin connecting section 74. The expandable backbone 66 allows the spacing between the staples 22a to be adjusted for the particular anastomosis to be performed. The backbone 66 allows expansion of the distance between staples from a distance of approximately 0.1 mm to a distance of approximately 1 to 4 mm, i.e., expansion of up to 40 times the original spacing. Alternately, the backbone 66 allows a different amount of expansion. The expanding backbone 66 also includes two openings 76 at opposite ends which may be engaged by holding pins (not shown) on an anastomosis system or staple holder. The opening 76 allow the backbone 66 to be easily expanded by relative motion of the holding pins. The connecting diamond members 72 are configured to collapse inwardly toward the backbone when the staples 22a engage the staple bending surface or surfaces 16a of the anvil. The collapsing of each diamond member 72 forces the corresponding staple 22a to separate from the diamond member 72 at a connecting section 74. The connecting section 74 is a frangible linkage connecting a staple 22a to a corresponding diamond member 72.

Figure 10B:
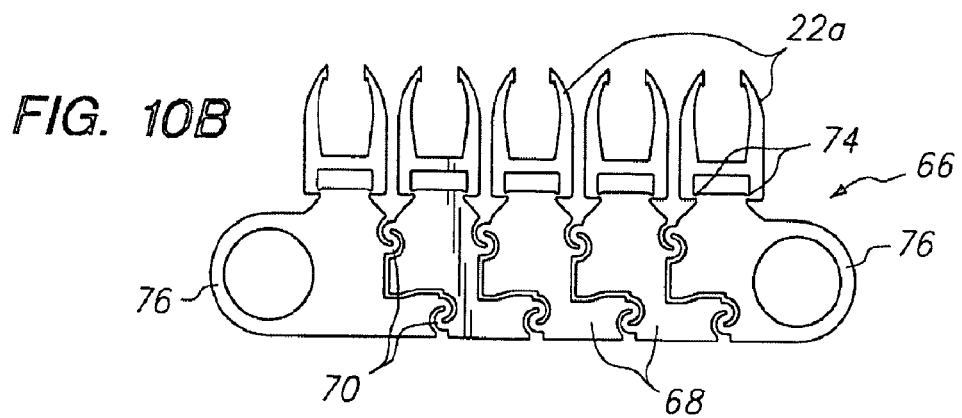

FIG. 10B illustrates another example of staples 22a detachably connected to a backbone 66. The staples 22a are each connected to the associated backbone elements 68 at two connecting sections 74. The staples 22a, backbone 66, and associated components are substantially as described above with regard to FIG. 10A.

Cutting Device

Figure 11:
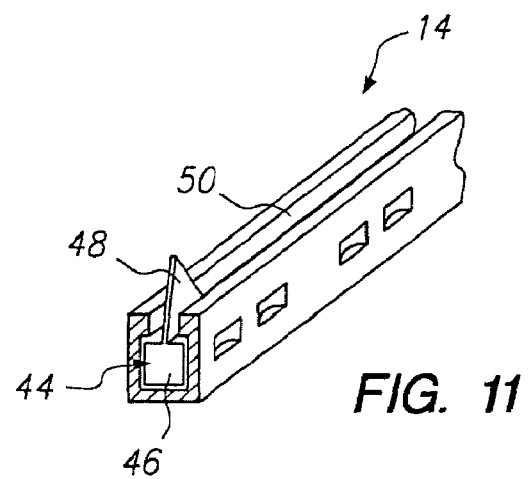
FIG. 11 is a perspective view of a portion of an anvil having a movable cutting device.

FIG. 11 shows a portion of an anvil arm 14 with a movable cutting device 44. The cutting device 44 includes a base 46 and a blade 48. The base 46 of the cutting device 44 is positioned in a longitudinal groove 50 in the anvil arm 14. After the anvil arm 14 has been inserted into the target vessel, the cutting device 44 may be moved longitudinally along the anvil arm 14 to form an incision in the target vessel.

Figure 12:
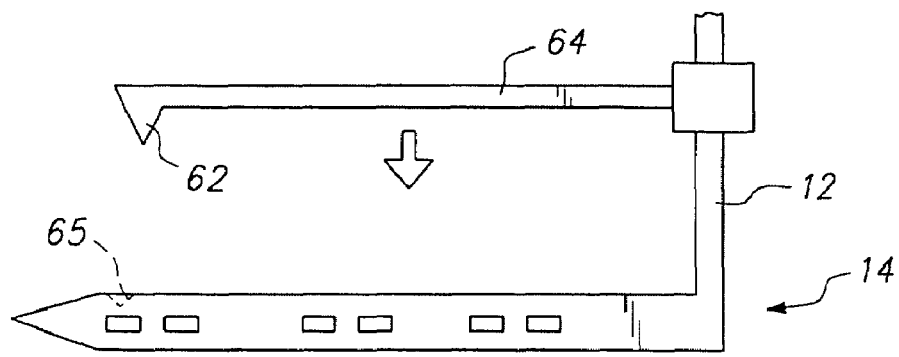
FIG. 12 is a side view of an anvil having an external cutting device.
Figure 12A:
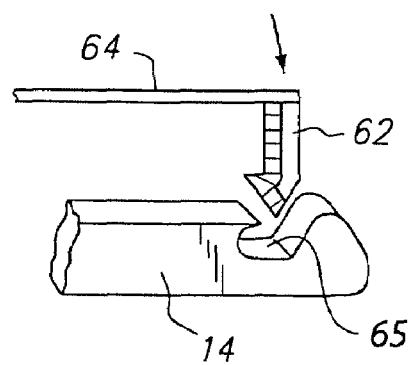
FIGS. 12A and 12B are side views of a portion of an anvil and two cutting devices that snap onto the anvil.
Figure 12B:
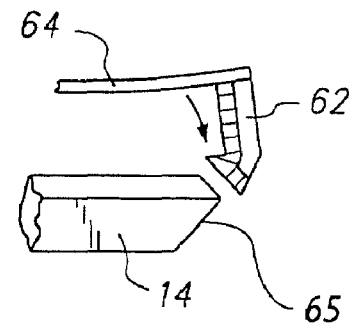

FIGS. 12, 12A, and 12B illustrate external cutting devices that are advanced onto the anvil arm 14 after the anastomosis procedure and cut an incision in the target vessel from an exterior of the target vessel as the anvil arm 14 is withdrawn. As shown in FIG. 12, a knife 62 is positioned on a knife arm 64 that is movable along the handle 12 of the anvil. The knife 62 is moved downward in a direction substantially parallel to the longitudinal axis of the handle 12 until the knife 62 engages a recess 65 in the anvil arm 14. The knife 62 is thereby positioned substantially at the anastomosis site. The end of the graft vessel is then placed substantially against the wall of the target vessel at the anastomosis site, over the knife 62 and knife arm 64. As the anvil arm 14 is withdrawn from the anastomosis site, the knife 62 forms an incision in the target vessel. The knife 62 and knife arm 64 exit the anastomosis site via the joint between the graft vessel and the target vessel. The withdrawal of the anvil arm 14, knife 62 and knife arm 64 leaves a gap in the wall of the target vessel that is approximately the same as the spacing between adjacent staples to minimize or eliminate leakage through that gap. Alternately, the knife 62 may be moveable relative to the handle 12 in at least one direction in addition to or instead of a direction substantially parallel to the longitudinal axis of the handle 12. For example, the knife 62 may be moveable in a direction substantially parallel to the wall of the target vessel to create an arteriotomy in the target vessel at the junction between the graft vessel and the target vessel.

FIGS. 12A and 12B illustrate two alternate examples of the knife 62 which snap onto a corresponding engagement surface 65 of the anvil arm 14 so that the knife 62 and anvil arm 14 are secured together for formation of the incision during removal of the anvil arm 14 from the anastomosis site.

Figure 13:
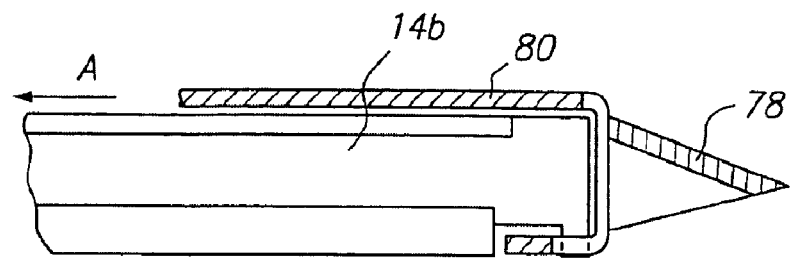
FIG. 13 is a side view of a portion of an anvil with an extendable cutting device.
Figure 14:
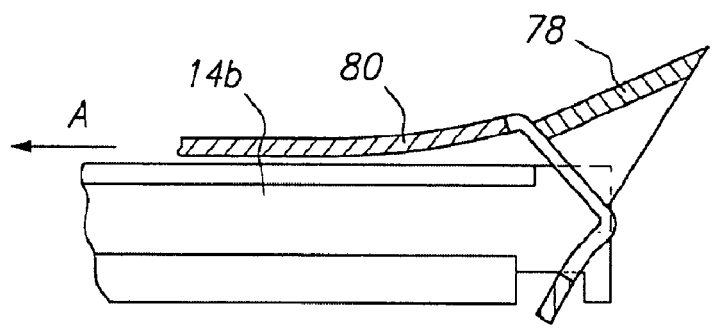
FIG. 14 is a side view of the anvil of FIG. 13 with the cutting device extended.

FIGS. 13-16 illustrate two variations of extendable cutting devices for making an incision in the target vessel while withdrawing the anvil arm 14 from the target vessel. FIG. 13 illustrates an anvil arm 14b having a blade 78 connected to a flexible blade support 80. When the blade support 80 is pulled in the direction of the arrow A with respect to the anvil arm 14b, the blade 78 moves from a forwardly extending position shown in FIG. 13 to an upwardly extending position shown in FIG. 14 as a result of flexure of the blade support 80. The blade 78 in the forwardly extending position may be used to form a small opening in the wall of the target vessel through which the anvil arm 14 is inserted into the target vessel. After an anastomosis has been performed, or while an anastomosis is performed, the blade 78 is moved to an upwardly angled or a vertical position in which the blade 78 is used to form an incision in the target vessel as the anvil arm 14b is removed from the target vessel.

Figure 15:
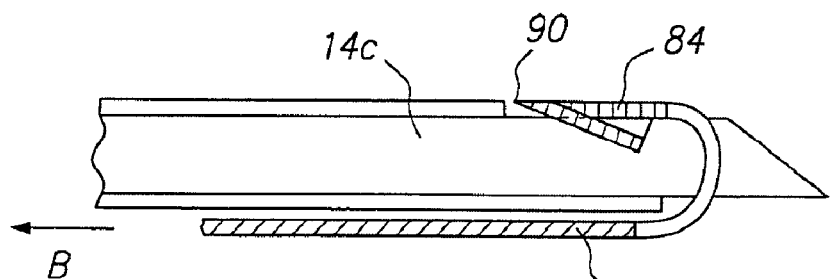
FIG. 15 is a side view of a portion of an anvil with an alternate extendable cutting device.
Figure 16:
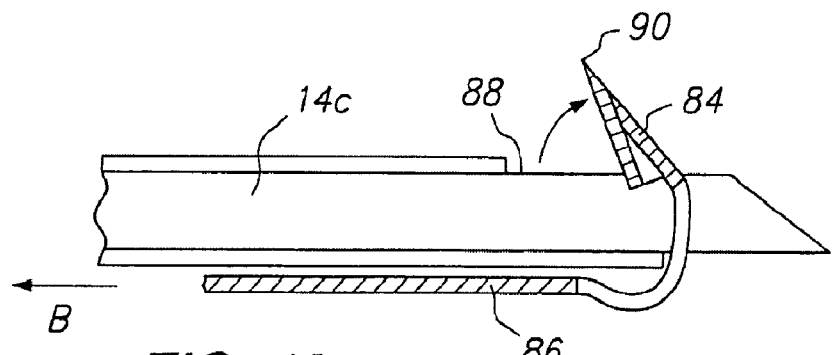
FIG. 16 is a side view of the anvil of FIG. 15 with the cutting device extended.

FIGS. 15-16 illustrate an alternate example of an anvil arm 14c having a blade 84 and a blade support 86. While the anvil arm 14c is inserted into the target vessel and during the anastomosis procedure, the blade 84 is positioned in a recess 88 in the anvil arm. The blade 84 may be moved from the position of FIG. 15 to the extended position of FIG. 16 by moving the blade support 86 in the direction of the arrow B with respect to the anvil arm. The blade 84 is flexible and stressed, such that freeing the blade 84 from the recess 88 causes the blade 84 to move to the extended position. Alternatively, the blade 84 may be extended automatically upon withdrawal of the anvil arm 14 when a blade tip 90 catches on an interior surface of the target vessel wall during withdrawal of the anvil arm.

The extendable cutting devices shown in FIGS. 13-16 are merely shown as examples of the type of cutting devices which may be used for making the incision. Once these cutting devices or blades have been extended from the anvil arm 14, they may be fixed to perform cutting as the anvil arm 14 is removed from the target vessel or the blades may be movable along the anvil arm 14 to make an incision prior to removal of the anvil arm 14 from the target vessel.

Anastomosis Tool

Figure 55:
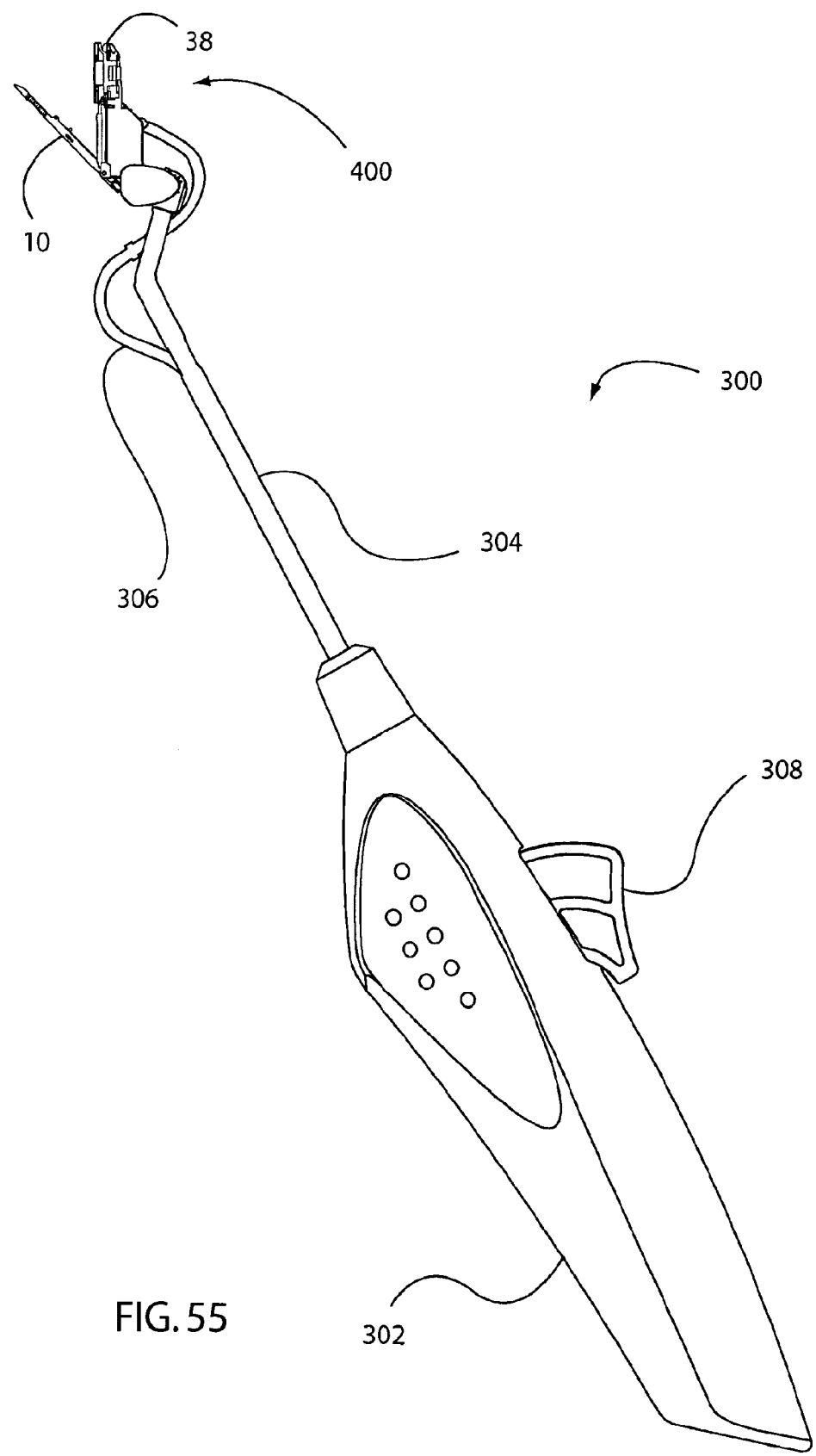
FIG. 55 is a side view of an anastomosis tool having a tissue effector and a handle.

Referring to FIG. 55, another exemplary anastomosis tool 300 is shown. The anastomosis tool 300 includes a handle 302, a shaft 304 connected to the handle 302, a cable housing 306 connected at one end to the handle 302, and a tissue effector 400 connected to both the shaft 304 and the cable housing 306. The anastomosis tool 300 may be configured differently, if desired. For example, the cable housing 306 may be omitted, and the cable or cables (not shown) or other force transmission members that would otherwise extend therethrough are instead routed through the shaft 304. The handle 302 and/or the tissue effector 400 may be detachable from the shaft 304 to allow for interchangeability of these components. In this way, the same handle 302 may be used to perform more than one anastomosis within a single patient, where a different tissue effector 400 may be connected to that handle 302 for each anastomosis. Further, the handle 302 may be constructed from materials that can be sterilized, such as by an autoclave, and reused. The handle 302 may assume any appropriate configuration; the shape and configuration of the handle 302 described herein is exemplary and not limiting. The shaft 304 may be a rigid hollow structure such as a tube of stainless steel, but may be shaped differently and/or fabricated from a different material. Further, the shaft 304 may be flexible at least in part, rather than rigid. Alternately, the shaft 304 may be omitted altogether, such that the handle 302 is connected to the tissue effector 400 by one or more cables or other force transmission members that would otherwise have extended through the shaft 304. The handle 302 may include a trigger 308 that provides for actuation of the anastomosis tool 300 based solely on a single input to that trigger 308, as described in greater detail below. Alternately, one or more other or additional inputs may be utilized to actuate the anastomosis tool 300. For example, actuation of the anastomosis tool 300 may be based on an input to one or more buttons in addition to the trigger 308.

The tissue effector 400 includes an anvil 10 and a staple holder 38. The tissue effector 400 may be permanently fixed to the shaft 304, or may be detachable from it such that is it decoupled from the handle 302. That is, tissue effectors 400 may be interchangeable. Alternately, the shaft 304 is not provided, and the tissue effector 400 is directly coupled to the handle 302. One end of the cable housing 306 may be fixed to the staple holder 38.

Figure 34:
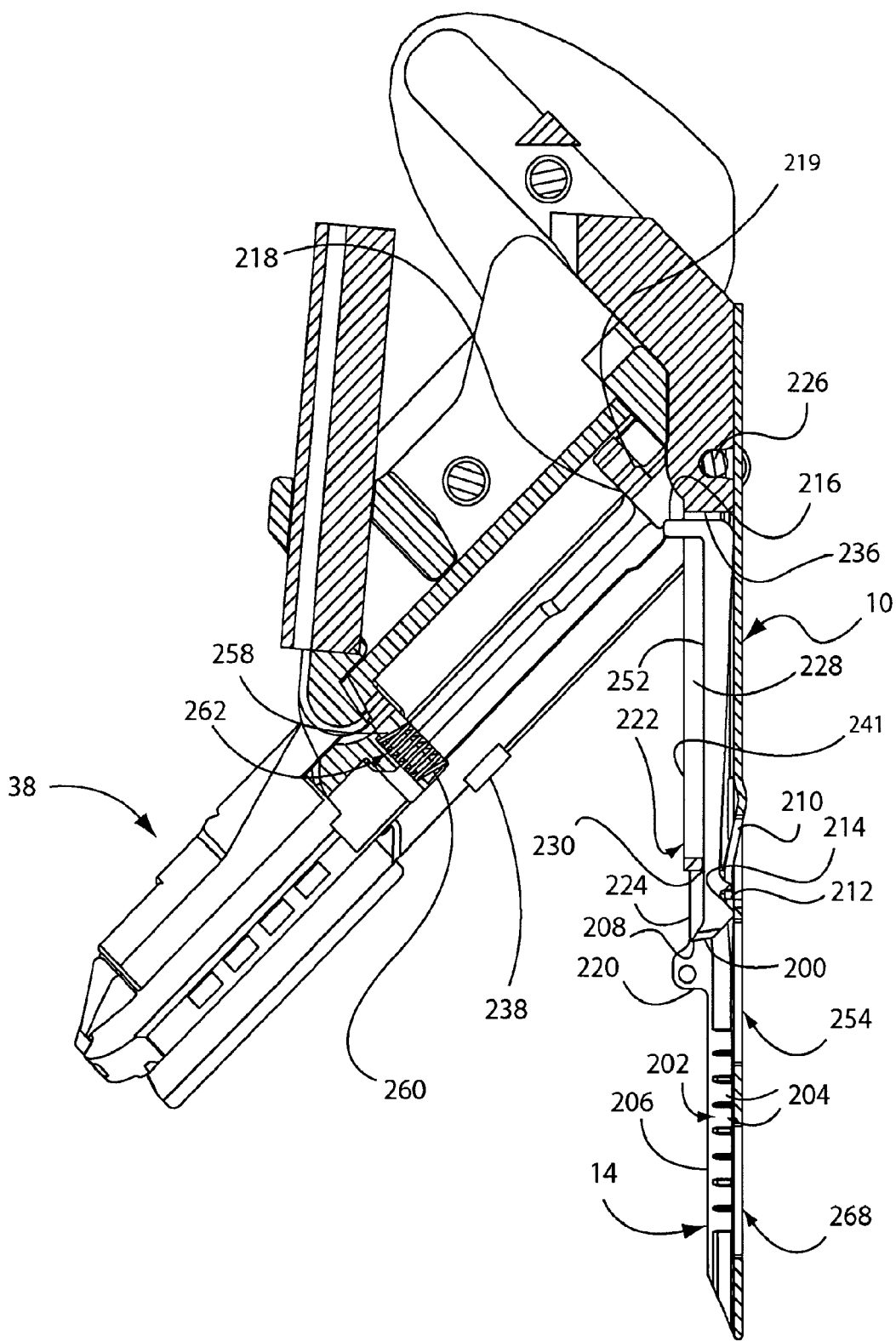
FIG. 34 is a side cutaway view of a first embodiment of an anvil, a cutter and a staple holder, where the anvil and staple holder are spaced apart from each other.
Figure 35:
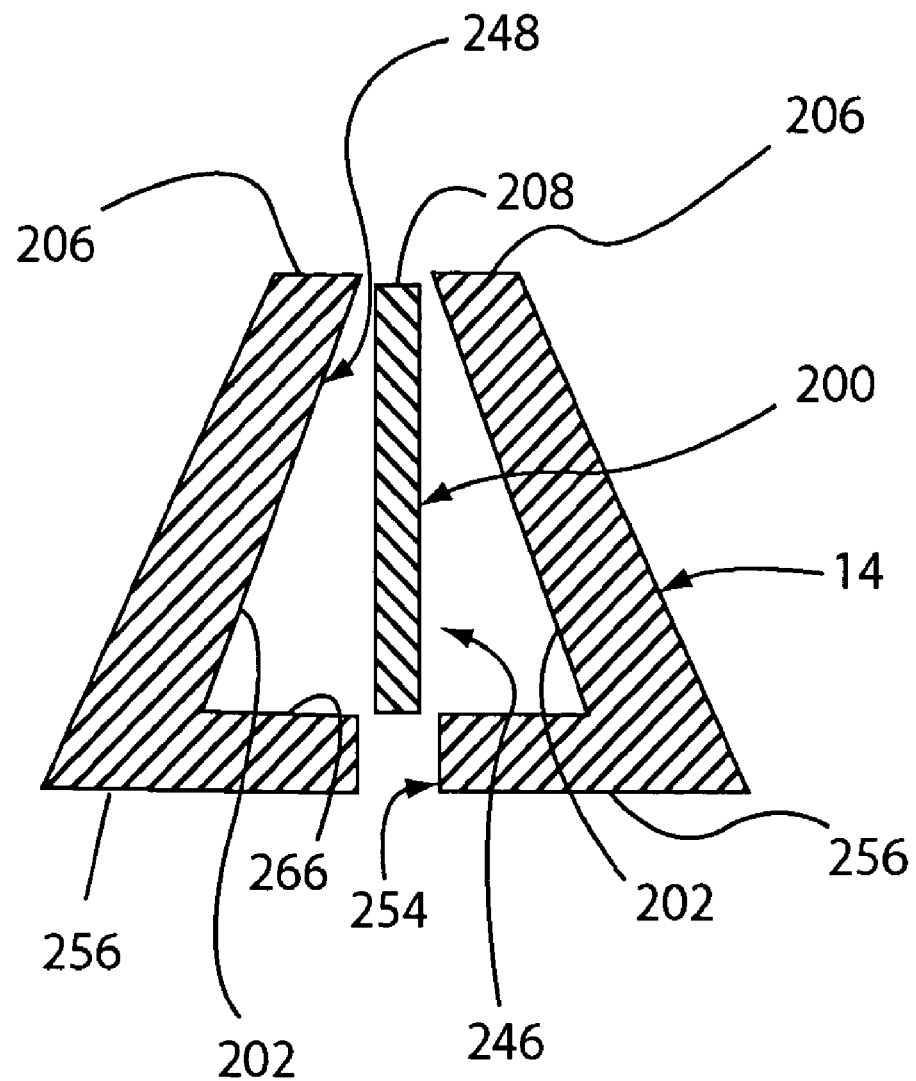
FIG. 35 is an end cross-section view of the anvil of FIG. 34.

The anvil 10 of the tissue effector 400 may be as described above, or may be configured differently. The anvil 10 may be formed from any material or combination of materials having a suitable stiffness. As one example, the anvil 10 is formed from stainless steel. As another example, at least part of the lower portion of the anvil 10 is formed from tungsten carbine for enhanced stiffness, and the upper portion of the anvil 10 is formed from stainless steel. Other or additional materials or combinations may be used. Advantageously, the anvil 10 also includes a cutter 200 that is moveable relative to the anvil 10 for making an incision in the wall of a target vessel. Referring to FIGS. 34 and 35, a tissue stop 220 is formed into or connected to the anvil 10. The portion of the anvil 10 distal to the tissue stop 220 is configured to penetrate the wall of a target vessel, and may be referred to as the anvil arm 14. A channel 246 is defined within the anvil arm 14, through which a cutter 200 is configured to move. The cutter 200 is narrower than the channel 246, such that interior surfaces 202 on either side of the channel 246 may guide the translation of the cutter 200 relative to the anvil arm 14. As used in this document, the term "translation" as used in regard to the cutter 200 refers to motion of the cutter 200 in the distal or proximal direction, whether or not the cutter 200 or a portion thereof moves upward or downward during that motion. For convenience, the direction substantially perpendicular to the longitudinal centerline of the anvil arm 14 toward the wall of the target vessel may be referred to as "upward", and the direction substantially perpendicular to the longitudinal centerline of the anvil arm 14 away from the wall of the target vessel may be referred to as "downward". However, the positioning of the anvil arm 14 in use is not limited to an orientation in which these directions correspond to absolute directions measured relative to the ground. Similarly, for convenience, motion upward or downward may be referred to as "vertical" motion, and motion substantially parallel to the longitudinal centerline of the anvil arm 14 may be referred to as "horizontal" motion.

Figure 36:
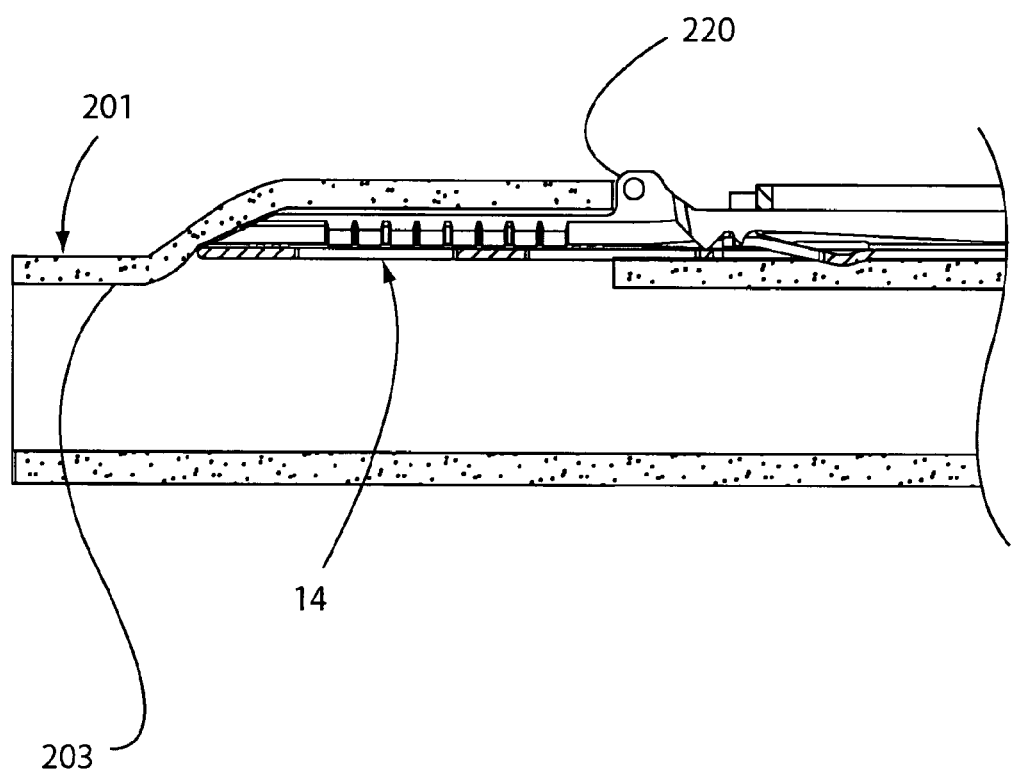
FIG. 36 is a side cutaway view of a portion of the anvil inserted into the lumen of a target vessel.

The anvil arm 14 includes a contact surface 206. Referring also to FIG. 36, in use, the contact surface 206 of the anvil arm 14 is placed substantially against the inner surface 203 of a target vessel 201. The contact surface 206 substantially defines a plane that is substantially parallel to the longitudinal centerline of the anvil arm 14. Alternately, the contact surface 206 is contoured and/or oriented differently. An upper opening 248 extends along at least a portion of the contact surface 206 in a direction substantially parallel to the longitudinal centerline of the anvil arm 14, and opens into the channel 246. The upper opening 248 may divide the contact surface 206 into symmetrical or asymmetrical sections. Further, the contact surface 206 may be formed by two substantially planar surfaces, by one substantially planar surface and a differently-shaped surface, or by another set of surfaces. Additionally, the contact surface 206 may be formed by two thin edges, each edge occurring at the intersection of a wall of the upper opening 248 and an outer surface of the anvil arm 14. The upper opening 248 need not extend proximally any further than the tissue stop 220. However, the upper opening 248 may extend proximal to the tissue stop 220, if desired. A first lower opening 254 and a second lower opening 268 are defined through a lower surface 256 of the anvil arm 14. The lower surface 256 of the anvil arm 14 may be substantially parallel to the contact surface 206 or may be oriented differently relative to the contact surface 206. Alternately, the first lower opening 254 and/or the second lower opening 268 do not extend completely through the anvil arm 14, and instead are depressions extending along at least part of a bottom surface 266 of the channel 246.

Cutter

Figure 37:
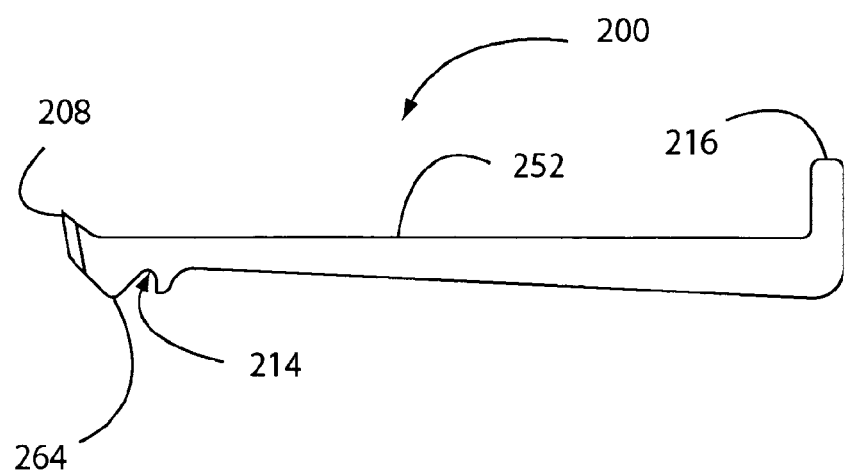
FIG. 37 is a side view of the cutter.
Figure 38:
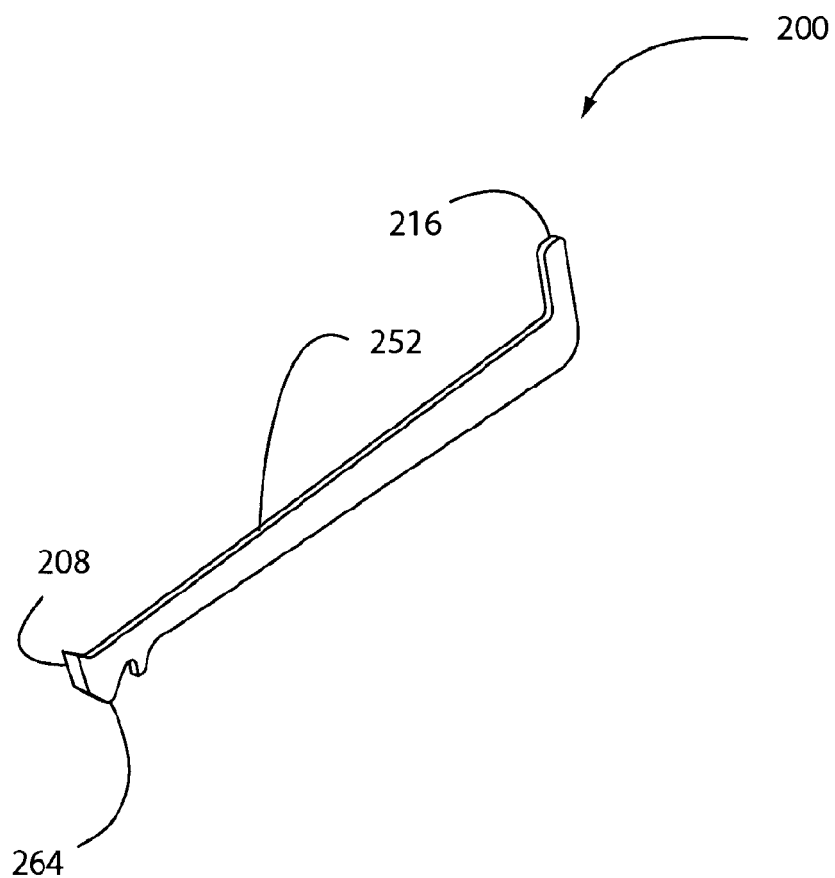
FIG. 38 is a perspective view of the cutter of FIG. 37.

Referring also to FIGS. 37-38, the cutter 200 may be a thin, rigid member, shaped such that it can be held within and/or moved along the channel 246 in the anvil arm 14. The cutter 200 has a substantially constant width along its entire length. Alternately, the width of the cutter 20 may vary along its length. The cutter 200 may be made of metal, ceramic, plastic, or other material, or from a combination of different materials. A sharp projection 208 extends upward from the cutter 200 at or near its distal end. The projection 208 is substantially triangular, but may be shaped differently. The projection 208 may be smooth or serrated, or otherwise shaped or formed. A portion of the projection 208 may be ground or otherwise honed to a sharp edge to facilitate the motion of the projection 208 through the tissue of the wall of a target vessel, as described in greater detail below. If so, the cutter 200 is composed of a material that can be sharpened adequately to cut tissue. Alternately, the cutter 200 may be flexible, at least in part. Further, the projection 208 may be located at a different position on the cutter 200 than at or near its distal end. An additional sharp point (not shown) may be provided at the distal end of the cutter 200, extending in a distal direction, in order to create an initial puncture or incision in the wall of the target vessel. Such a point may be as described in U.S. patent application Ser. No. 10/134,081, which is herein incorporated by reference in its entirety.

Figure 39:
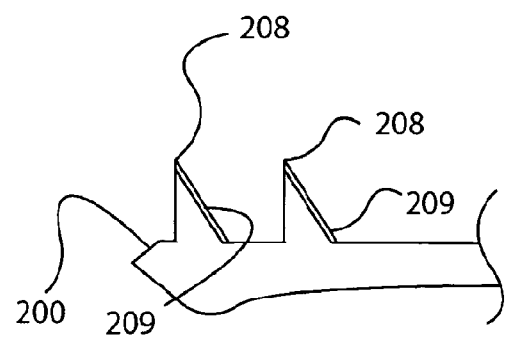
FIG. 39 is a side view of the distal end of a second embodiment of a cutter.
Figure 40:
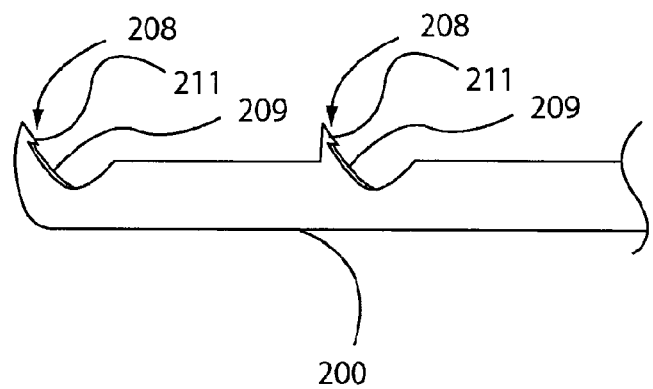
FIG. 40 is a side view of the distal end of a third embodiment of a cutter.
Figure 41:
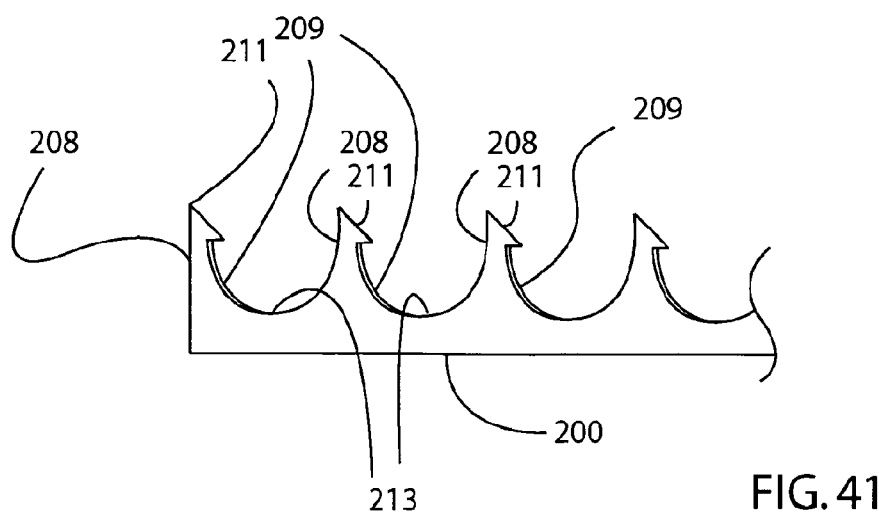
FIG. 41 is a side view of the distal end of a fourth embodiment of a cutter.
Figure 42:
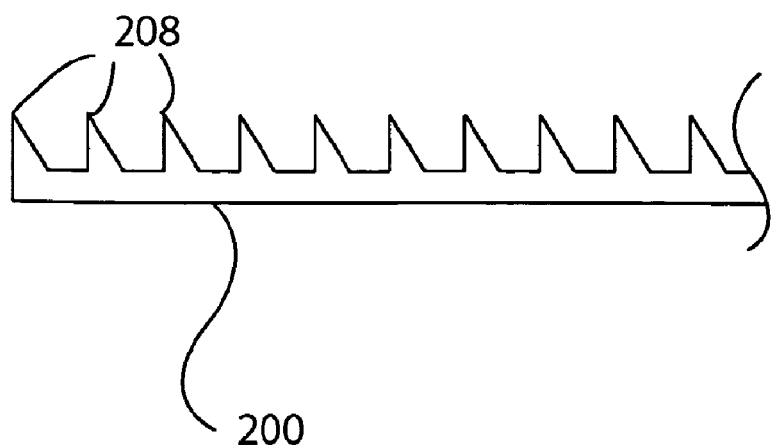
FIG. 42 is a side view of a portion of a fifth embodiment of a cutter.

One or more additional projections 208 may be provided, if desired. For example, two or more projections 208 may extend upward from the cutter 200. Where multiple projections 208 are used, they may cooperate with one another to create an incision in the wall of the target vessel. Referring also to FIG. 39, a second projection 208 extends upward from the cutter 200 proximal to a first projection 208. The projections 208 are both substantially the same triangular shape and the same size. However, the projections 208 may be shaped and sized differently. The projections 208 are both substantially planar, and are aligned such that both projections 208 lie in substantially the same plane. Alternately, at least one projection 208 is not substantially planar. Each projection 208 may include at least one sharpened or beveled edge 209 oriented to engage and incise the wall of the target vessel when the cutter 200 is translated, as described below. Referring to FIG. 40, at least two projections 208 extend upward from the cutter 200. The projections 208 each have a barb 211 at the tip. However, the barb 211 may be omitted from some or all of the projections 208. Under the barb 211, a sharpened or beveled edge 209 extends downward and proximally. The edge 209 may be straight or curved. The upper end of the edge 209 is distal to the lower, proximal end of the corresponding barb. The edge 209 of each projection 208 is oriented to engage and incise the wall of the target vessel when the cutter 200 is translated. Referring to FIG. 41, at least two projections 208 extend upward from the cutter 200, at least one of which has a barb 211 at its tip. The edge 209 associated with each projection 208 is more curved than the edge 209 shown in FIG. 40. Alternately, the edge 209 is substantially straight, or gently curved, or positioned on a portion of a larger curved segment 213 extending downward from and proximal to the barb 211. Referring to FIG. 42, a number of projections 208 may be placed along a length of the cutter 200. This length may be comparable to the desired length of the incision in the wall of the target vessel. These projections 208 may be substantially triangular as shown, or may be shaped differently. Where more than one projection 208 is used on the cutter 200, the projections 208 need not have the same configuration. For example, projections 208 such as the exemplary projections 208 shown in FIGS. 39-41 may be mixed together on the same cutter 200. Alternately, one or more of the projections 208 are moveable relative to the cutter 200, such that one or more projections 208 can be moved upward or downward relative to the cutter 200.

Figure 43:
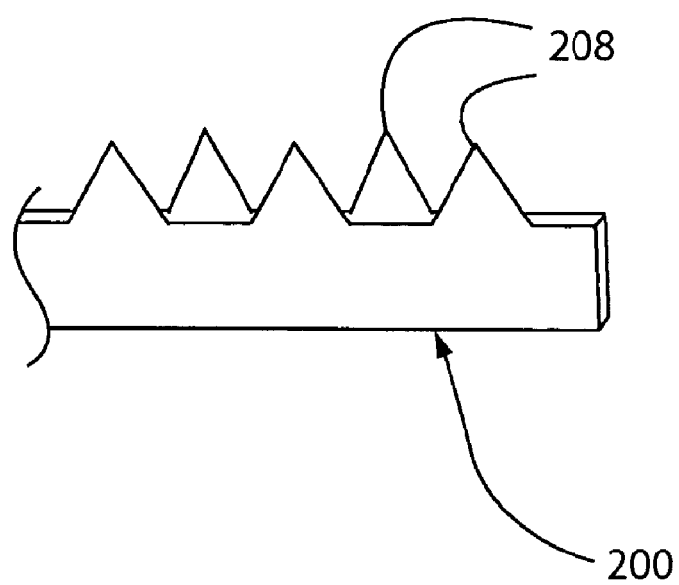
FIG. 43 is a side view of the distal end of a sixth embodiment of a cutter.

As another example of a configuration of the projections 208, referring to FIG. 43, the projections 208 extending upward from the cutter 200 each are substantially planar, and are aligned such that not all of the projections 208 lie in the same plane. In such a configuration, the projections 208 may create a wider incision in the wall of the target vessel than would be created if the projections 208 were substantially aligned. For example, one set of projections 208 may be aligned substantially in a first plane, and a second set of projections 208 may be aligned substantially in a second plane substantially parallel to the first plane. The second plane and the first plane may be oriented differently relative to one another, if desired. As another example, none of the projections 208 lie in a common plane with one or more other projections 208. Referring to FIGS. 39-42, by using multiple projections, the cutter 200 need not be translated as far to make an incision in the wall of the target vessel as it would if only a single projection 208 were used, as described in greater detail below.

Referring to FIGS. 115-118, another example of a cutter 200 is shown. This cutter 200 is an assembly that includes a projection 208 rotatable or otherwise movable from a stowed position in which it is substantially completely within the channel 246 in the anvil arm 14 (shown in FIG. 115) to an active position in which at least a portion of the projection 208 extends upward from the channel 246 in the anvil arm 14 (shown in FIGS. 116-117). The projection 208 may include an edge 209 that is beveled or sharpened, where that edge 209 may be oriented at least partially distally when the projection 208 is in the active position. Alternately, the edge 209 may be oriented at least partially proximally when the projection 208 is in the active position. The orientation of the edge 209 when the projection 208 is in the active position is related to the direction of motion of the projection 208 as it creates an incision in the target vessel 580, as is described in greater detail below. With reference to the active position, where the edge 209 is defined on a distally-facing surface of the projection 208, the proximally-facing surface of the projection 208 may be blunt. Similarly, where the edge 209 is defined on a proximally-facing surface of the projection 208, the distally-facing surface of the projection 208 may be blunt.

A member 848 is connected to the projection 208. The member 848 is at least partially rigid. An aperture 849 is defined through the projection 208. The distal end of the member 848, or a portion of the member 848 near its distal end, is received into or through that aperture 849 to connect to the projection 208. Alternately, the member 848 is connected to the projection 208 in a different way. The member 848 extends along the channel 246 in the anvil arm 14. A pusher 850 also extends along the channel 246 in the anvil arm 14. The pusher 850 is a substantially rigid body, having a distal end that is configured to engage the projection 208. The distal end of the pusher 850 may be beveled or otherwise shaped such that at least the upper portion of that distal end is angled or curved proximally. The distal end of the pusher 850 is configured to remain substantially in contact with the projection 208 in both the stowed position and the active position. Alternately, the pusher 850 engages the projection 208 in a different manner. The aperture 849 in the projection 208 may be located at a position lower than the longitudinal centerline of the pusher 850. Alternately, the aperture 849 is positioned differently relative to the pusher 850.

A spring 852 may be connected to or otherwise associated with the pusher 850. The spring 852 may be a leaf spring, a compression spring, or any other suitable type of spring or biasing element. The spring 852 is configured to press the pusher 850 downward against the bottom surface 266 of the channel 246 in the anvil arm 14 when the projection 208 is in the stowed position. In this way, the pusher 850 is held substantially in place when the projection 208 is in the stowed position. The spring 852 is also configured to release the pusher 850 and allow it to translate when the cutter 200 is in the active position. Optionally, a button 854 is configured to press the spring 852 downward and thereby hold the pusher 850 in place when the projection 208 is in the stowed position, and is movable to a position in which it no longer presses the spring downward and thereby releases the pusher 850 when the projection 208 is in the active position. The spring 852 may be connected to the button 854 rather than the pusher 850. A stop 856 may be connected to or formed into the channel 246 of the anvil arm 14, where that stop 856 is configured to engage the spring 852 or other portion of the cutter 200 and arrest its motion at a particular location, as described in greater detail below.

As another example of biasing the cutter 200 in a particular direction, a cavity 262 may be defined within the staple holder 38 or a separate component connected to the staple holder 38. A post 258 is positioned at the upper end of the cavity 262, where the post 258 is oriented downward. A biasing element 260 is connected at one end to the post 258. The biasing element 260 may be a coil spring, a leaf spring, a different type of spring, an elastomer, a wire form, or other structure or mechanism capable of exerting a biasing force. The biasing element 260 is positioned within and protected by the cavity 262, where the cavity 262 is used. The cavity 262 may be a cylindrical opening having a diameter substantially the same as the outer diameter of the biasing element 260, such that the cavity 262 restricts the biasing element 260 to motion substantially along the axis of the cavity 262 and thus directs the force exerted by the biasing element 260 in a substantially downward direction, preventing bending or other undesirable motion of the biasing element 260. The end of the biasing element 260 that is not connected to the post 258 contacts the cutter 200. As an example, the biasing element 260 may be a compression spring that is compressed between the post 258 and the cutter 200, resulting in a force on the cutter 200 that biases the cutter 200 downward. The cutter 200 is slidable relative to the biasing element 260, such that the biasing element 260 exerts a downward force on the cutter 200 at different locations along its upper surface 252 as the cutter 200 translates. Thus, at least the distal end of the cutter 200 is biased downward throughout its translation along the anvil 10. The entire cutter 200 may be biased downward, if desired. Alternately, the post 258 is omitted, and the biasing element 260 is fixed to an upper surface of the cavity 260. Alternately, the biasing element 260 is omitted, and the cutter 200 is biased downward in another way. For example, the cutter 200 may be constructed from an elastic or superelastic material that is formed in such a way as to produce a downward bias.

Referring to FIGS. 119-122, another embodiment of a cutter 200 is shown. In this embodiment, the cutter 200 is an assembly that includes a projection 208 rotatable or otherwise movable from a stowed position in which it is substantially completely within the channel 246 in the anvil arm 14 (shown in FIG. 119) to an active position in which at least a portion of the projection 208 extends upward from the channel 246 in the anvil arm 14 (shown in FIGS. 120-121). The projection 208 may include an edge 209 that is beveled or sharpened, where that edge 209 may be oriented at least partially distally when the projection 208 is in the active position. Alternately, the edge 209 may be oriented at least partially proximally when the projection 208 is in the active position. The orientation of the edge 209 when the projection 208 is in the active position is related to the direction of motion of the projection 208 as it creates an incision in the target vessel 580, as is described in greater detail below. With reference to the active position, where the edge 209 is defined on a distally-facing surface of the projection 208, the proximally-facing surface of the projection 208 may be blunt. Similarly, where the edge 209 is defined on a proximally-facing surface of the projection 208, the distally-facing surface of the projection 208 may be blunt. The projection 208 includes a lobe 858 defined therein or connected thereto, where the lobe 858 is located on the lower portion of the projection 208 with reference to the position of the projection 208 in the stowed position. The lobe 858 may be curved or rounded. A slot 860 is located in the bottom surface 266 of the channel 246 in the anvil arm 14. The slot 860 may extend completely through that bottom surface 266, or may simply be a depression or other feature defined in that bottom surface 266. When the cutter 200 is in the stowed position, at least part of the lobe 858 extends into that slot 860. An aperture 849 is defined in the projection 208. A clip 862 is connected to the projection 208 through the aperture 849. The clip 862 may be U-shaped, or shaped in any other suitable manner. The clip 862 may be configured to slide along at least one track 864 defined in or connected to at least one interior surfaces 202 of the channel 264.

A pusher 850 also extends along the channel 246 in the anvil arm 14. The pusher 850 is a substantially rigid body, having a distal end that is configured to engage the projection 208. The distal end of the pusher 850 may be beveled or otherwise shaped such that at least the lower portion of that distal end is angled or curved proximally. The distal end of the pusher 850 is configured to remain substantially in contact with the projection 208 in both the stowed position and the active position. Alternately, the pusher 850 engages the projection in a different manner. The aperture 849 in the projection 208 may be located at a position lower than the longitudinal centerline of the pusher 850. Alternately, the aperture 849 is positioned differently relative to the pusher 850. As described above, the pusher 850 may be substantially restrained when the projection 208 is in the stowed position and substantially freed when the projection 208 is in the active position.

Referring to FIGS. 125-128, another example of a cutter 200 is shown. The cutter 200 is an assembly that includes a projection 208 rotatable or otherwise movable from a stowed position in which it is substantially completely within the channel 246 in the anvil arm 14 (shown in FIG. 125) to an active position in which at least a portion of the projection 208 extends upward from the channel 246 in the anvil arm 14 (shown in FIGS. 126-127). At least one edge 209 of the projection 208 may be beveled or otherwise sharpened. A member 848 is connected to the projection 208. The member 848 is a cable or any other appropriate structure or mechanism. For example, the member 848 may be at least partially rigid. An aperture 849 is defined through the projection 208. The distal end of the member 848, or a portion of the member 848 near its distal end, is received into or through that aperture 849 to connect to the projection 208. Alternately, the member 848 is connected to the projection 208 in a different way. The member 848 extends along the channel 246 in the anvil arm 14.

The projection 208 includes a lobe 858 defined therein or connected thereto, where the lobe 858 is located on the lower portion of the projection 208 with reference to the position of the projection 208 in the stowed position. The lobe 858 may be curved or rounded. A notch 859 may be located between the lobe 858 and the remainder of the projection 208. The notch 859 may be curved, rounded, angled or otherwise configured. A slot 860 is located in the bottom surface 266 of the channel 246 in the anvil arm 14. The slot 860 may extend completely through that bottom surface 266, or may simply be a depression or other feature defined in that bottom surface 266. When the cutter 200 is in the withdrawal position, at least part of the lobe 858 extends into that slot 860. The projection 208 includes two sharp edges 209.

A centerpiece 868 may be secured within the channel 246. For example, the centerpiece 868 may be connected to one or more pins 870 that are connected to or formed into the anvil arm 14. Alternately, the centerpiece 868 is positioned at least partially above the channel 246, and/or may extend laterally from at least one edge of the channel 246, as shown in FIG. 143. The centerpiece 868 includes a slot 872 in its upper surface to allow the projection 208 to extend therethrough, and includes a longitudinally-extending free space 874 that allows the projection 208 to travel longitudinally therethrough. A receiving space 876 is defined at or near the distal end of the centerpiece 868, oriented downward. The receiving space 876 is located distal to a first cam surface 878, which is positioned lower than the uppermost part of the receiving space 876. Alternately, the centerpiece 868 is not used.

Referring back to FIGS. 34-35, an interior surface 202 is located on each side of the channel 246. Each interior surface 202 may be substantially planar, curved, or may be shaped differently. Further, each interior surface 202 may be oriented at an angle to vertical or substantially vertical. The interior surfaces 202 may be formed such that the channel 246 is substantially bilaterally symmetrical, or may be formed to result in a channel 246 that is not bilaterally symmetrical. The interior surfaces 202 of the channel 246 within the anvil arm 14 may include raised features 204 that correspond to depressed staple bending features (not shown) on the outer surface of the anvil arm 14. That is, if the staple bending features are stamped into the anvil arm 14, or formed in another way that causes deformation of the anvil arm 14, the depressed staple bending features result in corresponding raised features 204 on the interior surface 202 of the channel 246. The raised features 204 do not interfere with the motion of the cutter 200 through the channel 246. Alternately, the raised features 204 are not present on the interior surface 202 of the channel 246.

Shield

Figure 93:
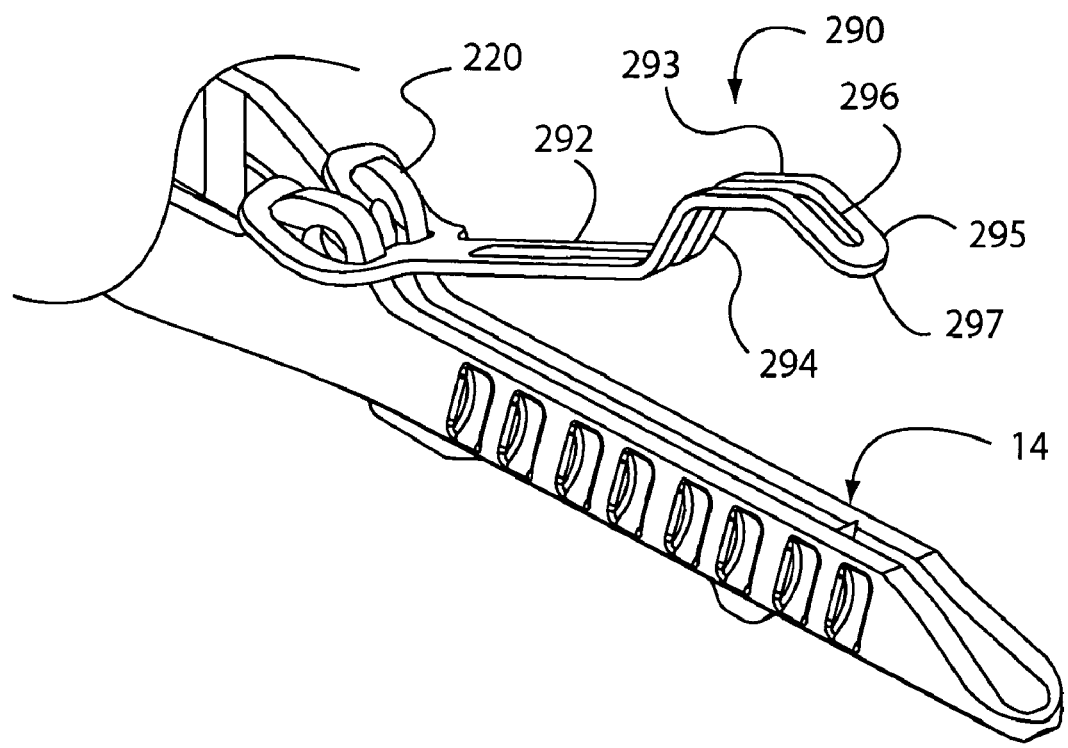
FIG. 93 is a perspective view of an anvil of a tissue effector, to which a shield is connected. The staple holder has been omitted from the tissue effector for clarity.
Figure 94:
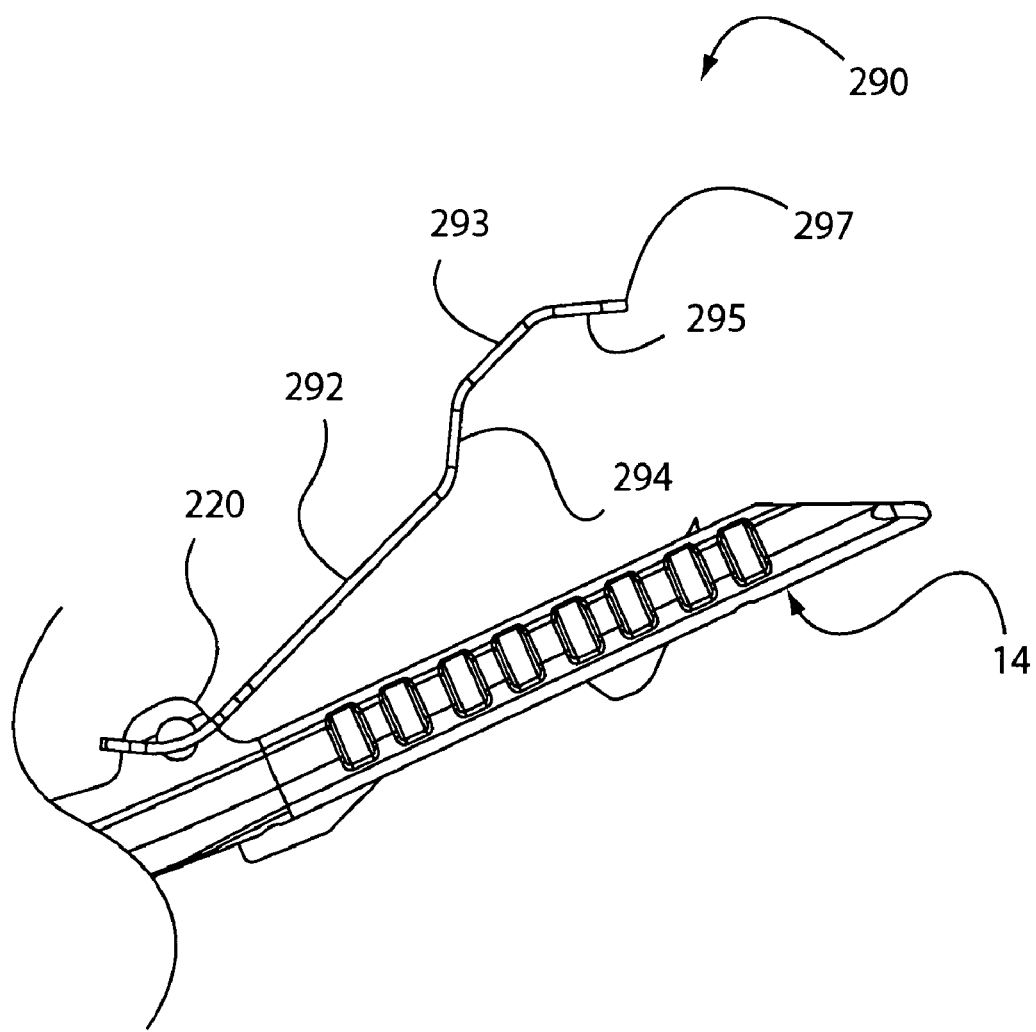
FIG. 94 is a side view of the anvil and shield of FIG. 93.

Optionally, referring to FIGS. 93-94, a shield 290 may be connected to the anvil arm 14, at or near the proximal end of the anvil arm 14. For example, the shield 290 may be connected to the anvil arm 14 in proximity to the tissue stop 220. Alternately, the shield 290 may be connected to a different location on the anvil arm 14, or to a portion of the anvil 10 other than the anvil arm 14. Alternately, the junction between the shield 290 and the anvil arm 14 performs the function of the tissue stop 220, and a separate tissue stop 220 is not provided. The shield 290 may be connected to or formed into the anvil arm 14 in any appropriate manner. As one example, the shield 290 may be pressure-fit to the anvil arm 14 at or near the tissue stop 220. Alternately, the shield 290 may be connected to the anvil arm 14 by welding, by adhesive, or by any other appropriate structure, mechanism, or method. The proximal end of the shield 290 is connected to the anvil arm 14, and the distal end of the shield 290 is free. Alternately, the shield 290 is connected to the anvil arm 14 in a different orientation. The shield 290 may be connected to the anvil arm 14 such that the free end of the shield 290 is biased upward relative to the anvil arm 14. However, the free end of the shield 290 need not be biased upward, or in any other direction, relative to the anvil arm 14. Alternately, the shield 290 may be biased downward relative to the anvil arm 14.

The shield 290 is configured to be positioned at least partially adjacent to the outer surface of the target vessel during the anastomosis procedure, as described in greater detail below. As one example of such a configuration, a proximal element 292 of the shield 290 is substantially straight, such that it substantially can contact the outer surface of the target vessel during the anastomosis procedure. A raised element 293 of the shield 290 at or near its distal end is raised relative to the proximal element 292 of the shield 290. A first ramp element 294 of the shield 290 connects the proximal element 292 of the shield 290 to the raised element 293 of the shield 290. A second ramp element 295 may extend distally and downward from the raised element 293 of the shield 290. At least a portion of the second ramp element 295, such as its distal end, is configured to contact the outer surface of the target vessel. This contact provides a limit to the motion of the shield 290 relative to the anvil arm 14 and causes the raised element 293 to be spaced apart from the outer surface of the target vessel. The second ramp element 295, or distal end of the raised element 293 if the second ramp element 295 is not used, is blunt to prevent damage to the outer surface of the target vessel upon contact therewith. Alternately, the shield 290 may be configured and/or shaped differently.

Optionally, an aperture 296 extends substantially longitudinally along at least a portion of the shield 290. The aperture 296 has a closed perimeter, or alternately may be open ended. The aperture 296 is substantially aligned with the channel 246 in the anvil arm 14. Thus when the projection 208 of the cutter 200 extends above the contact surface 236 of the anvil arm 14, at least a portion of the aperture 296 receives at least part of the projection 208 and allows it to slide freely. The aperture 296 extends along the shield 290 a sufficient distance to allow the projection 208 to slide freely throughout its entire travel, as described in greater detail below. A tip element 297 may be located at or near the distal end of the shield 290, oriented substantially transversely and closing the distal end of the aperture 296. The tip element 297 may be oriented differently, if desired. The aperture 296 need not be provided, such as where the shield 290 is configured to remain above and out of contact with the projection 208 throughout its path of motion. The shield 290 may be composed of polyethylene such that it is both flexible and durable. However, any other suitable material may be utilized if desired.

Figure 106:
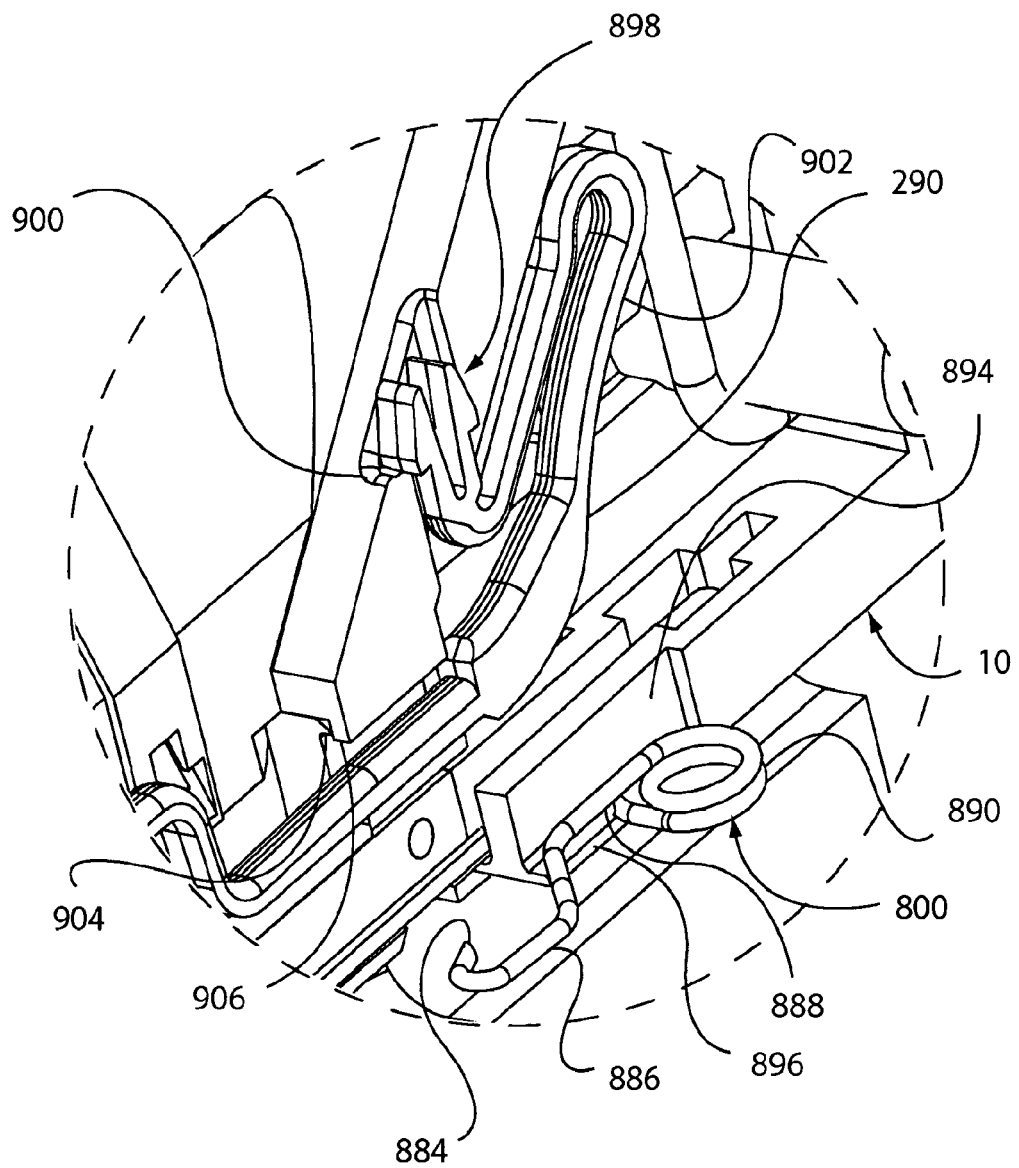
FIG. 106 is a detail perspective view of a tissue effector with a sealer detachably connected thereto, where the tissue effector includes a shield connected to the staple holder.

Alternately, referring to FIG. 106, the shield 290 may be connected to the staple holder 38. As one example, the shield 290 includes a snap feature 898 that connects to an aperture 900 in the staple holder 38. The snap feature 898 is compressible for insertion into the aperture 900, and expands after it is released. Friction between the snap feature 898 and the aperture 900, and/or interference between portions of the snap feature 898 above the aperture 900 and the structure in proximity to the aperture 900, hold the shield 290 in place. This snap feature 898 is utilized for ease of assembly; the shield 290 is connected to the staple holder 38 throughout the anastomosis procedure. Alternately, the shield 290 is connected to the staple holder 38 in a different manner. Alternately, the shield 290 is detachable from the staple holder 38. The shield 290 extends upward and proximally from its point of connection to the staple holder 38, then curves to extend downward and distally; this portion of the shield 290 may be referred to as the hinge 902. The remainder of the shield 290 extends substantially distally from the hinge 902 substantially as described above. The shield 290 may include an aperture 296 therein and/or be otherwise configured substantially as described above. Further, the shield 290 is utilized, and removed from the anastomosis site, in substantially the same manner as the configuration of shields 290 described above. By connecting the shield 290 to the staple holder 38 rather than the anvil 10, preparation of the graft vessel 404 and/or manufacture of the tissue effector 400 may be simplified. At least the hinge 902 of the shield 290 is composed of polyethylene or other flexible material. In this way, the hinge 902 can flex to allow the tissue effector 400 to move from the open position to the closed position.

Referring also to FIGS. 144-145, another example of a shield 290 connected to the staple holder 38 is shown. In this example, the shield 290 is connected to a location at or near the distal end of the staple holder 38. The shield 290 is connected to the staple holder 38 by a hinge 966. The hinge 966 may be oriented in a substantially transverse direction. Where the hinge 966 is used, the shield 290 may be flexible or rigid. Alternately, the shield 290 may be flexible, and fixed to the staple holder 38. Alternately, the shield 290 is connected to the staple holder 38 in any other suitable manner.

Tissue Effector

The tissue effector 400 may include one or more other features. Optionally, the anvil 10 and the staple holder 38 are configured to snap together when the tissue effector 400 moves to the closed position. Any suitable mechanism or structure may be used to hold the tissue effector 400 in the closed position. As an example, a first tab 904 extends from the tissue stop 220 or other portion of the anvil 10, and a second tab 906 extends from a corresponding location on the staple holder 38. As the tissue effector 400 moves to a closed position, at least one of the tabs 904, 906 flexes to accommodate the other tab 904, 906, until the first tab 904 is located above the second tab 906. Once the tissue effector 400 has been closed, the tabs 904, 906 are configured such that the tissue effector 400 cannot easily re-open. In this manner, the tissue effector 400 is positively held in the closed position.

Optionally, a safety feature 210 may be connected to the underside of the anvil 10. The safety feature 210 is biased toward the anvil 10 and the cutter 200. The safety feature 210 may be biased into the channel 246 within the anvil 10. Alternately, the safety feature 210 is connected to a different location, such as the underside of the anvil arm 14. The safety feature 210 may be flexible or rigid. The safety feature 210 includes a tip 212 that is oriented substantially transverse to the longitudinal centerline of the cutter 200. Alternately, the tip 212 may be oriented in a different direction. If the safety feature 210 is provided, the cutter 200 may include a safety recess 214 defined in it, corresponding to the tip 212 of the safety feature 210. The tip 212 is shaped and sized such that it can engage the safety recess 214. The tip 212 may be a bar or rod oriented substantially transverse to the direction of translation of the cutter 200, or may be shaped or oriented differently.

In FIG. 34, the staple holder 38 has not yet been moved into position to perform anastomosis. In this position, if the safety feature 210 is provided, the tip 212 of the safety feature 210 is biased upward to engage the safety recess 214. The engagement between the safety recess 214 and the tip 212 of the safety feature 210 substantially prevents translation of the cutter 200 within the channel 246. Thus, the cutter 200 and the projection 208 are prevented from deploying until the staple holder 38 has been moved into the appropriate position relative to the anvil arm 14, and inadvertent actuation of the cutter 200 is prevented.

Figure 58:
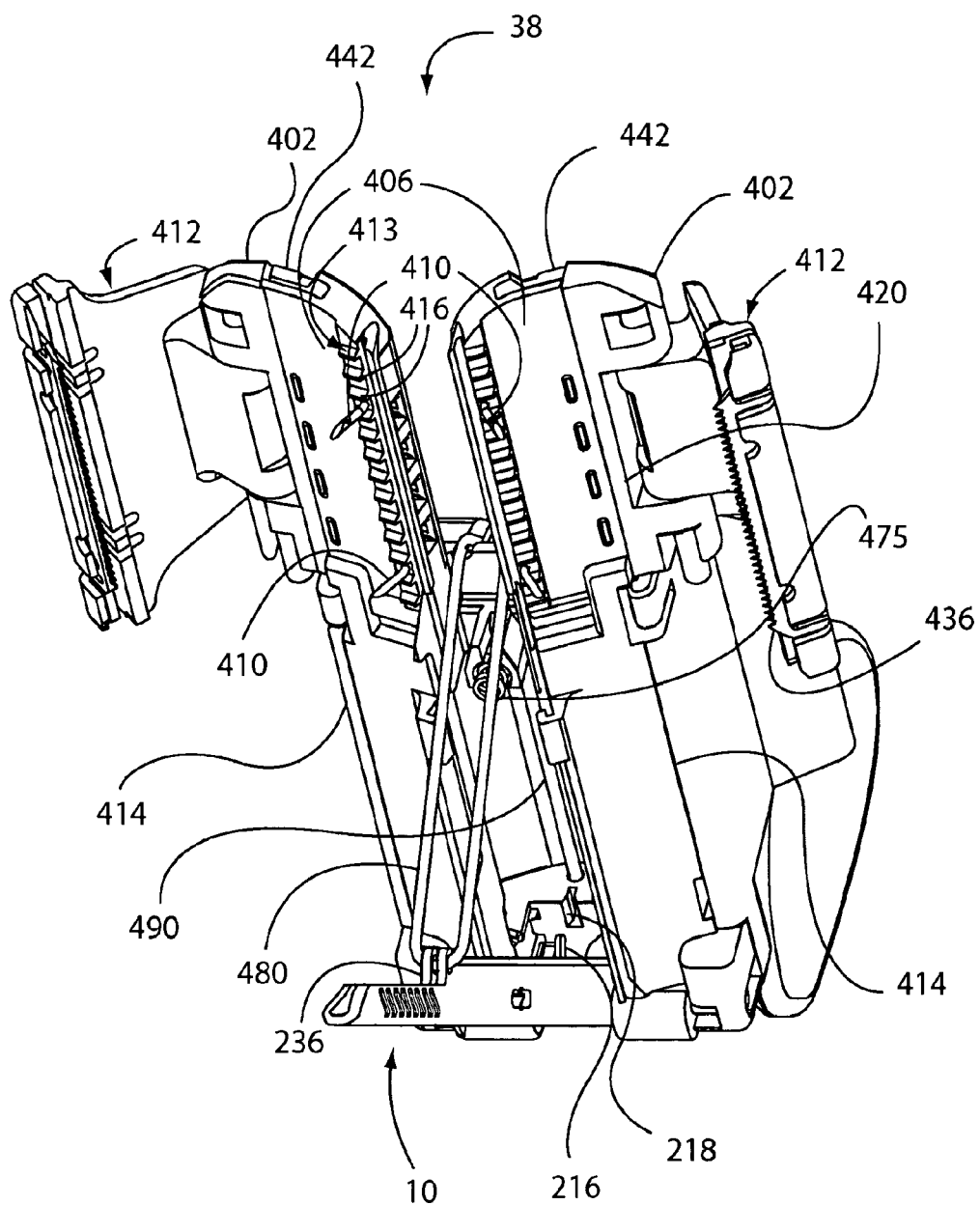
FIG. 58 is another perspective view of the tissue effector of FIG. 55 in the first position.
Figure 68:
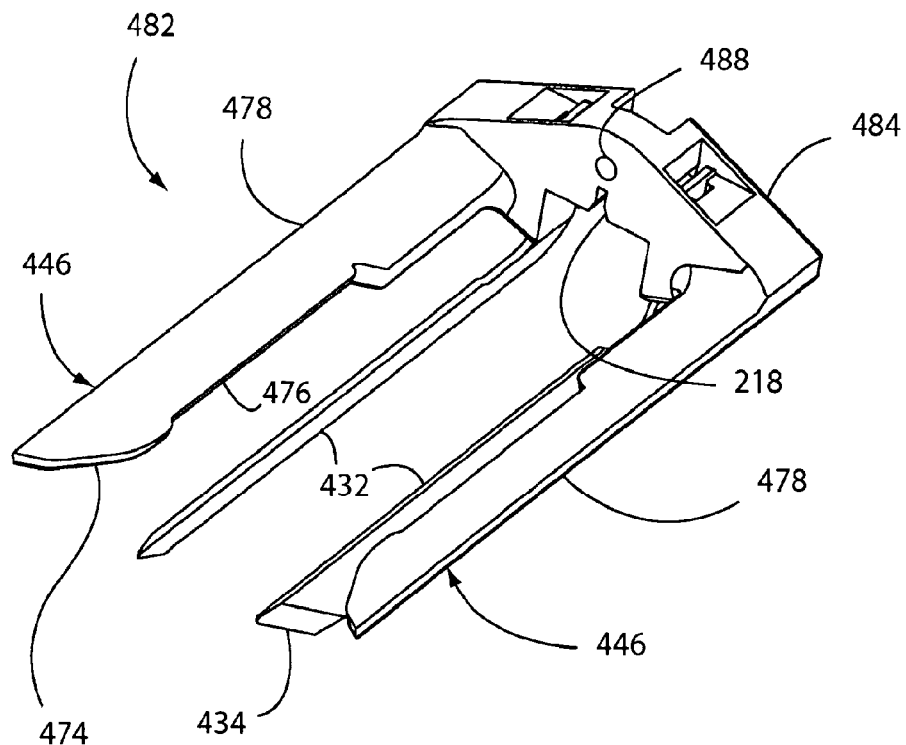
FIG. 68 is a perspective view of a sled used in the tissue effector of FIG. 55.
Figure 69:
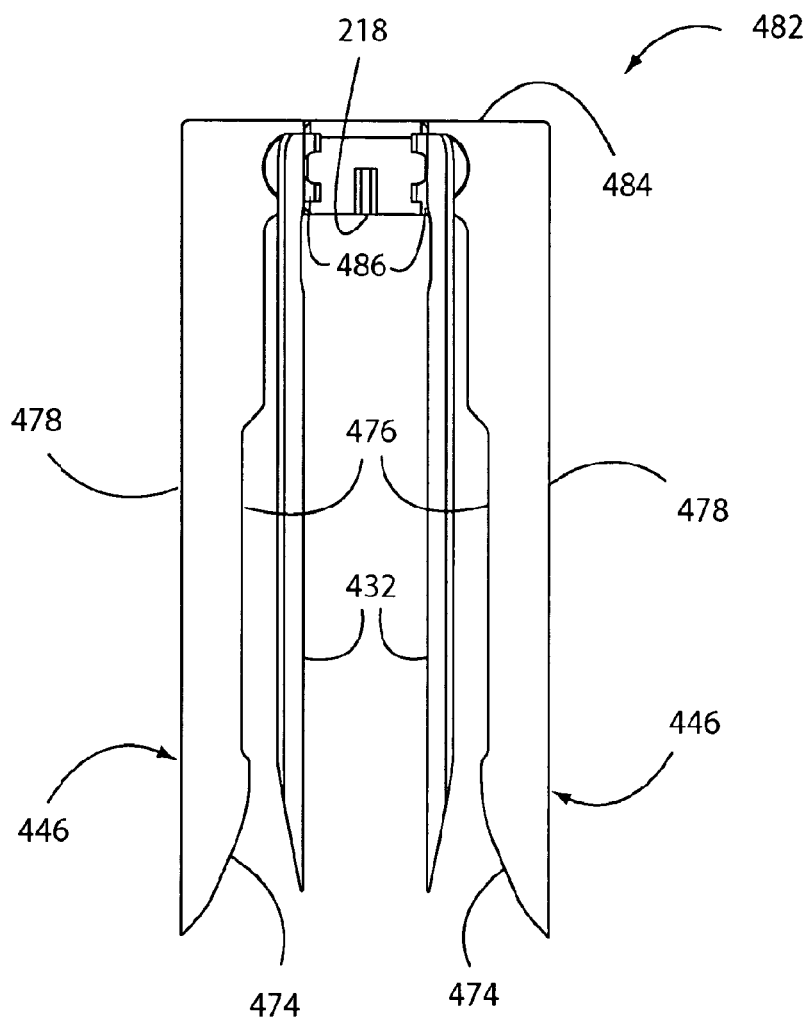
FIG. 69 is a bottom view of the sled of FIG. 68.

The cutter 200 may include an engagement member 216 extending upward from a location at or near its proximal end. The engagement member 216 instead may extend downward from the cutter 200 or to the side of the cutter 200. Further, the engagement member 216 may be positioned at a location other than at or near the proximal end of the cutter 200. The engagement member 216 is configured to engage at least a portion of a corresponding receiver 218 in the staple holder 38. Thus, after engagement between the engagement member 216 and the receiver 218, translation of the receiver 218 results in translation of the cutter 200. The receiver 218 is a structure that is at least partially open on its underside and that includes at least one surface 219 configured to engage the engagement member 216. As shown in FIG. 34, the surface 219 is a partially-curved surface shaped to receive the curved upper end of the engagement member 216. However, the receiver 218 may be a flat vertical surface, a curved surface, a structure such as an inverted cup that is open on its underside and that has a wall or walls encircling the engagement member 216, or any other structure or mechanism capable of engaging the engagement member 216 and urging it distally. Referring also to FIGS. 58 and 68-69, the receiver 218 may be defined in a sled 482, which is described in greater detail below.

Optionally, an anvil insert 222 is fixed to the anvil 10. As one example, the anvil 10 is wider proximal to the anvil arm 14, open at its top with a space therein. The anvil insert 222 can be inserted into the anvil 10 through the open top of the anvil 10, such that the anvil insert 222 is partially or completely positioned within the anvil 10. However, the anvil insert 222 may be connected to the anvil 10 in another way. Alternately, the anvil insert 222 is connected to and capable of motion relative to the anvil 10. Further, the anvil insert 222 instead may be connected to the proximal end of the anvil arm 14, or another location on the anvil arm 14. A cavity 228 is defined within the anvil insert 222. An aperture 230 is defined through the distal end of the anvil insert 222 into the cavity 228, connecting the channel 246 in the anvil arm 14 and anvil 10 to the cavity 228. The cutter 200 extends through the aperture 230, such that the distal end of the cutter 200 is positioned within the channel 246 and the proximal end of the cutter 200 is positioned within the cavity 228.

A cutter stop 236 may be formed into or connected to the anvil insert 222, or formed into or connected to the anvil 10 itself or another structure or mechanism. The cutter stop 236 may engage the proximal end of the cutter 200 if the cutter 200 is moved proximally to a defined position within the cavity 228, thereby restricting its proximal translation.

Figure 56:
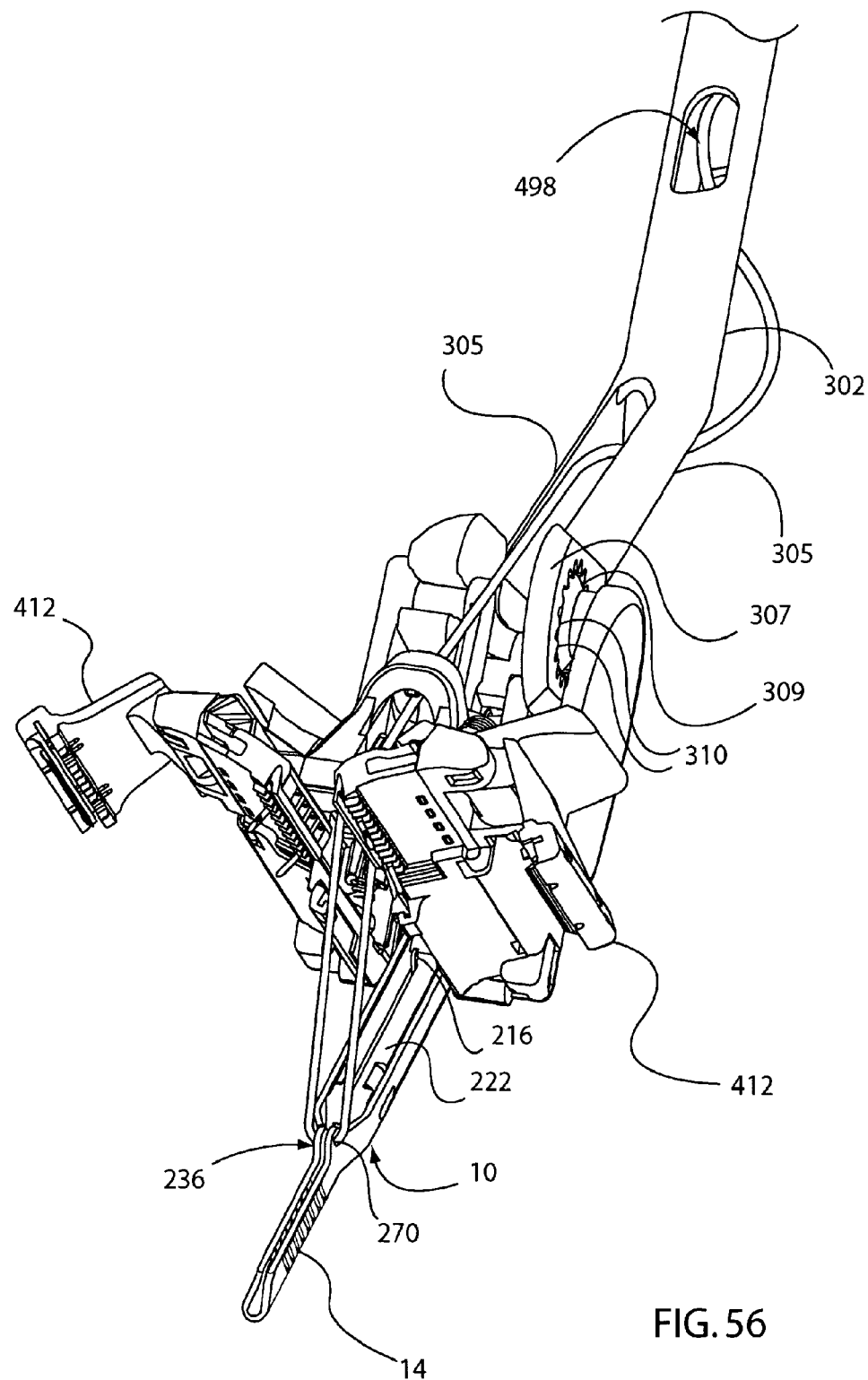
FIG. 56 is a perspective view of the tissue effector of FIG. 55 in first position.

Referring also to FIG. 56, the anvil 10 may include one or more attachment features 270. The attachment features 270 provide a location for attachment of one or more cables or other force transmission structures or mechanisms. As one example, the attachment features 270 may be one or more passages 270 through the cutter stop 236. The cutter stop 236 may include two or more spaced-apart members. If so, the attachment features 270 may be substantially aligned with one another, or offset from one another. However, the cutter stop 236 may be a single member, if desired. As another example, one or more of the attachment features 270 are separate from the cutter stop 236, and are positioned at a different location on the anvil 10. As another example, one or more of the attachment features 270 may extend in a direction from the anvil 10 that is other than upward.

The configuration of the attachment features 270 is related to the configuration of the cable or other force transmission structure or mechanism attached to it, such that the connection between them is secure. As one example, the cutter stop 236 includes two spaced-apart members, and the attachment features 270 are passages through the upper portion of each member of the cutter stop 236. Two separate cables are connected to the attachment features 270. The end of each cable is passed through one of the attachment features 270, after which it is welded, connected with adhesive, clamped, tied or otherwise secured to the cutter stop 236. Alternately, a single first cable is passed through each of the attachment features 270, such that the free ends of the first cable are spaced apart from the attachment features 270. In this way, no additional steps are needed to secure the first cable to the attachment features 270. However, the cable may be welded, connected with adhesive, clamped, tied or otherwise secured to the cutter stop 236, if desired. Alternately, the force transmission member or members may be connected to the anvil 10 in a different manner and/or location.

Figure 44:
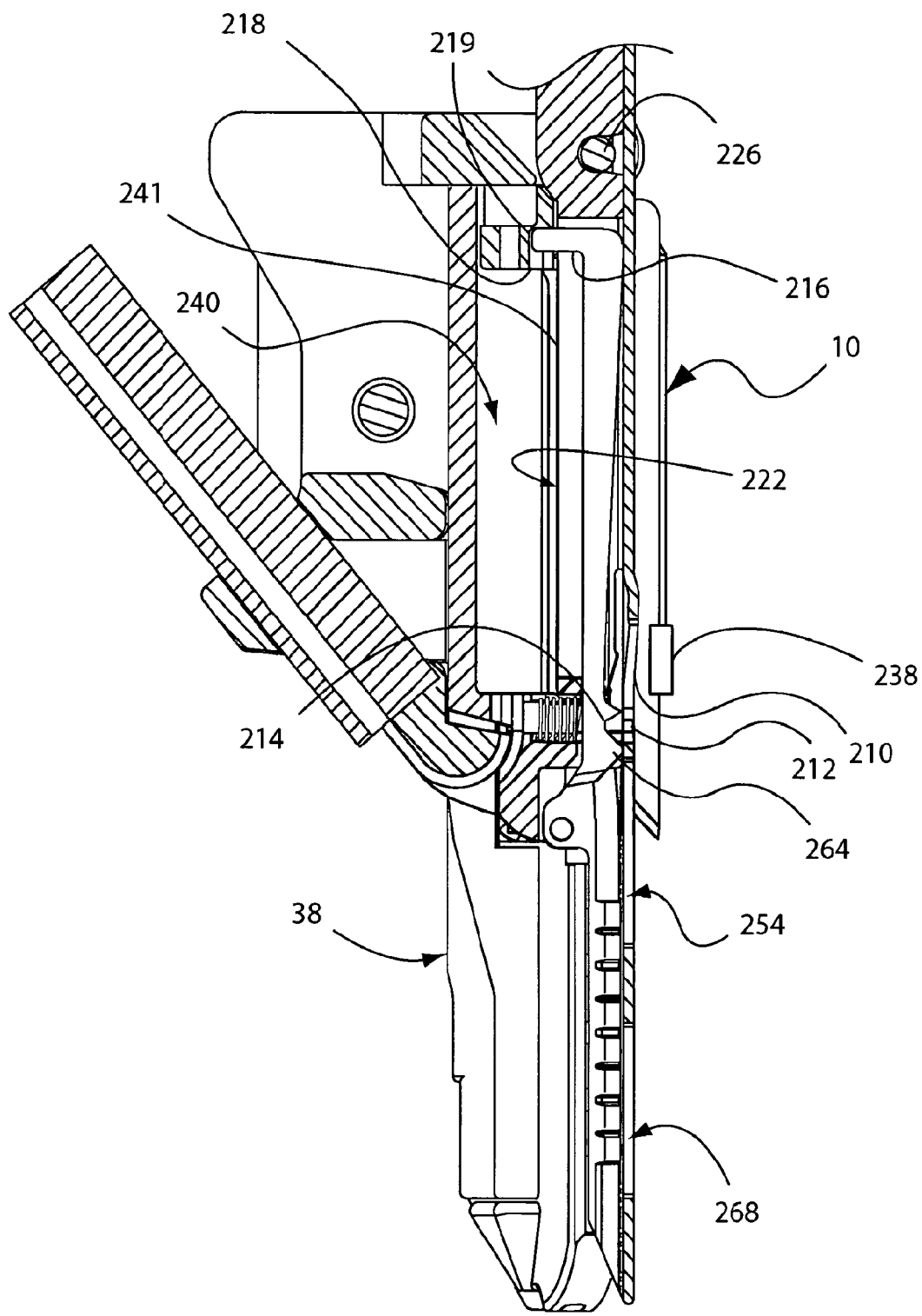
FIG. 44 is a side cutaway view of the anvil and staple holder of FIG. 34, where the cutter is in a first position.

Referring also to FIG. 44, the anvil 10 extends proximally to a pivot point such as a pin 226. The pivot point may be any other structure or mechanism that allows the anvil 10 to rotate about it. For example, the pivot point may be a four-bar linkage or other mechanism rather than the pin 226. By using a four-bar linkage or other mechanism, the staple holder 38 and the anvil 10 may be movable relative to one another in a simple manner such as rotation, or in a more complex manner. Alternately, the anvil insert 222 extends to the pin 226 instead of or in addition to the anvil 10. The pin 226 pivotally connects the staple holder 38 to the anvil 10. The pin 226 may be formed into or otherwise fixed to the staple holder 38 or anvil 10, if desired. The anvil 10 and/or anvil insert 222 may extend still further proximally from the pin 226. As one example, the anvil 10 extends proximally to the pin 226. The anvil insert 222 also extends proximally to the pin 226, and additionally extends as far as or further proximally to the proximal end of the anvil 10.

The staple holder 38 and the anvil 10 may be connected to one another in any other suitable manner and/or in any suitable location. As one example, the staple holder 38 and the anvil 10 may be connected to one another at the junction between the tissue effector 400 and the shaft 304. The staple holder 38 and/or anvil 10 may be movable toward the other. Alternately, the staple holder 38 is substantially fixed relative to the anvil 10. If so, the tissue effector 400 is substantially in the closed position throughout the anastomosis procedure. Fabrication and/or operation of the anastomosis tool 300 may be simplified if the tissue effector 400 remains in substantially the same position throughout the anastomosis procedure.

Figure 57:
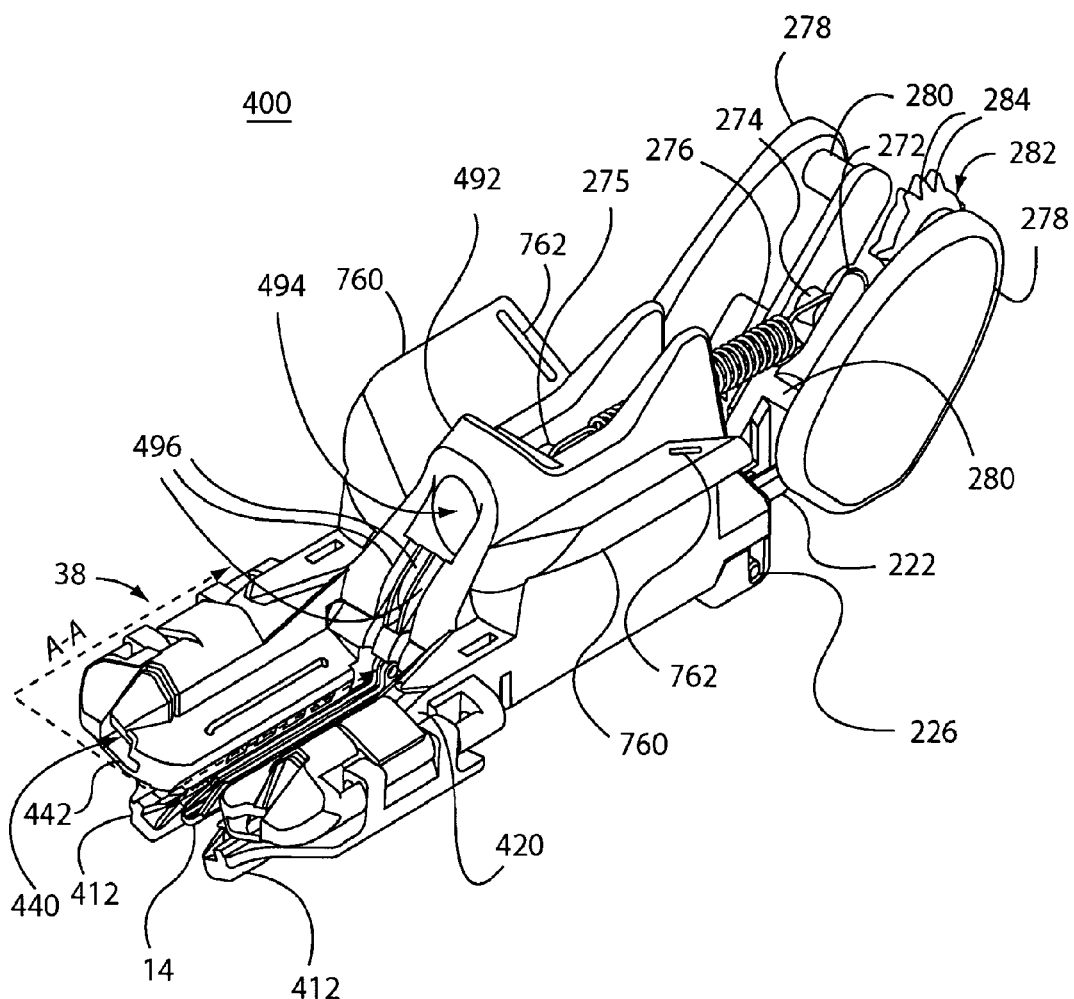
FIG. 57 is a perspective view of the tissue effector of FIG. 55 in a second position.

Referring also to FIG. 57, a proximal portion of the anvil insert 222 may be bent upward relative to a distal portion of the anvil insert 222. The proximal portion of the anvil insert 222 may be referred to as the spine 272. The spine 272 need not be bent upward relative to the proximal portion of the anvil insert 222, and instead may be bent downward or oriented substantially parallel to the proximal portion of the anvil insert 222. Alternately, the spine 272 is a separate structure or mechanism that is connected to the anvil insert 222. A post 274 may be defined in or connected to the spine 272. The post 274 may be cylindrical, or may be shaped differently. One end of a spring 276 is connected to the post 274. The spring 276 is a coil spring, but may be a different type of spring if desired. The other end of the spring 276 is connected to the staple holder 38, such as to an attachment member 275 defined in or connected to the staple holder 38. The attachment member 275 may be cylindrical, or may be shaped differently. The spring 276 may be connected to the post 274 and/or to the attachment member 275 by hooking an end of the spring 276 to at least one of the post 274 and the attachment member 275, by welding, by adhesive, or by any other appropriate structure, mechanism or method. The spring 276 may be connected to the staple holder 38 and/or the spine 272 in a different way, if desired. The spring 276 is sized and configured to be in tension, so as to bias the tissue effector 400 to an open position. That is, the spring 276 presses the staple holder 38 about the pin 226, toward the spine 272 of the anvil insert 222. Alternately, any other suitable structure, mechanism or method may be used to bias the tissue effector 400 to the open position. Alternately, the tissue effector 400 is not biased to the open position.

Optionally, one or more buttons 278 are connected to the spine 272. The wing or buttons 278 may be spaced apart from the spine 272 and connected to it by one or more connection members 280. The buttons 278 each may be sized and shaped for contact with a user's finger. For example, two buttons 278 may be sized and shaped such that a user may conveniently press one with a thumb and the other with a forefinger. The precise shape and size of the buttons 278 is not critical to the invention. Optionally, at least one button 278 is connected to a cog 282 that in turn connects to the shaft 304 of the anastomosis tool 300, as described in greater detail below. The cog 282 includes one or more teeth 284. Advantageously, the cog 282 is substantially circular, and the teeth 284 extend substantially radially outward from it.

Graft Vessel Handling Features

Figure 59:
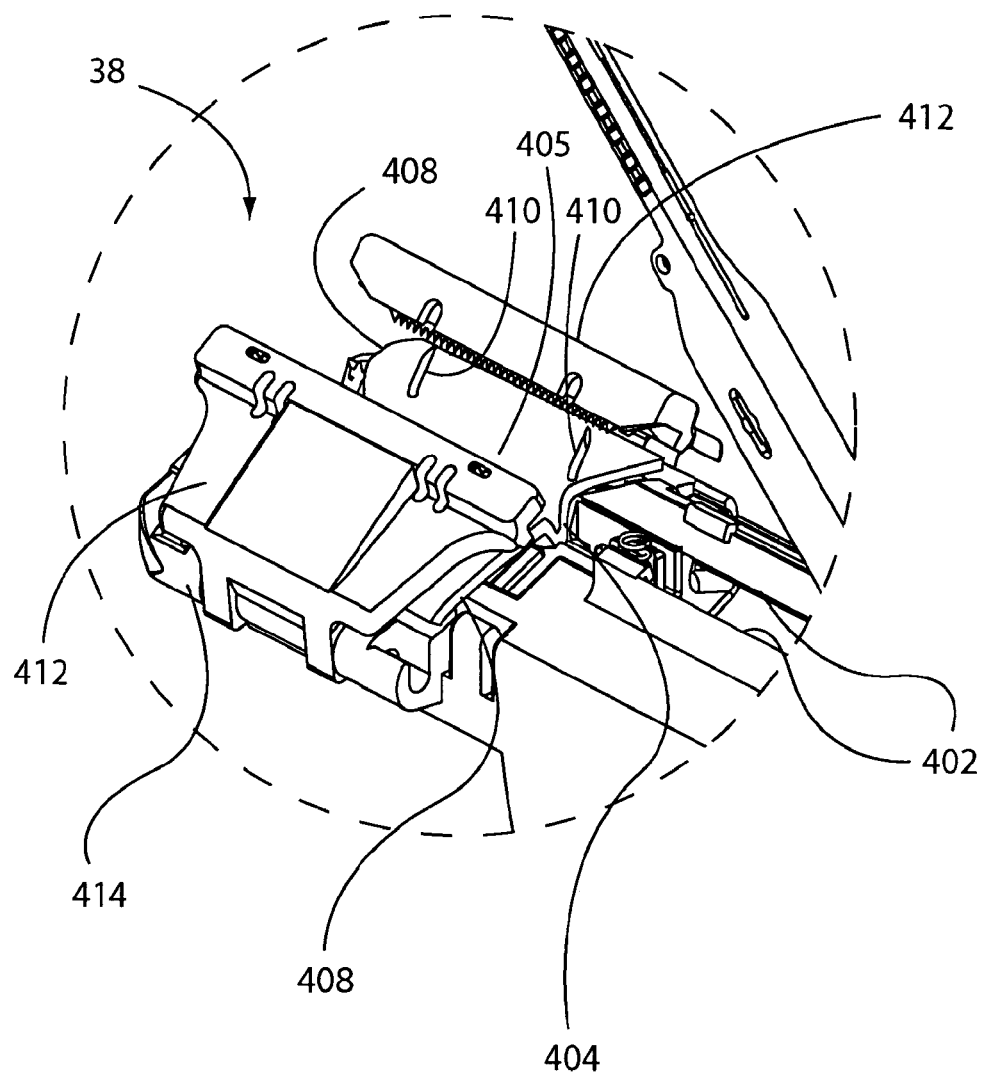
FIG. 59 is a perspective view of the tissue effector of FIG. 55 in the first position, with a graft vessel being connected to it.

Referring to FIG. 58, the underside of the staple holder 38 is seen. The staple holder 38 includes two arms 402, where those arms 402 are spaced apart from one another along at least part of their length, and/or at least at one end. More or fewer arms 402 may be provided. The arms 402 extend distally from the remainder of the staple holder 38. However, the arms 402 may be positioned differently, if desired. The arms 402 are generally linear in configuration, and the longitudinal centerlines of the arms 402 are substantially parallel to one another. However, the arms 402 may be shaped differently and/or oriented differently relative to one another. One or more of the arms 402 may be angled relative to a horizontal plane; for example, to facilitate connecting the flaps of the graft vessel to the wall of the target vessel. Referring also to FIG. 59, the arms 402 are spaced apart from one another along at least part of their length and/or at least at one end to allow a graft vessel 404 to be placed between them, and to allow the tissue effector 400 to be freed from the completed anastomosis. The arms 402 may be substantially fixed relative to one another. Alternately, at least one arm 402 may be movable relative to the other arm 402.

The underside of each arm 402 may include a flap receiving surface 406. Each flap receiving surface 406 is substantially flat across at least a portion of its area. Each flap 408 at the end of the graft vessel 404 is placed onto a corresponding flap receiving surface 406, and the main body of the graft vessel 404 extends between the arms 402 of the staple holder 38. Advantageously, each flap 408 is substantially flat against the corresponding flap receiving surface 406. One or more of the flap receiving surfaces 406 may include a ridged region 413 that has individual ridges 416 spaced apart from one another. The individual ridges 416 may be parallel to one another, or oriented differently. The ridges 416 extend away from the flap receiving surface 406. As one example, each flap receiving surface 406 includes a ridged region 413 in proximity to its inner edge. As used in this document in the context of the staple holder 38, the term "inner" refers to proximity to the space between the arms 402, and the term "outer" refers to distance from the space between the arms 402.

Advantageously, two flaps 408 are present at the end of the graft vessel 404. These flaps 408 may be created in any appropriate manner, such as by incising the end of the graft vessel 404 with a scalpel. However, the end of the graft vessel 404 may have more than two flaps 408. Further, the end of the graft vessel 404 may have a single flap 408. That is, a single incision may be made at the end of the graft vessel 404, substantially parallel to its centerline. As a result, a single flap 408 is created that extends substantially continuously around the circumference of the end of the graft vessel 404, where the opposite ends of the flap 408 are adjacent to the incision.

Optionally, one or more spikes 410 may extend outward from at least one of the flap receiving surfaces 406. As at least one of the flaps 408 is placed onto the corresponding flap receiving surface 406, one or more of the spikes 410 penetrate that flap 408 partially or completely, thereby assisting in holding the flap 408 in place against the flap receiving surface 406. Alternately, no flaps are created at the end of the graft vessel 404. Rather, an end of the graft vessel 404 is simply everted onto the flap receiving surfaces 406, spikes 410 and/or other part of the staple holder 38. Where the end of the graft vessel 404 is everted, the anastomosis procedure is performed in substantially the same manner as if one or more flaps 408 were utilized.

Graft Vessel Handling Features—Graft Clip

A graft clip 412 is connected to each arm 402. Each graft clip 412 may be configured to rotate relative to the corresponding arm 402. As one example, each graft clip 412 is pivotally connected to the corresponding arm 402 at or near the outer edge 414 of that arm 402. Alternately, at least one graft clip 412 is movable relative to the corresponding arm 402 in a different way, such as by sliding. Alternately, at least one graft clip 412 is initially a separate component from the arm 402, and is connectable to the corresponding arm 402. Each graft clip 412 is moveable between an open position and a closed position relative to the corresponding arm 402. The graft clip 412 is positioned relative to the flap receiving surface 406 on the corresponding arm 402 such that, in the closed position, the graft clip 412 is configured to engage a flap 408 of the graft vessel 404. The graft clip 412 may engage substantially all of the flap 408, or less than all of the flap 408. Optionally, the graft clip 412 may include ridges 416 corresponding to ridges 416 extending from the flap receiving surface 406.

Referring to FIG. 140, at least one graft clip 412 may be connected to the staple holder 38 at a location at or near the proximal end of the staple holder 38, such as in proximity to the proximal end of a corresponding arm 402 of the staple holder 38. The graft clips 412 may be connected to the staple holder 38 in any suitable manner. For example, at least one graft clip 412 may be pivotally connected to the staple holder 38 in such a way that the axis of rotation of the graft clip 412 is substantially perpendicular to the longitudinal axis of the staple holder 38. Alternately, at least one graft clip 412 has an axis of rotation oriented in a different direction. The graft clips 412 are separate and independent from one another. Alternately, the graft clips 412 are connected to one another. For example, the graft clips 412 may both be part of a single generally U-shaped assembly, with the base of that U-shaped assembly positioned at or near the proximal end of the staple holder 38.

Referring also to FIG. 58, alternately, the spikes 410 alone hold at least one flap 408 onto the corresponding flap receiving surface 406, and one or more graft clips 412 are not used. The spikes 410 are oriented at an angle that facilitates the opening of the tissue effector 400 after the flaps 408 are connected to the target vessel. Where the spikes 410 alone hold the flaps 408, the vein knives 432 that are described below may be omitted, because the staple holder 38 is disengaged from the flaps 408 simply by removal of the spikes 410 from the flaps 408. Thus, by eliminating the graft clips 412, construction of the tissue effector 400 may be simplified. Alternately, a structure or mechanism other than or in addition to the spikes 410 may be used to hold the flaps 408 onto the corresponding flap receiving surfaces 406.

Each graft clip 412 is locked or otherwise held in the closed position to securely hold the flap 408 between itself and the corresponding flap receiving surface 406. The pressure between the graft clip 412 and the flap receiving surface 406, alone or in conjunction with ridges 416 on the graft clip 412 and the flap receiving surface 406 and/or spikes 410 extending upward from the flap receiving surface, holds the flap 408 firmly in place. The spikes 410, if used, may engage the graft clip 412 when it is in the closed position. The ridges 416 on the graft clip 412 and the flap receiving surface 406, if used, engage opposite sides of at least one flap 408, thereby gripping the flap 408 firmly and resisting motion of the flap 408 in a direction substantially perpendicular to the orientation of the ridges 416. However, each graft clip 412 may be shaped or configured in any manner that allows it to participate in holding the corresponding flap 408 to the corresponding flap receiving surface 406.

Figure 59A:
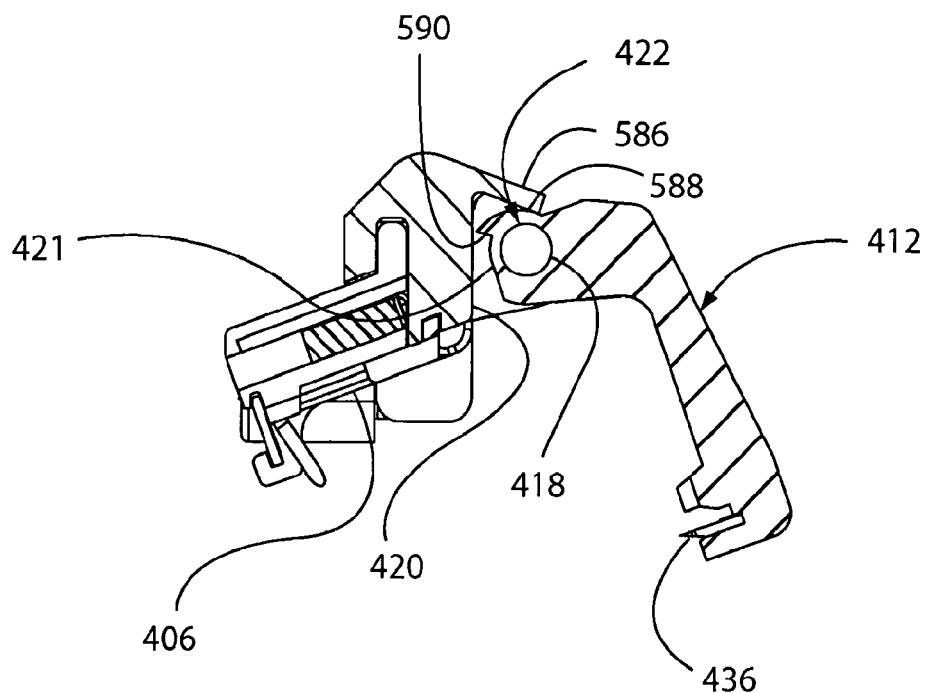
FIG. 59A is a detail cross-section view of a cam lock used in the tissue effector of FIG. 55, where the cam lock is in an open position.

The graft clip 412 may be locked or otherwise held in the closed position with any appropriate mechanism, structure or method. As one example, the graft clip 412 uses a cam lock to hold itself in the closed position. Referring also to FIG. 59A, the graft clip 412 is in an open position. In the open position, the graft clip 412 is positioned to receive a flap 408 of the graft vessel 404 between it and the flap receiving surface 406. The graft clip 412 is rotatable about an axle 418 that is spaced apart from a wall 420 defined on an arm 402 of the staple holder 38. The wall 420 may be perpendicular or otherwise angled to the flap receiving surface 406. The axle 418 is connected to the arm 402, and is substantially fixed relative to the wall 420. Alternately, the axle 418 is movable relative to the wall 420. The axle 418 extends substantially longitudinally, but may be angled relative to the longitudinal direction. Alternately, the axle 418 may be substantially transverse to the longitudinal direction, or may be oriented in a different manner relative to the staple holder 38. The arm 402 also includes an overhang 586 that extends outward and downward from the main portion of the arm 402. Alternately, the overhang 586 extends in a different direction. The overhang 586 may extend laterally outward at least as far as the longitudinal centerline of the axle 418, but need not do so.

The graft clip 412 includes a lobe 422 in proximity to the axle 418, where the lobe 422 has a non-circular cross section. The lobe 422 has a variable thickness, where thickness is defined as the distance between the surface of the axle 418 and the surface of the lobe 422. The lobe 422 includes a first portion 588 that has a relatively small thickness. When the graft clip 412 is in the open position, the first portion 588 is substantially adjacent to the overhang 586. The thickness of the first portion 588 of the lobe 422 is substantially equal to the distance between the axle 418 and the overhang 586. Alternately, the first portion 588 of the lobe 422 may have a different thickness. Moving counterclockwise along the lobe 422, its thickness increases, then decreases rapidly to form a step 590, which may be substantially aligned with the centerline of the axle 418. Continuing to move counterclockwise along the lobe 422, its thickness once again increases. The graft clip 412 may be a mirror image of the clip 412 shown in FIG. 59A, such that the thickness of the lobe 422 relative to the angular position thereon is reversed from the description above. Similarly, if the graft clip 412 is viewed from the opposite direction, the thickness of the lobe 422 will be reversed from the description above. The operation of the graft clip 412 is the same.

In the open position, which is the initial position of the graft clip 412, the first portion 588 of the lobe 422 is adjacent to the overhang 586. This first portion 588 may be substantially as thick as the distance between the axle 418 and the overhang 586. The portion of the lobe 422 adjacent to and immediately clockwise from the step 590 may be in contact with or in proximity to the wall 420. The graft clip 412 is rotated about the axle 418 from the open position to the closed position in a clockwise direction by the user or by a mechanism associated with the tissue effector 400. As this rotation begins, increasingly-thick portions of the lobe 422 move between the axle 418 and the overhang 586. As a result, the overhang 586, axle 418, and/or lobe 422 may flex to accommodate the increased amount of thickness of the lobe 422 between the axle 418 and the overhang 586. Further, this increase in thickness between the axle 418 and the overhand 586 may provide at least some resistance to the motion of the graft clip 412.

Figure 59C:
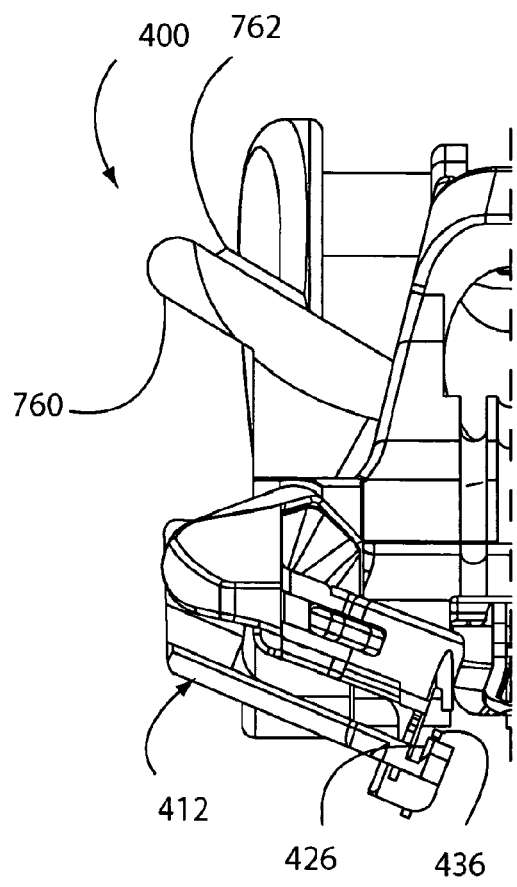
FIG. 59C is an end view of the left half of the tissue effector of FIG. 55, in the closed position.
Figure 60:
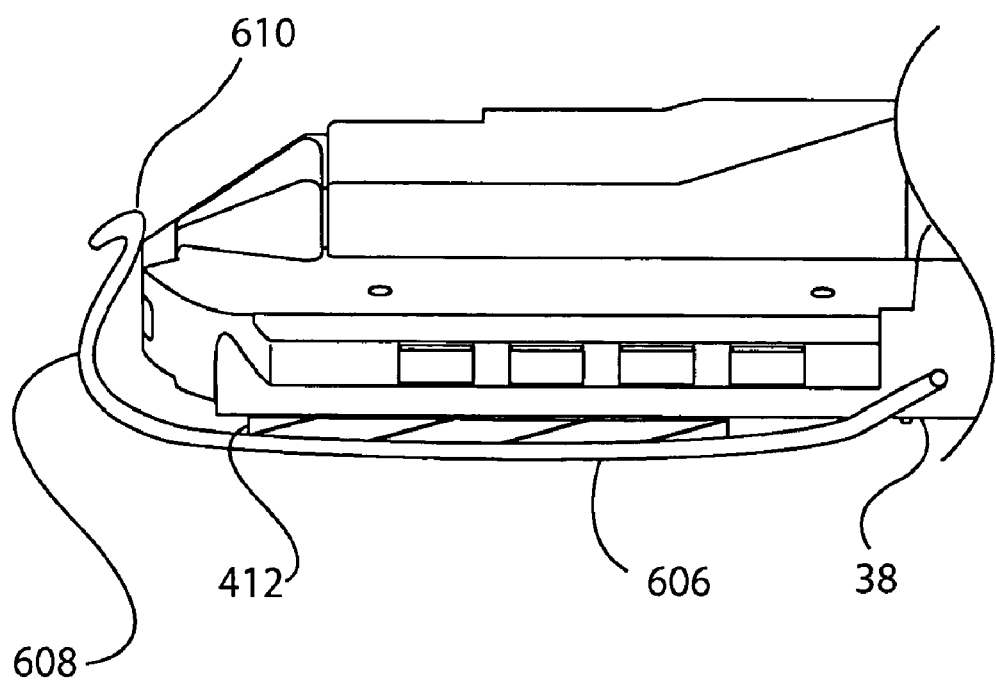
FIG. 60 is a detail side view of a portion of the tissue effector of FIG. 55, showing an embodiment of a graft clip.

Referring also to FIG. 60, as the rotation of the graft clip 412 continues, the step 590 encounters the overhang 586, then moves past the overhang 586. As a result, the thickness of the lobe 422 between the overhang 586 and the axle 418 decreases abruptly. The stiffness of the overhang 586 is such that the overhang 586 can flex enough to allow the graft clip 412 to rotate past the step 590. Rotation of the graft clip 412 may stop at or shortly after the motion of the step 590 past the overhang 586, such that the graft clip 412 stops at the closed position shown in FIG. 59C. Motion of the graft clip 412 in the counterclockwise direction would cause the step 590 to encounter the end of the overhang 586, stopping the rotation of the graft clip 412. Thus, the step 590 acts to hold the graft clip 412 in the closed position.

Alternately, a structure or mechanism other than a cam lock may be used to hold the graft clip 412 in a closed position. As one example, at least one elastic band (not shown) may be used to hold the graft clip 412 against the staple holder 38. Each elastic band may be fixed to either the graft clip 412 or the staple holder 38. As another example, the graft clip 412 and the corresponding arm 402 may each include corresponding magnets (not shown), such that magnetic force holds the graft clip 412 in contact with the arm 402 in the closed position.

As another example, referring to FIG. 60, a snap arm 606 may be used to hold the graft clip 412 in a closed position. The snap arm 606 is connected at one end to the corresponding arm 402. This connection may be a hinge, or may be any other connection that allows the snap arm 606 to move between an open position, in which the graft clip 412 may be opened, and a closed position, in which the graft clip 412 is held closed. The connection between the proximal end of the snap arm 606 and the arm 402 is made proximal to the flap receiving surface 406. Alternately, the connection between the snap arm 606 and the staple holder 38 is made at a different location. Alternately, a different part of the snap arm 606 than its proximal end is connected to the arm 402.

The distal end of the snap arm 606 includes a catch 608 that is shaped to engage the distal end of the corresponding arm 402. For example, the catch 608 may be curved such that a lobe 610 of the catch 608 is proximal to the distal end of the arm 402 when the snap arm 606 is in the closed position, thereby holding the snap arm 606, and the graft clip 412, in place. The catch 608 is at least partially flexible such that the catch 608 can be snapped down onto the distal end of the corresponding arm, thereby holding the snap arm 606 in the closed position. The catch 608 may be configured differently, if desired. When the snap arm 606 is in the closed position, at least a portion of the graft clip 412 is positioned between the snap arm 606 and the corresponding arm 402. Thus, in the closed position, the snap arm 606 presses the graft clip 412 against the arm 402, holding it in place. As a result, the graft clip 412 holds the corresponding flap 408 against the flap receiving surface 406.

Alternately, a separate snap arm 606 is not used, and the graft clip 412 itself includes a catch 608 that engages the corresponding arm 402 of the tissue effector 400. Alternately, the snap arm 606, or the graft clip 412 that includes a catch 608, is oriented differently, such as described above with regard to FIGS. 59A-59B.

Figure 61:
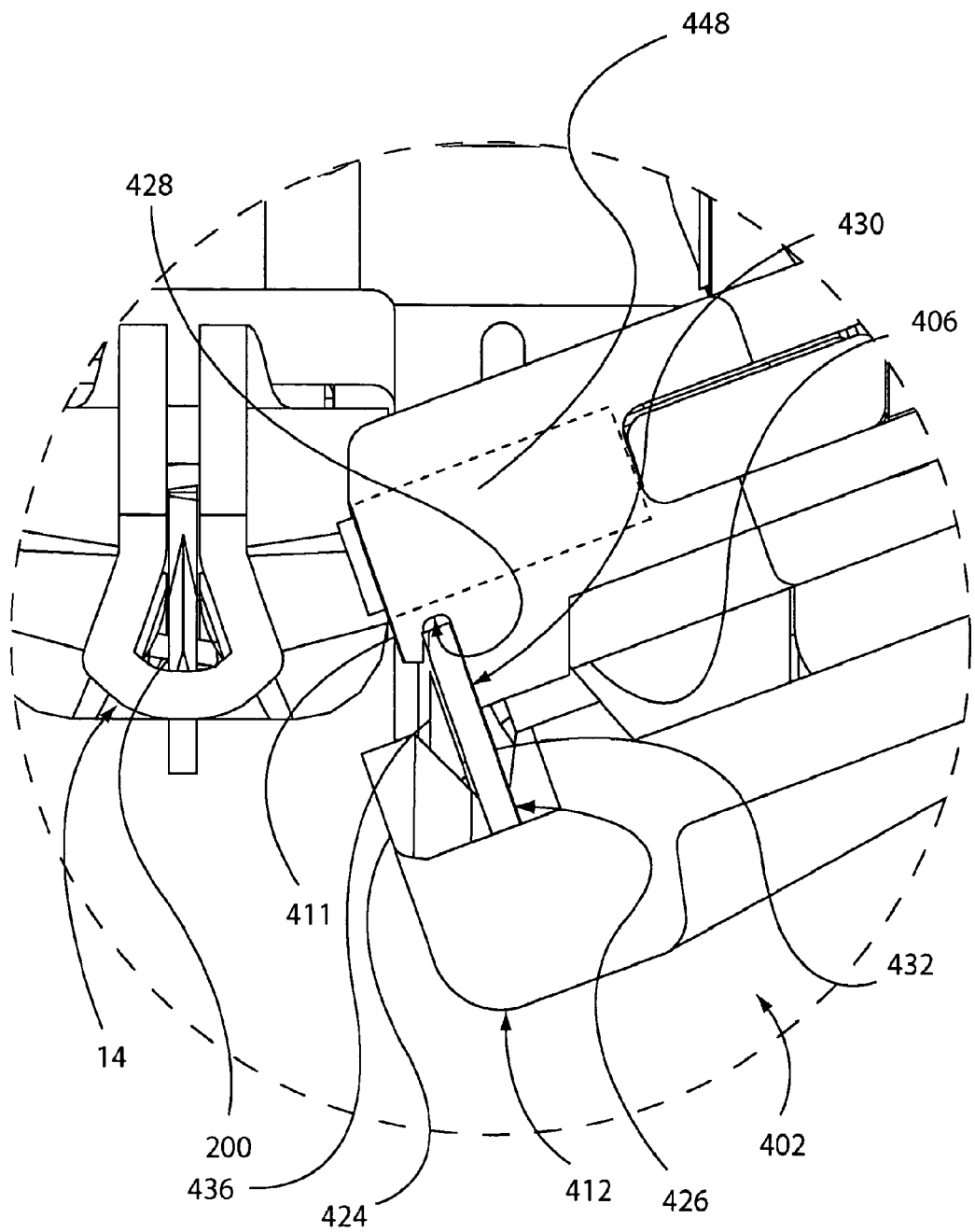
FIG. 61 is a detail end view of a portion of the tissue effector of FIG. 55.

Referring also to FIG. 61, in the closed position, each graft clip 412 is configured to press a flap 408 of the target vessel against the corresponding flap receiving surface 406. The flap 408 is not shown for clarity. In the closed position, the graft clip 412 and the flap receiving surface 406 are substantially fixed relative to one another. The graft clip 412 and the corresponding flap receiving surface 406 may be configured such that a portion of each would contact the other in the closed position, absent the flap 408. Thus, where the flap 408 is present, the graft clip 412 compresses the flap 408 against the flap receiving surface 406. Additionally, the graft clip 412 may include an overhang 424, which extends along at least a portion of the edge of the graft clip 412. The overhang 424 may be substantially parallel to and in proximity to the corresponding inner edge 411 of the arm 402 in the closed position. Alternately, the overhang 424 may be configured differently relative to the arm 402. The overhang 402 may bend the flap 408 and/or press, pinch or otherwise hold it against the corresponding edge of the arm 402.

As another example, referring to FIG. 140, at least one graft clip 412 includes a clamp 952 extending from it. The clamp 952 is configured to exert a force on the staple holder 38 and/or the corresponding arm 402 when the graft clip 412 is in the secure position. For example, the clamp 452 may be a tab extending from the graft clip 412 generally toward the staple holder 38. The clamp 452 is shaped such that its free end is laterally spaced inward from the intersection between the clamp 452 and the graft clip 452. The free end of the clamp 452 is spaced inward far enough such that, as the graft clip 412 moves to the secure position, the clamp 452 can be received onto the corresponding arm 402 or other part of the staple holder 38. As the graft clip 412 continues to move to the secure position, the clamp 452 contacts a corresponding arm 402 or other part or feature of the staple holder 38 and exerts a force such as in the lateral direction against that corresponding arm 402 or other part of the staple holder 38. The clamp 452 may exert such a force as a result of its configuration, where the shape of the clamp 452 causes friction or interference with the corresponding arm 402 or other part or feature of the staple holder 38. Alternately, at least one graft clip 412 is held in the secure position in a different or additional manner.

Graft Vessel Handling Features—Vein Knife

Still referring to FIG. 61, optionally a first channel 426 may be defined in the graft clip 412, and a corresponding second channel 428 may be defined in the corresponding arm 402. The first channel 426 and the second channel 428 are substantially linear and substantially aligned with one another. Alternately, the first channel 426 and the second channel 428 are configured differently, aligned differently with respect to one another and/or have a different cross-section. Each channel 426, 428 is open along one side, at least in part. The first channel 426 and the second channel 428 are oriented and aligned relative to one another such that the openings in the channels 426, 428 face one another to form a vein knife passage 430. The channels 426, 428 may be spaced apart from one another at least in part and still form the vein knife passage 430; that is, the vein knife passage 430 need not be bounded around its entire periphery. Alternately, the channels 426, 428 are oriented and aligned differently, and/or the vein knife passage 430 is formed differently. Each vein knife passage 430 is oriented such that, when the tissue effector 40 is in the closed position, the longitudinal centerline of the vein knife passage 430 is substantially parallel to the longitudinal axis of the anvil 10. Alternately, the vein knife passages 430 are aligned differently relative to the longitudinal axis of the anvil 10 when the tissue effector 400 is in the closed position.

Figure 62:
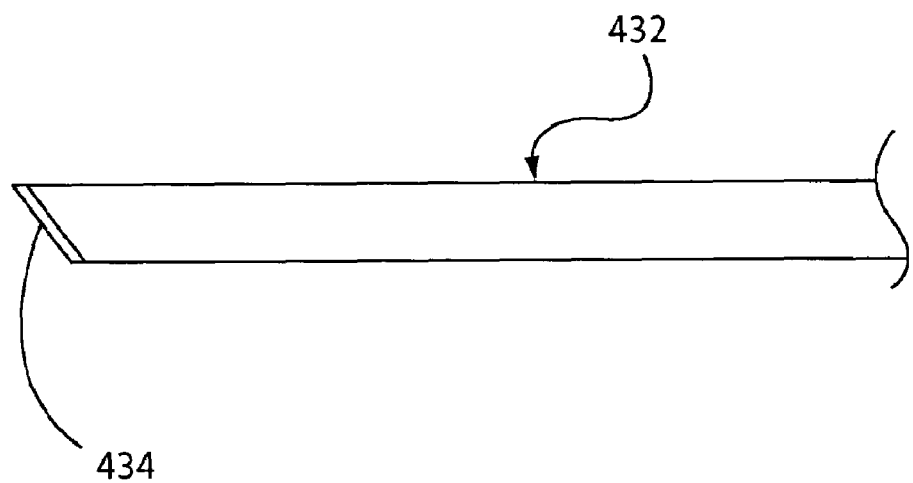
FIG. 62 is a side view of a vein knife used in the tissue effector of FIG. 55.

Referring also to FIG. 62, at least one vein knife passage 430 is configured to receive a corresponding vein knife 432. The fit between the dimensions of the vein knife 432 and the corresponding vein knife passage 430 is close enough that the vein knife passage 430 guides the vein knife 432 and substantially prevents wobbling or other disruption of the motion of the vein knife 432 as it travels along the vein knife passage 430, and loose enough to allow the vein knife 432 to slide easily along that vein knife passage 430 substantially without binding or interference. Each vein knife 432 has a blade 434 or other sharp element at its distal end. The blade 434 of at least one vein knife 432 may be angled. Alternately, the blade 434 of at least one vein knife may be curved or otherwise shaped. The proximal end of each vein knife 432 is connected to a sled, which is described in greater detail below. The vein knife 432 is configured to translate or otherwise move between a first position and a second position. In the first position, the blade 434 of the vein knife 432 is located proximal to the flap 408 held between the graft clip 412 and the flap receiving surface 406. The vein knife 432 translates or otherwise moves to the second position and cuts the flap 408 as it does so. In the second position, the blade 434 of the vein knife 432 is located adjacent or distal to the portion of the flap 408 held between the graft clip 412 and the flap receiving surface 406. The first and second positions are reversed when the vein knife 432 is moved in the opposite direction. Alternately, at least one vein knife 432 and corresponding vein knife passage 430 is omitted, and at least one flap 408 is released from the staple holder 38 after anastomosis simply by opening the corresponding graft clip 412.

Figure 63:
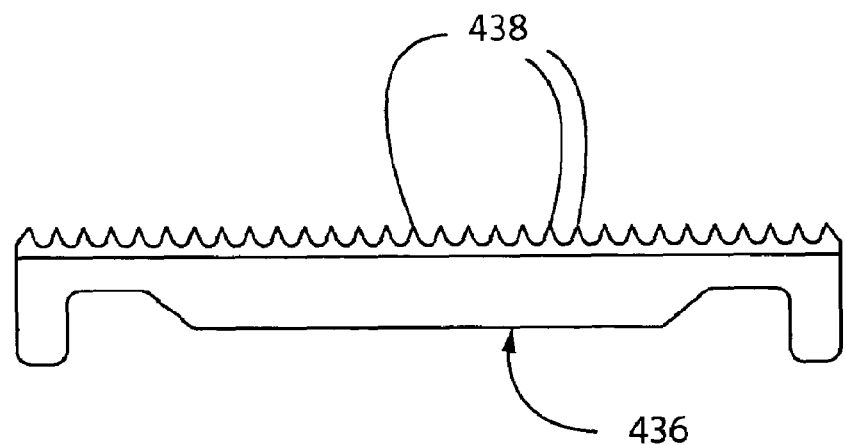
FIG. 63 is a side view of a graft clip blade used in the tissue effector of FIG. 55.

Optionally, one or more graft clip blades 436 are connected to at least one graft clip 412. Referring also to FIG. 63, one or more of the graft clip blades 436 may be serrated. Each graft clip blade 436 is located in and against one side of the first channel 426, such that it does not interfere with the motion of the vein knife 432. Alternately, one or more graft clip blades 436 are located in a different position on the corresponding graft clip 412 or arm 402. Serrations 438 on the graft clip blade 436 are oriented toward the open face of the first channel 426 in the graft clip 412. The serrations 438 may be sized and shaped in any appropriate manner. The serrations 438 assist in holding the flap 408 between the graft clip 412 and the flap receiving surface 406. That is, one or more of the serrations 438 may penetrate into or through the flap 408, thereby holding the tissue of the flap 408 substantially fixed relative to the graft clip 412 and the flap receiving surface 406. When the vein knife 432 translates along the vein knife passage 430 to incise the flap 408, the serrations 438 hold the flap 408. The motion of the vein knife 432 may apply stress to the tissue of the flap 408 such that the serrations 438 themselves act to cut the tissue of the flap 408. Thus, the cutting action may be a scissors-like action resulting from the relative motion of the vein knife 432 and the graft clip blade 436. More than one graft clip blade 436 can be provided in at least one vein knife passage 430. For example, two graft clip blades 436 may be located in one first channel 426, in and against two different sides of the first channel 426 and spaced apart from one another a sufficient distance to allow the vein knife 432 to slide therebetween. Other configurations or numbers of graft clip blades 436 may be utilized, if desired.

Figure 59B:
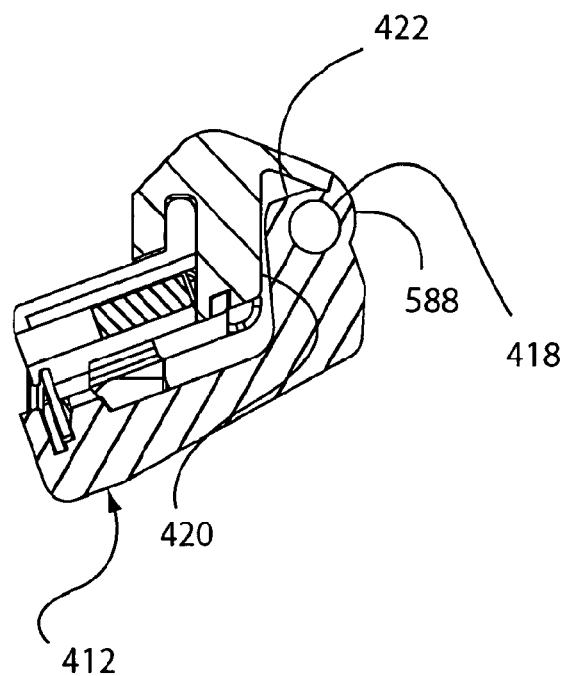
FIG. 59B is a detail cross-section view of the cam lock of FIG. 59A in a closed position.
Figure 59D:
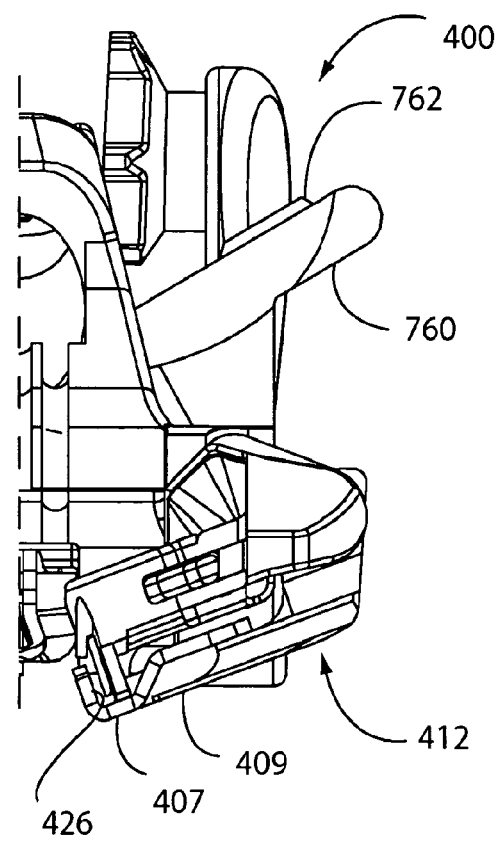
FIG. 59D is an end view of the right half of another embodiment of the tissue effector of FIG. 55, in the closed position.

Alternately, referring to FIG. 59D, at least one graft clip 412 may have a thinner cross-section than the graft clip 412 of FIGS. 59-59B. This thinner cross-section may be achieved by utilizing metal, such as sheet metal, to form at least part of the graft clip 412. However, metal need not be used in order for the graft clip 412 to be made thinner. As shown in FIG. 59C, the graft clip 412 may be an assembly having a first piece 407 connected to a second piece 409. The first piece 407 is located at or near the first channel 426 of the graft clip 412. Alternately, the graft clip 412 may be a single piece, or may be an assembly having additional components. The second piece 409 may be made of plastic or any other suitable material. Other materials may be used to form the pieces 407, 409 if desired. Advantageously, the graft clip blades 436 may be formed into the first piece 407, particularly where at least the first piece 407 of the graft clip 412 is metal. By forming the graft clip blades 436 into a portion of the graft clip 412 rather than connecting them to the graft clip 412, construction of the graft clip 412 may be simplified.

The use of a thinner graft clip 412 results in less compression of the surface of the heart, where the target vessel is a coronary artery and the anvil arm 14 is inserted into that coronary artery. The vertical distance between the bottom of the anvil arm 14 and the bottom of the graft clip 412 substantially defines the distance across which the heart tissue near the coronary artery is compressed as the tissue effector 400 moves from the open to the closed position. By decreasing that distance, the heart tissue around the coronary artery is compressed a lesser distance. As a result, the amount of force required to move the tissue effector 400 from an open position to a closed position, in which compressive force is applied against the heart tissue, may be decreased. This reduction in force may simplify the construction of the tissue effector 400.

Graft Vessel Handling Features—Graft Affixer

Optionally, referring to FIGS. 130-133, a graft affixer 910 is connected to or formed into the staple holder 38. The graft affixer 910 extends outward from the staple holder 38, and is oriented at least partially toward the anvil 10. The graft affixer 910 penetrates an end of the graft vessel 404 and holds the graft vessel 404 to the staple holder 38, as described in greater detail below. The graft affixer 910 may be any structure or mechanism configured to hold the graft vessel 404 to the staple holder 38. As one example, the graft affixer 910 may be a spike. The tip of the spike may be oriented toward the anvil 10, or in a different direction. As another example, the graft affixer 910 may be a hook. As another example, the graft affixer 910 may be a clip. The graft affixer 910 may include a barb (not shown) at or near its tip, or at a different location, in order to hold the graft vessel 404 more securely.

The graft affixer 910 is located between the arms 402 of the staple holder 38 slightly proximal to the two most-proximal connector bays 448. This proximal position of the graft affixer 910 allows the graft affixer 910 to engage a location on the graft vessel 404 that will be positioned at or near the heel of the anastomosis. Alternately, the graft affixer 910 is located directly between the two most-proximal connector bays 448. Alternately, the graft affixer 910 is located between the arms 402 of the staple holder 38, between or slightly distal to the two most distal connector bays 448. If so, the anvil arm 14 may be inserted into the target vessel 580 in the opposite direction, such that the graft affixer 910 engages a location on the graft vessel 404 that will be positioned at or near the toe of the anastomosis. Alternately, the graft affixed 910 is located at any other suitable location relative to the staple holder 38.

The graft affixer 910 may be composed of any appropriate material. As one example, the graft affixer 910 may be composed of plastically-deformable material, such as stainless steel. As another example, the graft affixer 910 may be composed at least in part of an elastic or superelastic material, such as nickel-titanium alloy.

The graft affixer 910 may be connected to the staple holder 38 in any appropriate manner. Referring also to FIGS. 131-132, the graft affixer 910 may be part of a graft affixer assembly 912. The graft affixer assembly 912 includes a base 914 connected to the graft affixer 910 by an arm 916. The base 914 engages the staple holder 38, such as by a friction fit. Alternately, the base 914 engages the staple holder 38 in a different way. The base 914 may be located proximal to the graft affixer 910 where the graft affixer 910 is positioned at or near the most proximal connector bays 448, or distal to the graft affixer 910 where the graft affixer 910 is positioned at or near the most distal connector bays 448. Alternately, the base 914 is positioned differently relative to the graft affixer 910. The arm 916 cantilevers the graft affixer 910 into the space between the arms 402 of the staple holder 38. The arm 916 may be shaped in any manner that connects the base 914 to the graft affixer 910 and that does not interfere with the operation of the tissue effector 400. Alternately, the graft affixer 910 is detachably connected to the staple holder 38, such as by a clip.

At least part of the graft affixer assembly 912 may be movable relative to the staple holder 38. Initially, the graft affixer assembly 912 has a first position relative to the staple holder 38 such that the graft affixer 910 extends outward from it by a first distance, far enough to allow the graft vessel 404 to be connected to it easily. The graft affixer assembly 912 is movable to a second position relative to the staple holder 38 such that the graft affixer 910 extends outward from the staple holder 38 by a second distance that is less than the first distance. In the second position, the graft affixer 910 still extends outward far enough to hold the graft vessel 404, but not so far as to interfere with the anvil 10 when the tissue effector 400 is in the closed position. At least part of the graft affixer assembly 912 may be moved from its initial position to a final position by contact between the base 916 and the anvil 10. For example, the base 916 may be friction-fit to an aperture 918 in the staple holder 38, such that contact between the anvil 10 and the base 916 overcomes the frictional force holding the base 916 to the aperture and causes the base 916 to slide within the aperture 918. As another example, the graft affixer assembly 912 may be biased toward a stop 920 defined in the staple holder 38, such that contact between the anvil 10 and the base 916 moves the graft affixer assembly 912 against that bias away from the stop 920. As another example, the base 916 remains substantially stationary as the anvil 10 moves toward the staple holder 38, and contact between the anvil 10 and the graft affixer 910 moves the graft affixer 910 away from the anvil 10 and/or deforms the graft affixer 910. Alternately, the graft affixer 910 is molded into, formed as an integral part of, glued onto, welded onto, fastened onto, or otherwise associated with the staple holder 38 directly, without the use of a graft affixer assembly 912.

Referring to FIG. 158, another example of a graft affixer 910 is shown. The graft affixer 910 of FIG. 158 is detachable from the staple holder 38, and/or may be used to provide additional sealing at the heel 587 of the anastomosis. The exemplary graft affixer 910 of FIG. 158 may also be referred to as the heel clip 910. The heel clip 910 includes a leg 1150 having a free end 1152. The free end 1152 of the leg 1150 may be substantially sharp or substantially blunt. A first tab 1154 extends outward from the leg 1150 of the heel clip 910. Alternately, the first tab 1154 extends from a different part of the heel clip 910. Moving away from the free end 1152 of the heel clip 910, a base 1156 of the heel clip 910 bends or angles away from the leg 1150. A second tab 1158 extends outward from the base 1156 of the heel clip 910. Alternately, the second tab 1158 extends from a different part of the heel clip 910. Continuing along the heel clip 910 away from the free end 1152 of the leg 1150, a prong 1160 extends from the base 1156. The prong 1160 may be oriented in substantially the same direction as the leg 1150. Alternately, the prong 1160 is oriented in a different direction from the leg 1150. The prong 1160 has a free end 1162 that may be substantially sharp or substantially blunt. The heel clip 910 may be fabricated from a single unit of material. Alternately, at least part of the heel clip 910 is fabricated separately and connected to a remainder of the heel clip 910 in any suitable manner, such as by welding.

The heel clip 910 is detachable from the staple holder 38, and may be detachably held by the staple holder 38 in any suitable manner. As one example, the staple holder 38 includes a ledge 1162 that engages the first tab 1154 and a notch 1164 that engages the second tab 1158. The ledge 1162 and the notch 1164 may be configured to hold the tabs 1154, 1158 such that the heel clip 910 is compressed at least slightly, thereby enhancing the connection between the heel clip 910 and the staple holder 38. The staple holder 38 may include a pocket 1157 or other surface or feature configured to receive at least part of the base 1156 of the heel clip 910. Alternately, the heel clip 910 may be detachably connected to the staple holder 38 in any other suitable manner.

Graft Vessel Handling Features—Measurement Feature

Referring also to FIG. 130, the staple holder 38 includes at least one measurement feature 922. Advantageously, two measurement features 922 are provided, one on each arm 402 of the staple holder 38, each having substantially the same length. Each measurement feature 922 is located on the staple holder 38 in such a way as to facilitate the placement of the graft vessel 404 relative to the staple holder 38, as described in greater detail below. Each measurement feature 922 may be shaped or configured in any suitable manner. For example, at least one measurement feature 922 is a raised area on an arm 402 of the staple holder 38, positioned relative to the graft affixer 910 to be able to assist in the positioning of the graft vessel 404 relative to the staple holder 38. Alternately, at least one measurement feature 922 is a depressed area on an arm 402 of the staple holder 38, one or more indicia defined on an arm 402 of the staple holder 38, or any other appropriate structure or mechanism. Alternately, at least one measurement feature 922 is configured differently. The measurement feature 922 has two spaced-apart ends. Alternately, at least one measurement feature 922 is two spaced-apart and unconnected indicia.

Staple Holder Components

Figure 64:
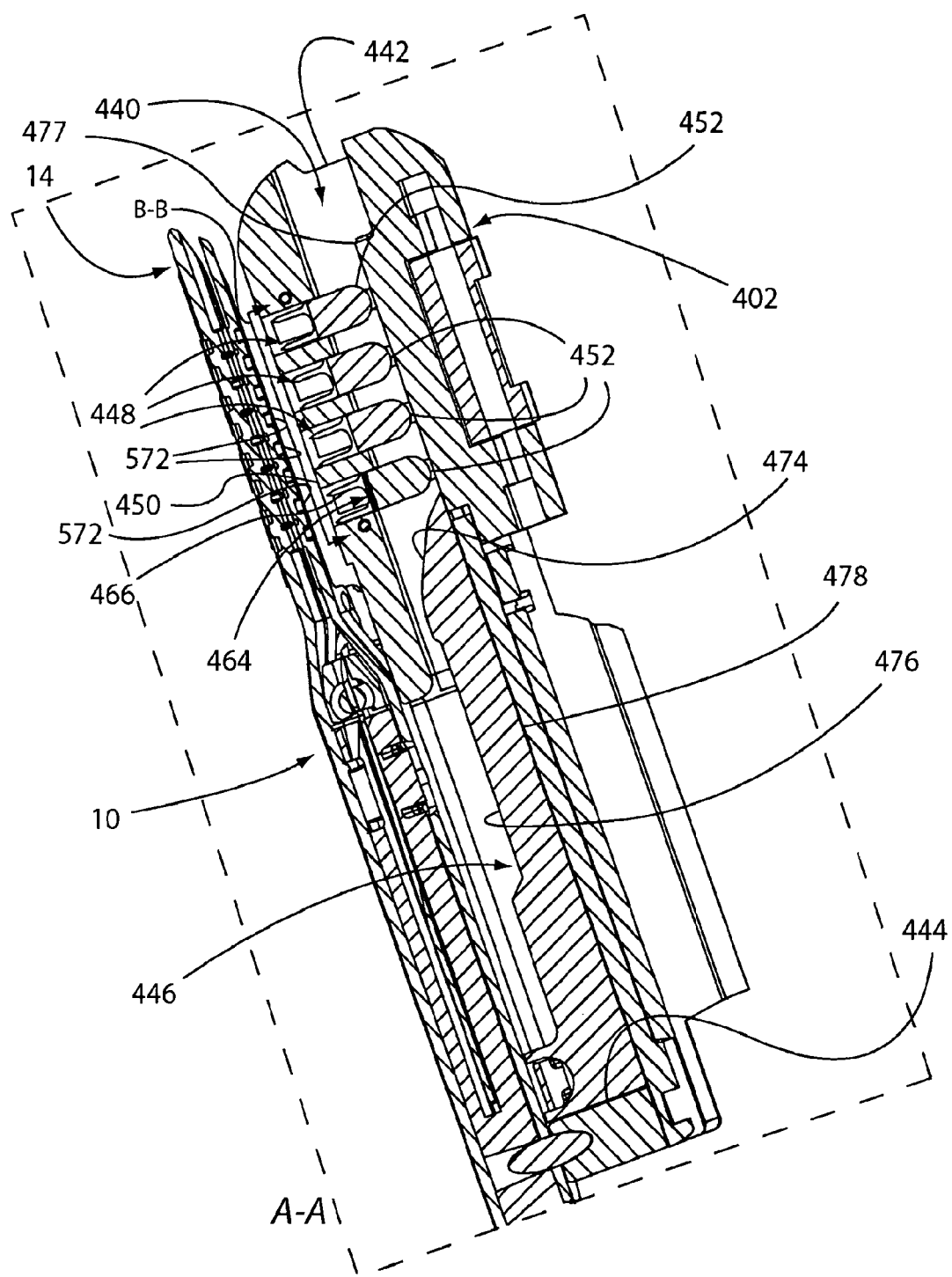
FIG. 64 is a cross-section view of section A-A of FIG. 57.

Referring also to FIG. 64, a cross-section of one arm 402 of the staple holder 38 is shown. The staple holder 38 is substantially symmetrical, such that the arm 402 shown is substantially a mirror image of the other arm 402. Alternately, the staple holder 38 is not symmetrical, and/or the arms 402 are not mirror images of one another. A passage 440 is defined within each arm 402. Each passage 440 extends substantially longitudinally within the corresponding arm 402, and the longitudinal centerline of each passage 440 is substantially parallel to the longitudinal centerline of the anvil 10 when the tissue effector 400 is in the closed position. Alternately, at least one passage 440 is oriented differently relative to its corresponding arm 402. The passage 440 may have a rectangular cross-section, or a different cross-section. Further, the dimensions of the passage 440 may be substantially constant along its entire length, or may change along at least part of its length. Optionally, the distal end 442 of the passage 440 is open, and/or the proximal end 444 of the passage 440 is open.

Figure 69A:
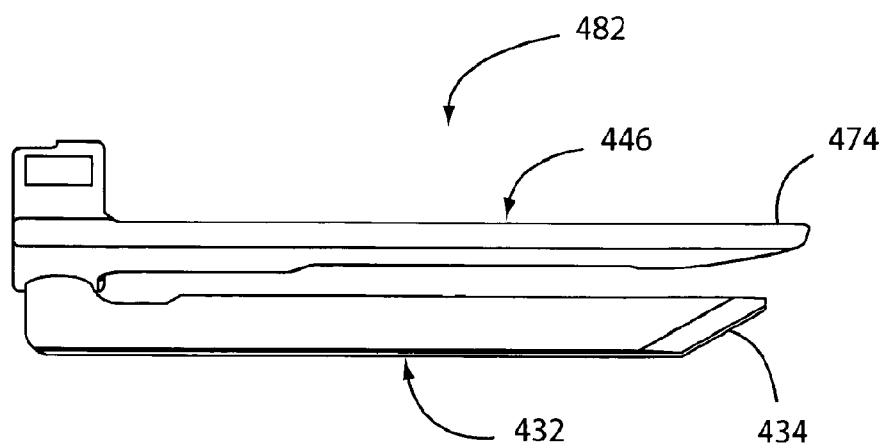
FIG. 69A is a side view of the sled of FIG. 68.

A ramp element 446 is configured to translate or otherwise move through at least a portion of each passage 440. Referring also to FIGS. 68-69A, the ramp elements 446 may be molded or otherwise formed into a unitary ramp element assembly 484, or may be molded or otherwise formed separately and then connected together. Alternately, the ramp elements 446 are not connected to one another. The ramp elements 446 may be formed from stainless steel, polymer or other appropriate material. The vein knives 432 are connected to the ramp element assembly 484 to form a sled 482. As an example, apertures 486 are defined in the ramp element assembly 484, and the proximal end of each vein knife 432 is sized and shaped to provide for a pressure or interference fit within the corresponding aperture 486. However, any other appropriate mechanism, structure or method may be used to connect each vein knife 432 to the ramp element assembly 484. Alternately, the ramp elements 446 and the vein knives 432 are cast, molded or otherwise formed as a single unit. The vein knives 432 may be fixed to the ramp element assembly 484, such that the ramp elements 446 and the vein knives 432 translate as a unit substantially simultaneously. Alternately, at least one ramp element 446 is moveable relative to at least one vein knife 432, or vice versa. As another example of the sled 482, each ramp element 446 is connected to the corresponding vein knife 432, but the ramp elements 446 are not connected to one another.

The sled 482 includes an attachment feature 488. The attachment feature 488 may be an aperture through a portion of the ramp element assembly 484 that is configured to receive a second cable 490 or other force transmission mechanism or structure. Where a cable is used and the attachment feature 488 is an aperture, the second cable 490 may be inserted into and/or through the attachment feature 488, and held in place there such as by tying off one end of the cable, by welding, by adhesive, or any other appropriate connection method. Alternately, the attachment feature 488 may be a ring, a hook, a raised area, a depression, or any other structure or mechanism appropriate for connection to a cable or other force transmission mechanism or structure.

Figure 123:
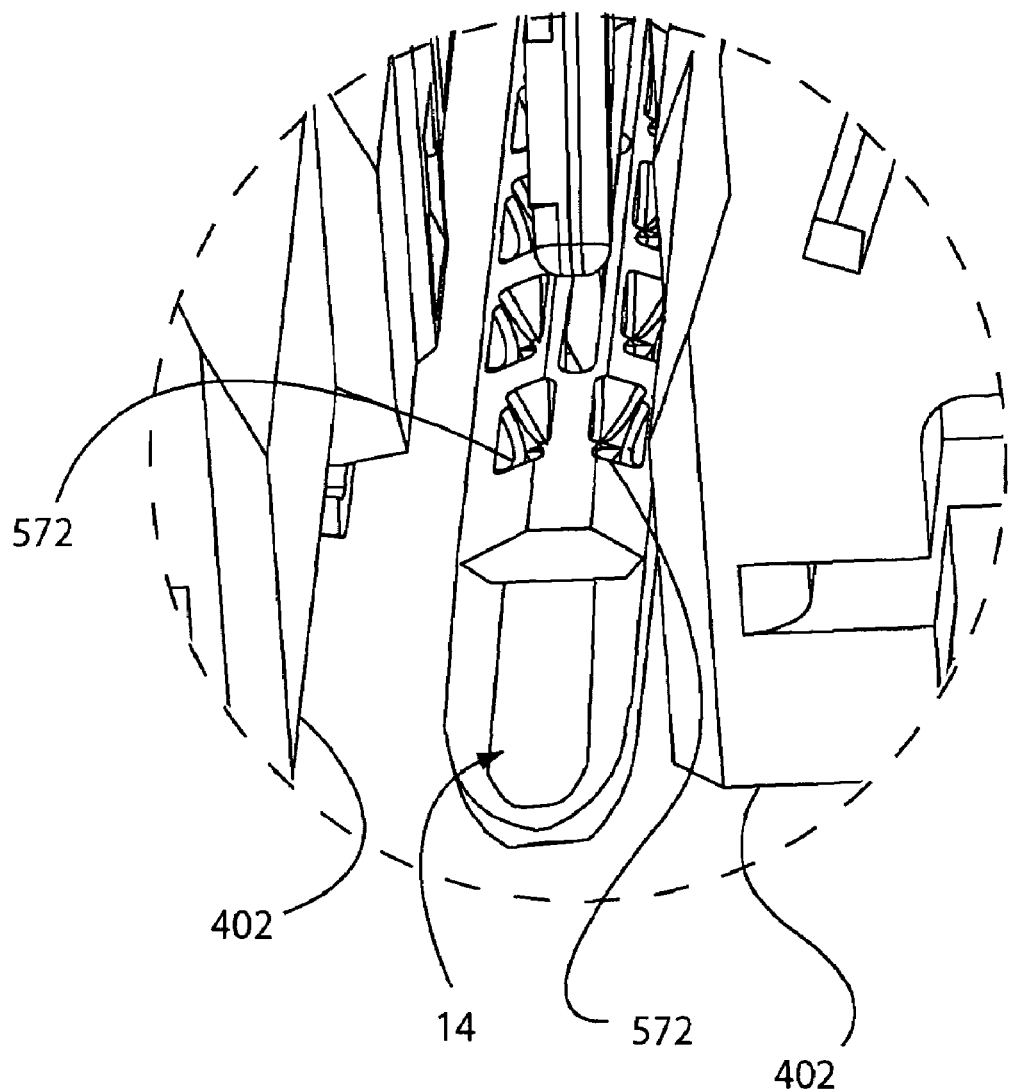
Figure 124:
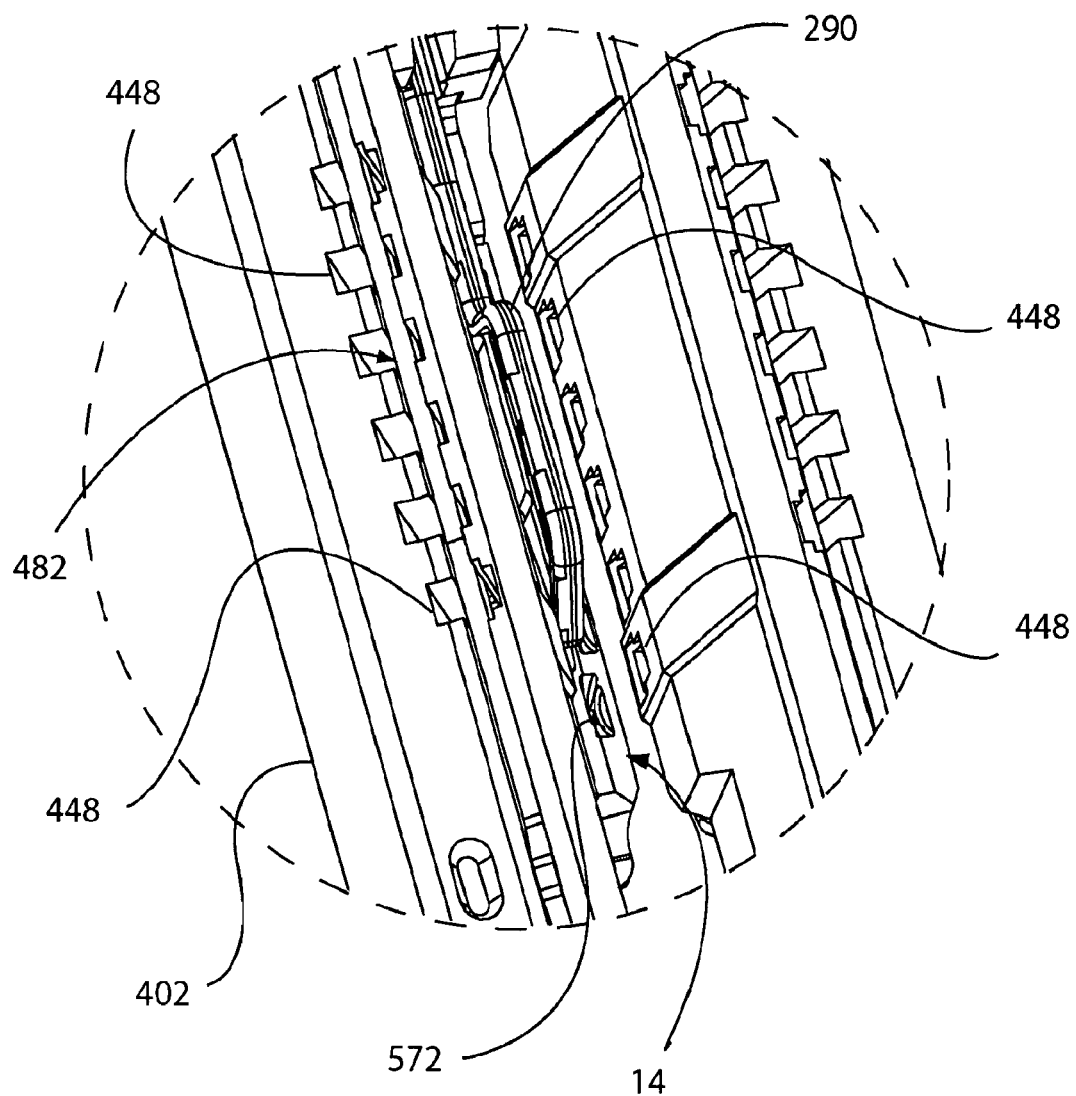

One or more connector bays 448 are defined in each arm 402, between the passage 440 within the arm 402 and an inner surface 450 of the arm 402. The connector bays 448 and the passages 440 are substantially hollow. The cross-sectional shape of each connector bay 448 is selected to allow it to receive and hold a staple or other connector, as described below. The connector bays 448 are oriented such that the longitudinal centerline of each connector bay 448 is substantially perpendicular to the longitudinal centerline of the corresponding passage 440. Alternately, at least one connector bay 448 is oriented differently relative to the corresponding passage 440. Each connector bay 448 has substantially the same cross-section and length. Alternately, at least one connector bay 448 has a different cross-section and/or length than at least one other connector bay 448. The connector bays 448 may be oriented relative to a local horizontal such that the longitudinal centerline of each connector bay 448 forms an angle of between 0° and 45° relative to that local horizontal. (The use of the term "horizontal" here and elsewhere in this document is used for convenience in description only, and does not restrict the orientation in which the anastomosis tool 300 may be used.) A different orientation may be used, if desired. As one example, the longitudinal centerline of each connector bay 448 may form an angle of greater than 45° relative to the local horizontal, as shown in FIG. 123. Such an angle may hold the lateral sides of the anastomosis closer together and thus may enhance sealing. To facilitate deployment at such an angle, bending features 572 on the anvil arm 14 may be located on an upper surface of the anvil arm 14 instead of its sides, as shown in FIG. 124. The bending features 572 correspond to the connector bays 448, each receiving an end of at least one connector 464 and facilitating its bending or deformation to a deployed configuration. Alternately, the bending features 572 may be positioned differently on the anvil arm 14. Alternately, at least one of the bending features 572 may be omitted. Where the connector bays 448 are significantly angled relative to the local horizontal, the arms 402 of the staple holder 38 may be made narrower, facilitating the use of the tissue effector 400 in both open-chest and closed-chest surgery.

Figure 65:
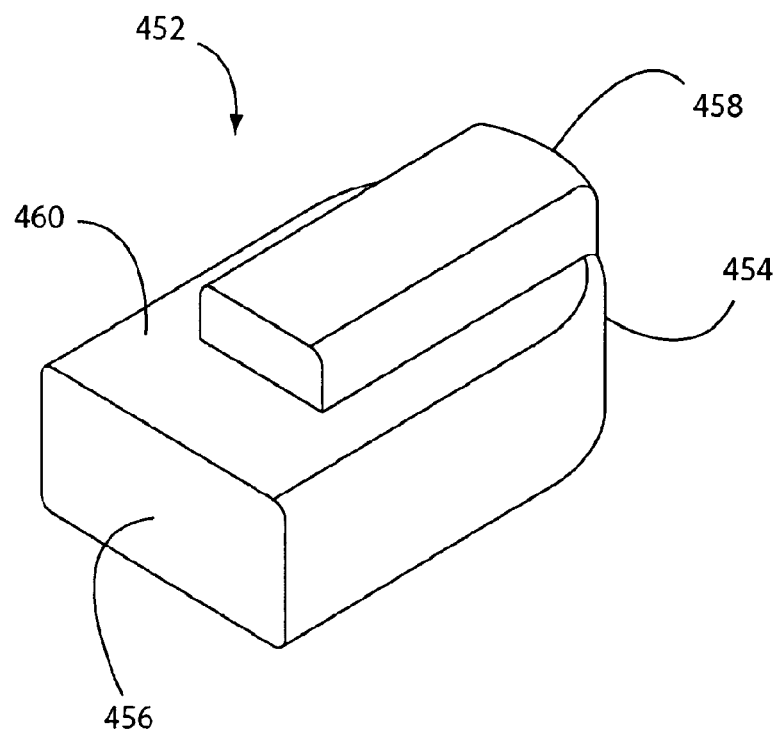
FIG. 65 is a perspective view of a connector deployer used in the arm of FIG. 64.
Figure 66:
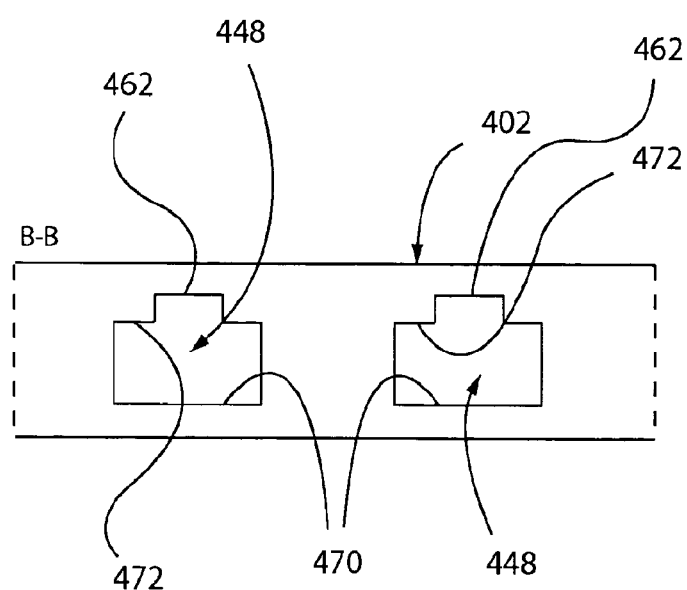
FIG. 66 is a side view of a portion of the arm of FIG. 64 as defined by the line B-B of FIG. 64.

Referring also to FIG. 65, at least one connector bay 448 is configured to receive a connector deployer 452. Each connector bay 448 is shaped to allow the corresponding connector deployer 452 to translate or otherwise move within it. The connector deployers 452 may be shaped in any appropriate manner. As one example, a connector deployer 452 is substantially curved at its outer end 454 and substantially flat at its inner end 456. The connector deployer 452 may vary in height along at least a portion of its length and/or width. As one example, a registration element 458 may extend upward from the upper surface 460 of the connector deployer 452. The registration element 458 may be formed into the connector deployer 452, or otherwise manufactured into it or connected to it.

Where a registration element 458 is used, the corresponding connector bay 448 is shaped accordingly. That is, the size, shape and orientation of the registration element 458 of the connector deployer 452 corresponds to the size, shape and orientation of a registration feature 462 of the connector bay 448. For example, where the connector deployer 452 and registration element 458 of FIG. 65 is used, the corresponding connector bay 448 is shaped as shown in FIG. 66. The registration element 458 translates along the registration feature 462 as the connector deployer 452 translates along the connector bay 448. In this way, the connector deployer 452 is maintained in a desired orientation throughout its translation relative to the connector bay 448, and the connector deployer 452 is prevented from cocking in the connector bay 448 during that translation. The connector deployers 452 and corresponding connector bays 448 may be shaped differently, if desired. The connector deployers 452 are all shaped substantially identically. Alternately, at least one of the connector deployers 452 is shaped differently from at least one of the others, and the corresponding connector bay or bays 448 are shaped accordingly. Optionally, a biocompatible lubricant such as sodium stearate may be used between at least one connector deployer 452 and the corresponding connector bay 448 to facilitate the translation of the connector deployer 452 relative to the connector bay 448.

Where multiple connector bays 448 are provided in each arm 410, at least the most-proximal and/or the most distal connector bays 448 may be offset relative to the other connector bays 448. Advantageously, the direction of offset is toward the longitudinal centerline of the anvil arm 14, as determined when the tissue effector 400 is in the closed position. Each connector bay 448 on one arm 410 may be at substantially the same longitudinal position on the arm as a corresponding connector bay 448 on the other arm 410. In this way, connector bays 448 on opposite arms 410 may be said to be paired. The two connector bays 448 in the most-proximal and/or most distal pair may be spaced apart from one another a distance less than the spacing between connector bays 448 in at least one of the remaining pairs, as a result of the offset of the most-proximal and/or most distal connector bays 448. As a result, the connectors 464 deployed by the most-proximal and/or most distal connector bays 448 may be spaced apart from one another by a lesser distance than exists between connectors 464 deployed from the remaining pairs of connector bays 448. Referring also to FIG. 135, this reduced spacing may enhance the seal of the anastomosis at its heel 587 and/or toe 585.

Each connector deployer 452 is moveable between a first position and a second position. In the first position, the outer end 454 of the connector deployer 452 extends at least partially into the passage 440. Alternately, the outer end of the connector deployer 452 does not extend into the passage 440. In the second position, the connector deployer 452 has translated relative to the corresponding connector bay 448 and completed its motion. The outer end 454 of the connector deployer 452 no longer extends into the passage 440. Alternately, the outer end 454 of the connector deployer 452 still extends into the passage 440 in the second position. Each connector deployer 452 translates or otherwise moves from the first position to the second position as a result of contact with the ramp element 446. This translation is described in greater detail below.

Referring also to FIG. 156, optionally, a biasing element 453 may be connected to or associated with at least one connector deployer 452. As one example, the biasing element 453 may be a coil spring. However, the biasing element 453 may be any other type of spring, or any other suitable structure or mechanism. The biasing element 453 may be molded into or otherwise connected to the corresponding connector deployer 452. The biasing element 453 may include a free end oriented substantially toward the anvil arm 14 when the tissue effector 400 is in the closed position. The longitudinal centerline of the biasing element 453 may be substantially parallel to the longitudinal centerline of the corresponding connector deployer 452. Alternately, the biasing element 453 may be oriented differently. A stop 455 is defined near the exit of the connector bay 448, or at any other suitable location along the length of the connector bay 448. The stop 455 is sized and positioned such that the biasing element 453 contacts the stop 455 as the connector deployer 452 is urged toward the anvil arm 14 to deploy the corresponding connector 464. Contact between the biasing element 453 and the stop 455 compresses the biasing element 453 or otherwise stores energy in the biasing element 453. Part of at least one connector deployer 452 may extend out of the corresponding connector 448 after that connector deployer 452 has deployed the corresponding connector 464. After that deployment, the stored energy in the biasing element 453 urges the connector deployer 452 away from the anvil arm 14 and away from the exit opening of the corresponding connector bay 448. In this way, at least part of at least one connector deployer 452 is moved back into the corresponding connector bay 448 and out of the space between the arms 402 after that connector deployer 452 deploys a connector 464. Alternately, more than one biasing element 453 is associated with at least one connector deployer 452. Alternately, in at least one connector bay 448, the biasing element 453 is connected to the connector bay 448, and the stop 455 is positioned on the corresponding connector deployer 452. Alternately, a single biasing element 453 may be connected to both a connector deployer 453 and the corresponding stop 455. Alternately, a biasing element 453 may be connected to the stop 455, and another biasing element 453 may be connected to the corresponding connector deployer 452, such that the two biasing elements 453 engage one another as the connector deployer 452 is urged toward the anvil arm 14.

Figure 67:
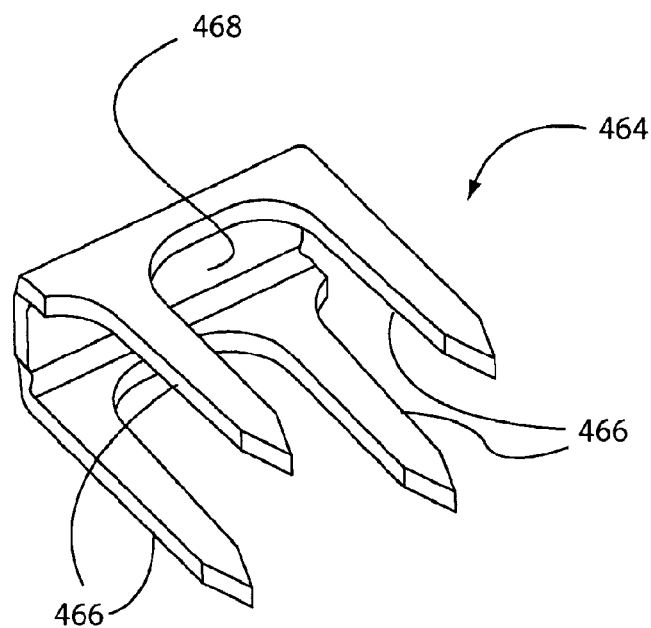
FIG. 67 is a perspective view of a staple configured to be deployed from the tissue effector of FIG. 55.

A connector 464 is placed in at least one connector bay 448. Each connector 464 may be any suitable anastomotic connector. In an exemplary embodiment shown in FIG. 64, the connector 464 is a staple. Each connector 464 is located closer to the inner surface 450 of the arm 402 than the corresponding connector deployer 452. The connector 464 may be configured as disclosed in pending U.S. patent application Ser. No. 10/309,519 filed on Dec. 4, 2002, which is hereby incorporated by reference in its entirety. Referring also to FIG. 67, the connector 464 may include four tines 466 extending from a base 468. The tines 466 may be offset from one another. A different configuration of connector 464 may be used, if desired. For example, at least one connector 464 may be a conventional wire staple. The connectors 464 utilized may be all of the same type, or different types of connectors 464 may be mixed within the staple holder 38. The connector 464 is constructed from 316L stainless steel, but may be constructed from a different type of stainless steel, or from a different material. For example, at least one connector 464 may be constructed from superelastic material, such as nickel-titanium alloy. Such a connector 464 may be self-deformable from an undeployed state to a deployed state. As another example, the connector 464 may be a connector other than a staple, such as a pin or clip. As another example, a single connector 464 may be detachably connected to at least one arm 402. The single connector 464 includes tines 466 spaced apart from one another along a base 468. The base 468 of the single connector 464 is longer than the base 468 of the exemplary connector 464 described above. Advantageously, the base 468 is sized to be substantially as long as the corresponding flap 408, although the base 468 may be longer or shorter if desired. The tines 466 extend from the base 468 at intervals along the base 468. Advantageously, the single connector 464 replaces a plurality of individual connectors 464 that otherwise would be deployed from the arm 402, and the location of the tines 466 along the base 468 substantially matches the locations where the tines 466 of the individual connectors 464 would have been located. Where the single connector 464 is utilized, the connector bays 448 and structures and mechanisms associated with the connectors bays 448 may be omitted. In this way, fabrication and/or operation of the tissue effector 400 may be simplified.

Each connector 464 is oriented in the connector bay 448 such that the tines 466 extend in a direction facing substantially out of the connector bay 448. Alternately, at least one connector 464 is oriented differently. The base 468 of the connector 464 may be in contact with the inner end 456 of the corresponding connector deployer 452 when that connector deployer 452 is in the first position, or may be spaced apart from the inner end 456 of that connector deployer 452 in the first position. When the connector deployer 452 is in the first position, the corresponding connector 464 is held within the connector bay 448 in any appropriate way. Referring also to FIG. 66, as one example, the tines 466 of each connector 464 may be biased against at least part of the corresponding connector bay 448. For example, at least one tine 468 may be biased against a lower surface 470 of the connector bay 448 and at least one other tine 469 may be biased against an upper surface 472 of the connector bay 448. The biasing force exerted by each tine 468 against the corresponding surface 470, 472 of the connector bay 448 holds the connector 464 in place when the connector deployer 452 is in the first position. The biasing forces exerted by the tines 468 are high enough to hold the connector 464 securely within the connector bay 448, and are low enough to allow the connector 464 to translate easily as a result of contact with the corresponding connector deployer 452. As another example, each connector 464 may be held in place in the corresponding connector bay 448 with a biocompatible substance that provides friction between that connector 464 and the connector bay 448, where the amount of force required to overcome that friction and move the connector 464 is selected to be less than the amount of deployment force to be exerted on the connector 464 by the corresponding connector deployer 452. The translation of a connector deployer 452 from the first position to the second position causes deployment of the corresponding connector 464, as described in greater detail below.

The ramp element 446 translates or otherwise moves within the passage 440, as described above. The distal end 474 of the ramp element 446 is configured to engage the outer ends 454 or other parts of the connector deployers 452 as it moves, causing those connector deployers 452 in turn to translate or otherwise move relative to their respective connector bays 448. As one example, the ramp element 446 is curved and/or angled at its distal end 474, where the curvature and/or angularity begins at or near the most distal point of the ramp element 446 and continues proximally along the inner surface 476 of the ramp element 446. That is, the ramp element 446 increases in width from its most distal point to a selected point spaced apart from and proximal to that most distal point. The ramp element 446 may be shaped such that the curvature and/or angularity of the distal end 474 is present on the inner surface 476 of the ramp element 446, and such that the outer surface 478 of the ramp element 446 is substantially flat against a wall of the passage 440. The ramp element 446 may be smoothly curved, along an arc, spline, or any other suitable curve that may have no inflection points or one or more inflection points. However, the ramp element 446 may be shaped in any other appropriate manner. The ramp element 446 may be translated distally along at least a portion of the passage 440. In the course of this translation, the distal end 474 of the ramp element 446 sequentially contacts at least the outer ends 454 of, and thereby actuates, the connector deployers 452, beginning with the most proximal and concluding with the most distal. Alternately, the ramp element 446 translates proximally to contact and actuate sequentially the connector deployers 452, beginning with the most distal and concluding with the most proximal. That is, the sled 482 may translate or otherwise move either distally or proximally to actuate the connector deployers 452. Alternately, the ramp element 446 is configured to move in such a manner that at least a component of its motion is toward the inner surface 450 of the arm 402, such that the ramp element 446 engages more than one connector deployer 452 at a time. Thus, the ramp element 446, another component of the sled 482, or a different component may actuate the connector deployers 452 serially or in parallel.

Optionally, one or more of the connector deployers 452 are omitted from the tissue effector 400, such that the ramp element 446 and/or a different component of the sled 482 directly contacts one or more of the staples 464 to urge that staple or staples 464 out of the corresponding arm 402. That is, the intermediate mechanism between the sled 482 and at least one of the staples 464 may be omitted. If so, the sled 482 and/or at least one connector 464 are configured such that contact between them urges the connector 464 in the desired direction. For example, one or more of the staples 464 may include a structure analogous to the connector deployer 452 formed into it, where that structure is implanted into the patient along with the connector 464. This additional structure is small, and is positioned outside the lumen of both the graft vessel and the target vessel, such that its presence in the patient has no effect. Such a structure may be composed of stainless steel or other biocompatible material, or from bioabsorbable material that is gradually absorbed by the patient. Such biocompatible and bioabsorbable materials are standard in the art.

Optionally, one or more of the connector bays 448 may be omitted from one or more of the arms 402 of the staple holder 38. For example, if the staples 464 are deployed in parallel, the staples 464 may be connected to the sled 482 or other component such as by adhesive, where that connection is able to withstand an amount of force less than the force with which the deployed connector 464 grips the graft vessel 404 and the target vessel 580. As a result, after the staples 464 are deployed into tissue and grip the vessels 404, 580 and the sled 482 or other component is pulled away from the anastomosis, the connection between each connector 464 and the sled 482 or other component is broken, thereby freeing the staples 464 from the staple holder 38.

Cables, Cable Housing, and Shaft

Figure 74:
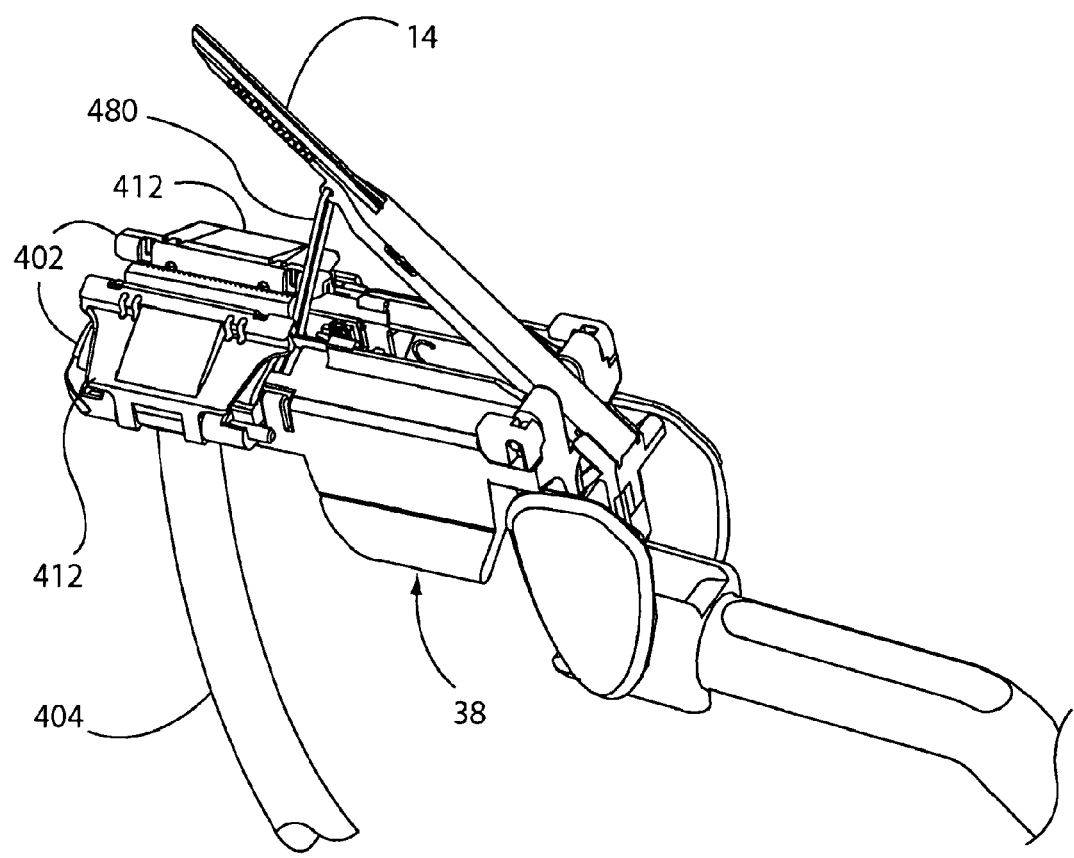
FIG. 74 is a perspective view of the tissue effector of FIG. 55 with a graft vessel loaded onto it.

Referring also to FIGS. 58 and 74, the anvil 10 may be connected to a force transmission mechanism such as a first cable 480. As described above, the anvil 10 may include a cutter stop 236 having one or more attachment features 270 to which the first cable 480 is connected. However, the first cable 480 may be connected to a different or an additional part of the anvil 10.

The sled 482 is connected to a force transmission mechanism such as a second cable 490. As described above, the sled 482 includes an attachment feature 488 to which the second cable 490 is connected. However, the second cable 490 may be connected to a different or an additional part of the sled 482. Alternately, one or both of the cables 480, 490 are not used, and a different force transmission mechanism is used instead. For example, one or both force transmission mechanisms may be a chain, a shaft, one or more gears, one or more tubes for handling pressurized gas or vacuum, conductive elements for carrying electricity, and/or other appropriate mechanisms.

Alternately, the tissue effector 400 may be configured differently, and/or the cables 480, 490 may be attached to the tissue effector 400 differently. As one example, referring to FIG. 154, the first cable 480 extends through part of the anvil 10 and is then connected to the staple holder 38. An axle 1082 may be defined in or connected to the anvil 10. The first cable 480 may be routed along a path that, moving distally, travels along a portion of the anvil 10, then under the axle 1082, then distal to the axle 1082, then upward to the staple holder 38, where that first cable 480 may be connected to the staple holder 38 in any suitable manner. As one example, an end of the first cable 480 is connected to an termination element 1084. The termination element 1084 is wider than an aperture or passage 1086 in the staple holder 38 through which a portion of the first cable 480 enters. The termination element 1084 is on the other side of the aperture or passage 1086 than the anvil 10. Thus, the termination element 1084 prevents the first cable 480 from slipping out of the aperture or passage 1086. Alternately, the end of the first cable 480 may be knotted, forming a knot having a diameter larger than that of the aperture or passage 1086; the termination element 1084 is omitted. Alternately, the first cable 480 may be connected to the staple holder 38 in any other suitable manner. The first cable 480 is routed through the tissue effector 400 in such a way that tension exerted on the first cable 480 causes the tissue effector 400 to move to the closed position. The axle 1082 acts to convert proximal motion of the first cable 480 into force acting downward on the staple holder 38.

The second cable 490 may also, or instead, be configured in the tissue effector 400 in a different manner. As one example, referring to FIG. 154, the second cable 490 may be connected to the sled 482, or a structure or mechanism connected to or associated with the sled 482, in any suitable manner. A termination element 1084 may be utilized in conjunction with an aperture or passage 1088 in the sled 482 or a structure or mechanism connected to or associated with the sled 482. The termination element 1084 may be as described above with regard to the termination element 1084 of the first cable 480. Alternately, the end of the second cable 490 may be knotted, forming a knot having a diameter larger than that of the aperture or passage 1088; the termination element 1084 is omitted. The second cable 490 is routed through the tissue effector 400 in such a way that tension exerted on the second cable 490 causes the sled 482 to move, thereby causing the staple holder 38 to deploy a plurality of connectors 464.

The sled 482, or a structure or mechanism connected to the sled 482, may include a receiver 218 At least part of the receiver 218 may be oriented at least partially toward the anvil 10. Alternately, the receiver 218 is oriented differently. The receiver 218 is configured to engage the engagement member 216 extending from the cutter 200, such that motion of the sled 482 causes the receiver 218 to move the engagement member 216 and thus the cutter 200. The receiver 218 and the engagement member 216 may be shaped, sized and/or configured in any manner that allows them to engage one another upon and/or after actuation of the first cable 480 when the tissue effector 400 is in the closed position. As one example, the engagement member 216 may be a protrusion in an upper portion of the cutter 200, and the receiver 218 may be a protrusion that extends substantially downward, such that when the tissue effector 400 is in the closed position the receiver 218 is aligned with, and extends lower than an upper part of, the engagement member 216, such that proximal motion of the receiver 218 causes the receiver 218 to contact the engagement member 216 and urge it proximally.

Optionally, a cutter slide 1092 may be slidable along at least part of the anvil 10. The cutter slide 1092 may be part of the cutter 200, or connected to the cutter 200. The cutter slide 1092 includes a engagement member 216. As one example, the engagement member 216 may be a step or shoulder in an upper portion of the cutter slide 1092. The cutter slide 1092 may be connected to a cutter pull 1096 in any suitable manner. As one example, a crimp 1098 may be used to crimp the cutter pull 1096 to the cutter slide 1092. However, any other structure, mechanism or method may be used to connect the cutter pull 1096 to the cutter slide 1092. The cutter pull 1096 may be a wire fabricated from stainless steel, nitinol or any other suitable metallic or nonmetallic material. Alternately, the cutter pull 1096 may be a cable or other structure or mechanism. The cutter pull 1096 is also connected to the cutter 200 and/or the projection 208. In this way, motion of the cutter slide 1092 causes the cutter 200 and/or the projection 208 to move, as described in greater detail below.

Referring also to FIGS. 58, 74, the cables 480, 490 extend proximally from the tissue effector 400. Optionally, a cable housing 306 is provided. The cable housing 306 is a tube that is at least partially flexible, through which at least a portion of the cables 480, 490 extend. Two or more lumens or passages may be present in the cable housing 306, such that each cable 480, 490 extends through a different lumen or passage of the cable housing 306. Referring also to FIG. 57, the staple holder 38 may include a collar 492. The collar 492 may be formed into the staple holder 38, or formed separately from and attached to the staple holder 38. The collar 492 includes a passage 494 therethrough. The diameter of the passage 494 may be substantially the same as the outer diameter of the cable housing 306, such that the distal end of the cable housing 306 may be received into and/or through the collar 492 and held therein. Similarly, the shape of the passage 494 may substantially correspond to the shape of the distal end of the cable housing 306. The distal end of the cable housing 306 is fixed to the collar 492 via a friction fit, adhesive, welding, or any other appropriate structure, mechanism or method. The cable housing 306 need not have a uniform shape, size or cross-section along its entire length. Alternately, the distal end of the cable housing 306 may connect to a different portion of the tissue effector 400, or may not connect to the tissue effector 400 at all. Additionally, the cable housing 306 may pass over and/or connect to one or more of the connection members 280 of the tissue effector 400, and/or one or more other components of the tissue effector 400.

One or more channels 496 may be defined on the surface of the staple holder 38 distal to the collar 492. Each channel 496 receives a cable 480, 490. At least one channel 496 may be curved in a convex manner, such that the corresponding cable 480, 490 curves as well. The convex curvature causes the most distal part of that channel 496 to be located between the upper and lower ends of the channel 496. The cable 480, 490 in that channel 496 may be under tension, such that it follows the curvature of that channel 496. Thus, each channel 496 causes the cable 480, 490 received therein to curve back in a proximal direction. For example, the second cable 490 is connected to the sled 482. Tension on the second cable 490 that results from proximal motion of its proximal end also results in distal motion of the sled 482.

Cables, Cable Housing, and Shaft—Shaft Articulation

The shaft 304 may be articulated to allow the tissue effector 400 to be placed in two or more different orientations relative to the handle 302. As one example of articulation, referring also to FIG. 56, the shaft 304 may be bifurcated at its distal end, forming two spaced-apart arms 305. The cable housing 306 passes between the arms 305, such that the arms 305 constrain the potential lateral motion of the cable housing 306. Alternately, the cable housing 306 does not pass between the arms 305. At least one arm 305 forms or connects to a paddle 307 at its distal end. The cable housing 306 extends in a curved configuration, such as an S-shaped or serpentine configuration, between the shaft 304 and the tissue effector 400. The paddle or paddles 307 may be substantially planar and parallel to one another. A receiving opening 309 is provided through at least one paddle 307, each opening corresponding to a cog 282 of the tissue effector 400. One or more detents 310 are present along the perimeter of the receiving opening 309, corresponding to the teeth 284 of the cog 282. The teeth 284 are configured to engage the detents 310 in the receiving opening 309. The button 278 connected to the cog 282 may be connected to the spine 272 with a single connection member 280 spaced apart from the cog 282, or may be connected to the spine 272 with one or more flexible connection members 280. As a result, the buttons 278 can be compressed together, such that the teeth 284 are moved out of engagement with the corresponding detents 310. The cog 282 thus can be moved to a position out of contact with the receiving opening 309, such that it is located between the paddles 307. Consequently, the cog 282 and the tissue effector 400 can be freely rotated to a desired orientation. The buttons 278 are then released, such that the cog 282 re-enters the receiving opening 309 and the teeth 284 engage the detents 310 in the receiving opening 309 once again. Alternately, the cog 282 engages a corresponding gear or other structure or mechanism in or on the shaft 304, such that motion of the corresponding gear rotates the cog 282. Alternately, the cog 282 is connected to the shaft 304 or one or more components in and/or on the shaft 304 in such a way that the cog 282 can be rotated or otherwise manipulated as desired. Alternately, the tissue effector 38 is connected to the shaft 304 with a mechanism or structure other than or in addition to the cog 282.

The cog 282 allows the tissue effector 38 to be oriented at a plurality of positions relative to the shaft 304. That is, the cog 282 allows the tissue effector 38 to move such that the longitudinal centerline of the tissue effector 38 may be positioned at more than one angle relative to the longitudinal centerline of the shaft 304. The cog 282 or other mechanism may allow the tissue effector 38 to move smoothly through a range of orientations relative to the handle 302, or may allow the tissue effector 38 to move among two or more discrete orientations relative to the handle 302. Thus, the tissue effector 38 is orientable to two or more different positions relative to the handle 302. The relative motion between the tissue effector 38 and the shaft 304 allows the tissue effector 38 to be utilized on target vessels having a number of different orientations within the patient, while allowing convenient access by the surgeon or other medical professional. That is, the surgeon may hold the handle 302 in a single convenient position, and orient the tissue effector 38 into a selected position relative to the shaft 304 and handle 302 that is optimal for use with a particular target vessel. Optionally, the arms 305 or a mechanism connected to the arms may be capable of rotation relative to the shaft 304, providing additional freedom of motion for the tissue effector 38. Alternately, the cog 282 is not present, and the arms 305 otherwise allow motion of the tissue effector 38 relative to the shaft 304. Alternately, the tissue effector 400 is fixed relative to the shaft 304.

Referring also to FIGS. 140-141, another example of an articulated shaft 304 is shown. The tissue effector 400 may be connected to the shaft 304 by a hinge 956. A locktab 954 may be connected to the shaft 304 and/or the tissue effector 400 in proximity to the hinge 956. The tissue effector 400 may include an interface member or members 957 connected to the hinge 956. The interface member or members 957 may be rounded in proximity to their connection with the hinge 956, and at least one interface member 957 may include an aperture 955 therethrough to receive the hinge 956. Alternately, the tissue effector 400 is connected to the shaft 304 by any other suitable mechanism that allows the tissue effector 400 to be oriented in two or more discrete positions relative to the shaft 304. For example, a ball joint may be utilized instead of, or in addition to, the hinge 956. The locktab 954 may be connected to the shaft 304 and/or the tissue effector 400 in any suitable manner. As one example, the locktab 954 is itself connected to the shaft 304 by a locktab hinge 958. The locktab hinge 958 may be oriented substantially perpendicular to the hinge 956, or may be oriented differently relative to the hinge 956.

The locktab 954 may be movable from a first position, as shown in FIG. 140, to a second position, as shown in FIGS. 141 and 142. When the locktab 954 is in the first position, the tissue effector 400 is rotatable or otherwise movable relative to the shaft 304, such that the surgeon may place the tissue effector 400 in a desired position relative to the shaft 304. When the locktab 954 is in the second position, the tissue effector 400 is substantially locked in place relative to the shaft 304, such that the tissue effector 400 is maintained substantially in place during the anastomosis procedure. In the first position, the free end of the locktab 954 may be spaced apart from the shaft 304, and in the second position, the free end of the locktab 954 may be in proximity to the shaft 304. Alternately, the locktab 954 may be oriented differently in the first position and/or the second position.

When the locktab 954 is in the second position, it maintains the tissue effector 400 substantially in its selected orientation in any suitable manner. As one example, the locktab 954 may use a cam lock 960 to hold itself in the second position. The cam lock 960 may be configured substantially as the cam lock described above that may be utilized to hold at least one graft clip 412 in the closed position. If so, the cam lock 960 may include a lobe 962 at or near its distal end. The hinge 956 may extend out of the sides of the shaft 304. If so, a first flange 974 extends from the hinge 956 on one side of the shaft 304, and a second flange 976 extends from the hinge 304 on the other side of the shaft 304 and on the side of the locktab 954 facing substantially away from the shaft 304. The hinge 956 extends through the walls of the shaft 304, and through the apertures 955 of the interface member or members 957. A third flange 978 may extend outward from the hinge 956 adjacent to at least one of the interface members 957, where that at least one interface member 957 is between the third flange 978 and the locktab 954. The locktab hinge 958 may extend through or into part of the hinge 956.

As the cam lock 960 rotates about the locktab hinge 958 from the first position to the second position, an increasingly greater cross-section of the lobe 962 moves between the second flange 976 and the outer wall of the shaft 304. As a result, the second flange 976 is pulled away from the outer wall of the shaft 304. At the same time, the third flange 978 pulls the interface member or members 957 into contact with the inner surface of the shaft 304 or other part of the shaft 304. After the cam lock 960 has moved to the second position, the third flange 978 exerts enough force on the interface member or members 957 such that at least one interface member 957 is substantially friction-fit against the shaft 304. As a result, the tissue effector 400 is substantially restrained in a desired position relative to the shaft 304.

Alternately, where a different mechanism than a hinge 956 is used for articulation, then the cam lock 960 may exert a force on that mechanism to hold it in place relative to the shaft 304 when the locktab 954 is in the second position. Alternately, any other suitable structure, mechanism and/or method may be utilized to hold the locktab 954 in the second position.

Referring also to FIG. 55, the shaft 304 may be substantially hollow along at least part of its length, starting at its proximal end and continuing distally. The entire shaft 304 may be substantially hollow. An aperture 498 or other opening is located in the wall of the shaft 304 at a point along its length where it is hollow. Thus, the aperture 498 provides access to the lumen of the shaft 304. The cable housing 306 extends through the aperture 498 into the lumen of the shaft 304. Alternately, the cable housing 306 does not enter the lumen of the shaft 304, and instead is attached to the outer surface of the shaft 304 with adhesive, clips, pins, and/or any other appropriate attachment mechanisms, structures or methods. If so, the shaft 304 need not include a lumen. Alternately, the cable housing 306 does not connect to the shaft 304 at all, and instead connects to the handle 302 directly. If so, the shaft 304 need not include a lumen, and may be solid.

Handle

Figure 70:
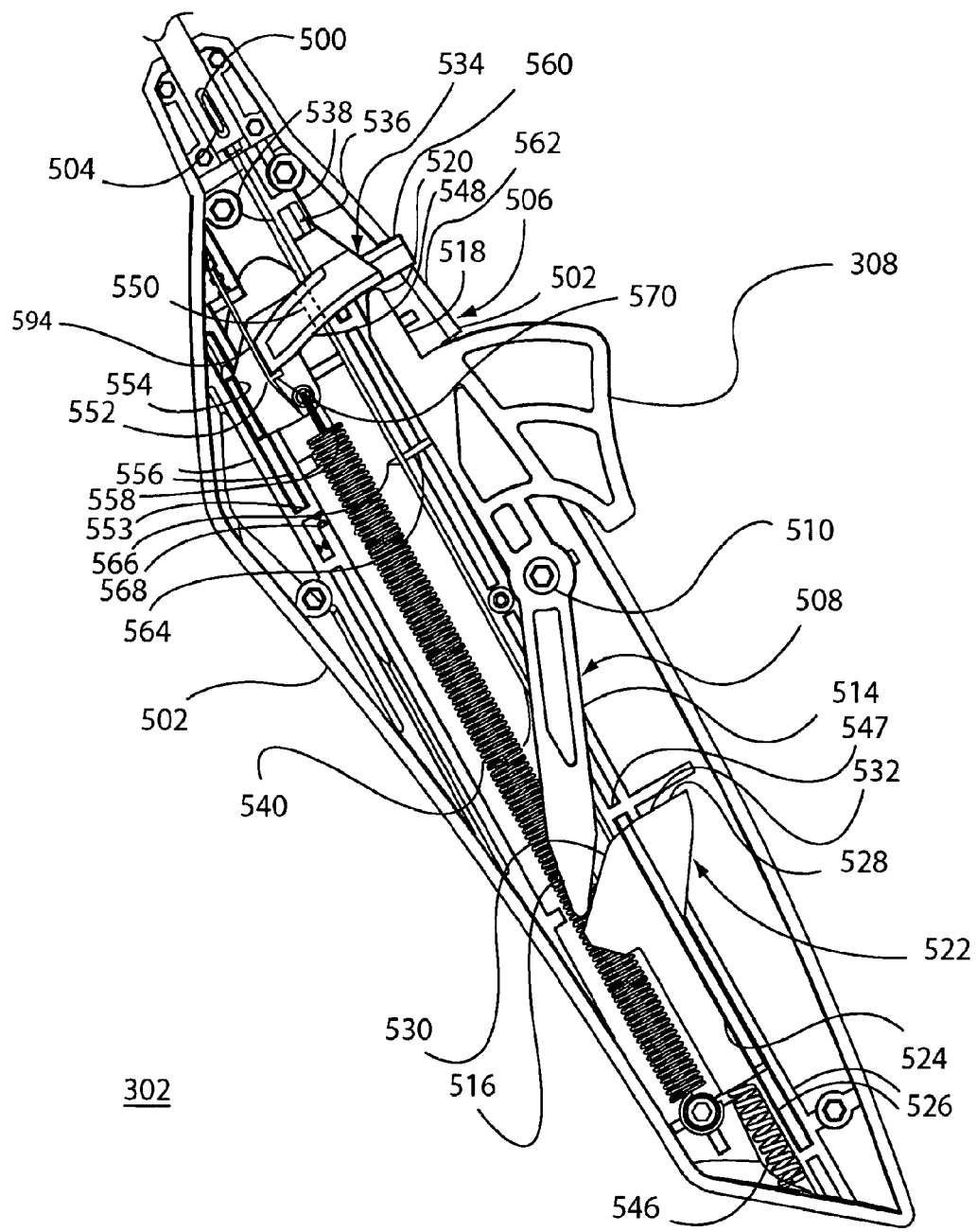
FIG. 70 is a side cross-section view of the handle of FIG. 55 in a first position.

The proximal end of the shaft 304 is connected to the handle 302. The handle 302 may be configured in any suitable manner. As one example, the handle 302 may include two or more individual handle shell members 502 that are connected to one another. Alternately, the handle 302 may be constructed differently. The shaft 304 may be fixed to the handle 302 such that it does not substantially move relative to the handle 302. Referring also to FIG. 70, as one example, a member 500 extends from one handle shell member 502 into the hollow interior of the handle 302. That member 500 may connect at its other end to the other handle shell member 502. The proximal end of the shaft 304 includes a corresponding aperture 504, such that the member 500 fits within the aperture 504. The aperture 504 is substantially the same size as the cross-section of the member 500. When the shell members 502 are assembled, the member 500 engages the aperture 504 of the shaft 304 and holds the shaft 304 in place. Alternately, a member 500 extends from each handle shell member 502, and those members 500 both engage the aperture 504 of the shaft 304. As another example, ribs (not shown) may be defined in the inner surface of the handle, and a corresponding retainer (not shown) is defined at or near the proximal end of the shaft. The retainer is wider than the shaft 304, and has a selected thickness. The ribs are spaced apart from one another substantially the same distance as the thickness of the retainer. The ribs thus substantially prevent the shaft 304 from translating proximally or distally. The handle 302 may engage the retainer with a registration feature or other structure or mechanism to substantially prevent rotation of the shaft 304 about its longitudinal axis. Alternately, the handle 302 holds the shaft 304 in a different way.

The handle 302 has a substantially hollow interior. Where the shaft 304 includes a lumen, the lumen of the shaft 304 opens into the interior of the handle 302. The cables 480, 490 extend out of the lumen of the shaft 304 into the hollow interior of the handle 302. Alternately, the cables 480, 490 extend through the cable housing 306 directly into the handle 302, bypassing the shaft 304.

Figure 78:
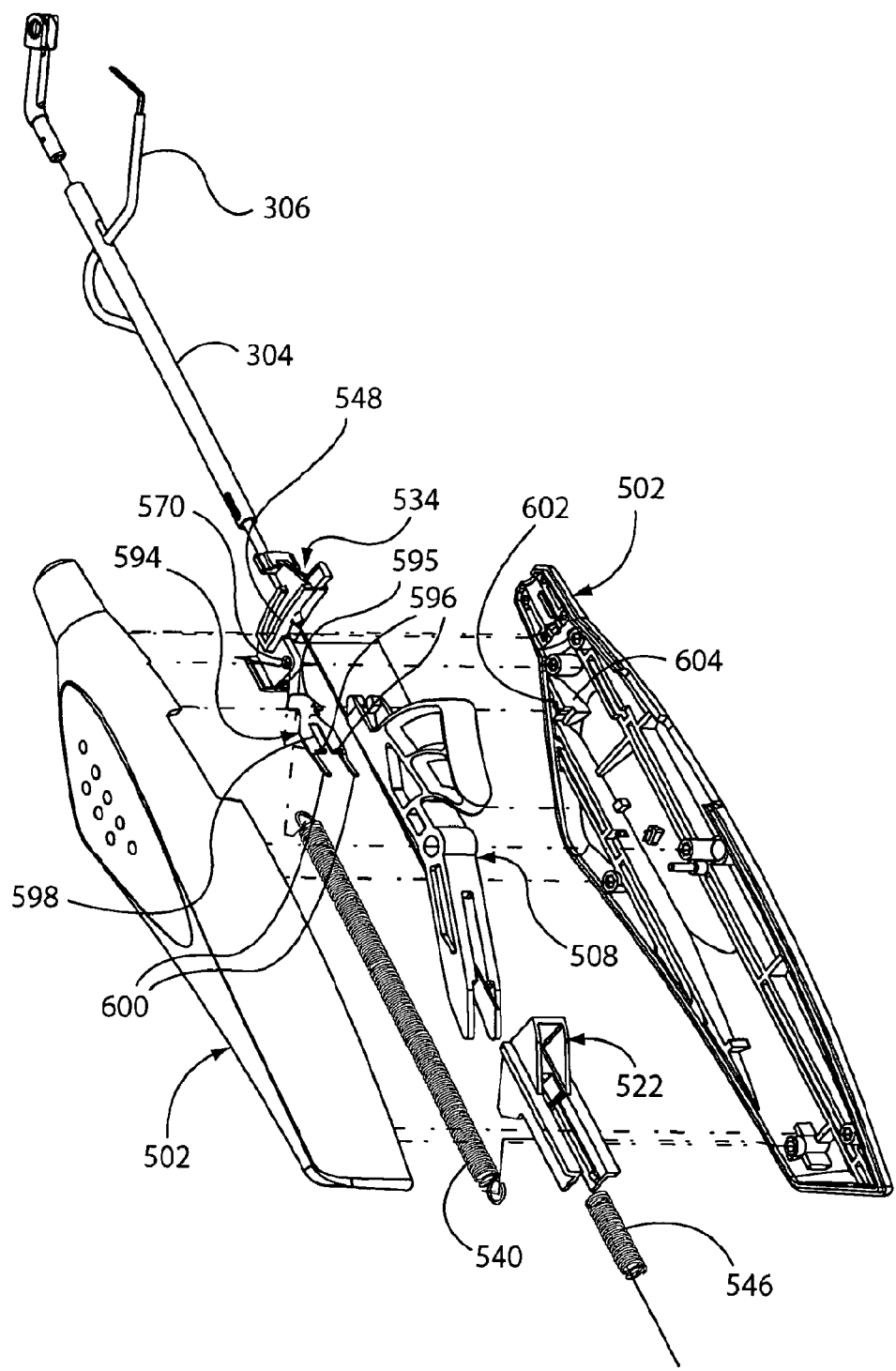
FIG. 78 is an exploded view of the handle of the anastomosis tool. The use of the same reference symbols in different figures indicates similar or identical items.

One or more mechanisms within the handle 302 are utilized to actuate the tissue effector 38 via the cables 480, 490. Alternately, at least some of those mechanisms are separate from the handle 302. Referring to FIGS. 70 and 78, one example of such mechanisms is shown. A single input to the anastomosis tool 300 via the trigger 308 actuates the anastomosis tool 300. Alternately, one or more additional inputs to the anastomosis tool 300 are required, such as actuation of a safety switch or depression of a second feature. The trigger 308 initially extends outward from the upper surface of the handle 302 through an aperture 506 in the handle 302. Alternately, the trigger 308 initially extends from a different surface of the handle 302. Alternately, the trigger 308 is initially flush with the surface of the handle 302, or otherwise configured. The handle 302 may be shaped ergonomically for ease of operation. For example, as shown in FIGS. 70 and 78, the handle 302 is curved and tapered slightly toward its proximal end, and substantially bilaterally symmetrical, such that the proximal end of the handle 302 can be gripped easily with either the left or the right hand. Alternately, the handle 302 may be ergonomically configured in a different way for ease of actuation by the user. The trigger 308 is positioned on the handle 302 such that it can be actuated conveniently by a user's thumb. Alternately, the trigger 308 could be placed on the underside of the handle 302 for actuation with the index finger of either hand. More than one finger may be used to actuate the trigger 308 and/or other mechanisms for actuating the anastomosis tool 300.

The trigger 308 is connected to a rocker 508. The trigger 308 may be formed into the rocker 508, or otherwise connected to it. The rocker 508 is located inside the handle 302. Alternately, the rocker 508 is located at least partly outside the handle 302. The rocker 508 is rotatably mounted to a rocker axle 510. The rocker axle 510 extends from one interior surface of the handle 302, and may extend to a different interior surface of the handle 302 to provide additional stiffness and/or stability to the rocker axle 510. Alternately, the rocker axle 510 may connect to the handle 302 in a different way.

The rocker 508 includes a proximal arm 514 extending proximally to the rocker axle 510. The proximal arm 514 may be formed into the rocker 508, or otherwise connected to it.

Figure 71:
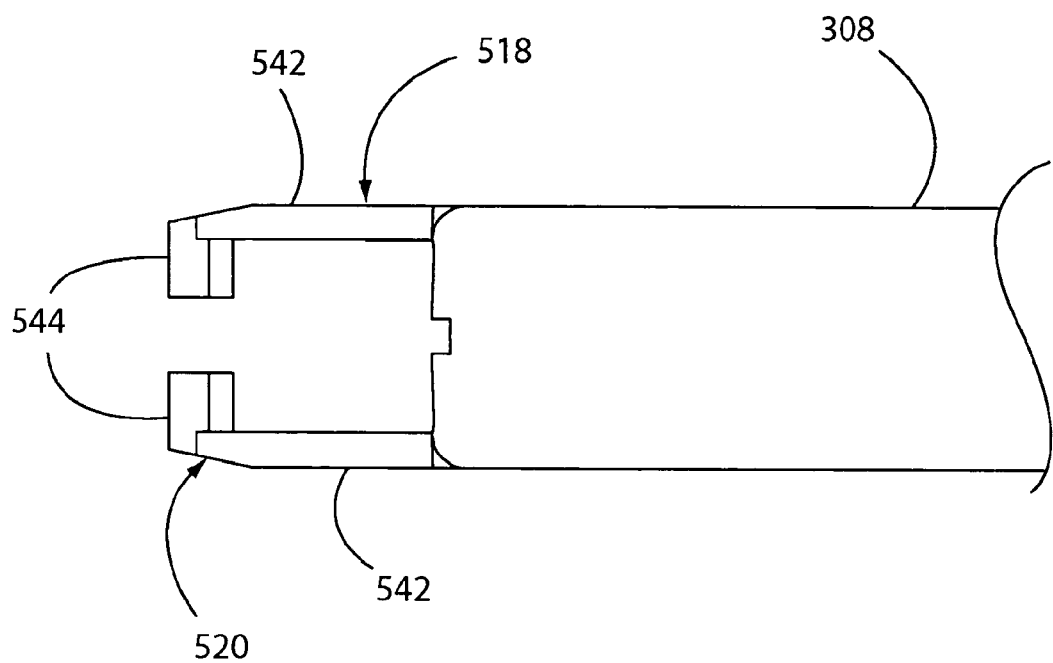
FIG. 71 is a top view of a portion of a rocker utilized in the handle of FIG. 55.

The proximal end 516 of the proximal arm 514 may be tapered to a curved or rounded surface. Alternately, the proximal end 516 of the proximal arm 514 is shaped differently. Alternately, the entire proximal arm 514 is tapered. The rocker axle 510 is located proximal to the trigger 308. As a result, depression of the trigger 308 causes rotation of the rocker 508 such that the proximal end 516 of the proximal arm 514 moves upward. Alternately, the trigger 308 and the rocker axle 510 are positioned differently relative to one another. The rocker 508 also includes a distal arm 518 extending distal to the trigger 308, where the distal arm 518 has a distal end 520. The distal arm 518 may be formed into the rocker 508, or otherwise connected to it. Referring also to FIG. 71, at least a portion of the distal arm 518 may be bifurcated into two or more spaced-apart members 542. A post 544 may be located at the distal end of each member 542. At least one post 544 substantially may take the shape of a cylindrical or rectangular solid. Each post 544 is angled relative to the corresponding member 542, protruding at least partly inward. This angle may be substantially ninety degrees, or any other angle. Alternately, at least one post 544 extends outward from the corresponding member. The posts 544 are spaced apart from one another by a distance that is less than the distance separating the spaced-apart members 542. Alternately, at least one post 544 is located at a position on the corresponding member 542 other than its distal end. As one example, at least one post 544 may be positioned a short distance proximal to the distal end of the corresponding member 542.

Because the rocker axle 510 is located proximal to the trigger 308, depression of the trigger 308 causes the distal end 520 of the distal arm 518 to move downward. Alternately, the arms 514, 518 of the rocker 508 are configured to move in another manner when the trigger 308 is depressed. Alternately, the rocker 508 may be shaped or configured differently than described above.

A proximal slider 522 is also included within the handle 302. The proximal slider 522 includes at least one flange 524 extending laterally from at least one side thereof. Advantageously, a flange 524 extends from each side of the proximal slider 522 for stability. Additional flanges 524 may be provided, if desired. Ribs 526 are molded, formed, connected or otherwise attached to the inner surface of the handle 302. Two ribs 526 are spaced apart from one another a distance substantially equal to the thickness of the corresponding flange 524, such that each flange 524 is configured to slide therebetween. Each pair of ribs 526 substantially constrains the motion of the corresponding flange 524. Where the ribs 526 are substantially linear, and ribs 526 and corresponding flanges 524 are utilized on opposite sides of the proximal slider 522, the ribs 526 substantially linearly constrain the motion of the corresponding flange 524. A spring 546 is connected at one end to the handle 302, and is connected to or engages the proximal slider 522. The spring 546 is in compression, and thereby biases the proximal slider 522 distally. A stop 547 may be connected to or defined in the inner surface of one or more of the handle shell members 502, where the stop or stops 547 are located distal to the proximal slider 522. The stop or stops 547 act to restrain the distal motion of the proximal slider 522, thereby defining a position that is the most distal the proximal slider 522 can travel. Alternately, a different or additional mechanism, structure or method may be used to bias the proximal slider 522 distally. Alternately, the spring 546 is initially neither in tension nor compression, but is compressed by the rocker 508 during at least a portion of its travel.

The spring 546 stores energy within itself when it is in tension. Alternately, an energy storage device could be used in lieu of the spring 546. As one example, the energy storage device is a reservoir or cylinder of pressurized gas. Valves, tubing and/or other structure may be used to route the pressurized gas to desired locations in the handle 302 such that the energy stored in the gas is used to bias the proximal slider 522 distally, and/or to perform other actuation functions within the handle 302 and/or the tool 300. The gas may be carbon dioxide, nitrogen, a different gas, air, or a combination of gases. As another example, a cylinder or source of vacuum may be used as an energy storage device. Valves, tubing and/or other structure may be used to route the vacuum to desired locations in the handle 302 such that the vacuum can be used to bias the proximal slider 522 distally, and/or to perform other actuation functions within the handle 302 and/or the tool 300. That is, compressed gas may be used for controlling the operation of the tool 300 instead of or in addition to providing energy storage. As another example, a battery may be used as an energy storage device. Wiring and actuators such as solenoids or motors may be provided within the handle 302 such that the stored electrical energy in the battery is used to bias or hold the proximal slider 522 distally, and/or to perform other actuation functions within the handle 302 and/or the tool 300. That is, electromagnetic energy may be used for controlling the operation of the tool 300 instead of or in addition to providing energy storage. Where such an alternate energy storage device is provided, the trigger 308 may be configured differently, such that actuation of the anastomosis tool 300 may be performed simply by contacting the trigger 308 with a finger, or moving the trigger 308 through a more limited range of motion. Alternately, the trigger 308 may be omitted altogether, and the anastomosis tool 300 may be actuated remotely by a computer, dedicated control station, handheld computing device, or other device.

A contact feature 528 is defined on the distal surface of the proximal slider 522. Alternately, the contact feature 528 is a separate element connected to the proximal slider 522. The contact feature 528 is configured to engage the proximal end 516 of the proximal arm 514 at or after the time the trigger 308 is depressed, as described in greater detail below. The contact feature 528 is angled proximally and downward along a lower portion 530 thereof, and is substantially vertical along an upper portion 532 thereof. Alternately, the contact feature 528 is shaped and/or angled differently.

The first cable or cables 480 are connected to the proximal slider 522 in any appropriate way. As an example, at least one aperture or port (not shown) may be formed in the proximal slider 522, and at least one cable 480 is inserted into at least one aperture and secured thereto. As other examples, an end of the cable or cables 480 may be wound around all of or a portion of, crimped to, welded to, or secured by adhesive to the proximal slider 522. The proximal arm 514 of the rocker 508 may be bifurcated to allow the first cable or cables 480 to extend substantially along the longitudinal centerline of the handle 302 and between the bifurcations substantially without interference. Similarly, the lower portion 530 of the contact feature 528 may be bifurcated as well. Where both the proximal arm 514 and the contact feature 528 are bifurcated, the two are aligned such that they contact one another during at least a portion of the travel of the rocker 508.

A distal slider 534 is also included within the handle 302. The distal slider 534 includes a flange 536 extending outward from at least one side thereof. Advantageously, a flange 536 extends from each side of the distal slider 534 for stability. Additional flanges 536 may be provided, if desired. Ribs 538 are molded, formed, connected or otherwise attached to the inner surface of the handle 302. Two ribs 538 are spaced apart from one another a distance substantially equal to the thickness of the corresponding flange 536, such that each flange 536 is configured to slide therebetween. Each pair of ribs 538 substantially constrains the motion of the corresponding flange 536. Where the ribs 538 are substantially linear, and ribs 538 and corresponding flanges 536 are utilized on opposite sides of the distal slider 534, the ribs 538 substantially linearly constrain the motion of the corresponding flange 524.

A contact surface 548 is defined on at least a portion of the proximal surface of the distal slider 534. The contact surface 548 may be curved or angled. As one example, the contact surface 548 has a concave curvature. Other shapes or configurations of the contact surface 548 may be utilized. Alternately, the contact surface 548 is located on a portion of the distal slider 534 other than its proximal surface. The distal slider 534 may include a passage 550 through it to allow the cables 480, 490 to pass therethrough. Alternately, the passage 550 is not provided in the distal slider 534, and the distal slider 534 is bifurcated or otherwise shaped to allow the cables 480, 490 to pass through it. Alternately, the cables 480, 490 are routed through the handle in such a way as to bypass the distal slider 534 altogether.

The distal slider 534 may include a lower guide 552. The lower guide 552 extends downward from the remainder of the distal slider 534, and may extend proximal to the contact surface 548. Further, the lower guide 552 may be thinner than the remainder of the distal slider 534. Alternately, the lower guide 552 is not included in the distal slider 534, or may be configured differently relative to the remainder of the distal slider 534. Optionally, the lower guide 552 may include a flange 554 extending outward from at least one side thereof. Advantageously, a flange 554 extends from each side of the lower guide 552 for stability. Additional flanges 554 may be provided, if desired. These flanges 554 provide additional stability to the distal slider 534. Ribs 556 are molded, formed, connected or otherwise attached to the inner surface of the handle 302. Two ribs 556 are spaced apart from one another a distance substantially equal to the thickness of the corresponding flange 554, such that each flange 554 is configured to slide therebetween. Each pair of ribs 556 substantially constrains the motion of the corresponding flange 554. Where the ribs 556 are substantially linear, and ribs 556 and corresponding flanges 554 are utilized on opposite sides of the distal slider 534, the ribs 556 substantially linearly constrain the motion of the corresponding flange 554.

A spring 540 is connected at one end to the distal slider 534 and at the other end to the handle 302. An aperture 558 may be provided in the lower guide 552, or in another part of the distal slider 534. One end of the spring 540 includes a hook or similar structure, which is received into and held by the aperture 558. Alternately, the spring 540 is connected to the distal slider 534 in a different way. The spring 540 is in tension, and thereby biases the distal slider 534 proximally. Alternately, a different or additional mechanism, structure or method may be used to bias the distal slider 534 proximally. The spring 540 stores energy within itself when it is in tension. Alternately, an energy storage device such as a reservoir or container of pressurized gas, a battery, or other energy storage device such as described above with regard to the spring 546 could be used in lieu of the spring 540.

Referring also to FIG. 78, a holder 594 is connected to the inner surface of the handle 302. This connection may be accomplished in any appropriate manner. As one example, a slot 602 may be defined in a member 604 or between two separate members 604 extending inward from the inner surface of each shell member 502, wherein a portion of the holder 594 is held by the slot 602 such as by a pressure fit. The distal end 595 of the holder 594 is held by the slot 602 such that it does not substantially move. Alternately, a different part of the holder 594 is held by the slot 602, and/or the distal end 595 of the holder 594 is free to move. Moving proximally from the distal end 595 of the holder 594, the holder 594 is bifurcated by an opening 598 that extends substantially longitudinally. Two spaced-apart members 600 extend substantially proximally, each member 600 on an opposite side of the opening 598. At least the members 600 of the holder 594 have some flexibility, such that the members 600 can move up or down in response to force applied to them. However, the members 600 are stiff enough to remain in a neutral position until that force is applied.

A stop 596 extends upward from each member 600. The stops 596 are positioned and shaped to engage the bottom edge 570 of the contact surface 548 of the distal slider 534. The holder 594 is substantially restrained against longitudinal motion by its engagement with the slots 602 in the shell members 502 ad/or members 604 defined in or on the shell members 502. Thus, by engaging the bottom edge 570 of the contact surface 548 of the distal slider 534, the stops 596 substantially restrain the distal slider 534 against proximal motion under the influence of the spring 540. The stops 596 are stiff enough, and extend upward enough, to provide this restraint. For example, the stops 596 may be curved to match the curvature of the contact surface 548, such that they contact a portion of the contact surface. Alternately, contact between the distal slider 534 and the rocker 508 prevents the distal slider 534 from substantially moving proximally. This contact occurs between the contact surface 548 of the distal slider 534 and the distal tip 520 of the distal arm 518 of the rocker 508. Alternately, this contact occurs between other or additional components of the distal slider 534 and/or the rocker 508.

The second cable 490 is connected to the distal slider 534 in any appropriate way. As an example, at least one aperture or port (not shown) may be formed in the distal slider 534, and at least one cable 480 is inserted into at least one aperture and secured thereto. As other examples, an end of the cable or cables 480 may be wound around all of or a portion of, crimped to, welded to, or secured by adhesive to the distal slider 534. The second cable 490 may have an amount of slack in it when the distal slider 534 is in the first, predeployment position shown in FIG. 70. The amount of slack, if any, is related to the distance traveled by the distal slider 534 during actuation, as described in greater detail below.

Optionally, the distal slider 534 includes a verification stub 560. The verification stub 560 extends substantially upward from the upper end of the distal slider 534. Alternately, the verification stub 560 extends from a different portion of the distal slider 534, or in a different direction. The verification stub 560 may extend into or through a slot 562 through the handle 302. Because it is connected to the distal slider 534, the verification stub 560 moves along the slot 562 in the handle 302 when the distal slider 534 moves during operation, as described below. As a result, the position of the verification stub 560 may be used to confirm visually whether a particular anastomosis tool 300 has been actuated or not. That is, the verification stub 560 may be located in a first position before the anastomosis tool 300 is actuated, and in a second position after the anastomosis tool 300 is actuated, such that the user can determine whether the anastomosis tool 300 has been actuated by viewing the position of the verification stub 560.

Optionally, the rocker 508 includes a ratchet 564 extending substantially downward from a location distal to the rocker axle 510. Alternately, the ratchet 564 extends in a different direction. The ratchet 564 includes a member 566 at its lower end extending substantially transverse to the remainder of the ratchet 564. Alternately, the member 566 extends in a different direction. Alternately, the member 566 is a notch or other element defined in the ratchet 564. The ratchet 564 moves in conjunction with the rocker 508. Thus, when the trigger 308 is depressed and the distal end of the rocker 508 moves downward, the ratchet 564 moves downward as well. A pawl feature 568 is configured to engage the member 566 of the ratchet 564 after the ratchet 564 has moved downward a particular distance, allowing the ratchet 564 to continue to move downward after engagement, but preventing the ratchet 564 from moving back upward past the pawl feature 568 after engagement.

Fluid-Driven Actuator

Alternately, the rocker 508, sliders 522, 534, and/or other mechanisms in the handle 302 are not used, and a different mechanism or mechanisms are used to actuate the tissue effector 400 and complete the anastomosis. For example, a fluid-driven actuator may be used, where a container of gas within the handle 302 or a connection to a tank, reservoir or other storage device outside the handle 302 provides gas under pressure to a switching assembly or other mechanism. The switching assembly utilizes and/or directs the pressure of the gas to successively actuate the components of the tissue effector 400. Vacuum or liquid may be used instead of gas, if desired. As another example, the handle 302 may include an electromechanical assembly under analog or digital control, such that actuation of the trigger 308 or other component causes actuation of the tissue effector.

The fluid-driven actuator may be any mechanism that is configured to operate the tissue effector 400. Such operation may include moving the tissue effector 400 from the open to the closed position, moving the tissue effector 400 from the closed to the open position, and/or deploying connectors from the tissue effector 400.

Fluid-Driven Actuator—Control Member

Referring to FIGS. 148-149, a handle 302 of the anastomosis tool 300 may include an exemplary fluid-driven actuator 1000. The fluid-driven actuator 1000 includes a control member 1002 movable within a first chamber 1004. Referring also to FIG. 152, the control member 1002 is operationally connected to the trigger 308, as described in greater detail below. The control member 1002 may be generally rod-shaped, and the first chamber 1004 may be generally cylindrical. Alternately, the control member 1002 and/or the first chamber 1004 may be shaped differently. At least one sealing element 1006 extends from the control member 1002. Each sealing element 1006 may be an O-ring or any other suitable structure or mechanism that substantially seals against the control member 1002 and the wall of the first chamber 1004. Each sealing element 1006 may be connected to the control member 1002 in any suitable manner. As one example, where the sealing element 1006 is an O-ring, the sealing element 1006 may be friction-fit or pressure-fit to the control member 1002. As another example, the diameter and/or cross-section of the control member 1002 may be reduced at the interface of the control member 1002 and at least one sealing element 1006, forming an indentation into which the sealing element 1006 may be seated securely.

At least one rib 1008 may extend from the control member 1002 adjacent to at least one sealing element 1006. Each rib 1008 may be integral with, or may be a separate element fixed to, the control member 1002. Advantageously, one rib 1008 extends from the control member 1002 on either side of at least one sealing element 1006. Thus, the two ribs 1008 substantially trap the corresponding sealing element 1006 therebetween, substantially restraining the sealing element 1006 from sliding or otherwise moving relative to the control member 1002 during motion of the control member 1002. At least one outer edge 1007 of at least one rib 1008 may be beveled, curved or similarly shaped. Advantageously, the ribs 1008 do not extend far enough from the sealing element 1006 to contact the wall of the first chamber 1004. Thus, a substantially ring-shaped passage exists between each rib 1008 and the wall of the first chamber 1004, allowing gas to travel through that passage as described in greater detail below. Alternately, at least part of at least one rib 1008 may contact the wall of the first chamber 1004. If so, the part of each rib 1008 that contacts the wall of the first chamber 1004, and/or the wall of the first chamber 1004, advantageously may be coated with polytetrafluoroethylene or other lubricious coating or substance to facilitate motion of each rib 1008 that contacts the wall of the first chamber 1004.

A biasing element 1009 such as a spring is connected to the control member 1002, to the wall of the first chamber 1004, and/or to the body of the handle 302. The biasing element 1009 biases the control member 1002 to a first position within the first chamber 1004, as shown in FIG. 149. The distal end of the control member 1002 may extend out of the distal end of the first chamber 1004 when the control member 1002 is in the first position. The part of the control member 1002 that extends out of an end of the first chamber 1004 advantageously remains within the body of the handle 302.

One or more tabs 1014 may extend outward from the control member 1002 at a location on the control member 1002 outside the first chamber 1004. At least one tab 1014 may have two opposed ends, one of which is connected to the control member 1002, and the other of which is free. The free end of each tab 1014 may be oriented at least partially in the proximal direction. The tabs 1014 extend from the control member 1002 a sufficient distance such that they do not enter the first chamber 1004 when movement of the control member 1002 moves the tabs 1014 toward the first chamber 1004. Instead, the tabs 1014 contact a surface 1016 of a body 1018 in which the first chamber 1004 is defined, thereby stopping motion of the control member 1002. In this way, the control member 1002 may be moved from a first position to a second position. At least one of the first position and the second position of the control member 1002 may be defined within a range of locations in the first chamber 1004. The free ends of the tabs 1014 include ramp surfaces 1015 that engage the end of the first chamber 1004. Upon application of greater force to the control member 1002, the ramp surfaces 1015 of the tabs 1014 are pressed inward toward the longitudinal axis of the control member 1002 as a result of contact between the ramp surfaces 1015 and the end of the first chamber 1004. After the tabs 1014 have moved inward a sufficient amount, the control member 1002 is free to move along the first chamber 1004 until its end opposite the tabs 1014 contacts the corresponding end of the first chamber 1004. This contact stops the motion of the control member 1002 at a defined third position. Alternately, the tabs 1014 are not movable into the first chamber 1004.

Referring also to FIGS. 148 and 152, a slot 1017 may be defined in the end of the control member 1002 that extends out of the first chamber 1004. The slot 1017 is configured to receive a transverse member 1032 connected to the trigger 308. The transverse member 1032 may be oriented substantially perpendicular to the longitudinal axis of the control member 1002. Alternately, the transverse member 1032 is oriented differently relative to the longitudinal axis of the control member 1002. The trigger 308 also may include one or more projections 1034 each configured to engage a corresponding depression or other receiver (not shown) in the inner surface of a casing 1071 of the handle 302 or a structure or mechanism associated with the handle 302. The trigger 308 thus rotates about the axis defined by the one or more projections 1034. The transverse member 1032 is positioned between the surface of the trigger 308 depressed by the surgeon and the axis of rotation defined by the one or more projections 1034. As a result, rotation of the trigger 308 about its axis of rotation causes the transverse member 1032 to travel in an arc. As shown in FIG. 152, that arc may be directed proximally. Motion of the transverse member 1032 in an arc in the proximal direction pushes the control member 1002 proximally, as a result of contact between the transverse member 1032 and the slot 1017 in the control member 1002. Alternately, the trigger 308 and/or the control member 1002 are configured in a different manner that converts the actuation of the trigger 308 to motion of the control member 1002.

Fluid-Driven Actuator—Clamping Member

Referring also to FIG. 149, the exemplary fluid-driven actuator 1000 also includes a clamping member 1010 movable within a second chamber 1012. Referring also to FIG. 148, the distal end of the clamping member 1010 is connected to the first cable 480 in any suitable manner. As one example, the distal end of the clamping member 1010 extends out of the distal end of the second chamber 1012, and includes a hook 1020 defined therein or connected thereto. A segment of the first cable 480 near the proximal end thereof is placed into the hook 1020, and may be wound repeatedly about the hook 1020 if desired. The proximal end of the first cable 480 is oriented distally, and is substantially parallel to a remaining segment of the first cable 480. A crimp 1022 compresses the proximal end of the first cable 480 against a remaining segment of the first cable 480, securing the proximal end of the first cable 480 to a remainder of itself, and thereby securing the first cable 480 to the hook 1020. Alternately, the first cable 480 may be connected to the clamping member 1010 by a ferrule, by tying, adhesive, winding, or in any other suitable manner.

The clamping member 1010 may be generally rod-shaped, and the second chamber 1012 may be generally cylindrical. The second chamber 1012 may have a first diameter at a distal part thereof, and a second, larger diameter at a proximal part thereof. Alternately, the clamping member 1010 and/or the second chamber 1012 may be shaped differently. At least one sealing element 1006 extends from the clamping member 1010. The sealing element or elements 1006, and their attachment to the clamping member 1010, may be as described above with regard to the control member 1002. At least one rib 1008 may extend from the clamping member 1010 adjacent to at least one sealing element 1006, as described above with regard to the control member 1002. At least one rib 1008 may be located in the wider portion of the second chamber 1012. When the clamping member 1010 is in a first position, as shown in FIG. 149, that rib 1008 may be positioned at the distal end of the wider portion of the second chamber 1012, against a ledge 1024 defined in the second chamber 1012 by the reduction in diameter of the second chamber 1012 in the distal direction. Contact between that rib 1008 and the ledge 1024 restrains the clamping member 1010 from motion distal to its first position. The clamping member 1010 may be biased to the first position by tension in the first cable 480, which acts to pull the clamping member 1010 distally such that the rib 1008 in the wider portion of the second chamber 1012 is brought into contact with the ledge 1024.

Fluid-Driven Actuator—Firing Member

The fluid-driven actuator 1000 also includes a firing member 1026 movable within a third chamber 1028. Referring also to FIG. 148, the distal end of the firing member 1026 is connected to the second cable 490 in any suitable manner. As one example, the distal end of the firing member 1026 extends out of the distal end of the third chamber 1028, and includes a hook 1020 defined therein or connected thereto. The second cable 490 may be connected to the hook 1020 of the firing member 1026 in substantially the same manner as described above with regard to the connection of the first cable 480 to the hook 1020 of the clamping member 1010. Alternately, the second cable 490 may be connected to the firing member 1026 in any suitable member, whether or not the firing member 1026 includes a hook 1020. The second cable 490 is also connected to the sled 482, directly or indirectly.

The firing member 1026 may be generally rod-shaped, and the third chamber 1028 may be generally cylindrical. The third chamber 1028 may have a first diameter at a distal part thereof, and a second, larger diameter at a proximal part thereof. Alternately, the firing member 1026 and/or the third chamber 1028 may be shaped differently. At least one sealing element 1006 extends from the firing member 1026. The sealing element or elements 1006, and their attachment to the firing member 1026, may be as described above with regard to the control member 1002. At least one rib 1008 may extend from the firing member 1026 adjacent to at least one sealing element 1006, as described above with regard to the control member 1002. At least one rib 1008 may be located in the wider portion of the third chamber 1028. When the firing member 1026 is in a first position, as shown in FIG. 149, that rib 1008 may be positioned at the distal end of the wider portion of the third chamber 1028, against a ledge 1030 defined in the third chamber 1028 by the reduction in diameter of the third chamber 1028 in the distal direction. Contact between that rib 1008 and the ledge 1030 restrains the firing member 1026 from motion distal to its first position. The firing member 1026 may be biased to the first position by tension in the second cable 490, which acts to pull the firing member 1026 distally such that the rib 1008 in the wider portion of the third chamber 1028 is brought into contact with the ledge 1030.

Fluid-Driven Actuator—Passages

A gas inlet 1036 opens into the first chamber 1004. A gas inlet orifice 1038 exists at the intersection of the gas inlet 1036 and the first chamber 1004. The gas inlet 1036 may receive pressurized gas from, for example, the cylinder 1046 shown in FIG. 153. A gas outlet 1040 also opens into the first chamber 1004. A gas outlet orifice 1042 exists at the intersection of the gas outlet 1040 and the first chamber 1004. The gas outlet 1040 may vent gas out of the body 1018 and/or the handle 302.

A plurality of passages interconnect each chamber 1004, 1012, 1028 to at least one other chamber 1004, 1012, 1028. The passages may be substantially round in cross-section, or may be shaped in any other suitable manner. An orifice exists at each connection between a chamber 1004, 1012, 1028 and a passage. The location of each orifice in a corresponding chamber 1004, 1012, 1028 is selected in conjunction with the location of the sealing elements 1006 along the members 1002, 1010, 1026 to produce a desired motion of the clamping member 1010 and the firing member 1026 upon depression of the trigger 308. As described in greater detail below, the fluid-driven actuator 1000 transitions among two or more discrete states upon the introduction of pressurized gas into the fluid-driven actuator and the application of force to the trigger 308 to control the position of the control member 1002.

Fluid-Driven Actuator—Working Fluid

Where the handle 302 includes a fluid-driven actuator 1000, the handle 302 is configured to accommodate the working fluid, be it gas or liquid, that is utilized by the fluid-driven actuator 1000. Referring to FIGS. 152-153, as one example, the handle 302 may include a cylinder receiving space 1044 configured to receive a gas cylinder 1046. The gas cylinder 1046 may hold pressurized gas of any suitable type, such as carbon dioxide, nitrogen or argon. The gas cylinder 1046 is a standard commercially-available item that holds a suitable volume of gas at a desired pressure. The gas cylinder 1046 includes a neck end 1047 configured to be punctured to release gas stored within.

The gas cylinder 1046 is held within the cylinder receiving space 1044 by a knob 1048 that is movable relative to the handle 302. The knob 1048 may be configured in any suitable manner. As one example, the knob 1048 includes a spindle 1049 that has at least one thread 1050 that is received in corresponding threads 1052 located on an inner surface of a spindle receiving space 1053 located at the proximal end of the handle 302. Rotation of the knob 1048 thus causes the knob 1048 to both rotate and advance. However, the knob 1048 may move in any other suitable manner relative to the handle 302. For example, the knob 1048 may simply be slidable. Alternately, the knob 1048 and the spindle receiving space 1053 are located at a different position relative to the handle 302. An O-ring 1045 or other sealing element may be connected to the spindle 1049 in any suitable manner. For example, the O-ring 1045 may be held in a notch defined in the spindle 1049, or may be held between threads 1050 of the spindle 1049. The O-ring 1045 is sized and positioned to seal substantially the cylinder receiving space 1044, such that gas substantially does not exit the cylinder receiving space 1044 past the spindle 1049. The cylinder receiving space 1044, gas cylinder 1046, spindle 1049, and spindle receiving space 1053 are all substantially aligned about their longitudinal axes, which are oriented substantially parallel to the longitudinal axis of the handle 302. Alternately, those components are oriented in a different manner relative to the handle 302 and/or to one another. The distal end of the spindle 1049 may be curved to correspond to the curvature of the proximal end of the gas cylinder 1046. Alternately, the distal end of the spindle 1049 may be flat, or may be shaped in any other suitable manner.

The handle 302 may include at least one stop 1054 that extends into the spindle receiving space 1053. The stop 1054 may include a pin 1056 connected to a spring 1058 or other biasing element that biases at least part of the pin 1056 into the spindle receiving space 1053. Alternately, the stop 1054 may be any other suitable mechanism or structure, such as a tab or prong that extends into the spindle receiving space 1053 without being biased by a spring 1058 or other biasing element. Alternately, the stop 1054 may be omitted. A first notch 1060 in the spindle 1049 engages the stop 1054. Contact between the first notch 1069 and the stop 1054 prevents the spindle 1049 from being rotated out of the spindle receiving space 1053, and thereby prevents removal of the gas cylinder 1046 from the cylinder receiving space 1044. When the knob 1048 is moved toward an activation position, the first notch 1060 does not interfere with the resulting motion of the spindle 1049, and the threads 1050 on the spindle 1049 rotate such that at least part of the stop 1054 is located between adjacent threads on the spindle 1049 during motion of the knob 1048. A second notch 1062 may engage the stop 1054 after the knob 1048 has been moved to the activation position. Contact between the second notch 1062 and the stop 1054 stops the motion of the spindle 1049 when the knob 1048 has been moved to the activation position. Optionally, the notches 1060, 1062 are opposite ends of a groove defined in the spindle 1049.

A spike 1064 extends into the cylinder receiving space 1044, and is sized, shaped and located to contact and puncture the neck end 1047 of the gas cylinder 1046. For example, the spike 1064 may be located at the distal end of the cylinder receiving space 1044, oriented substantially in the proximal direction. Alternately, the spike 1064 is located in a different location in the cylinder receiving space 1044, and/or is oriented differently. Referring also to FIG. 149, the spike 1064 includes an aperture 1066 defined therein. The aperture 1066 is located on the spike 1064 at a position that allows gas to flow out of the gas cylinder 1046 and into the aperture 1066 after the spike 1064 has punctured the neck end 1047 of the gas cylinder 1046.

Fluid-Driven Actuator—Pressure Regulation Assembly

Optionally, referring to FIGS. 163-166, the aperture 1066 of the spike 1064 may be connected to a pressure regulation assembly 1070. The pressure regulation assembly 1070 may include a pressure control member 1072 positioned within a regulator space 1078 defined in the handle 302. The pressure control member 1072 may be a rod, or may be shaped or configured in any other suitable manner. A biasing element 1074 may be configured to bias the pressure control member 1072 and the spike 1064 toward the gas cylinder 1046. The biasing element 1074 may be any structure or mechanism that is suitable for biasing the pressure control member 1072 distally. As one example, the biasing element 1074 is a coil spring, and at least part of the pressure control member 1072 is received within that coil spring. The biasing element 1074 may be substantially fixed at one end by any suitable structure, mechanism or method. As one example, a stop 1076 is fixed to the wall of the regulator space 1078, such as by a friction fit, a pressure fit, or an interference fit, or by welding or by adhesive. Alternately, an end of the biasing element 1074 is directly connected to the wall of the regulator space 1078 or to the body of the handle 302. For example, an end of the biasing element 1074 may be molded into the handle 302.

The pressure control member 1072 may have a smaller cross-section closer to its distal end than to its proximal end. For example, the pressure control member 1072 may be shaped to include a cylinder having a smaller diameter closer to the proximal end of the pressure control member 1072, and a cylinder having a larger diameter closer to the distal end of the pressure control member 1072. One or more ribs 1008 may extend from the pressure control member 1072, where such ribs 1008 may be configured substantially as described above. Advantageously, one rib 1008 extends from the pressure control member 1072 on either side of at least one sealing element 1006. Thus, the two ribs 1008 substantially trap the corresponding sealing element 1006 therebetween, substantially restraining the sealing element 1006 from sliding or otherwise moving relative to the pressure control member 1072 during motion of the pressure control member 1072. One or more sealing elements 1006 may also, or instead, be located in an annular groove 1170 define in the pressure control member 1072. Alternately, one or more sealing elements 1006 may be connected to the pressure control member 1072 in a different manner. The gas inlet 1036 is a passage is connected to the regulator space 1078. An orifice O14 exists in the wall of the regulator space 1078 at the intersection between the gas inlet 1036 and the regulator space 1078. A passage P7 operationally connects the aperture 1066 of the spike 1064 to the regulator space 1078. An orifice O15 exists in the wall of the regulator space 1078 at the intersection between the passage P7 and the regulator space 1078.

The knob 1048 may be rotatable or otherwise movable between two positions. Initially, the knob 1048 is in a neutral position that substantially does not exert force on the gas cylinder 1046. The knob 1048 is rotatable or otherwise movable to an activation position, in which the spindle 1049 exerts a force on the gas cylinder 1046, pressing it into contact with the spike 1064. When the knob 1048 is in the activation position, the spike 1064 has punctured the neck end of the gas cylinder 1046. Optionally, the knob 1048 includes an indicator 1080, such as a substantially planar tab extending from the proximal end of the knob 1048. When the indicator 1080 is in a particular position, it provides positive confirmation that the gas cylinder 1046 has been punctured. The indicator 1080 may be configured in any suitable manner. As one example, where the indicator is a substantially planar tab, its orientation relative to the handle 302 and/or a marker on the handle 302 confirms that the knob 1048 is in the activation position and that the gas cylinder 1046 has been punctured by the spike 1064.

Alternately, the gas cylinder 1046 is not used; instead, gas is stored in a reservoir (not shown) defined within the handle 302. Where the gas cylinder 1046 is not used, the spike 1064, the cylinder receiving space 1044, and other components utilized to hold and/or control the gas cylinder 1046 and the gas flow therefrom need not be provided. Rather, upon activating the knob 1048, gas is released from the reservoir into the gas inlet 1036. Any suitable mechanism for regulating the pressure at the gas inlet 1036 may be utilized. Alternately, the gas cylinder 1046 is not used, and the handle 302 or other part of the anastomosis tool 300 receives pressurized gas from a source outside the handle 302. Such an energy source located outside the tool may be characterized as an external utility. Examples of an external utility include a pressurized gas feed provided at a wall outlet or on a portable gas supply. The external utility may be connected to the gas inlet 1036 of the handle 302 in any suitable manner, such as via a hose or other suitable connecting structure or mechanism. The pressure may be regulated at the source outside the handle 302, such that pressure regulation need not be provided within the anastomosis tool 300.

Graft Vessel Preparation

The graft vessel 404 is harvested from the patient in a conventional manner. The graft vessel 404 may be a saphenous vein, radial artery, mammary artery, or any other appropriate blood vessel. Alternately, the graft vessel 404 may be harvested from a different person or from a cadaver. Alternately, a xenograft or an artificial graft vessel may be provided.

Graft Vessel Preparation—Retractor Mount

Figure 79:
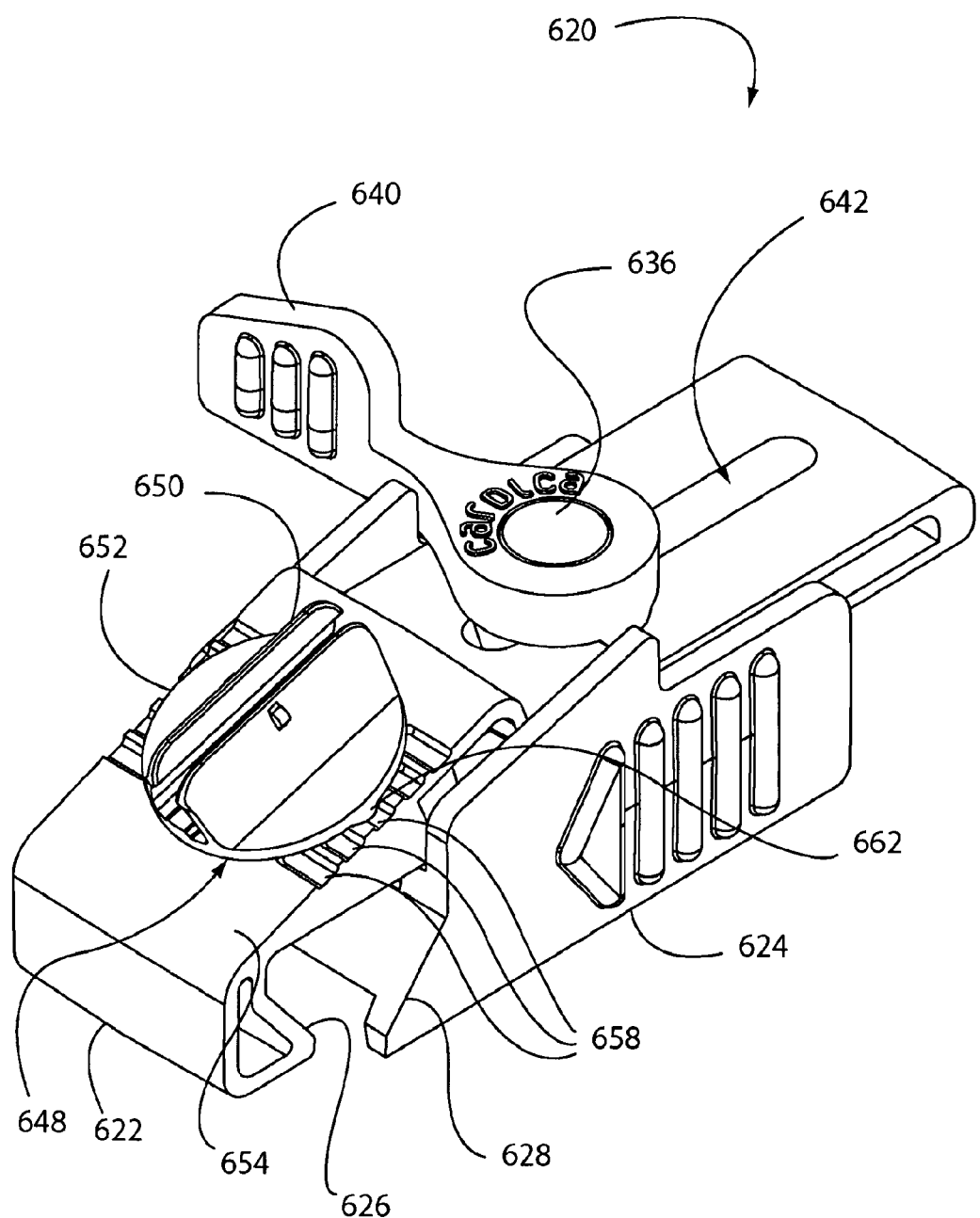
FIG. 79 is a perspective view of a retractor mount used in preparing a graft vessel for anastomosis.
Figure 80:
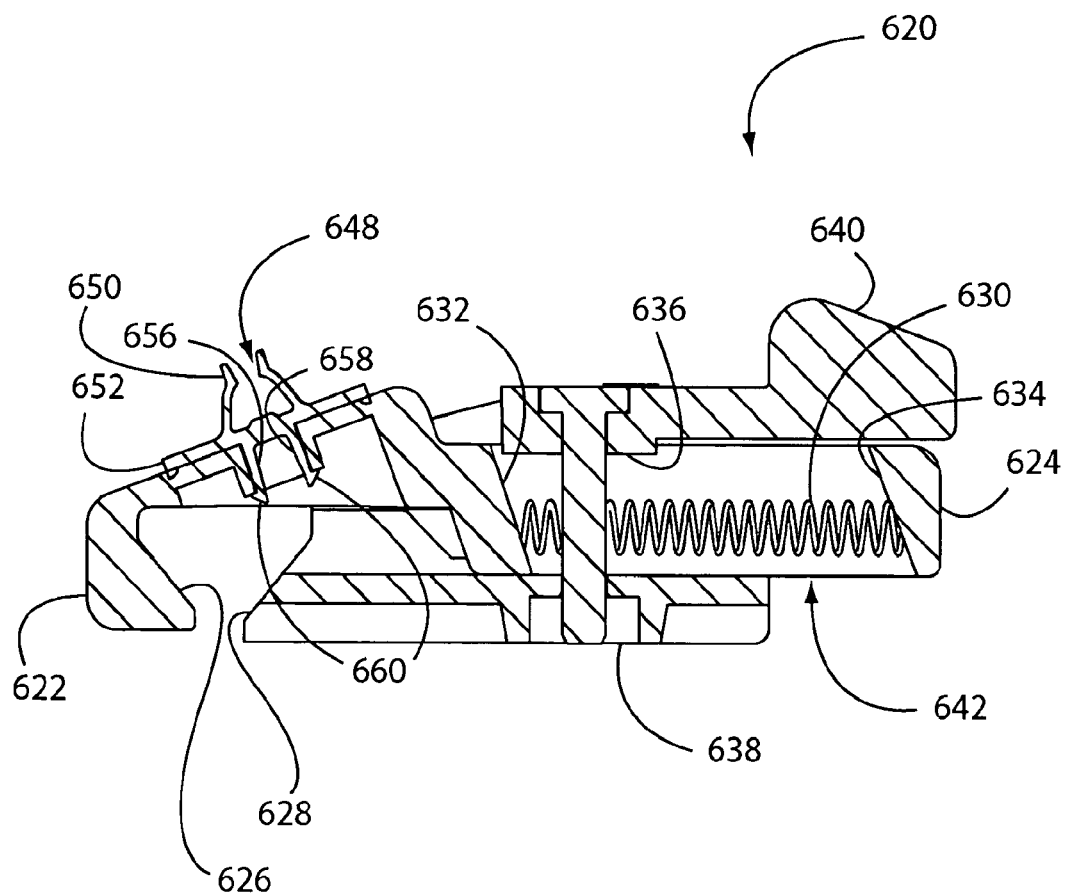
FIG. 80 is a side cross-section view of the retractor mount of FIG. 79.
Figure 80A:
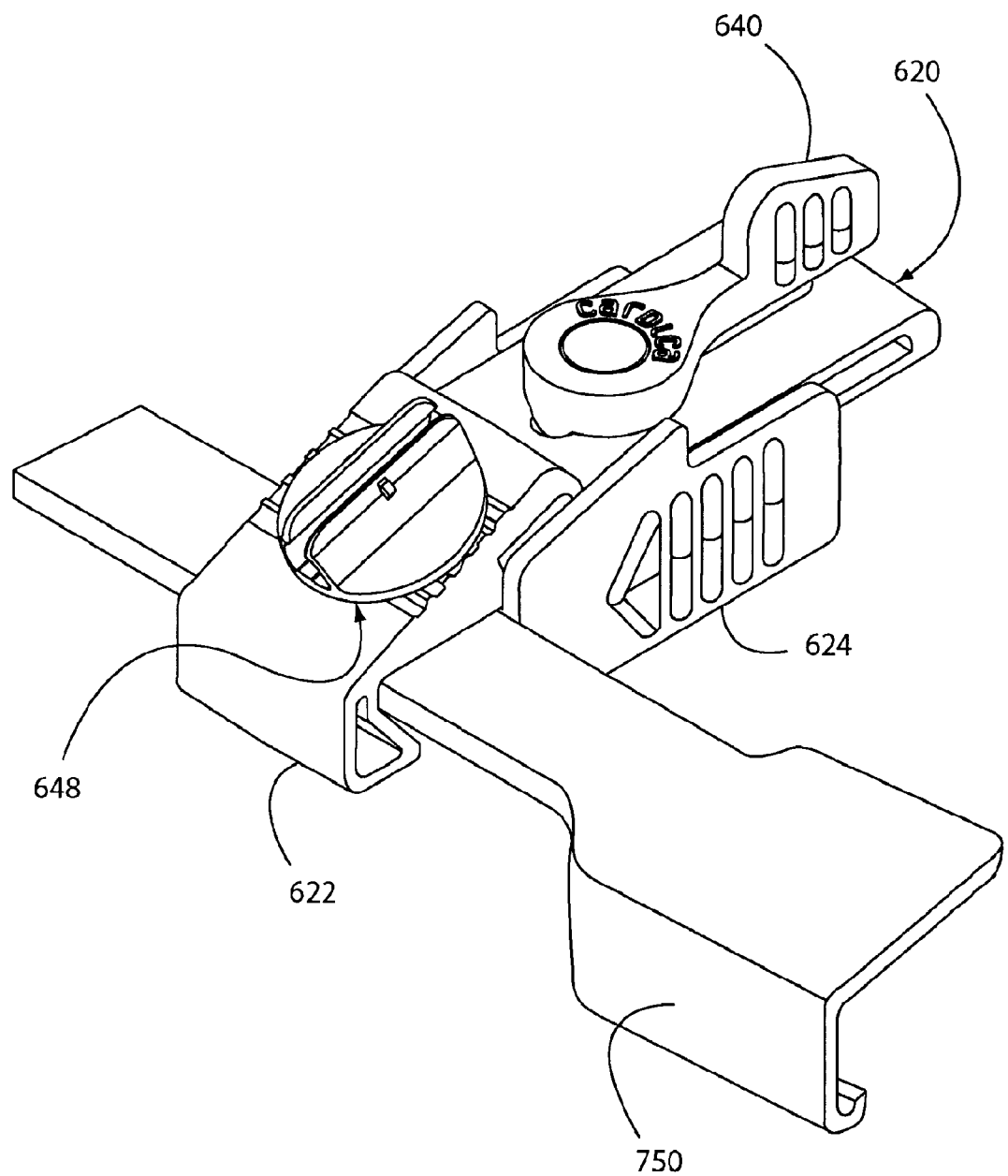
FIG. 80A is a perspective view of the retractor mount of FIG. 79 mounted on a standard surgical retractor.

The graft vessel 404 can be prepared in any appropriate manner for anastomosis to a target vessel. As one example, a system including one or more preparation tools may be used to prepare the graft vessel for anastomosis. Referring to FIGS. 79-80A, a retractor mount 620 is shown. The retractor mount 620 is detachably connected to a standard surgical retractor 750 used for an open-chest surgical procedure. The retractor mount 620 may include a first clamp element 622 and a second clamp element 624, which are movable relative to one another. As one example, the clamp elements 622, 624 are slidable relative to one another. The first clamp element 622 includes a first engagement feature 626 at its distal end, and the second clamp element 624 includes a second engagement feature 628 at its distal end. The first engagement feature 626 is located distal to the second engagement feature 628. The engagement features 626, 628 are configured to engage the retractor 750, such as by clamping onto at least a portion of that refractor 750. That clamping may result from biasing the engagement features 626, 628 toward one another. Such bias may be provided by one or more compression springs 630 positioned relative to the clamp elements 622, 624. For example, the first clamp element 622 may include a first wall 632 and the second clamp element 624 may include a second wall 634 proximal to the first wall 632, between which at least one spring 630 is positioned. The spring or springs 630 act in compression to push the engagement features 626, 628 toward one another. The engagement features 626, 628 are moved apart by applying a force opposite to the bias provided by the spring or springs 630, thereby moving the engagement features 626, 628 away from one another. When that force is removed, the engagement features 626, 628 move closer to one another, such as to clamp onto the retractor 750.

The retractor mount 620 may include a post 636 connected at one end to a washer 638 or other structure and at the other end to an actuator 640. The actuator 640 is shaped and finished to be grasped and rotated by a user. The actuator 640 is configured to compress the clamp elements 622, 624 together in order to hold them in a selected position. Such compression substantially prevents relative motion of the clamp elements 622, 624 by increasing the friction between them to an amount greater than the biasing force. For example, the actuator 640 may be actuated to restrain the clamp elements 622, 624 to facilitate positive engagement between the retractor mount 620 and the retractor 750. The compression exerted by the actuator 640 may be in a direction substantially perpendicular to the direction of translation of the clamp elements 622, 624 relative to one another. The actuator 640 may apply compression in any appropriate manner. As one example, the first clamp element 622 includes a longitudinal slot 642 that allows it to translate relative to the post 636. The actuator 640 may include a ledge 644 protruding from its underside 646 that is sized and shaped to extend only into the slot 642. The distance that the ledge 644 extends below the underside 646 is selected such that the clamp elements 622, 624 can slide freely relative to one another when the ledge 644 is positioned in the slot 642. When the actuator 640 is rotated about the post 636, the ledge 644 comes out of the slot 642 and presses down the first clamp element 622, compressing it against the second clamp element 624. The ledge 644 and slot 642 are shaped and finished such that the ledge 644 can come out of the slot 642 upon application of force to the actuator 640. Optionally, a surface of at least one clamp element 622, 624 and/or the actuator 640 is configured to include at least one gripping feature (not shown). The gripping feature or features are located to assist in holding the clamp elements 622, 624 together when the retractor mount 620 clamps the retractor 750. Such gripping features may include raised areas, areas of increased surface roughness, or other features. If one or more gripping features are used, the actuator 640 may exert less compression on the clamp elements 622, 624 to hold them together than if the gripping features were not present. Further, the actuator 640 may be omitted altogether if the gripping features provide sufficient resistance to motion between the clamp elements 622, 624 when the retractor mount 620 clamps the retractor 750. Alternately, the retractor mount 620 may be permanently connected to, or constructed as an integral part of, a surgical retractor.

The retractor mount 620 may include a holder 648. The holder 648 may be moveable relative to another portion of the retractor mount 620. For example, the holder 648 may be rotatable relative to another portion of the retractor 620. The holder 648 includes a clip 650 configured to engage an anastomosis tool 300 and/or another component of the system for preparing the graft vessel for anastomosis. The holder 648 also includes a base 652 connected to the clip 650. The holder 650 may be moveable among two or more discrete positions, or may move smoothly through a range of positions. As one example, the base 652 is a disc-shaped element, and the holder 648 is rotatable among two or more discrete positions. The base 652 is positioned on or adjacent to a surface 654 of the first clamp element 622. The surface 654 is oriented to place tools held by the holder 648 in a useful orientation relative to the patient. Alternately, the base 652 is positioned on the second clamp element 624 or a different portion of the retractor mount 620. A spindle 656 extends from the base 652 into a tube 658 extending into or through the surface 654 of the first clamp element 622. Where the spindle 656 extends all the way through the tube 658, at least one flange 660 extends laterally from the spindle 656 to hold the spindle 656 in the tube 658 and prevent it from sliding out.

The surface 654 includes two or more troughs 658 defined therein. The troughs 658 are substantially linear, and substantially parallel to one another. Alternately, the troughs 658 may be oriented differently. At least one stub 662 extends downward from the base 652. Each stub 662 is sized and shaped to engage a trough 658 in the surface 654. Such engagement substantially prevents free rotation of the holder 648 relative to the surface 654. The base 652 is held against the surface 654, and therefore the stub or stubs 662, are each held against a corresponding trough 658, with a force related to the length and rigidity of the spindle 656. The flange 660 prevents gross upward motion of the spindle 656 and therefore the holder 648, such that the holder 648 is capable of limited motion perpendicular to the surface 654 at least partially as a result of flexibility of the spindle 656. The depth of each trough 658, and the distance that each stub 662 extends downward from the base 652 into the corresponding trough 658, act to hold the base 652 in the selected position. Correspondingly, the depth of each trough 658 and the distance that each stub 662 extends downward from the base 652 is related to the force required to remove that stub 662 from engagement with the trough 658 and cause the base 652 to rotate. Each stub 662 is shaped, and the cross-section of each trough 658 is shaped, to allow the stub 662 to move out of the trough 658 upon the application of force about the longitudinal axis of the spindle 656. The amount of force is selected to be low enough to allow the holder 648 to be rotated by hand, but high enough to allow the holder 648 to maintain a selected position in use. The number of troughs 658 determines the number of rotational positions to which the base 652 can be rotated. Advantageously, two or more stubs 662 extend from the edge of the base 652. Alternately, other structures or mechanisms are provided to allow the base 652 to rotate and maintain a selected position relative to the surface 654. The clip 650 of the holder 648 may be fixed to the base 652, such that the clip 650 rotates or otherwise moves along with the base 652. Thus, a tool or other object held by the clip 650 rotates or otherwise moves along with the base 652. Alternately, the holder 648 and the surface 654 are configured to allow substantially continuous rotational motion of the holder 648 relative to the surface 654. In such a configuration, the troughs 658 on the surface 654 and the stub or stubs 662 on the holder 648 may be omitted. As an example of such a configuration, a spring (not shown) is connected at one end to the base 652 of the holder 648 and at the other end to the tube 658, where the spring is configured to pull the base 652 into contact with the surface 654. The amount of force exerted by the spring is large enough to hold the base 652 substantially against the surface 654 at any selected rotational orientation, and is small enough to allow for rotation of the holder 648 relative to the surface 654 upon application of a reasonable amount of rotational force by the operator. As another example of such a configuration, frictional force between the base 652 and the surface 654 is sufficient to hold the base 652 in a selected rotational orientation. Such frictional force may result from the surface finish of the base 652 and/or the surface 654.

Graft Vessel Preparation—Transfer Clamp Assembly

Figure 81:
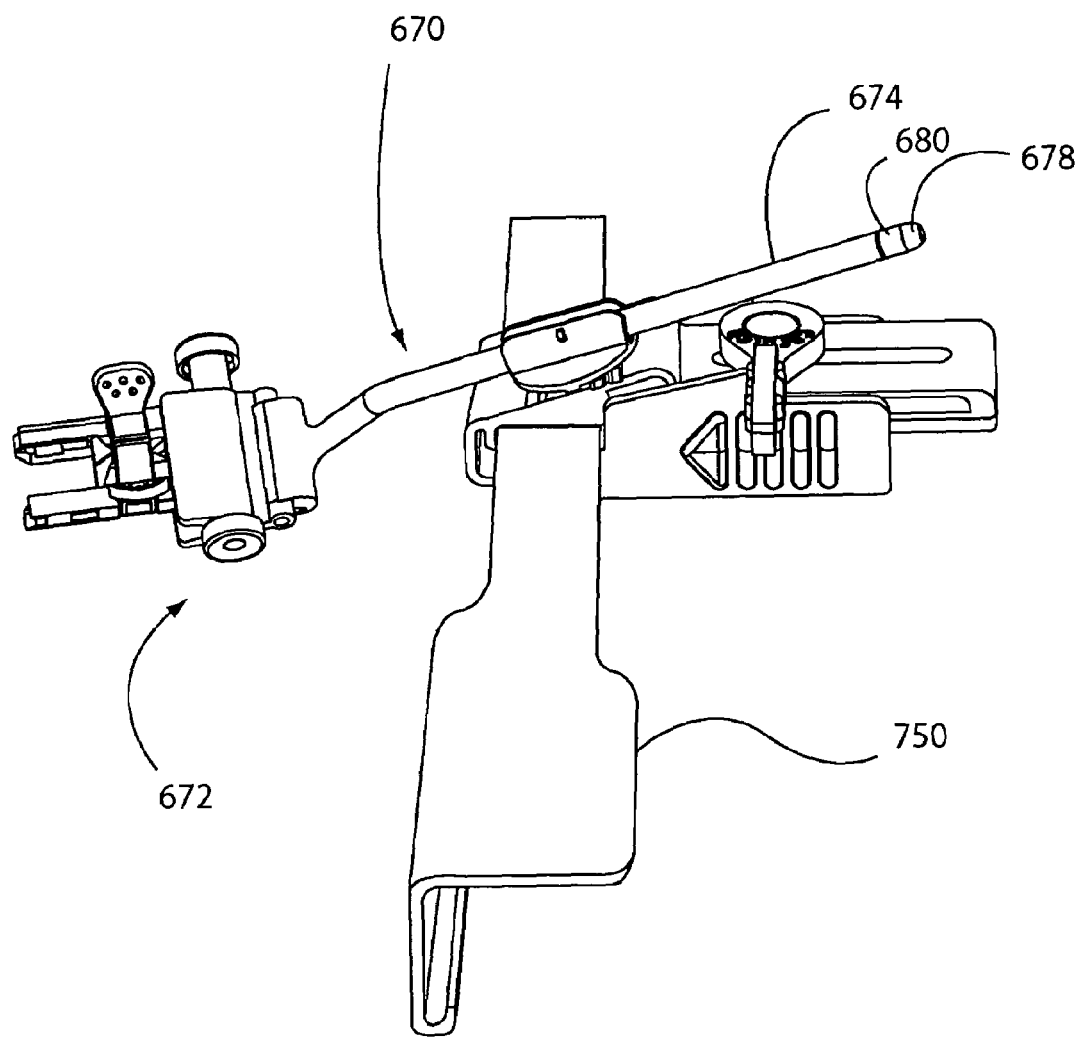
FIG. 81 is a perspective view of a transfer clamp assembly used in preparing a graft vessel for anastomosis, where the transfer clamp assembly includes a transfer clamp and an extension arm.
Figure 82:
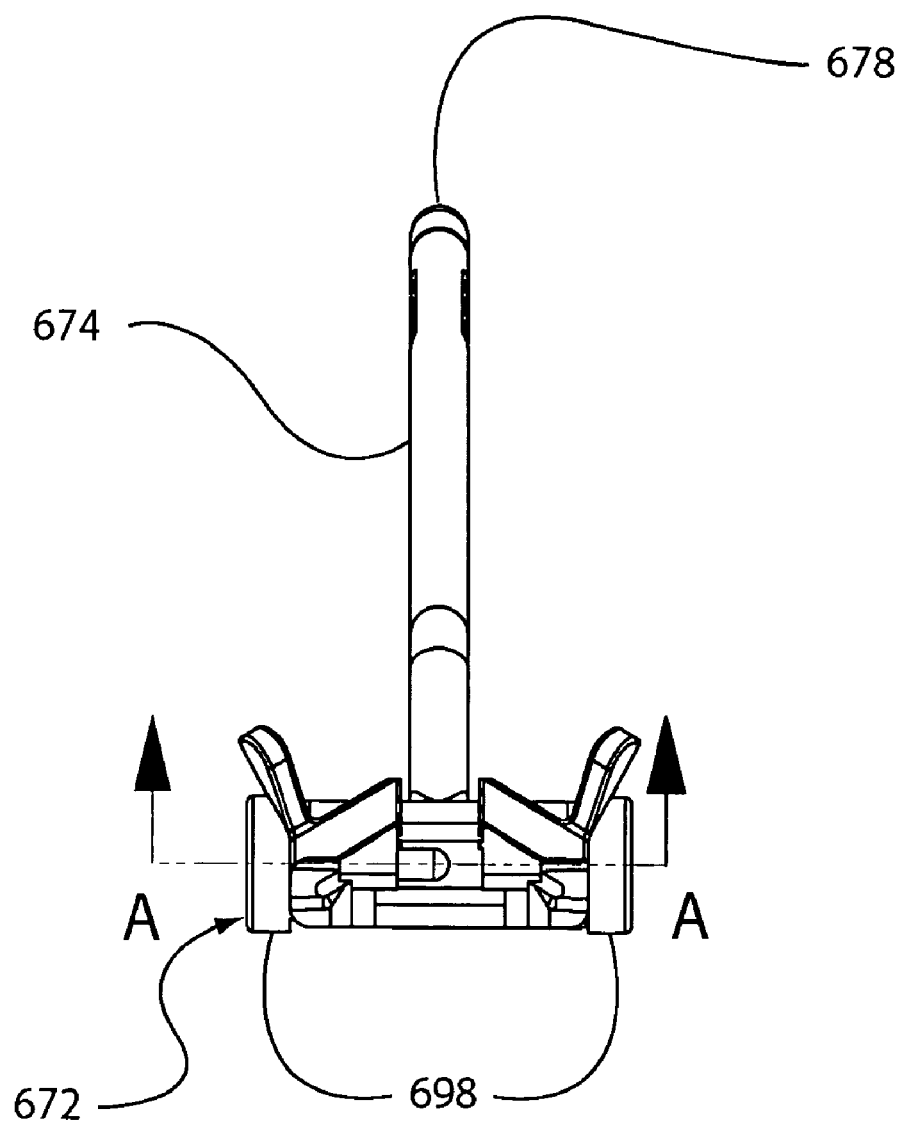
FIG. 82 is an end view of the transfer clamp of FIG. 81 in an open position.
Figure 82A:
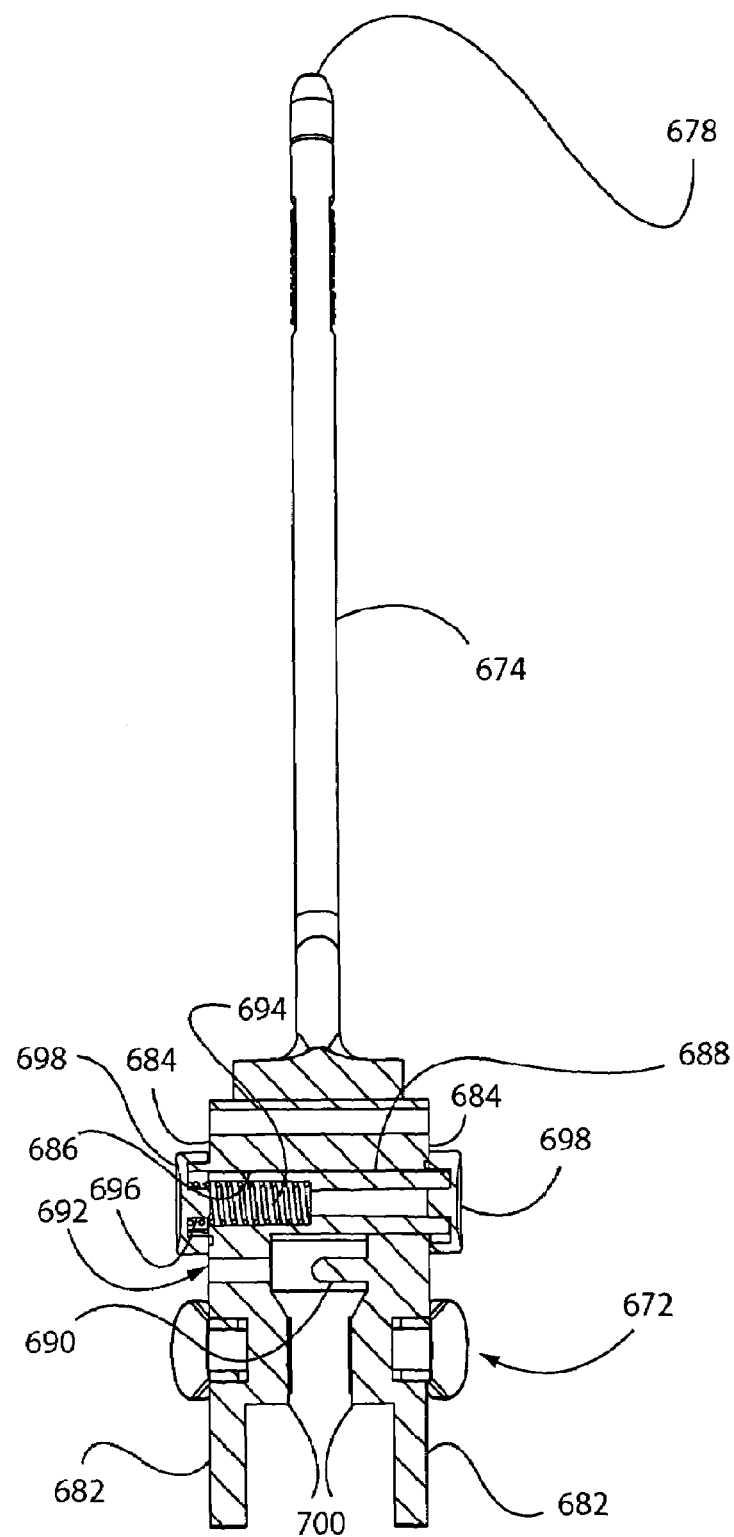
FIG. 82a is a top cross-section view of the transfer clamp along the lines A-A of FIG. 82.

Referring to FIGS. 81-82A, a transfer clamp assembly 670 is another tool that may be used in the preparation of a graft vessel for anastomosis. The transfer clamp assembly 670 includes a transfer clamp 672 connected to an extension arm 674. The extension arm 674 may be detachably connected to or permanently fixed to the transfer clamp 672. Optionally, the extension arm 674 may be omitted. The transfer clamp assembly 670 is connectable to the retractor mount 620. For example, the extension arm 674 and clip 650 may be configured such that the extension arm 674 snaps into the clip 650 and is held securely by it. The extension arm 674 may be detachably connected to the holder 648 or other portion of the retractor mount 620. Alternately, the extension arm 674 is omitted, and the transfer clamp 672 itself is connected to the holder 648 or other portion of the refractor mount 620. Alternately, the transfer clamp assembly 670 is permanently connected to the retractor mount 620. The extension arm 674 is configured to connect to the holder 648 and hold the transfer clamp 672 is a position in proximity to the site where an anastomosis is performed. Such proximity may be desirable where the graft vessel is a mammary artery, or where the anastomosis is to be performed after a proximal anastomosis at one end of the graft vessel.

Optionally, a poke-through tip 678 is connected to the extension arm 674 in any appropriate manner. As one example, the poke-through tip 678 includes a tubular or hollow sleeve 680 at its proximal end, where the sleeve 680 is configured to fit over a portion of an end of the extension arm 674. The poke-through tip 678 may be connected to the extension arm 674 in any appropriate manner. As one example, the extension arm 674 has an annular depression (not shown) defined therein, and the poke-through top 678 includes an annular ridge (not shown) defined therein, such that the annular ridge can be received in the annular depression to mechanically hold the poke-through tip 678 onto the extension arm 674. As another example, friction between the sleeve 680 and the extension arm 674 holds the poke-through tip 678 in place. As another example, an adhesive or other substance, mechanism and/or structure may be used in conjunction with the sleeve 680, or without the sleeve 680, to secure the poke-through tip 678 to the extension arm 674. As another example, the poke-through tip 678 is formed into the extension arm 674. The poke-through tip 678 may be positioned at the free end of the extension arm 674. Alternately, the poke-through tip is positioned at a different location on the extension arm 674. The poke-through tip 678 may be made of a thermoplastic elastomer, such as the C-FLEX® brand thermoplastic elastomer of Consolidated Polymer Technologies, Inc., a polymer, a plastic, or any other soft, durable material. Alternately, the poke-through tip 678 is substantially rigid. The rigid poke-through tip 678 may be tubular, or have a different shape. The poke-through tip 678 has at least one dimension greater than the length of the longest spike 410, to prevent interference between them. Alternately, a poke-through tip 678 is connected to a separate tool, such as a dedicated poke-through tool.

Referring to FIGS. 81-85, the transfer clamp 672 includes two arms 682 extending distally from a base 684. The arms 682 are substantially parallel to one another. Alternately, the arms 682 may be oriented differently relative to one another. The arms 682 are biased to a closed position, and may be moved apart to an open position. One of the arms 682 may be formed into the base 684 or otherwise fixed to the base 684, while the other arm 682 may be movable relative to the base 684 and biased toward the fixed arm 682. However, both arms 682 may be moveable relative to the base 684. Each movable arm 682 is configured to translate laterally relative to the base 684. The arms 682 are sized, shaped and spaced relative to one another such that a portion of an anastomosis tool can be received onto the arms 682 when they are in the open position, as described in greater detail below.

The base 684 may include a channel 686 defined laterally therein. At least one arm 682 may be connected to or include a corresponding runner 688 sized and shaped to translate within the channel 686. The interaction between the runner 688 and the channel 686 guides the translation of the runner 688, and thus the translation of the arm 682 connected to the runner 688. The channel 686 and runner 688 may be configured in any appropriate manner. As one example, the channel 686 and the runner 688 are both substantially cylindrical, and the diameter of the runner 688 is slightly less than the diameter of the channel 686. The base 684 includes an opening into the channel 686 to allow the runner 688 to connect to the remainder of the arm 682 and slide relative to the channel 686.

The arms 682 may be biased to a closed position with a spring 694. Advantageously, the spring 694 is a coil spring, but may be a leaf spring or other type of spring. One end of the spring 694 is fixed relative to the base 684, and the other end of the spring 694 is connected to a portion of the movable arm 682, such as the runner 688. The spring 694 is connected to the base 684 and the movable arm 682 such that the arms 682 are biased to the closed position and the user must overcome the biasing force of the spring 694 to increase the distance between the arms 682. The spring 694 may be positioned within the channel 686, or at a different location in the transfer clamp 672. The spring 694 may be connected to the arm 682 and/or base 684 by molding a portion of it into the corresponding component, securing an end of the spring 694 to a stub 696, or utilizing any other appropriate structure, mechanism or method. Alternately, the spring 694 is simply trapped within the channel 686 without being positively connected to the arm 682 and/or base 684. Where the spring 694 is a coil spring, its axial centerline is substantially collinear with the axial centerline of the channel 686. Alternately, two or more springs 694 may be used instead of a single spring, if desired.

At least one arm 682 may include a registration pin 690 or other registration feature, and the corresponding arm 682 may include a registration aperture 692 or other corresponding registration feature. The registration pin 690 is substantially parallel to and spaced apart from the channel 686. When the arms 682 are in the open position, the registration pin 690 is outside of the registration aperture 692. As the distance between the arms 682 decreases, the registration pin 690 is received into the registration aperture 692 of the other arm 682 and slides relative to the registration aperture 692. Because the motion of the arm 682 is constrained by both the registration pin 690 and the channel 686, the arms 682 are aligned, and remain in a desired orientation relative to one another. That is, the simultaneous linear motion of the registration pin 690 along the registration aperture 692 and the runner 688 along the channel 686 constrains the arms 682 to a plane. Alternately, at least a portion of the registration pin 690 remains within the corresponding registration aperture 692 at all times during motion of the arm or arms 682.

Optionally, at least one finger pad 698 is connected to the base 684 and/or at least one arm 682. The finger pads 698 may be substantially centered relative to the longitudinal centerline of the channel 686 in the base 684. As a user compresses the finger pads 698 toward one another, a longitudinal force is exerted on and compresses the spring 696, and the runner 688 translates within the channel 686, increasing the distance between the arms 682. The finger pads 698 may be shaped in any appropriate manner. Further, one or more of the finger pads 698 may be formed integrally with the corresponding base 684 or arm 682, if desired. Advantageously, the finger pads 698 are spaced apart a distance such that they can be operated by the user with a single hand, such as by pressing the finger pads 698 with the thumb and forefinger.

Each arm 682 includes at least one jaw 700. The jaws 700 on different arms are opposed to one another, such that a jaw 700 on one arm 682 faces a corresponding jaw 700 on the other arm 682. At least one jaw 700 may extend laterally away from the corresponding arm 682 toward the other arm 682. Further, the jaws 700 may instead or additionally extend in a direction perpendicular to the arms 682, above a plane defined by the longitudinal centerlines of the arms 682.

Optionally, at least one set of corresponding jaws 700 each includes a shim 702 extending upward from a remainder of the jaw 700 to provide a more secure grip for a graft vessel, as described in greater detail below. Each corresponding shim 702 is sized and shaped in substantially the same manner. For example, each corresponding shim 702 may be substantially rectangular. However, the shims 702 may be shaped differently, if desired.

Each jaw 700 is formed into or otherwise fixed to the corresponding arm 682. Alternately, at least one jaw 700 is movable relative to the corresponding arm 682, in which case the corresponding arm 682 may be fixed relative to the base 684. Optionally, at least one jaw 700 includes a gripping surface 704 defined thereon or connected thereto. The gripping surface 704 may be any surface finish, treatment, element or other structure, mechanism or feature to facilitate gripping a graft vessel between corresponding jaws 700. As one example, each gripping surface 704 includes a number of raised elements defined therein, alternating with depressions or other surface. As another example, the gripping surfaces 704 may have a high degree of surface roughness.

At least one cutting block 710 may be connected to at least one arm 682. Each cutting block 710 is movable relative to the corresponding arm 682. For example, each cutting block 710 may be rotatably connected to the corresponding arm 682, where the axis of rotation is parallel to the longitudinal axis of that arm 682. However, at least one cutting block 710 may be connected to the corresponding arm 682 in a different manner. Each cutting block 710 includes a first element 712 having an end 714 and a cutting surface 716, and a second element 718 angled relative to the first element 712. Each end 714 has an upper edge 715. Both the first element 712 and the second element 718 may be connected to or formed as a unit with a third element 722 that extends to the corresponding arm 682, where the third element 722 is rotatable or otherwise movable relative to that arm 682. Alternately, the second element 718, or the first element 712, extend to and connect to the corresponding arm 682. At least one second element 718 may include at least one gripping surface 720 defined thereon or connected thereto. The gripping feature or features 720 may be any structure or mechanism that facilitates actuation of the second element 718 by a user. As one example, the gripping surfaces 720 on a second element 718 may be a number of bumps formed in or connected to that second element 718. As another example, the gripping surface 720 may be a rubberized or rough surface on the second element 718.

Figure 73:
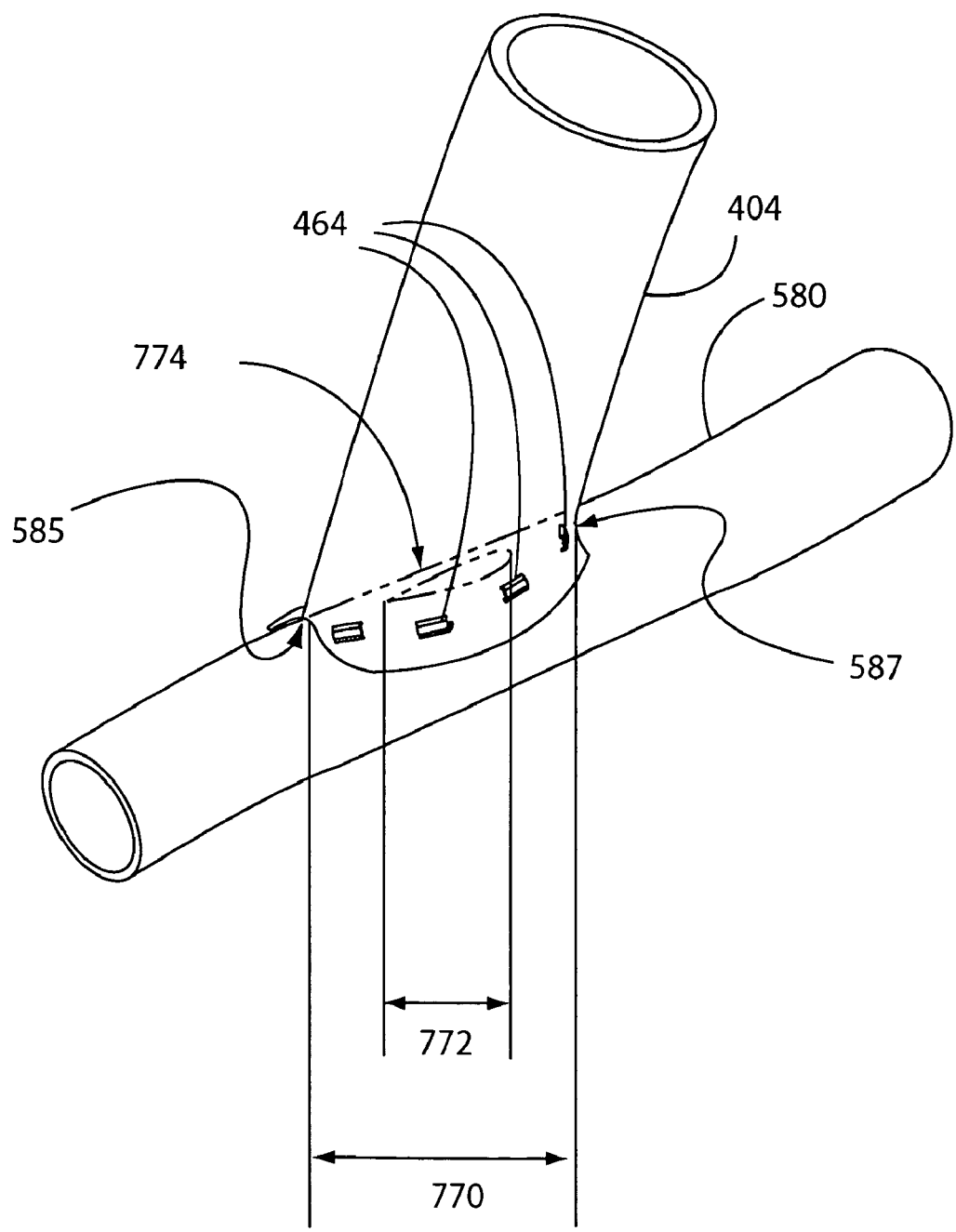
FIG. 73 is a perspective view of a completed anastomosis.

The upper edges 715 of the ends 714 of the cutting blocks 710 are substantially the same length as one another, and are substantially parallel to one another. The length of each upper edge 715 is related to the length of the anastomosis between the graft vessel 404 and the target vessel 580. Referring also to FIG. 73, the anastomosis length 770 is measured along the longitudinal axis of the target vessel 580, and is the distance between the two most longitudinally-distant points of contact between the perimeter of the end of the graft vessel 404 (the perimeter being substantially continuous and adjacent to the roots 405 of the flaps 408) and the side of the target vessel 580. As part of the anastomosis procedure, an arteriotomy 774 may be made in the target vessel, where that arteriotomy has a known length. The arteriotomy length 772 is measured along the longitudinal axis of the target vessel 580, and is the distance between the two most longitudinally-distant ends of the arteriotomy. The arteriotomy in the target vessel 580 is enclosed by the circumference of the end of the graft vessel 404, and the anastomosis length 770 is greater than the arteriotomy length 772, thereby preventing leakage at the anastomosis site.

The graft vessel 404 is angled relative to the parallel upper edges 715 such that one end of each edge 715 is positioned substantially at one side of the graft vessel 404 and the other end of each edge 715 is positioned substantially at the opposite side of the graft vessel 404. That is, the graft vessel 404 is positioned such that the edges 715 of the cutting blocks 710 define a chord across the graft vessel 404, where the chord has a length substantially equal to the length of the edges 715. In this way, the end of the graft vessel 404 can be prepared to a substantially constant preselected length, and the graft vessel 404 is held across the entire length of the chord. Further, graft vessels 404 of different widths each can be prepared such that the roots 405 of the flaps 408 each have the same substantially constant preselected length, simply by changing the angle of the graft vessel 404 relative to the edges 715 of the cutting blocks. The length of the chord across the graft vessel 404 is substantially equal to the anastomosis length 770. Further, the length of the chord across the graft vessel 404 is substantially equal to the length of the roots 405 of the flaps 408, and thus is related to the size of the flaps 408. The arteriotomy length 772 may be substantially constant across different sizes of graft vessel 404. By ensuring that the roots 405 of the flaps 408 are prepared to a preselected length across a spectrum of sizes of graft vessels 404, the anastomosis length 770 in turn is ensured to be longer than the arteriotomy length 772, thereby preventing leakage.

Figure 84:
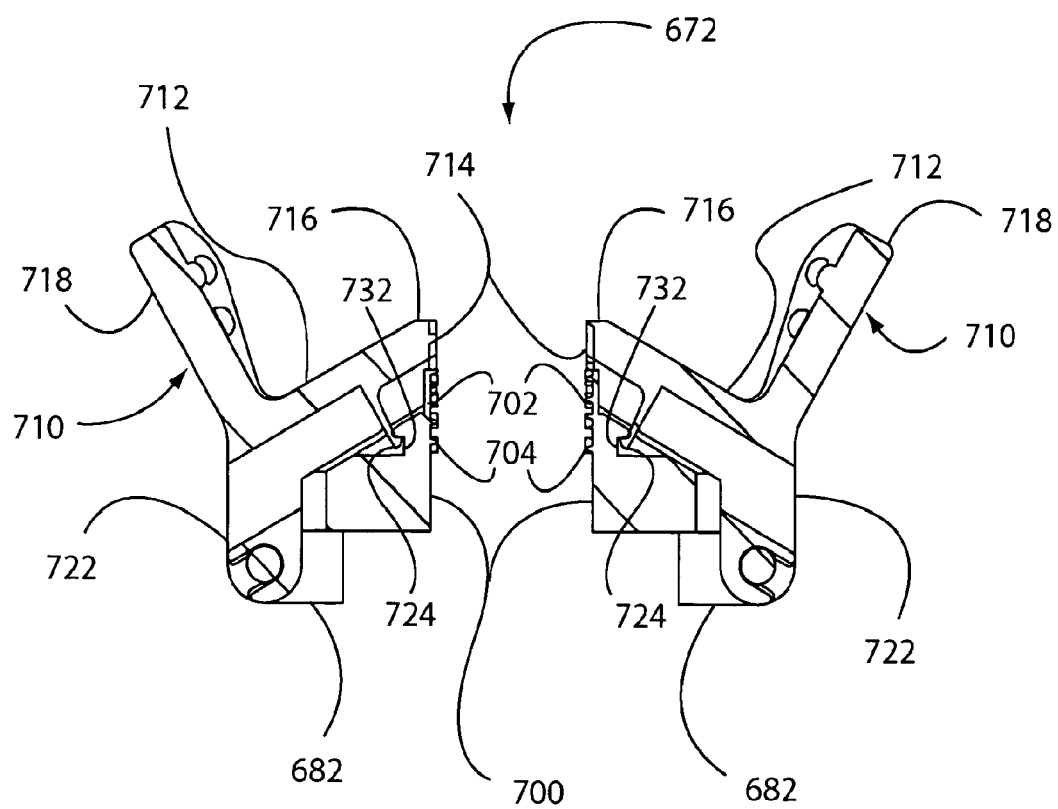
FIG. 84 is an end cross-section view of the transfer clamp of FIG. 81 in an open position, where cutting blocks are in a closed position relative to the transfer clamp.
Figure 85:
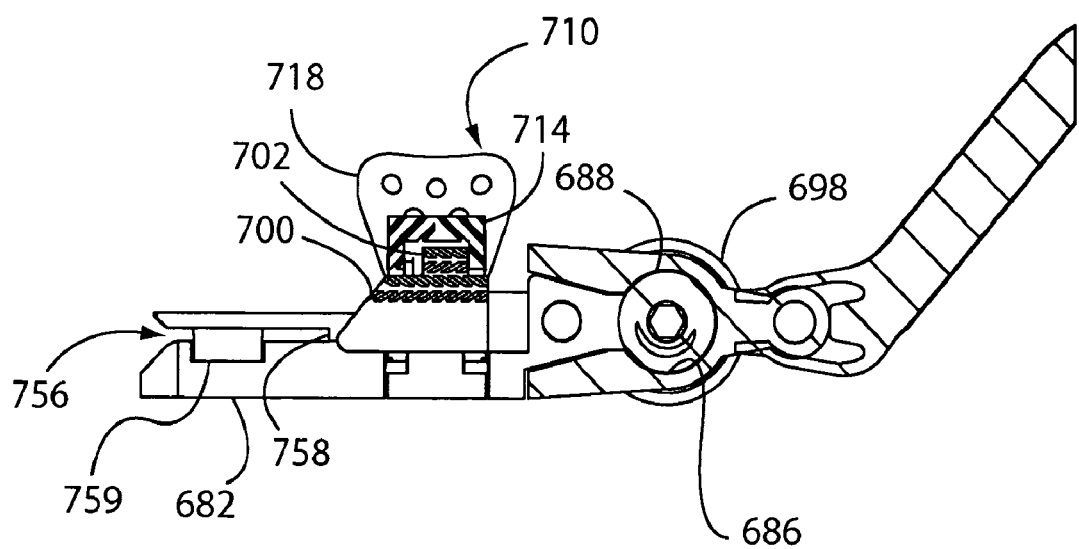
FIG. 85 is a side cross-section view of the transfer clamp of FIG. 81.

The shims 702 may be sized to be shorter than the length of the corresponding jaw 700 and/or the upper edge 715 of the cutting block 710. However, the shims 702 may be as long as, or longer than, the corresponding jaw 700 and/or the upper edge 715 of the cutting block 710. Each shim 702 may be longitudinally offset from the longitudinal center of the corresponding jaw 700 and/or cutting block 710. Referring in particular to FIG. 84, each shim 702 extends above the corresponding jaw 700 to a location below the upper edge 715 of the corresponding cutting block 710. In this way, adequate clearance is provided between the shims 702 and the staple holder 38 of the anastomosis tool 300 when the transfer clamp 672 is opened, as described below.

Referring to FIGS. 81-85, each cutting block 710 is moveable between an open position for receiving a graft vessel and a closed position for holding a graft vessel. Each cutting block 710 is positioned at a longitudinal position on the corresponding arm 682 that is substantially the same as the longitudinal position of the jaw 700 of that arm 682. In the closed position, the ends 714 of the first elements 712 of the cutting blocks 710 are positioned in proximity to and substantially above the gripping surfaces 704 of the corresponding jaws 700 and substantially above the corresponding jaws 700.

Figure 86:
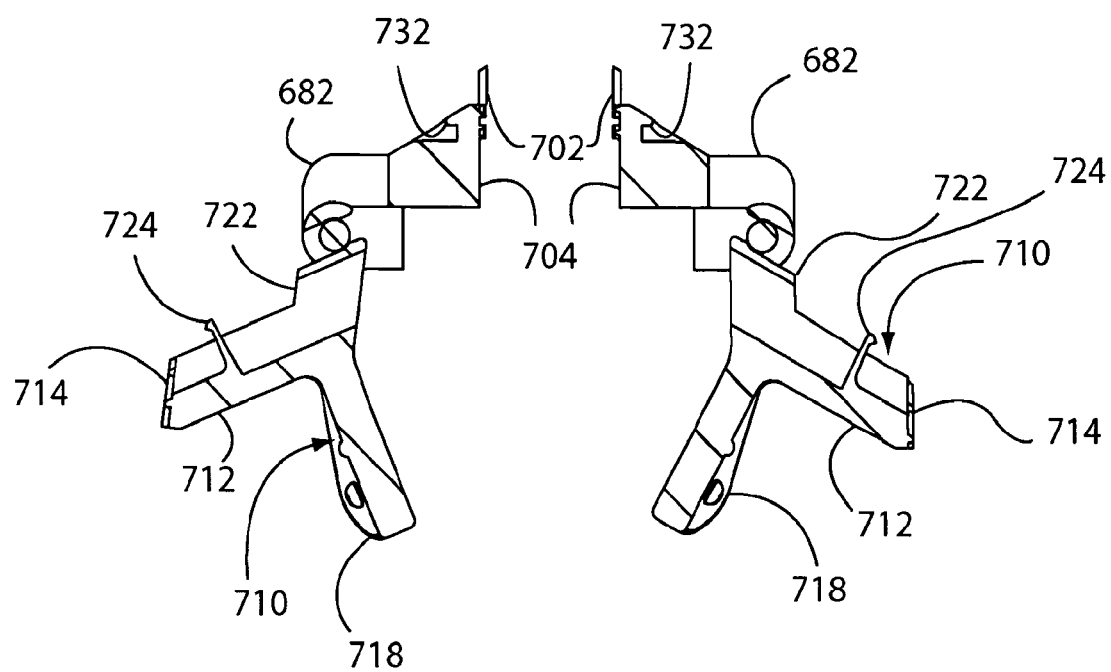
FIG. 86 is an end cross-section view of the transfer clamp of FIG. 81 in an open position, where cutting blocks are in an open position relative to the transfer clamp.

Referring also to FIG. 86, at least one of the cutting blocks 710 may include a snap 724 extending downward from it. The snap 724 may be configured in any appropriate manner to engage a corresponding receiver 726 defined in or connected to the corresponding jaw 700. As one example, the snap 724 may include a leg 728 connected at one end to the corresponding cutting block 710, and a ledge 730 connected to the other end of the leg 728, where the ledge 730 extends at an angle to the leg 728. The ledge 730 may be straight or curved. As a result, the snap 724 may have an L-shaped or J-shaped cross section. Alternately, the ledge 730 is connected to a different portion of the leg 728, or is omitted. The receiver 726 in the jaw 700 is shaped to engage the ledge 730 of the corresponding snap 724 when the cutting block 710 is in the closed position. That is, contact between the receiver 726 and the ledge 730 restrains the ledge 730 from moving out of the receiver 726 until a predetermined amount of force is applied. As one example, the receiver 726 includes a notch 732 defined therein. As the cutting block 710 is rotated toward the jaw 700, the ledge 730 contacts the surface of the jaw 700 in proximity to the receiver 726. The application of force on the cutting block 710 toward the jaw 700 causes the snap 724 to deflect, allowing the ledge 730 to move into the corresponding receiver 726 and engage the corresponding notch 732 therein.

Figure 83:
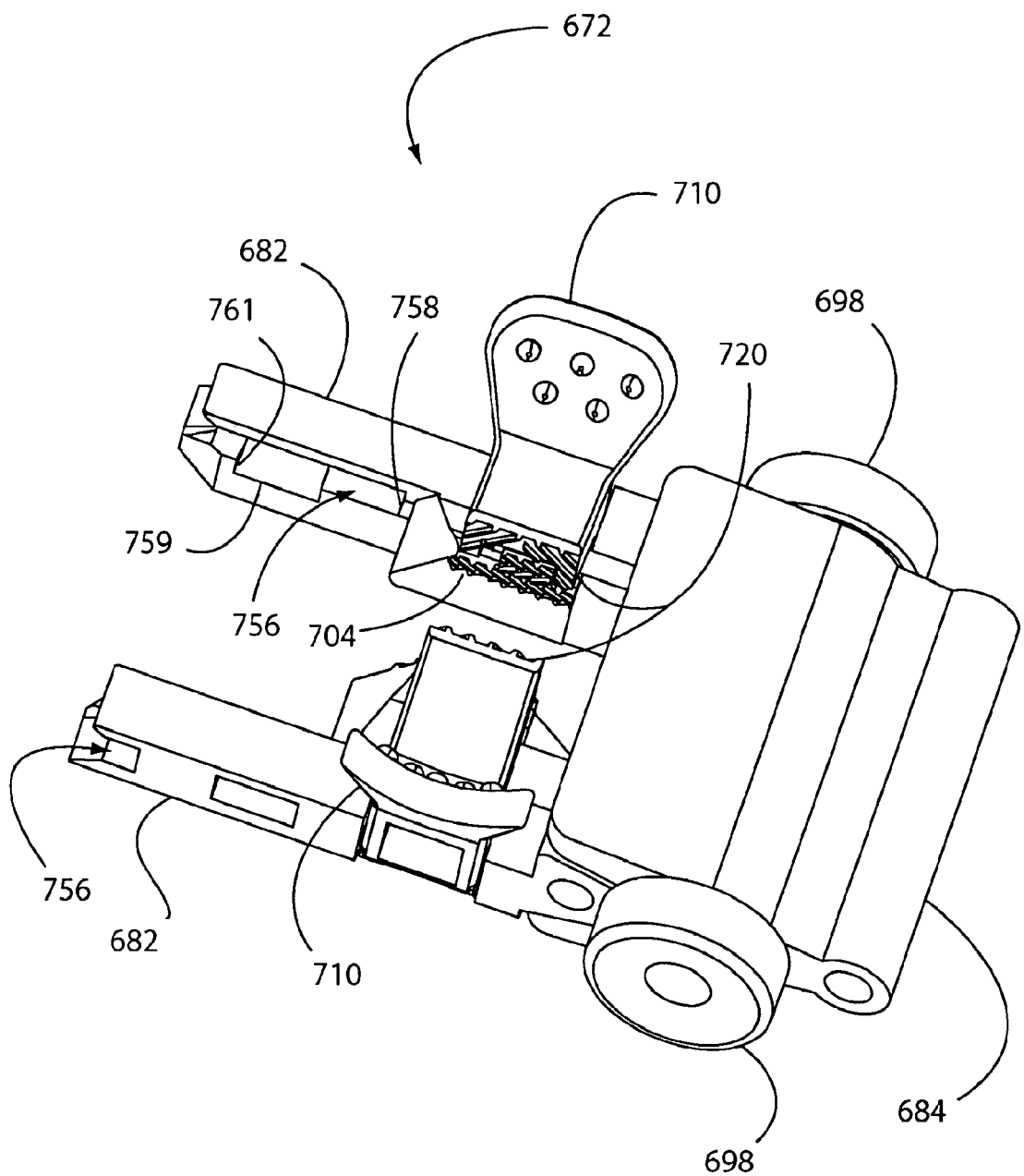
FIG. 83 is a perspective view of the transfer clamp of FIG. 81.

Referring also to FIG. 83, a slot 756 extends along each arm 682 of the transfer clamp 672. Each slot 756 is shaped and sized to receive a corresponding wing 760 of the staple holder 38. The slots 756 may be angled such that the staple holder 38 can be inserted only in a single orientation, to ensure that the flaps 408 are positioned appropriately relative to the anvil 10 and the staple holder 38. Further, the slots 756 are spaced apart from one another a particular distance such that the wings 760 each can be received into a corresponding slot 756. At the proximal end of each slot 756 is a wall 758. A notch 759 may be formed into at least one arm 682, where each notch 759 opens into a corresponding slot 756 and faces the space between the arms 682. Each notch 759 is positioned to engage the bump 762 on a particular wing 760, as described below.

Graft Vessel Preparation—Graft Manipulator

Figure 87:
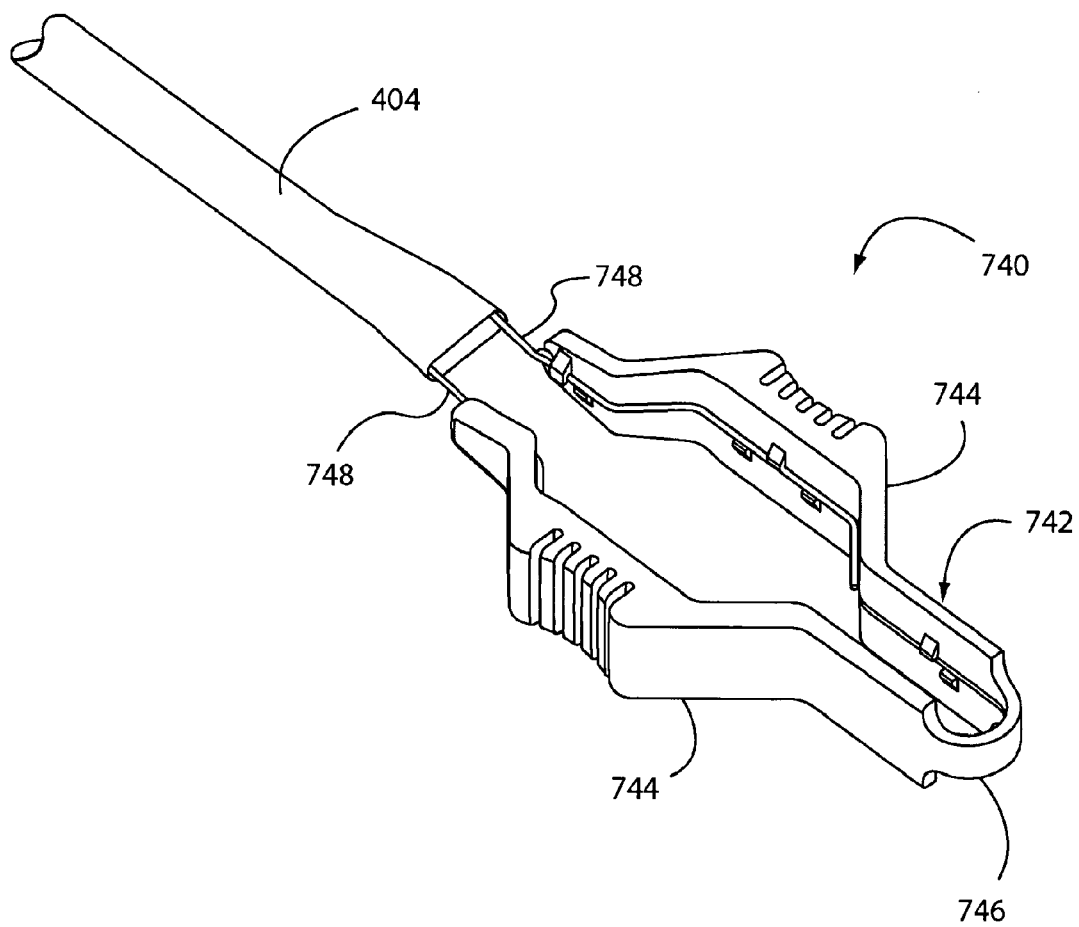
FIG. 87 is a perspective view of a graft manipulator.

Referring to FIG. 87, a graft manipulator 740 is shown. The graft manipulator 740 includes a handle 742 with two arms 744 biased apart from one another at their distal ends and connected together, such as with a base 746, at their proximal ends. The handle 742 may be a unitary structure, such as a single piece of molded plastic. The degree to which the distal ends of the arms 744 are biased apart may be related to the size and shape of the base 746 that connects the arms 744, and the properties of the material used to form the base 746. A prong 748 extends from the distal end of each arm 744. Each prong 748 may be connected to the corresponding arm 744, or formed into the corresponding arm 744. The prongs 748 are sized such that both can fit into an end of a graft vessel 404 at the same time, and are finished and contoured to do so without damaging the end of the graft vessel 404. As one example, each prong 748 is a thin metal rod with a blunt distal end. Each prong 748 is connected to the corresponding arm 744 by a pressure fit, by one or more clips, by adhesive, or by any other appropriate mechanism, structure or method. Because the distal ends of the arms 744 are biased apart, the prongs 748 at the distal ends of the arms 744 are biased apart as well.

Alternately, one or more of the retractor mount 620, the transfer clamp assembly 670, and/or the graft manipulator 740 are not utilized. Instead, one or more other preparation tools may be used, such as the graft vessel preparation device of U.S. Pat. No. 6,554,764 to Vargas et. al., which is hereby incorporated by reference in its entirety.

Alternately, where the staple holder 38 includes a graft affixer 910, the retractor mount 620, the transfer clamp assembly 670, and/or the graft manipulator 740 need not be utilized, and other specialized preparation tools need not be used, as described in greater detail below.

Preparing the Graft Vessel

Referring to FIGS. 79-80A, to prepare a graft vessel 404 for anastomosis, the retractor mount 620 is attached to a refractor 750. To do so, the clamp elements 622, 624 are slid relative to one another to create a gap between the engagement features 626, 628. This sliding is performed against the bias that urges the engagement features 626, 628 toward one another. The retractor mount 620 is then moved relative to the retractor 750 such that a portion of the retractor 750 is positioned between the engagement features 626, 628. The clamp elements 622, 624 are then released, and the engagement features 626, 628 move toward one another to the closed position and engage the retractor 750. Next, the actuator 640 is rotated to compress the clamp elements 622, 624 together and hold them in the closed position, secured to the retractor 750. Alternately, the retractor mount 620 is connected to the retractor 750 in a different manner.

The transfer clamp assembly 670 is then connected to the retractor mount 620. For example, the extension arm 674 is snapped into engagement with the clip 650 of the holder 648, where the clip 650 holds the extension arm 674 by a pressure fit. The transfer clamp assembly 670 is then rotated to a desired position, by rotating the holder 648. The holder 648 is retained in the desired position by engagement between the stub or stubs 662 of the holder 648 and the corresponding trough or troughs 658 of the refractor mount 620. The transfer clamp assembly 670 may be connected and/or oriented relative to the retractor mount 620 in a different way, if desired.

Next, referring to FIG. 87, the arms 744 of the graft manipulator 740 are pressed together by the user, overcoming the bias that urges the distal ends of the arms 744 apart. As a result, the prongs 748 of the graft manipulator 740 are brought into proximity with or contact with one another. The prongs 748 are then inserted into the lumen of the graft vessel 404, and pressure on the arms 744 of the graft manipulator 740 is gradually released. The prongs 748 move apart due to the biasing apart of the distal ends of the arms 744, resulting in the end of the graft vessel 404 flattening and becoming taut. The force exerted by the graft manipulator 740 is controlled such that the end of the graft vessel 404 is flattened, but not damaged or overly stretched. Such force control is accomplished such as by selecting the material and size of the base 746 of the graft manipulator 740, as described above. Optionally, the graft vessel 404 may be marked, such as with ink, along a length thereof. Referring also to FIG. 73, this marking may end at or near the location on the graft vessel 404 that will be positioned at the toe 585 of the anastomosis. The toe 585 of the anastomosis is the end of the anastomosis at which the outer surface of the graft vessel 404 forms an obtuse angle with the outer surface of the target vessel. The heel 587 of the anastomosis is the opposite end of the anastomosis, at which the outer surface of the graft vessel 404 forms an acute angle with the outer surface of the target vessel.

Referring also to FIG. 83, the user then compresses the finger pads 698 toward one another, causing the arms 682 of the transfer clamp 672 to move to the open position against the bias that urges them toward the closed position. Referring also to FIG. 87, the graft manipulator 740 is then moved relative to the transfer clamp 672 to place the graft vessel 404 between the arms 682 of the transfer clamp 672. The graft vessel 404 is placed between the arms 682 such that it is located between the opposed jaws 700 of the arms 682. The cutting blocks 710 are initially configured such that the ends 714 of each first element 712 is in proximity to the jaw 700 of the corresponding arm 682. The snap 724 of each cutting block 710 may engage the corresponding receiver 726 to hold the cutting block 710 in that position. Thus, the graft vessel 404 is also placed between the opposed ends 714 of the first elements 712 of the cutting blocks 710. The graft vessel 404 may be oriented such that the marked toe of the graft vessel 404 is oriented distally.

The graft manipulator 740 is used to angle the graft vessel 404 relative to the edges 715 of the cutting blocks 710 such that one end of each edge 715 is positioned substantially at one side of the graft vessel 404 and the other end of each edge 715 is positioned substantially at the opposite side of the graft vessel 404. As described above, this defines a chord of a known length across the graft vessel 404. Advantageously, the graft vessel 404 is positioned such that its end extends at least 5 millimeters above the edges 715 of the cutting blocks 710. Because the transfer clamp assembly 670 is held by the retractor mount 620, a single user can manipulate the graft vessel 404 relative to the transfer clamp 672 easily.

Figure 88:
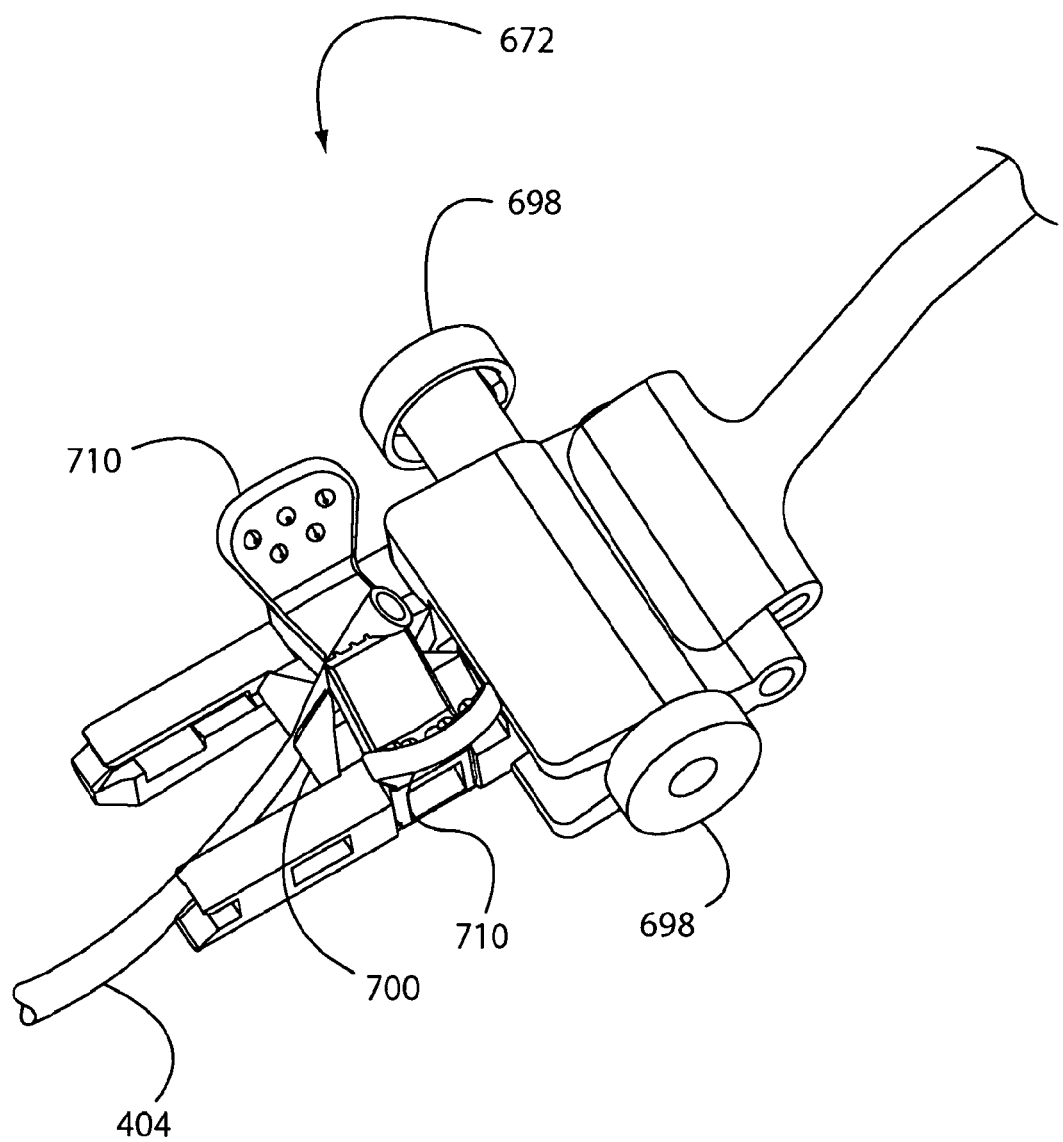
FIG. 88 is a perspective view of the transfer clamp of FIG. 81 holding a graft vessel.

The finger pads 698 are then released by the user, allowing the arms 682 of the transfer clamp 672 to return to a closed position. Referring also to FIG. 88, the jaws 700 and the ends 714 of the first elements 712 of the cutting blocks 710 close onto and hold the graft vessel 404. The gripping surfaces 704 of the jaws 700 and the gripping surfaces 720 of the cutting blocks 710 facilitate engagement with the graft vessel 404, such that the graft vessel 404 is held securely in the selected orientation. That is, the jaws 700 and/or cutting blocks 710 hold the graft vessel 404 at the selected angle relative to the edges 715 of the cutting blocks 710. That selected angle is related to the constant-length chord defined on the graft vessel 404 by the edges 715 of the cutting blocks 710. The graft vessel 404 can be reoriented by compressing the finger pads 698 together again and moving the graft manipulator 740 relative to the transfer clamp 672. The arms 744 of the graft manipulator 740 are then compressed together again such that the prongs 748 can be removed from the lumen of the graft vessel 404, and the graft manipulator 740 is set aside.

Figure 89:
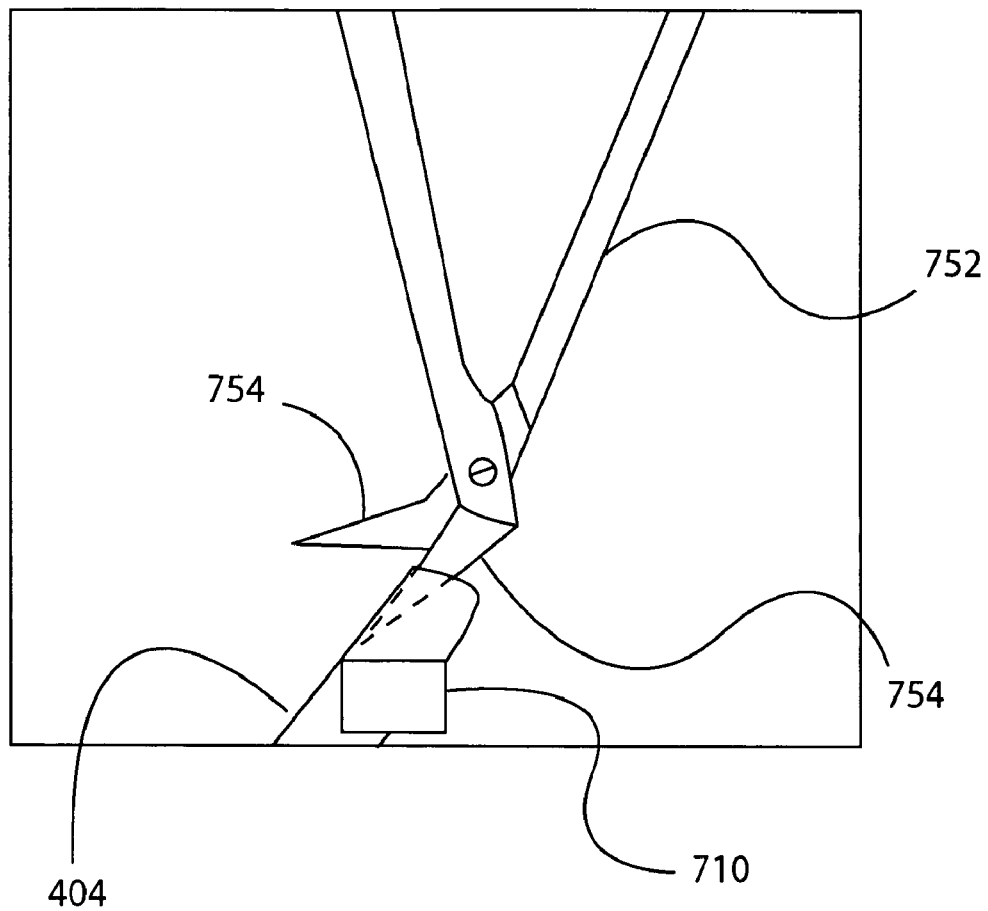
FIG. 89 is a schematic side view of the graft vessel held within the transfer clamp.
Figure 90:
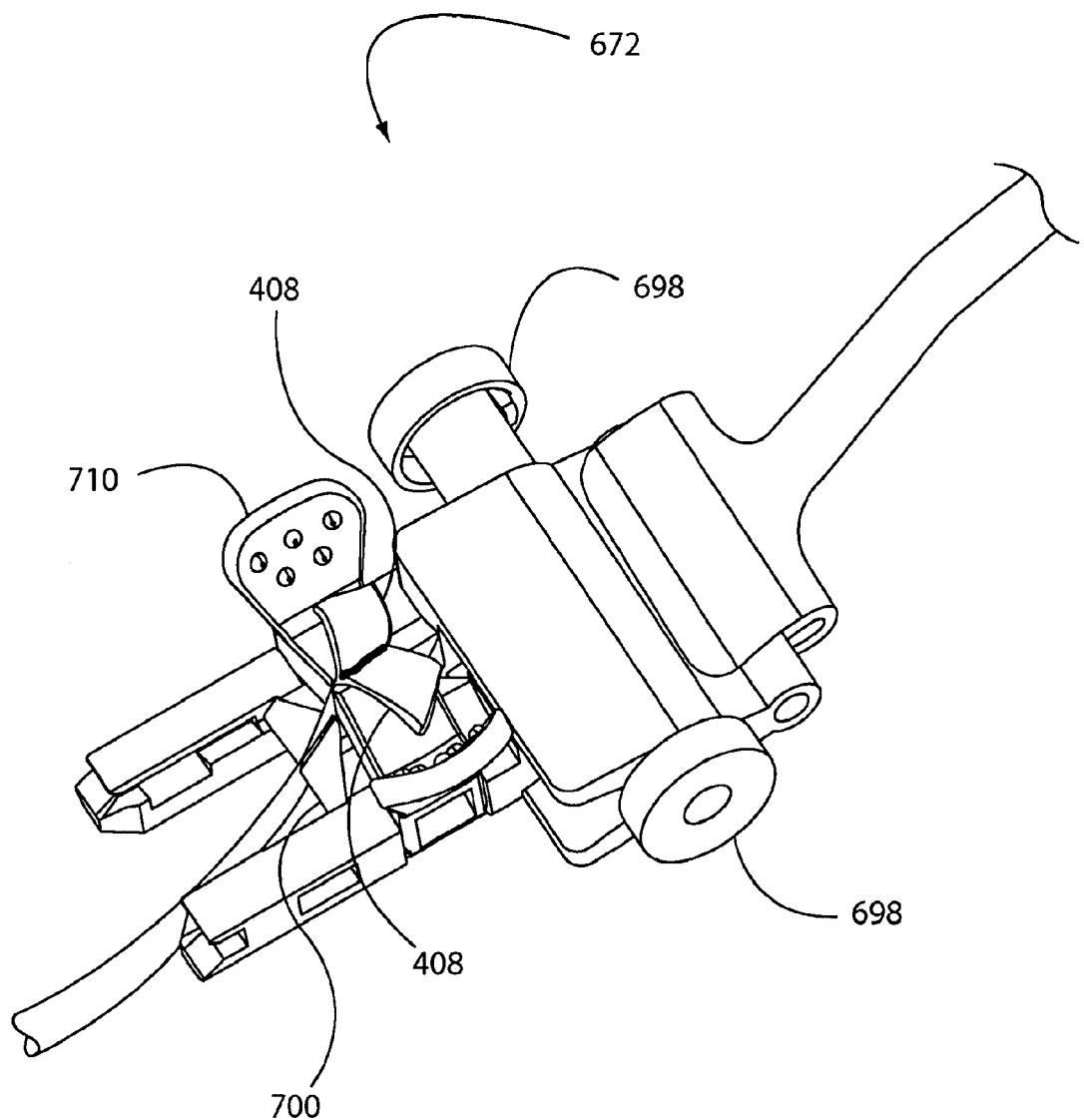
FIG. 90 is a perspective view of the transfer clamp of FIG. 81 holding a graft vessel, at the end of which flaps have been formed.

One or more flaps 408 are then created in an end of the graft vessel 404. Referring also to FIG. 89, a scissors 752 may be used to create the flaps. The scissors 752 have two jaws 754 movable relative to one another. The scissors 752 may be Potts scissors or any other appropriate surgical scissors. The jaws 754 of the scissors are moved apart from one another, and one of the jaws 754 is inserted into the lumen of the graft vessel 404. The scissors 752 are then closed to make a substantially straight incision in the graft vessel 404 substantially longitudinally along the graft vessel 404. Advantageously, the first incision is made along the line marked on the outer surface of the graft vessel 404. The incision is continued until the upper surfaces of the second elements 718 of the cutting blocks 710 are reached. That is, the upper surfaces of the second elements 718 of the cutting blocks 710 act as stops. A second incision is then made in the end of the graft vessel 404, substantially opposite from the first incision. The second incision is also substantially straight and substantially longitudinal, and is stopped by the upper surfaces of the second elements 718 of the cutting blocks 710. As a result of the two incisions, two tissue flaps 408 are created, each of which ends substantially at the upper surfaces of the second elements 718 of the cutting blocks 710. Thus, as described above, the length of the root 405 of each flap 408 is substantially equal to the anastomosis length 770 and to the length of the upper edge 715 of each cutting block 710. The flaps 408 are substantially the same size and shape as one another. Alternately, the flaps 408 are sized and/or shaped differently. Alternately, only a single incision is made in the graft vessel 404 to form a single flap 408, or more than two incisions are used to create more than two flaps 408. Alternately, a scalpel or other mechanism or structure may be used instead of or in addition to the scissors 752 to create the flap or flaps 408 at the end of the graft vessel 404.

Figure 91:
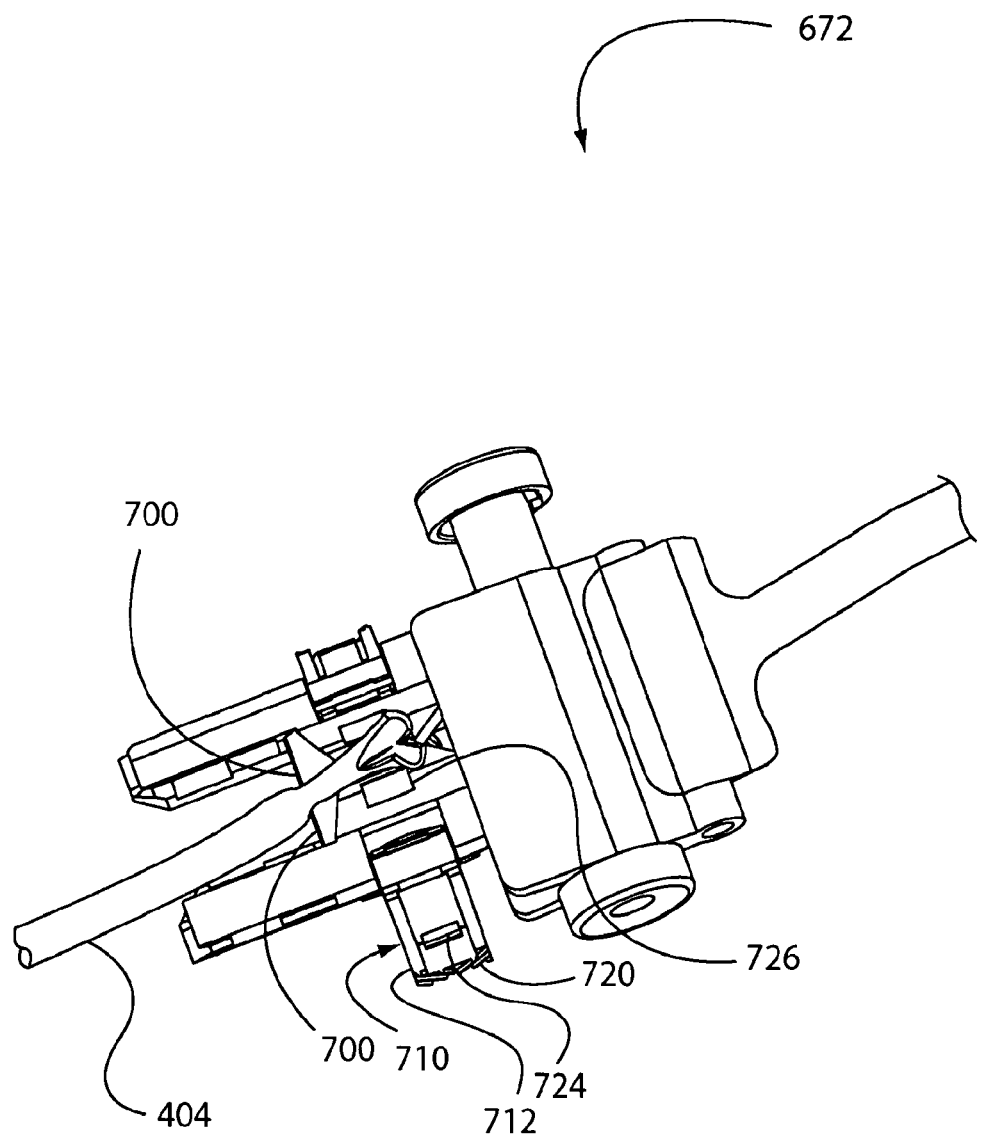
FIG. 91 is a perspective view of the transfer clamp of FIG. 81 holding a graft vessel, with cutting blocks in an open position.

Referring also to FIG. 91, after the incisions have been made in the graft vessel 404, the cutting blocks 710 are moved to the open position, such that the ends 714 of the first elements 712 of the cutting blocks 710 are positioned away from the graft vessel 404. Where a snap or snaps 724 are used, the snap or snaps 724 are disengaged from the corresponding receiver or receivers 726. Each cutting block 710 may be disengaged from the corresponding receiver 726 and/or moved to an open position by gripping or pushing the gripping surface 720 on the second element 718 of the cutting block 710. The cutting blocks 710 are configured to rotate from the open to the closed position, as described above. Alternately, at least one cutting block 710 is configured to slide relative to the corresponding arm 744, or rotate about an axis that is not parallel to the axis of rotation of a different cutting block 710. Alternately, the cutting blocks 710 may be configured to be completely removed from the transfer clamp 672 rather than moved to an open position. After the cutting blocks 710 have been moved to the open position, the jaws 700 hold the graft vessel 404 in place at substantially the same angle at which it was previously held, as a result of the bias urging the arms 682 and thus the jaws 700 together. The cutting blocks 710 may be moved to the open position to avoid interference with the staple holder 38 or other component of the anastomosis tool 300 when the transfer clamp assembly 670 engages at least part of the anastomosis tool 300. Alternately, the cutting blocks 710 may be configured to remain in the closed position and avoid interference with the staple holder 38 or other component of the anastomosis tool 300. If so, at least one cutting block 710 optionally may be integrated with the corresponding jaw 700. Alternately, at least one cutting block 710 is omitted altogether, such that there is no need to move cutting blocks 710 from an open position to a closed position. Instead, the incision or incisions made to create the flaps 408 are stopped by surfaces of the jaws 700, arms 744 and/or other structure or structures.

Figure 92:
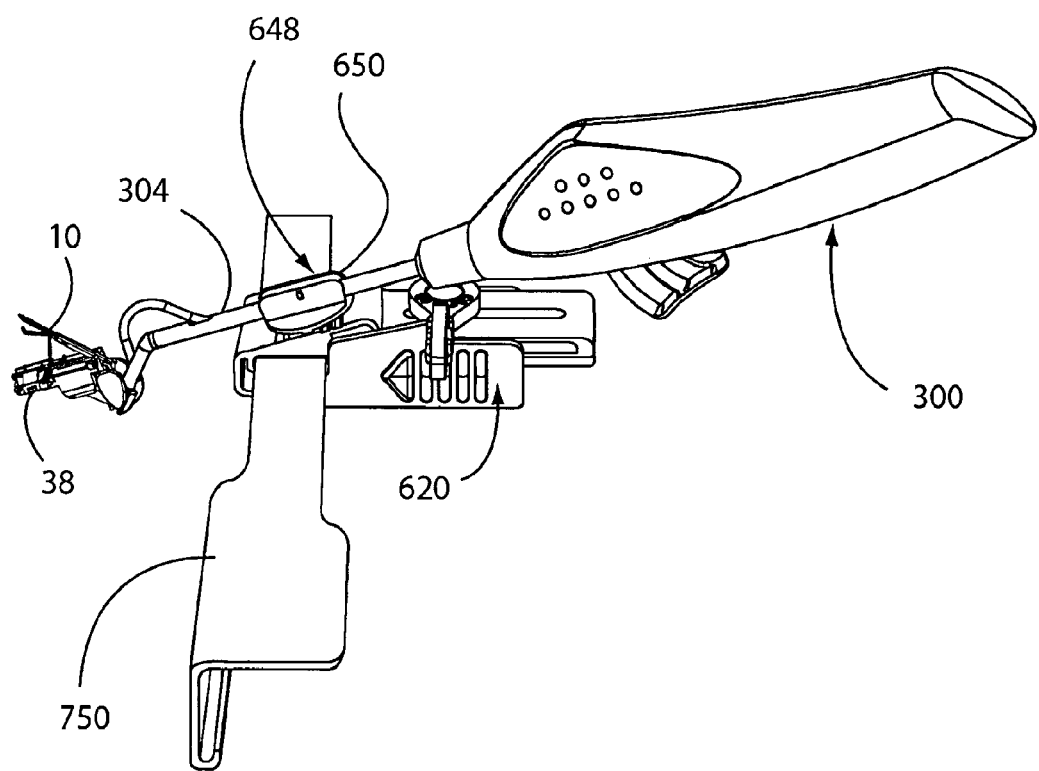
FIG. 92 is a perspective view of an anastomosis tool connected to the retractor mount of FIG. 79.

The transfer clamp assembly 670 is then disconnected from the retractor mount 620, and held by the user or rested in a secure position within the patient's chest. Alternately, the transfer clamp assembly 670 may be held by another person, or placed in a different location. Referring also to FIG. 92, the anastomosis tool 300 is then connected to the retractor mount 620. For example, the shaft 304 of the anastomosis tool 300 may snap into the clip 650 of the holder 648, wherein the clip 650 holds the shaft 304 with a pressure fit. However, the anastomosis tool 300 may be connected to the retractor mount 620 in a different way, if desired. The anastomosis tool 300 may be oriented such that the anvil 10 is oriented substantially upward. Where the graft clips 412 are used, they are moved to the open position if they are not already in the open position.

Next, the transfer clamp 672 is slid onto the staple holder 38. Referring also to FIGS. 57 and 59C-D, the staple holder 38 includes one or more wings 760 extending outward therefrom. Each wing 760 may include at least one bump 762 defined thereon. The bump or bumps 762 may be positioned on an upper surface of the corresponding wing 760, and may be oriented substantially laterally. As the transfer clamp 672 is moved toward the staple holder 38, each wing 760 of the staple holder 38 is received into a corresponding slot 756. The shape of the slots 756 defines the path of travel of the transfer clamp 672 relative to the wings 760 and therefore relative to the staple holder 38. Advantageously, the slots 756 are substantially linear, resulting in translation of the transfer clamp 672 relative to the staple holder 38. However, the slots 756 may define a different path if desired. As the transfer clamp 672 slides relative to the staple holder 38, each flap 408 slides between the anvil 10 and an arm 402 of the staple holder 38. The flaps 408 may be held with forceps or another tool or tools during this sliding. As the transfer clamp 672 slides relative to the wings 760, the bump 762 on at least one wing 760 enters the corresponding slot 756. The combined thickness of the wing 760 and the bump 762 is slightly larger than the height of the slot 756. However, the material of the wing 760 and bump 762, and/or the material of the corresponding arm 682, has enough compliance to allow for compression of the wing 760 and bump 762 and/or expansion of the corresponding slot 756. Further, the entrance to each slot 756 is shaped and/or finished to allow smooth entry of the bump 762 into that slot 756. As each bump 762 continues to translate, it enters a corresponding notch 759. The height of the notch 759 is larger than the height of the slot 756 and at least as large as the combined thickness of the wing 760 and bump 762, thereby allowing the bump 762 to move into that notch 759 freely.

Sliding of the transfer clamp 672 continues until each wing 760 encounters the wall 758 at the proximal end of the corresponding slot 756, at which time motion of the transfer clamp 672 stops. Each notch 759 has a substantially vertical distal end 761. Motion of the transfer clamp 672 away from the wall 758 causes contact between the distal end 761 of the notch 759 and the bump 762. This contact prevents the bump 762 from re-entering the slot 756, and thereby prevents the transfer clamp 672 from disconnecting from the staple holder 38. That is, the notches 759 and corresponding bumps 762 provide for positive engagement between the transfer clamp 672 and the staple holder 38. At the time translation of the transfer clamp 672 stops, the bump 762 of each wing 760 may be in close proximity to the distal end 761 of each notch 759, or in contact with the distal end 761 of each notch 759. This proximity limits the linear travel of the transfer clamp 672 relative to the staple holder 38 while the two are connected together. By minimizing or substantially elimination motion between the transfer clamp 672 and the staple holder 38 after positive engagement with one another, the staple holder 38 and the transfer clamp 672 are registered relative to one another in a desired position. The flaps 408 are thereby registered with the staple holder 38 in a desired position relative to the flap receiving surfaces 406 and/or other elements of the staple holder 38. In this way, the transfer clamp 672 reliably positions the flaps 408 at a preselected location relative to the staple holder 38. This preselected location is such that each flap 408 is positioned in proximity to a corresponding flap receiving surface 406, and such that each flap 408 extends distal to the most distal connector bay 448 of the arm 402 of the staple holder 38 and proximal to the most proximal connector bay 448 of the arm 402 of the staple holder 38. In this way, each flap 408 is positioned relative to the staple holder 38 such that each connector 464 held within the corresponding arm 402 of the staple holder 38 is deployable through that flap 408. Next, referring also to FIGS. 58-59, each flap 408 is draped onto the corresponding flap receiving surface 406 of the corresponding arm 402. Forceps or a different tool may be used to place each flap 408 onto at least one spike 410 extending from the flap receiving surface 406. The shims 702 are configured to hold the graft vessel 404 substantially in the middle thereof, in order to facilitate draping the flaps 408 onto the spikes 410 without substantially crinkling the flaps 408 or the graft vessel 404. Each shim 702 extends above the corresponding jaw 700 to a location below the upper edge 715 of the corresponding cutting block 710. Thus, after the cutting blocks 710 are moved to the open position, the shims 702 hold the graft vessel 404 at a location spaced apart from and underneath the flaps 408. This space between the shims 702 and the flaps 408 allows the flaps 408 to be tensioned when placed on the spikes 410. The flaps 408 are tensioned when they are placed onto the spikes 410, without tensioning them to the point where tissue elasticity is lost. By providing tension in the flaps 408, particularly at the locations on the flaps 408 that correspond to the heel 587 and the toe 585 of the anastomosis, sealing of the anastomosis is facilitated. After the flap 408 is placed onto one or more spikes 410, the poke-through tip 678 of the extension arm 674 is used to push the flap 408 down onto the one or more spikes 410. The spike or spikes 410 then hold the corresponding flap 408 in place. Advantageously, each flap 408 engages two or more spikes 410, and each flap 408 is held substantially taut.

The spikes 410 alone are sufficient to hold the flaps 408 onto the arms 402 of the staple holder 38. Where graft clips 412 are used, the graft clips 412 are moved to the closed position after the flaps 408 have been pushed down onto the spikes 410. The graft clips 412 provide additional holding force to secure the flaps 408 to the arms 402 of the staple holder 38. Optionally, where the arms 410 of the staple holder 38 are sufficiently close to one another to hold the graft vessel 404 in its unprepared state, the transfer clamp 672 may be omitted. If so, the flaps 38 may be prepared in place as the graft vessel 404 is held between the arms 410, and then secured to the spikes 410.

After the flaps 408 have been secured to the staple holder 38, the finger pads 698 are compressed to move the arms 682 of the transfer clamp 672 apart from one another. Such motion of the arms 682 also causes the arms 682 to move away from the staple holder 38, freeing it. Referring also to FIG. 84, each shim 702 extends above the corresponding jaw 700 to a location below the upper edge 715 of the corresponding cutting block 710. In this way, as the arms 682 move away from one another, the shims 702 substantially do not interfere with the staple holder 38, allowing the transfer clamp 672 to be detached from the anastomosis tool 300. Alternately, the shims 702 may be flexible, and may be positioned higher relative to the upper edge 715 of the corresponding cutting block. In this way, the shims 702 flex upon contacting the staple holder 38, allowing the transfer clamp 672 to open and release the staple holder 38. The anastomosis tool 300 is ready for performing anastomosis, and the transfer clamp assembly 670 may be set aside.

Alternately, where the staple holder 38 includes a graft affixer 910, the graft vessel 404 may be prepared differently, without the use of the retractor mount 620, the transfer clamp assembly 670, and/or the graft manipulator 740. Referring to FIG. 133, a single incision 924 is made at an end of the graft vessel 404. The incision 924 extends substantially longitudinally along the graft vessel 404. The incision 924 may be made with any appropriate surgical tool, such as a Potts scissors. When the incision 924 is made, the graft vessel 404 may be held by hand, with a surgical clamp, or in any other suitable manner. Advantageously, the incision 924 is substantially one centimeter long, although it may be longer or shorter if desired.

Referring also to FIGS. 130-132 and 134, the graft vessel 404 is moved between the arms 402 of the staple holder 38, such that the incised end thereof is in proximity to the staple holder 38. The graft vessel 404 is then connected to the graft affixer 910. Advantageously, a location on the graft vessel 404 close to and proximal to the incision 924 is connected to the graft affixer 910; this location corresponds to the heel of the anastomosis to be performed and may be referred to as the heel of the graft vessel 404. Alternately, a different location on the graft vessel 404 is connected to the graft affixer 910. The graft vessel 404 is connected to the graft affixer 910 in any suitable manner. As one example, where the graft affixer 910 is a spike, the graft vessel 404 is pushed down onto the spike or the leg 1150 such that it penetrates a wall of the graft vessel 404 in whole or in part. The graft vessel 404 may be everted onto the spike or the leg 1150. A poke-through tip 678 such as described above, or similar structure or mechanism, optionally may be provided and utilized to push the graft vessel 404 onto the spike or the leg 1150. The poke-through tip 678 may be connected to a rod or other member (not shown) to facilitate its use. Similarly, where the graft affixer 910 is a hook, the graft vessel 404 is pushed onto the hook such that it penetrates a wall of the graft vessel 404 in whole or in part. As another example, where the graft affixer 910 is a clip, the graft vessel 404 is clipped and held by the clip. The graft vessel 404 may be everted into the clip. Where the graft affixer 910 is configured differently, the graft vessel 404 is connected to it in any suitable manner.

Next, the graft vessel 404 is angled relative to the arms 402 of the staple holder 38, as the heel of the graft vessel 404 is held substantially at a known position by the graft affixer 910. That is, the graft affixer 910 registers the heel of the graft vessel 404 to the staple holder 38. The graft vessel 404 is angled relative to at least one measurement feature 922 such that one end of the measurement feature 922 is positioned substantially at one side of the graft vessel 404 and the other end of the measurement feature 922 is positioned substantially at the opposite side of the graft vessel 404. That is, the graft vessel 404 is positioned such that at least one measurement feature 922 defines a chord across the graft vessel 404. In this way, the end of the graft vessel 404 can be prepared to a substantially constant preselected length corresponding to the length of at least one measurement feature 922. Further, graft vessels 404 of different widths each can be handled simply by changing the angle of the graft vessel 404 relative to at least one measurement feature 922. The length of the chord across the graft vessel 404 is substantially equal to the anastomosis length 770. The arteriotomy length 772 may be substantially constant across different sizes of graft vessel 404. By ensuring that the graft vessel 404 is prepared substantially to a preselected chord length relative to the staple holder 38 across a spectrum of sizes of graft vessels 404, the anastomosis length 770 in turn is ensured to be longer than the arteriotomy length 772, thereby preventing leakage.

The flap 408 is then everted onto the arms 402 of the staple holder 38. If one or more spikes 410 extend outward from at least one of the flap receiving surfaces 406 of the staple holder 38, the flap 408 is everted onto one or more of those spikes 410. As the flap 408 is placed onto the corresponding flap receiving surface 406, one or more of the spikes 410 penetrate the flap 408 partially or completely, thereby assisting in holding the flap 408 in place against the flap receiving surface 406. The poke-through tip 678 or other tool optionally may be used to push the flap 408 down onto the one or more spikes 410. The spike or spikes 410 then hold the corresponding flap 408 in place. Advantageously, each flap 408 engages two or more spikes 410, and each flap 408 is held substantially taut. Alternately, at least one graft clip 412 is used to hold the flap 408 to the staple holder 38, instead of or in addition to at least one spike 410.

Optionally, referring to FIG. 155, the tissue effector 400 may be movable to a graft preparation position relative to the shaft 304. In the graft preparation position, the staple holder 38 is oriented at least partially upward, or at least partially toward the user, to facilitate the connection of the graft vessel 404 to it. The tissue effector 400 may be movable to the graft preparation position in any suitable manner. As one example, the shaft 304 may simply be rotated about its longitudinal axis within the clip 650 of the retractor mount 620, such that the staple holder 38 is oriented at least partially upward. As another example, where the cog 282 is used, the user may depress at least one of the buttons 278, disengaging the teeth 284 of the cog 282 from the detents 310 of the receiving opening 309. The tissue effector 400 is then rotated to the graft preparation position. The buttons 278 are then released, allowing the teeth 284 of the cog 282 to engage once again the detents 310 of the receiving opening 309. The cog 282 is thus held securely in place in its new orientation. As another example, where the articulated shaft includes a hinge 956 and a locktab 954 such as shown in FIGS. 140-141, the tissue effector 400 may be rotated about the hinge 956 until it reaches the graft preparation position. The locktab 954 is then rotated about the locktab hinge 958 from the first position to the second position, thereby substantially locking the tissue effector 400 in place in the graft preparation position.

Preparation of the graft vessel 404, where the graft affixer 910 is used, has been described in terms of a graft vessel 404 having a single incision 924 at an end thereof, such that a single flap 408 is formed. However, a graft vessel 404 having multiple incisions 924 in an end thereof, and therefore multiple flaps 408, may be utilized with a staple holder 38 having a graft affixer 910. Alternately, no flaps 408 are present in the graft vessel 404, and the end of the graft vessel 404 is everted onto the graft affixer 910. Further, the refractor mount 620, the transfer clamp assembly 670, and/or the graft manipulator 740 need not be used in conjunction with a staple holder 38 having a graft affixer 910. However, one or more of those tools may be used, if desired.

Operation of Anastomosis Tool—Pre-Deployment Configuration

Referring also to FIG. 70, the anastomosis tool 300 is initially in a pre-deployment configuration. In this configuration, the distal arm 518 of the rocker 508 is at an uppermost position, the trigger 308 correspondingly extends outward from the handle 302 to its greatest extent, and the proximal arm 514 of the rocker 508 is at a lowermost position. The distal end 520 of the distal arm 518 of the rocker 508 may engage the contact surface 548 of the distal slider 534 at or near the uppermost end of the contact surface 548. This contact may be between the posts 544 of the distal arm 518 and the contact surface 548, and/or between another portion of the distal arm 518 and the contact surface 548. The stops 596 of the holder 594 hold the distal slider 534 substantially in place against the proximal bias exerted by the spring 540. Alternately, where the holder 594 is not used, contact between the rigid distal arm 518 and the contact surface 548 holds the distal slider 534 substantially in place against the proximal bias exerted by the spring 540. In the pre-deployment configuration, the proximal end 516 of the proximal arm 514 may be spaced apart from the lower portion 530 of the proximal slider 522, or may be in contact with the lower portion 530 of the proximal slider 522. The proximal slider 522 is biased distally to its most distal possible position. Alternately, the proximal slider 522 is positioned differently in the pre-deployment configuration. Alternately, the rocker 508 and/or the trigger 308 may be in a different position in the pre-deployment configuration, particularly where the rocker 508 and/or trigger 308 are shaped or configured differently than shown in FIG. 70. If so, the rocker 508 may engage the proximal slider 522 and/or the distal slider 534 in a different manner than described above.

Figure 77:
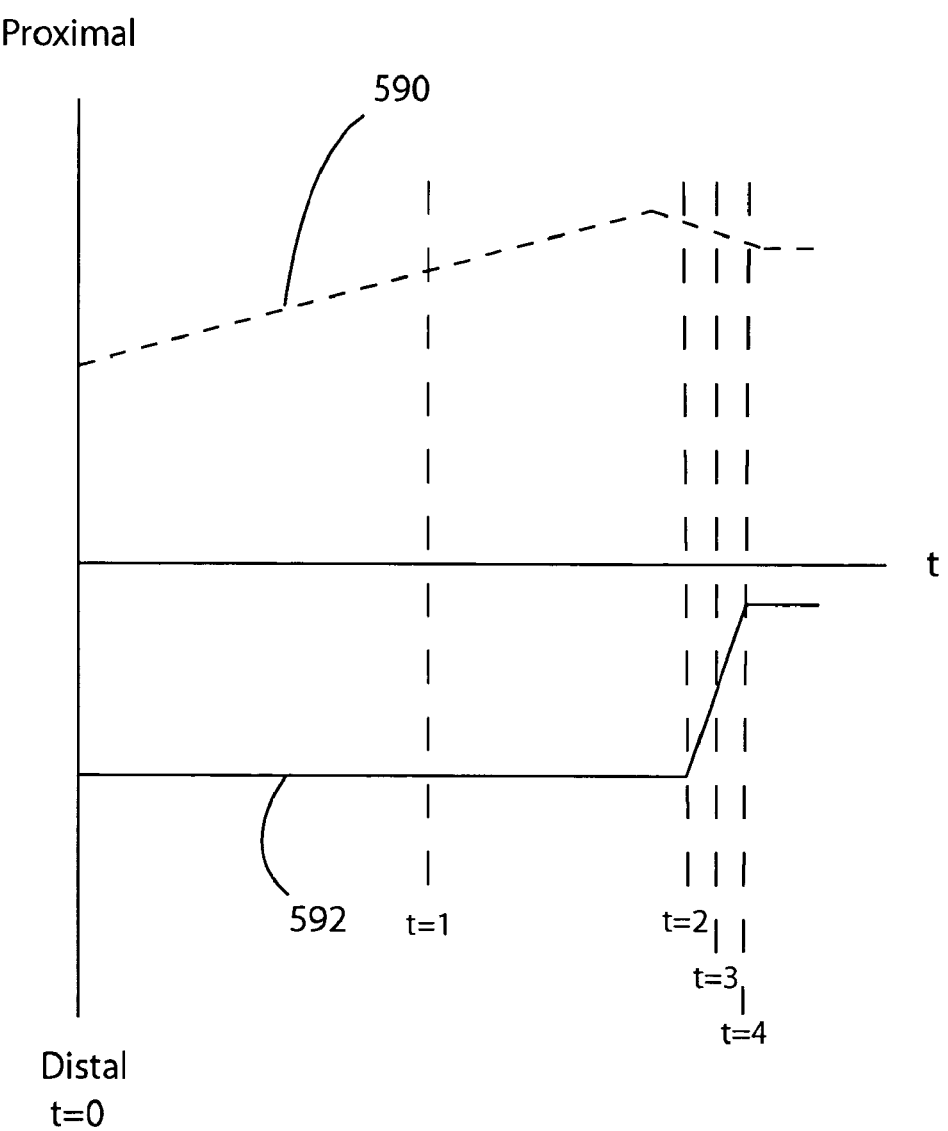
FIG. 77 is a graph qualitatively illustrating the positions of the distal slider and the proximal slider of the handle over time, with regard to an arbitrary point between them.

Referring also to FIG. 77, when the handle 302 is in the pre-deployment configuration, the time is t=0. The position 590 of the proximal slider 522 is at an initial position, and the position 592 of the distal slider 534 is also at an initial position. The positions 590, 592 of the sliders 522, 534 on the graph of FIG. 77 are qualitative, and are shown with respect to an arbitrary point selected between them. That is, the graph of FIG. 77 illustrates an exemplary set of motions of the sliders 522, 534 over time.

The first cable or cables 480 are connected to the proximal slider 522 and the second cable 490 is connected to the distal slider 534, as described above. In the pre-deployment configuration, both cables 480, 490 include some slack, such that a small initial motion of the trigger 308 takes up the slack and causes the cables 480, 490 to become tensioned. In this way, small motions of the trigger 308 before deployment is intended do not begin the actuation of the anastomosis tool 300. Alternately, one or more of the cables 480, 490 are tensioned in the pre-deployment configuration.

Figure 72:
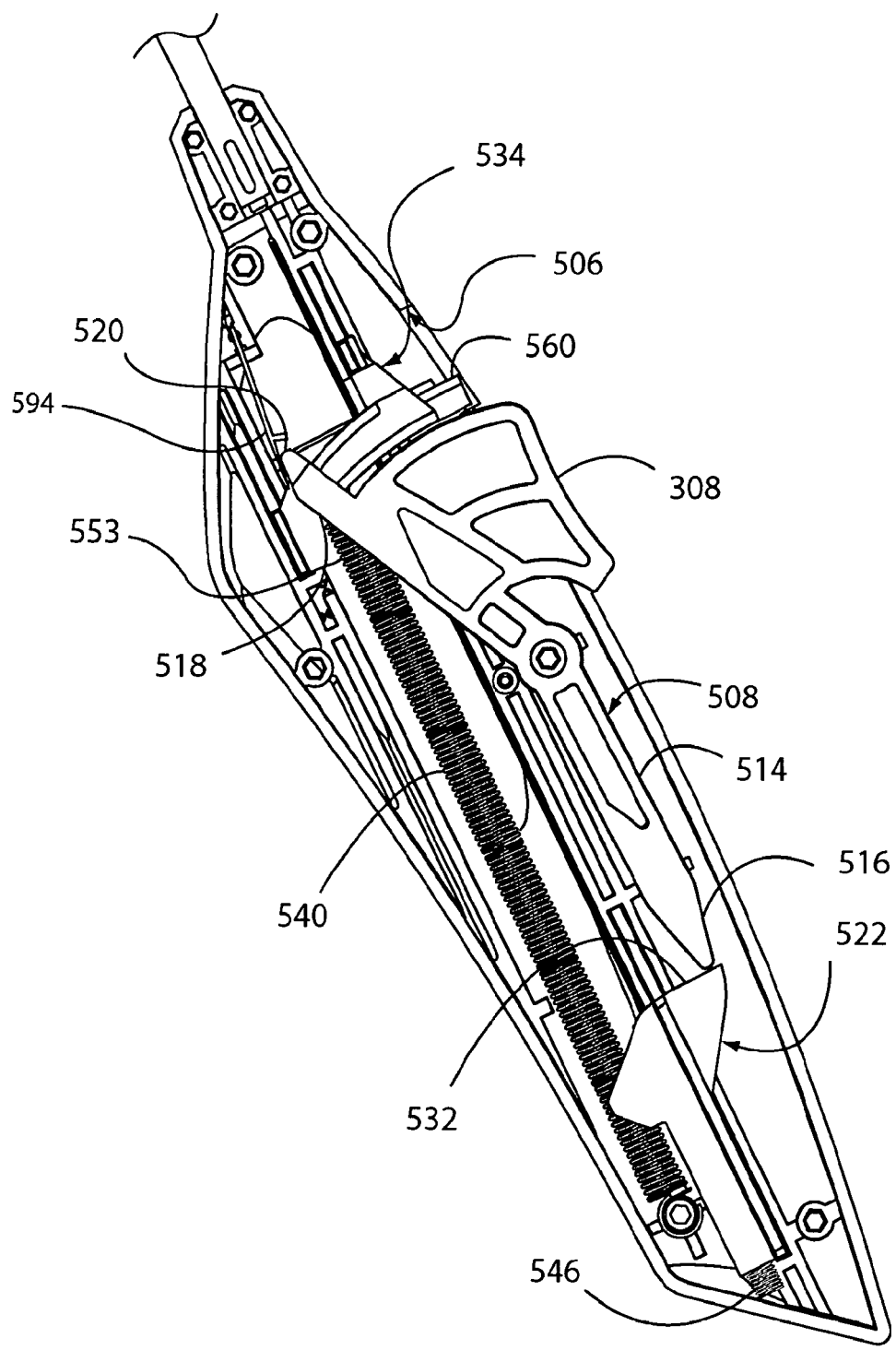
FIG. 72 is a side cross-section view of the handle of FIG. 55 in a second position.

The second cable 490 is also connected to the sled 482 in the tissue effector 400, as described above. Referring also to FIGS. 64 and 68-69, in the pre-deployment configuration the sled 482 is positioned such that each ramp element 446 is located within the corresponding passage 440 in the corresponding arm 402, proximal to the connector bays 448. Similarly, in the pre-deployment configuration the sled 482 is positioned such that each vein knife 432 is located proximal to the vein flap 408 held between the graft clip 412 and the corresponding flap receiving surface 406. Alternately, the sled 482 is positioned differently in the pre-deployment configuration. For example, each ramp element 446 may be positioned initially in a location distal to the connector bays 448. Referring also to FIG. 72, each flap 408 is held between a graft clip 412 and a flap receiving surface 406 as described above, such that the graft vessel 404 extends between the arms 402 of the tissue effector 400. The flaps 408 are held on the undersides of the arms 402. Each flap 408 may be held by the corresponding graft clip 412 such that a portion of the flap 408 at its root 405, which is the portion of the flap 408 at or in proximity to its intersection with the tubular portion of the graft vessel 404, is exposed. The root 405 of each flap 408 may be positioned to contact the outer surface of the target vessel 580, as described in greater detail below.

Optionally, the orientation of the tissue effector 400 may be changed relative to the handle 302. Thus, the tissue effector 400 can be oriented relative to the target vessel such that the anvil arm 14 is aligned with it, and the handle 302 can be placed in a convenient position for the user. As one example, to re-orient the tissue effector 400, the user depresses the buttons 278, disengaging the teeth 284 of the cog 282 from the detents 310 of the receiving opening 309. The tissue effector 400 is then rotated to the desired orientation. The buttons 278 are then released, allowing the teeth 284 of the cog 282 to engage once again the detents 310 of the receiving opening 309. The cog 282 is thus held securely in place in its new orientation. As another example, where the articulated shaft includes a hinge 956 and a locktab 954 such as shown in FIGS. 140-141, the tissue effector 400 is rotated about the hinge 956 until it reaches the desired position. The locktab 954 is then rotated about the locktab hinge 958 from the first position to the second position, thereby substantially locking the tissue effector 400 in place in the selected position.

Operation of Anastomosis Tool—Anvil Insertion

Figure 75:
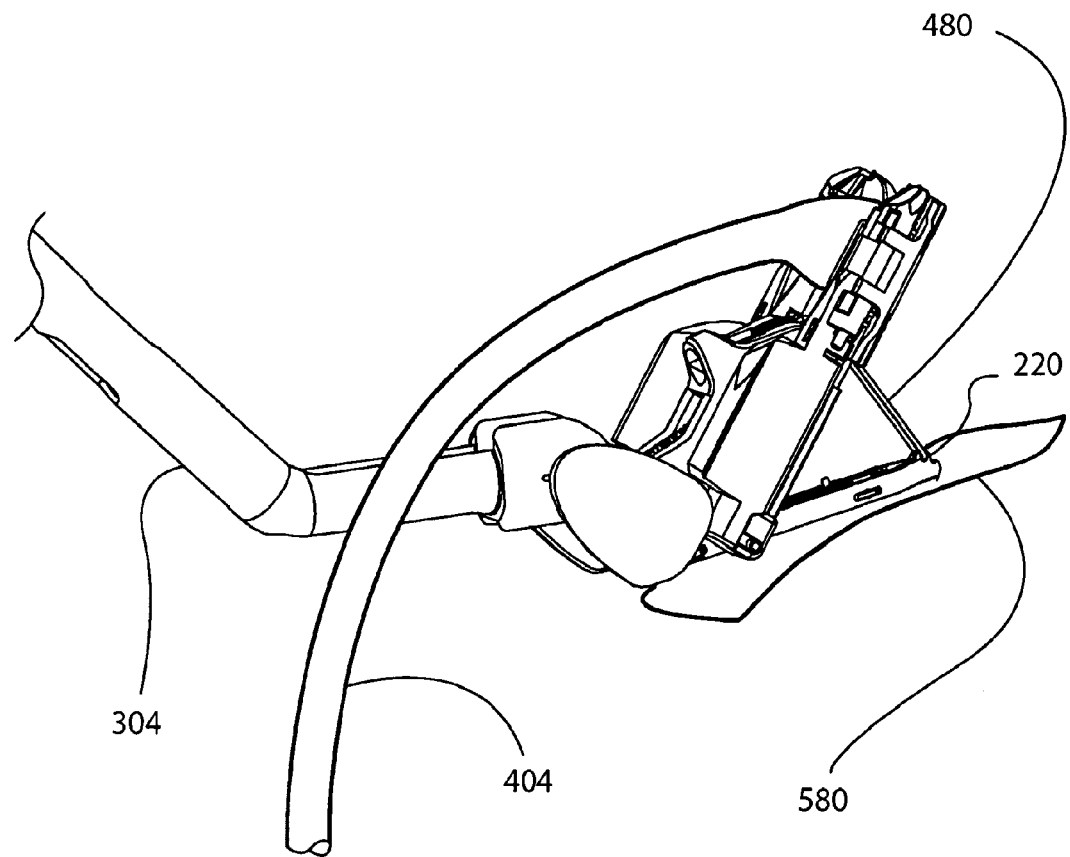
FIG. 75 is a perspective view of the tissue effector of FIG. 74, where the anvil of the tissue effector has been inserted into the lumen of a target vessel.

Referring to FIGS. 34 and 74, in the pre-deployment configuration, the distal end of the anvil arm 14 is spaced apart from the staple holder 38. Referring also to FIG. 75, the anvil arm 14 is inserted through the wall of the target vessel 580. The target vessel 580 may be a coronary artery, if the anastomosis tool 300 is used in the course of a CABG procedure, or any other appropriate bodily vessel or structure. Advantageously, the anvil arm 14 has a cross-section small enough to allow it to enter the target vessel 580 easily and to result in minimal or no leakage from the target vessel after the anvil arm 14 is removed. The distal tip of the anvil arm 14 may be sharp such that the anvil arm 14 itself penetrates the wall of the target vessel 580, resulting in an opening in the wall of the target vessel 580 substantially the same size as the cross-section of the anvil arm 14. Alternately, a sharp retractable projection, such as but not limited to the blade 78 of FIGS. 13-14 or the blade 84 of FIGS. 15-16, is provided at the distal end of the anvil arm 14. The retractable projection is extended to allow the distal end of the anvil arm 14 to penetrate the wall of the target vessel 580, then retracted into the anvil arm 14. The retractable projection may be a wire, a blade, a substantially conical member, a screw or a screw-tipped rod, or any other sharp structure or mechanism capable of penetrating the wall of the target vessel 580. Such a retractable projection alternately may be as described in U.S. patent application Ser. No. 10/134,081, which is herein incorporated by reference in its entirety. As another example, a separate mechanism or structure is used to penetrate the wall of the target vessel 580, and the anvil arm 14 is later inserted through that penetration. If so, the distal end of the anvil arm 14 may be substantially blunt. Alternately, the cutter 200 includes a sharp point at its distal end, where that sharp point extends out of the distal end of the anvil arm 14 to puncture the wall of the target vessel 580. If so, the cutter 200 may be actuated in a direction the reverse of that described below.

Referring also to FIGS. 36 and 75, after insertion, the distal end of the anvil arm 14 enters the lumen of the target vessel 580. The anvil arm 14 is advanced into the target vessel 580 until a tissue stop 220 on the anvil arm 14 encounters the edge of the penetration in the wall of the target vessel 580. The tissue stop 220 is substantially flat and/or blunt, and extends upward or in another direction relative to the anvil arm 14 to increase the height and/or width of the anvil arm 14. The tissue stop 220 increases the cross-section of the anvil arm 14 such that the anvil arm 14 cannot easily move further into the penetration in the wall of the target vessel 580 after the tissue stop 220 encounters the outer wall of the target vessel 580. Because the tissue stop 220 is blunt, it does not penetrate the wall of the target vessel 580 or act to expand the size of the existing penetration. Thus, the distance between the distal end of the anvil arm 14 and the tissue stop 220 substantially determines how much of the anvil arm 14 is allowed into the lumen of the target vessel 580.

Optionally, the distal end of the anvil arm 14 is stabilized after insertion into the target vessel 580. This stabilization may be performed by, for example, extending pins (not shown) from the staple holder 38 to the anvil arm 14, where the pins act to hold the distal end of the anvil arm 14 substantially in place. The pins may be sized and shaped to fit into depressions, slots or other features on the anvil arm 14. In this way, potential deflection of the distal end of the anvil arm 14 may be further reduced without the need for increasing the stiffness of the anvil arm 14. After the connectors 464 have been deployed, the pins are retracted or otherwise moved away from the anvil arm 14, freeing it. Different or additional mechanisms, structures or methods may be used to stabilize the anvil arm 14. Optionally, a different part of the anvil arm 14 is stabilized in addition to or instead of the distal end of the anvil arm 14.

Figure 95:
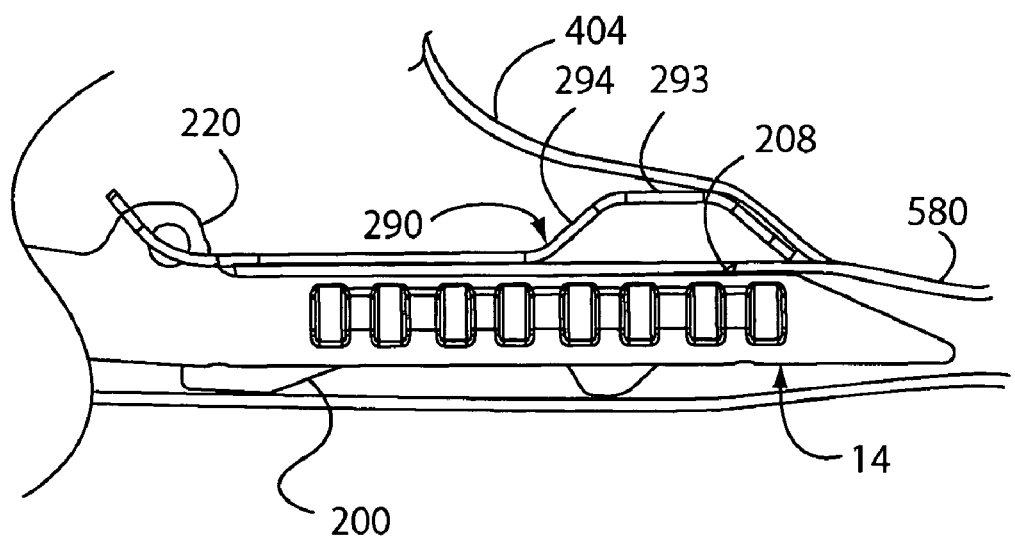
FIG. 95 is a side cross-section view of the anvil and shield of FIG. 93.

Referring also to FIGS. 93-95, when the anvil arm 14 is inserted into the lumen of the target vessel 580, the distal end of the shield 290 is spaced apart from the anvil arm 14. As a result, as the distal end of the anvil arm 14 enters the lumen of the target vessel 580, the distal end of the shield 290 is spaced apart from the distal end of the anvil arm 14 and does not enter the anvil entry hole 584. Consequently, the shield 290 remains outside the target vessel 580, and at least part of the shield 290 may be spaced apart from the wall of the target vessel 580. The location of the connection between the shield 290 and the anvil 10 remains outside the target vessel 580. Alternately, referring to FIGS. 106 and 144-145, where the shield 290 is connected to the staple holder 38, the shield 290 is in greater proximity to the staple holder 38 than to the anvil arm 14. The tissue effector 400 is in the open position, with at least part of the staple holder 38 spaced apart from the wall of the target vessel 580. Consequently, the shield 290 remains outside the target vessel 580, and at least part of the shield 290 may be spaced apart from the wall of the target vessel 580.

Operation of Anastomosis Tool—Closing Tissue Effector

Next, referring to FIGS. 44 and 70, an operator depresses the trigger 308 of the anastomosis tool 300. As a result, the rocker 508 begins to rotate about the rocker axle 510, such that the distal arm 518 moves downward and the proximal arm 514 of the rocker 508 moves upward. As the trigger 308 is depressed, the distal end 520 of the distal arm 518 moves downward. The stops 596 of the holder 594 continue to hold the distal slider 534 substantially in place against the proximal bias exerted by the spring 540. Thus, the distal slider 534 does not substantially move as the trigger 308 is initially depressed. The contact surface 548 of the distal slider 534 is curved to substantially match the travel of the distal end 520 of the distal arm 518. That is, the radius of curvature of the contact surface 548 relative to the rocker axle 510 is substantially the same as the path of motion of the distal end 520 of the distal arm 518 as the rocker 508 rotates, and thus does not substantially interfere with the motion of the distal arm 518. If the holder 594 is not used, the distal end 520 of the distal arm 518 holds the distal slider 534 in substantially the same position as the distal arm 518 moves relative to the contact surface 548, due to the match between the curvature of the contact surface 548 and the motion of the distal end 520 of the distal arm 518. Alternately, the contact surface 548 is configured differently. Further, the distal slider 534 may be configured to move as the trigger 308 is initially depressed, if desired.

The proximal end 516 of the proximal arm 514 moves upward as the trigger 308 is depressed, and contacts the lower portion 530 of the contact feature 528 of the proximal slider 522 if it is not initially in contact with the proximal slider 522. As the proximal end 516 of the proximal arm 514 continues to move upward, it continues to engage the lower portion 530 of the contact feature 528 of the proximal slider 522. The lower portion 530 of the contact feature 528 is shaped such that a component of force exerted by the proximal end 516 of the proximal arm 514 on that lower surface 530 is converted into a substantially translational force acting on the proximal slider 522 to urge it proximally. As one example, the lower portion 530 of the contact feature 528 is angled proximally and downward. Further, the ribs 526 and corresponding flanges 524 of the proximal slider 522 substantially linearly constrain the motion of the proximal slider. The angle of the lower surface 530 relative to the arcuate motion of the proximal end 516 of the proximal arm 514 results in the conversion of the substantially arcuate motion of the proximal end 516 of the proximal arm 514 to substantially linear motion of the proximal slider 522.

Thus, the upward motion of the rocker 508 against the lower portion 530 of the contact feature 528 of the proximal slider 522 urges the proximal slider 522 in the proximal direction, against the bias of the spring 546 connected to the proximal slider 522 and the handle 302. Referring also to FIG. 77, this is time t=1, the proximal slider 522 has moved proximally from time t=0, and the distal slider 534 has remained in substantially the same position it occupied at time t=0. As the proximal slider 522 moves proximally, it takes up slack in the first cable or cables 480 connected thereto, if slack is present. The first cable or cables 480 are fixed to the anvil 10. Because the anvil 10 is in turn fixed relative to the shaft 304, the proximal motion of the first cable or cables 480 removes slack from, then tensions, the first cable or cables 480. The first cable or cables 480 pass through at least a portion of the cable housing 306. As described above, the cable housing 306 curves between the shaft 304 and the tissue effector 400. The tension in the first cable or cables 480 causes the cable housing 306 to move. That is, the tension in the first cable or cables 480 acts upon the flexible cable housing 306, causing its curvature to decrease. Although the cable housing 306 is at least partially flexible, the cable housing 306 possesses stiffness longitudinally. Thus, as the curvature of the cable housing 306 decreases, the distal end of the cable housing 306 moves distally. Referring also to FIG. 58, the staple holder 38 is biased away from the anvil 10 by a biasing element 475, which tends to move the tissue effector 400 to an open position. The biasing element 475 may be a coil spring, leaf spring, or any other structure or mechanism capable of applying a biasing force. When the tension in the first cable or cables 480 causes the distal end of the cable housing 306 to move distally, the distal end of the cable housing 306 exerts a force on the anvil 10 that overcomes the bias of the biasing element 475, causing the anvil 10 to rotate about a pivot point such as the pin 226 to a standby position. In this way, the anvil arm 14 remains substantially stationary within the target vessel 580, while the staple holder 38 rotates.

Alternately, where the tissue effector 400 of FIG. 154 is used, tension is applied to the first cable 480. This tension may be applied by any suitable mechanism in the handle 302, such as the spring-actuated mechanism of FIG. 70, the gas-actuated mechanism of FIGS. 148-153, or any other suitable mechanism configured to move the tissue effector 400 from an open position to a closed position and to deploy at least one connector from the tissue effector 400. The first cable 480 is routed through at least part of the anvil 10 and then upward to the staple holder 38, to which it is connected. The axle 1082 directs the first cable 480 upward to the staple holder 38. Advantageously, the axle 1082 is located at a position in the anvil 10 that remains outside the lumen of the target vessel 580. As tension is applied to the first cable 480, moving it proximally, the axle 1082 changes the direction of the motion of the first cable 480 such that it pulls the staple holder 38 toward the anvil 10. The staple holder 38 thus rotates about a pivot point such as the pin 226 until reaching the closed position. In this way, the anvil arm 14 remains substantially stationary within the target vessel 580, while the staple holder 38 rotates. Alternately, the staple holder 38 and anvil 10 may be actuated to move between the position shown in FIG. 34 and the position shown in FIG. 44 by any structure, mechanism or method.

Alternately, a second cable housing (not shown) is provided. If so, the first cable or cables 480 may extend through the cable housing 306 as described above, and the second cable or cables 490 may extend through the second cable housing. In this way, the forces exerted along the first cable or cables 480 and cable housing 306 are substantially isolated from the forces acting along the second cable or cables 490 and the second cable housing.

Referring also to FIGS. 29-31, 44 and 76, as the staple holder 38 and anvil 10 move closer together, the staple holder 38 holds a root 405 of each flap 408 against or in proximity to the outer surface of the target vessel 580. For clarity, the flaps and graft vessel are not shown in FIG. 44. That is, the roots 405 of the flaps 408 are apposed to the outer wall of the target vessel 580. As a result, a portion of the intimal layer of the graft vessel 404 at the root 405 of each flap 408 is placed against the outer wall of the target vessel 580. The flaps 408 are held by the staple holder 38 in a substantially fixed position relative to the surface of the target vessel 580, such that the end of the graft vessel 404 is substantially immobile relative to the wall of the target vessel 580. Thus, the position of the end of the graft vessel 404 relative to the wall of the target vessel 580 remains substantially unchanged throughout the duration of the anastomosis procedure. Further, after the anvil arm 14 has been inserted into the lumen of the target vessel 580, the contact surface 206 of the anvil arm 14 is substantially in contact with the inner surface of the wall of the target vessel 580. The perimeter of the end of the graft vessel 404 defines a closed area on the wall of the target vessel. The location of a connection made between the end of the graft vessel 404 and the wall of the target vessel is substantially registered with an opening made within the closed area in the wall of the target vessel, regardless of the order in which the connection and the opening are made. Further, the position of the end of the graft vessel 404 relative to the wall of the target vessel 580 substantially maintains position registration throughout the duration of the anastomosis procedure relative to the opening in the wall of the target vessel through which the anvil arm 14 is inserted.

As the staple holder 38 and anvil 10 move together, the engagement member 216 engages the receiver 218. As described above, the receiver 218 may be defined in the sled 482. However, the receiver 218 may be a separate component from the sled 482. Alternately, when the tissue effector 400 is in the closed position, the engagement member 216 of the cutter 200 or the cutter slide 1092 does not engage the receiver 218. Instead, the engagement member 216 and the receiver 218 are positioned relative to one another such that motion of the receiver 218 as a result of motion of the second cable 490, as described below, brings the engagement member 216 and the receiver 218 into contact such that the engagement member 216 is placed into motion as well. Further, if the optional safety feature 210 is utilized, the relative motion of the staple holder 38 and the anvil 10 causes the staple holder 38 to contact the safety feature 210 and urge it downward against its upward bias. Consequently, the tip 212 of the safety feature 210 is moved downward out of engagement with the safety recess 214 of the cutter 200. Alternately, another structure or mechanism is configured to engage the safety feature 210 when the staple holder 38 and anvil 10 are moved together, so as to urge the tip 212 out of the safety recess 214. Thus, in the standby position, the cutter 200 is freed for translation along the channel 246.

Optionally, an interface structure 238 may be connected to or formed into the staple holder 38. The interface structure 238 engages the anvil 10 or a component associated with the anvil 10 as the staple holder 38 and the anvil 10 move to the standby position, such as by snapping onto a corresponding feature (not shown) on the anvil 10. By doing so, the interface structure 238 holds the staple holder 38 substantially fixed relative to the anvil 10, in order to maintain registration between the target vessel, the graft vessel, the anvil 10 and the staple holder 38. The interface structure 238 may be a tab, rail, bump, or any other feature that is capable of engaging a corresponding feature and holding the staple holder 38 substantially fixed relative to the anvil 10. Alternately, the interface structure 238 is formed into or connected to the anvil 10 and engages a corresponding feature on the staple holder 38.

Referring also to FIG. 95, as the staple holder 38 and the anvil 10 move toward the closed position the shield 290 remains outside the target vessel 580, between the end of the graft vessel 404 and the outer surface of the target vessel 580. As the staple holder 38 presses the flaps 408 against the outer surface of the target vessel 580, the flaps 408 and/or the graft vessel 404 contact the shield 290 and press it toward the outer surface of the target vessel 580. The proximal element 292 and the second ramp element 295 of the shield 292 are thus pressed into substantial contact with the outer surface of the target vessel 580. At least part of the anvil arm 14 is in contact with the corresponding inner surface of the target vessel 580, providing support for the shield 290. Contact between the second ramp element 295 of the shield 290 and the outer surface of the target vessel 580 supports the raised element 293 and holds the raised element 293 spaced apart from the outer surface of the target vessel 580. Alternately, the proximal element 292 and/or the second ramp element 295 of the shield 290 move toward the target vessel 580 but are not pressed into substantial contact with the target vessel 580. Alternately, one or more different or additional parts of the shield 290 are pressed into contact with the outer surface of the target vessel 580. The raised element 293 holds a portion of the tissue of the graft vessel 404 apart from the outer surface of the target vessel 580. Further, the raised element 293 substantially prevents contact between the cutter 200 and the tissue of the target vessel 580, as described in greater detail below. The shield 290 and the aperture 296 in the shield are substantially aligned with the anvil arm 14 both before and after the staple holder 38 and the anvil 10 have moved to a closed position relative to one another. Referring also to FIGS. 106 and 144-145, where the shield 290 is connected to the staple holder 38 instead of the anvil 10, as the staple holder 38 and the anvil 10 move toward the closed position the shield 290 remains outside the target vessel 580, between the end of the graft vessel 404 and the outer surface of the target vessel 580. At least part of the shield 290 may contact the outer surface of the target vessel 580 when the tissue effector 400 is in the closed position. Where the shield 290 is connected to the staple holder 38, it may be sized and configured, and may act, in substantially the same manner as if it were connected to the anvil 10.

Where the graft affixer 910 is utilized, it may be movable from a first position when the tissue effector 400 is in the open position to a second position when the tissue effector 400 is in the closed position. Referring also to FIG. 131, if the graft affixer 910 is movable relative to the staple holder 38, it initially occupies a first position relative to the staple holder 38. In the first position, the graft affixer 910 extends a first distance outward from the staple holder 38 that facilitates penetration of the flap 408. Referring also to FIG. 132, as the anvil 10 and staple holder 38 move closer to one another toward the closed position, the anvil 10 contacts the base 914 of the graft affixer assembly 912 and exerts force on it. This force urges the graft affixer assembly 912 away from the anvil 10. This force may act against a frictional force resulting from the friction fit of the base 914 with the aperture 918, or against a biasing force that biases the graft affixer assembly 912 to the first position. The aperture 918 may act to guide the motion of graft affixer assembly in a substantially linear manner. As the graft affixer assembly 912 moves away from the anvil 10, the graft affixer 910 moves relative to the staple holder 38 such that it extends a second distance outward from the staple holder 38 that is less than the first distance, but that is still sufficient to hold the graft vessel 404. Further, the graft affixer 910 thus does not interfere substantially with the anvil 10 when the graft affixer 910 is in the second position. As the anvil 10 and the staple holder 38 reach the closed position, the graft affixer 910 may penetrate the tissue of the target vessel 580 at least partially. Alternately, the base 914 of the graft affixer assembly 912 does not substantially move as the tissue effector 400 moves from the open position to the closed position, and contact between the anvil 10 and the graft affixer 910 causes the graft affixer 910 to slide, deform or otherwise transition from its first distance outward from the staple holder 38 to its second distance outward from the staple holder 38.

Where the graft affixer 910 is the heel clip 910 of FIG. 158, the tissue effector 400 also moves from the open position to the closed position as described above. As the staple holder 38 moves closer to the anvil 10, the free end 1152 penetrates completely through the wall of the target vessel 580. Alternately, an arteriotomy or other opening has already been formed in the target vessel 580, and the free end 1152 of the leg 1150 enters the target vessel 580 through that opening without penetrating the wall of the target vessel 580.

As the staple holder 38 moves closer to the anvil 10, the free end 1152 of the leg 1150 contacts the anvil 10. A bending feature (not shown) may be formed in the anvil 10 such that the free end 1152 of the leg 1150 contacts the bending feature upon contacting the anvil 10. Additionally, or instead, the leg 1150 may be curved in proximity to its free end 1152. The leg 1150 begins to deflect as it is pressed into contact with the anvil 10 by motion of the staple holder 38, where such deflection may be assisted by the bending feature and/or the curvature of the leg 1150. As the movement of the tissue effector 400 to the closed position exerts force on the heel clip 910, the heel clip 910 continues to be held by the staple holder, such as by engagement between the first tab 1154 and the ledge 1164, the second tab 1158 and the notch 1164, and/or the base 1156 and the pocket 1157. As the tissue effector 400 continues to move to the closed position, the heel clip 910 continues to bend. This bending may occur at the junction between the base 1156 and the leg 1150 and/or at one or more locations along the leg 1150. The junction between the base 1156 and the leg 1150 may be sized and/or shaped to concentrate bending at that junction, if desired. Further, as the tissue effector 400 continues to move to the closed position, the free end 1162 of the prong 1160 contacts and then penetrates the outer surface of the target vessel 580. The free end 1162 may penetrate partially or completely through the wall of the target vessel.

When the tissue effector 400 has reached the closed position, referring to FIGS. 159-160, the heel clip 910 is in a closed position. The leg 1152 has been bent such that its free end 1152 may be oriented at least partially upward. Further, the free end 1152 of the leg 1150 may penetrate into the wall of the target vessel 580 either partially or completely when the heel clip 910 is in the closed position. In the closed position, tissue of the target vessel 580 is compressed between the leg 1150 and the base 1156 of the heel clip 910. Further, the heel clip 910 may engage the tissue of the target vessel 580 by penetration by the free end 1152 of the leg 1150 and/or the free end 1162 of the prong 1160, thereby providing additional security. As the heel clip 910 moves to the closed position, the first tab 1152 moves inward as the leg 1150 is bent. When the heel clip 910 is in the closed position, the first tab 1152 has moved inward enough such that the first tab 1152 no longer engages the ledge 1162. In this way, the heel clip 910 is freed from the staple holder 38, such that the heel clip 910 is detached from the staple holder 38 upon its deformation to the closed position.

Alternately, the staple holder 38 may be constructed to deploy a plurality of heel clips 910 around the perimeter of the anastomosis, in lieu of staples or other connectors 464. In this way, construction of the tissue effector 400 may be greatly simplified. That is, the sled 482, the connector bays 448, the connector deployers 452, and/or other components of the staple holder 38 may be simplified or omitted. Instead, a plurality of heel clips 910 may be detachably connected to the staple holder 38 in the locations that would otherwise be occupied by the connector bays 448. Graft preparation proceeds substantially as described above, with the exception that the flaps 408 would be pushed down onto the leg 1150 of each heel clip 910. Alternately, no flaps 408 are incised in the graft vessel 404, and an end of the graft vessel 404 is everted onto and pushed down onto the legs 1150 of the heel clips 910. Deployment of the heel clips 910 to connect the graft vessel 404 to the target vessel 580 is performed by deformation of the heel clips 910, as described above. By placing the heel clips 910 at the locations corresponding to those at which the connectors boys 448 would have placed the connectors 464, the tissue effector 400 completes the anastomosis.

Referring also to FIG. 70, the user continues to depress the trigger 308. As a result, the rocker 508 continues to rotate about the rocker axle 510 such that the distal end 520 of the distal arm 518 continues to move downward, and the proximal end 516 of the proximal arm 514 continues to move upward. As the proximal end 516 of the proximal arm 514 continues to move upward, its contact with the lower portion 530 of the contact feature 528 of the proximal slider 522 continues to urge the proximal slider 522 proximally. When the proximal end 516 of the proximal arm 514 has reached a position at or near the intersection between the two portions 530, 532 of the contact feature 528, the proximal slider 522 has moved substantially as far proximally as it will move during actuation of the anastomosis tool 300. Further, when the proximal end 516 of the proximal arm 514 has reached that position, the staple holder 38 and the anvil arm 14 are still in the standby position. Referring also to FIG. 77, this is time t=2, at which the proximal slider 522 has moved proximally from its position at time t=1, and has reached its most proximal position. The distal slider 534 is in substantially the same position that it was in at time t=1.

Operation of Anastomosis Tool—Deploying Connectors

The user continues to depress the trigger 308. As the proximal end 516 of the proximal arm 514 continues to move upward, it moves past the intersection between the two portions 530, 532 of the contact feature 528, thereby contacting the upper portion 532 of the contact feature 528. The upper portion 532 of the contact feature 528 provides substantially no resistance to the continued rotation of the rocker 508, because it is substantially vertical or angled in a proximal direction as it extends upward. The proximal end 516 of the proximal arm 514 thus moves upward rapidly. Alternately, the speed of the motion of the proximal end 516 of the proximal arm 514 is controlled to be the same as or slower than its speed while it contacts the lower portion 530 of the contact feature 528. During the upward motion of the proximal end 516 of the proximal arm 514, the proximal slider 522 may move distally at least slightly due to the arcuate motion of the proximal end 516 of the proximal arm 514 relative to the non-arcuate upper portion 532 of the contact feature 528.

As the proximal end 516 of the proximal arm 514 moves upward along the upper portion 532 of the contact feature 528, the distal end 520 of the distal arm 518 continues to move downward along the contact surface 548 of the distal slider 534. As described above, the posts 544 at the distal end 520 of the distal arm 518 are spaced apart from one another, such that a gap is present between them. The distal arm 518 may contact the contact surface 548 via the posts 544 during at least a portion of its travel. As the distal end 520 of the distal arm 518 moves downward, the posts 544 reach the bottom edge 570 of the contact surface 548. The rocker 508, the proximal slider, and the distal slider 534 are positioned relative to one another and shaped such that the posts 544 reach the bottom edge 570 of the contact surface 548 at substantially the same time that the proximal end 516 of the proximal arm 514 reaches the intersection between the two portions 530, 532 of the contact feature 528 of the proximal slider 522.

Referring also to FIG. 78, when the posts 544 reach the bottom edge 570 of the contact surface 548, they contact the members 600 of the holder 594. As the distal end 520 of the distal arm 518 continues to move downward, the posts 544 thereby press the members 600 downward. As a result, the stops 596 are moved out of engagement with the bottom edge 570 of the contact surface 548, such that the stops 596 no longer contact the distal slider 534. Consequently, the stops 596 no longer restrain the distal slider 534 against proximal motion under the influence of the spring 540. The width of the lower guide 552 is less than the width of the gap between the posts 544, and the lower guide 552 is substantially aligned with the gap between the posts 544. Thus, after the stops 596 have been pushed below the bottom edge 570 of the contact surface 548 of the distal slider 534, the lower guide 552 is free to slide through the gap between the posts 544 and through the proximal end of the holder 594. The proximal motion of the distal slider 534 thus takes up the slack (if any) in the second cable 490 connected to the distal slider 534, then causes that second cable 490 to move proximally. Referring also to FIG. 77, this is time t=3, at which the distal slider 534 has rapidly moved proximally from its position at time t=2, and the proximal slider 522 has moved slightly in the distal direction from its position at time t=2.

Referring also to FIG. 58, this proximal motion of the second cable 490 urges the sled 482, which also is connected to the second cable 490, into motion. As described above, at least one channel 496 is defined in the staple holder 38, and the second cable 490 is guided by a corresponding channel 496. The staple holder 38 is shaped such that the channel 496 curves and causes the second cable 490 to curve back in a proximal direction. The second cable 490 is connected to the sled 482. Thus, the curvature of the channel 496 causes the second cable 490 to curve, such that the proximal motion of the second cable 490 pulls the sled 482 distally. In this way, proximal motion of the distal slider 534 causes the sled 482 to move distally.

Referring also to FIGS. 64 and 68-69, the sled 482 includes one or more ramp elements 446, each movable within a corresponding passage 440 in an arm 402 of the staple holder 38, as described above. Initially, the sled 482 is positioned such that each ramp element 446 is proximal to the most proximal connector bay 448 connected to the corresponding passage 440. Thus, as the second cable 490 is tensioned and moved proximally by the distal slider 534, and the sled 482 moves distally as a result, each ramp element 446 moves distally in its corresponding passage 440. Alternately, the sled 482 is positioned initially such that each ramp element 446 is distal to the most distal connector bay 448. As the second cable 490 is tensioned and moved proximally, the second cable pulls each ramp element 446 proximally, deploying the connectors 464 in a similar manner but in the reverse order.

For convenience in describing the deployment of staples 464, the motion of one ramp element 446 through the corresponding passage 440 will be described; the motion of each additional ramp element 446 through its corresponding passage 440 occurs in the same or a similar manner. Referring to FIG. 64, as the ramp element 446 moves distally from its initial position, its distal end 474 contacts the most proximal connector deployer 452. As described above, each connector deployer 452 initially is in a first position in which its outer end 454 extends into the passage 440. When the distal end 474 of the ramp element 446 contacts the most proximal connector deployer 452, it urges that connector deployer 452 into the corresponding connector bay 448. The distal end 474 of the ramp element 446 may be shaped such that its inner surface 476 curves or angles relative to the direction of travel of the ramp element 446. Thus, when the distal end 474 of the ramp element 446 encounters the outer end 454 of the most proximal connector deployer 452, a component of the force it exerts on the connector deployer 452 is substantially parallel to the longitudinal centerline of the corresponding connector bay 448. That centerline may be substantially perpendicular to the direction of travel of the ramp element 446, or may be otherwise oriented relative to the direction of travel of the ramp element 446.

As a result of contact with the distal end 474 of the ramp element 446, the connector deployer 452 begins to move through the corresponding connector bay 448, away from the passage 440. A connector 464 is located in the connector bay 448, inward from the connector deployer 452. The tines 466 of the connector 464 initially may be biased against at least part of the corresponding connector bay 448 as described above, or the connector 464 may otherwise be held within the connector bay 448 prior to motion of the connector deployer 452. As the connector deployer 452 moves, it exerts a force on the corresponding connector 464, overcoming the force with which the connector 464 is initially held in place and pushing the connector 464 inward. As the connector 464 is urged inward, the registration element 458 (if used) translates along the registration feature 462 of the connector bay 448. The registration element 458 reduces or eliminates lateral cocking of the connector deployer 452 during its translation through the connector bay 448, such that the connector deployer 452 is maintained in substantially the same orientation throughout its travel.

Referring also to FIG. 61 (in which the graft vessel and target vessel are not shown for clarity), as the connector deployer 452 urges the connector 464 out of the connector bay 448, the tines 466 of the connector 464 move out of the connector bay 448, penetrate the root 405 of the flap 408 held against the inner surface 450 of the arm 402, then penetrate the wall of the target vessel 580. One or more of the arms 402 may be angled relative to a horizontal plane to facilitate connecting the flaps of the graft vessel 404 to the wall of the target vessel 580, where that angle is chosen to place connectors in a desired orientation relative to the surface of the target vessel 580. Advantageously, the staples 464 enter the target vessel substantially perpendicular to it. However, the staples 464 can enter the target vessel at a different angle, and/or at different angles relative to one another.

After the tines 464 have completely penetrated the wall of the target vessel, they encounter corresponding staple bending features 572 in the anvil arm 14. The staple bending features 572 are depressions in the surface of the anvil arm 14, aligned with the connector bays 448 such that at least one tine 466 of at least one connector 464 encounters a staple bending feature 572 upon being pushed out of its connector bay 448. One or more of the staple bending features 572 may be configured differently, or may be omitted altogether. As the connector deployer 452 continues to urge the connector 464 out of the connector bay 448 and toward the anvil arm 14, the tines 466 of the connector 464 are pressed into the staple bending features 572. Thus, the force transmitted from the ramp element 446 to the connector deployer 452 presses the tines 466 into the staple bending features 572, causing them to deflect. The tines 466 may be deflected in any direction suitable for holding the flap 408 to the graft vessel 404. Optionally, the staple bending features 572 may be omitted. If so, the tines 466 simply engage the surface of the anvil arm 14. Alternately, where the connectors 464 are not staples, the staple bending features 572 are not needed. For example, where the connectors are clips, microrivets or other structures or mechanisms that are not staples, the staple bending features 572 need not be provided. Alternately, where the connectors 464 are superelastic staples configured to close without the need for contact with an anvil, the staple bending features 572 need not be provided.

Where the most proximal connector bay 448 and/or the most distal connector bay 448 in an arm 402 is offset toward the longitudinal centerline of the anvil arm 14 relative to one or more other connector bays 448, the connector deployer 452 in each offset connector bay 448 is actuated substantially as described above. The ramp element 446 may contact each such connector deployer 452 at a location offset from the longitudinal centerline of that connector deployer 452. As a result, the ramp element 446 may contact less area of each offset connector deployer 452 as compared to its contact with the other connector deployers 452. However, such contact is sufficient to urge each connector deployer 452 along the corresponding offset connector bay 448 to deploy the connector 464 in that connector bay 448. When the widest portion of the distal end 474 of the ramp element 446 encounters the outer end 454 of the connector deployer 452, the connector deployer 452 reaches the end of its stroke through the connector bay. The connector 464 and the corresponding staple bending feature or features 572 are configured such that the deflection of the tines 446, and thus the deployment of the connector 464, is substantially complete when the corresponding connector deployer 452 reaches the end of its stroke. The ramp element 446 then continues its motion through the passage 440 to encounter the next connector deployer 452, such that the staples 464 in each arm 402 are deployed sequentially. Alternately, the ramp element 446 and passage 440 are configured such that the ramp element 446 moves in substantially the same direction as the connector deployers 452, or is otherwise connected to the connector deployers 452, such that two or more of the connector deployers 452 are actuated substantially simultaneously. That is, the connector deployers 452 may be actuated in series, in parallel, or in a different way. For example, the connector deployers 452 may be selectively actuated, such that a selected number of staples 464 can be deployed. The user can deploy a selected number of staples 464 based on the size of the graft vessel 404 or other relevant factors. That is, the staple line (the length along the target vessel 580 along which staples 464 are deployed) is adjustable. Such adjustment may be performed in any appropriate manner, such as by adjusting the distance traveled by each ramp element 446 during deployment of the staples 464. Alternately, other mechanisms or structures may be used to deploy the staples 464 from the connector bays 448 in a desired sequence.

As described above, the staple holder 38 includes two spaced-apart arms 402. A ramp element 446 proceeds distally through a corresponding passage 440 in each arm 402. Further, the connector bays 448 in each arm 402 are aligned in a substantially bilaterally symmetric manner. Thus, as the sled 482 translates distally, the distal end 474 of each ramp element 446 encounters a connector deployer 452 at substantially the same time, such that a connector 464 is deployed from each arm 402 at substantially the same time. As a result, the staple holder 38 sequentially deploys pairs of staples 446 into tissue as the ramp elements 446 move distally. Alternately, the connector bays 448 are staggered, such that staples 464 from each arm 402 are deployed at different times than staples from the other arm 402.

Optionally, the sled 482 also includes vein knives 432. Each vein knife 432 translates through a corresponding vein knife passage 430 defined by a first channel 426 in the graft clip 412 and a second channel 428 in the flap receiving surface 406, as described above. The distal end 434 of each vein knife 432 is sharp, and may be a blade 434. As described above, the vein knives 432 are initially in a first position, where the distal end 434 of each vein knife 432 is located proximal to the root 405 of the corresponding flap 408. As the second cable 490 is tensioned and pulled toward the handle 302 by the distal slider 534, the sled 482 moves distally. The vein knives 432, which are connected to the sled 482 move distally as well through the corresponding vein knife passages 430.

As each vein knife 432 moves distally, its sharp distal end 434 engages the proximal edge of the root 405 of the corresponding flap 408, entering the tissue of the flap 408 and beginning to make an incision therein. The serrations 438 on the graft clip blades 436 assist in holding the flap 408 as the corresponding vein knife 432 incises it. Alternately, those serrations 438 may assist in incising the flap 408, depending on their configuration. In addition, the serrations 438 may assist in holding the excess tissue incised from each flap 408, after the vein knife 432 has made an incision through the entire flap. The vein knives 432 do not extend as far in the distal direction as the ramp elements 446. Thus, as the sled 482 translates distally, the distal end 474 of each ramp element 466 reaches any given longitudinal position before the blade 434 of the corresponding vein knife 432. Consequently, the ramp element 466 causes a staple 446 to deploy at a particular longitudinal position before the corresponding vein knife 432 extends the incision in the flap 408 to that longitudinal position. By stapling before incising at any given longitudinal position, each flap 408 is held securely as it is cut by the corresponding vein knife 432. Alternately, at any given longitudinal position, the flap 408 is incised during or before deployment of a staple 446 at that position. Each vein knife 432 is positioned to cut the flap 408 far enough from the deployed staples 446 to minimize or eliminate interference with these staples 446, but close enough to the staples 446 to cut away excess tissue on the flap 408 that is not needed for the finished anastomosis.

Operation of Anastomosis Tool—Creating Opening in Target Vessel

Figure 45:
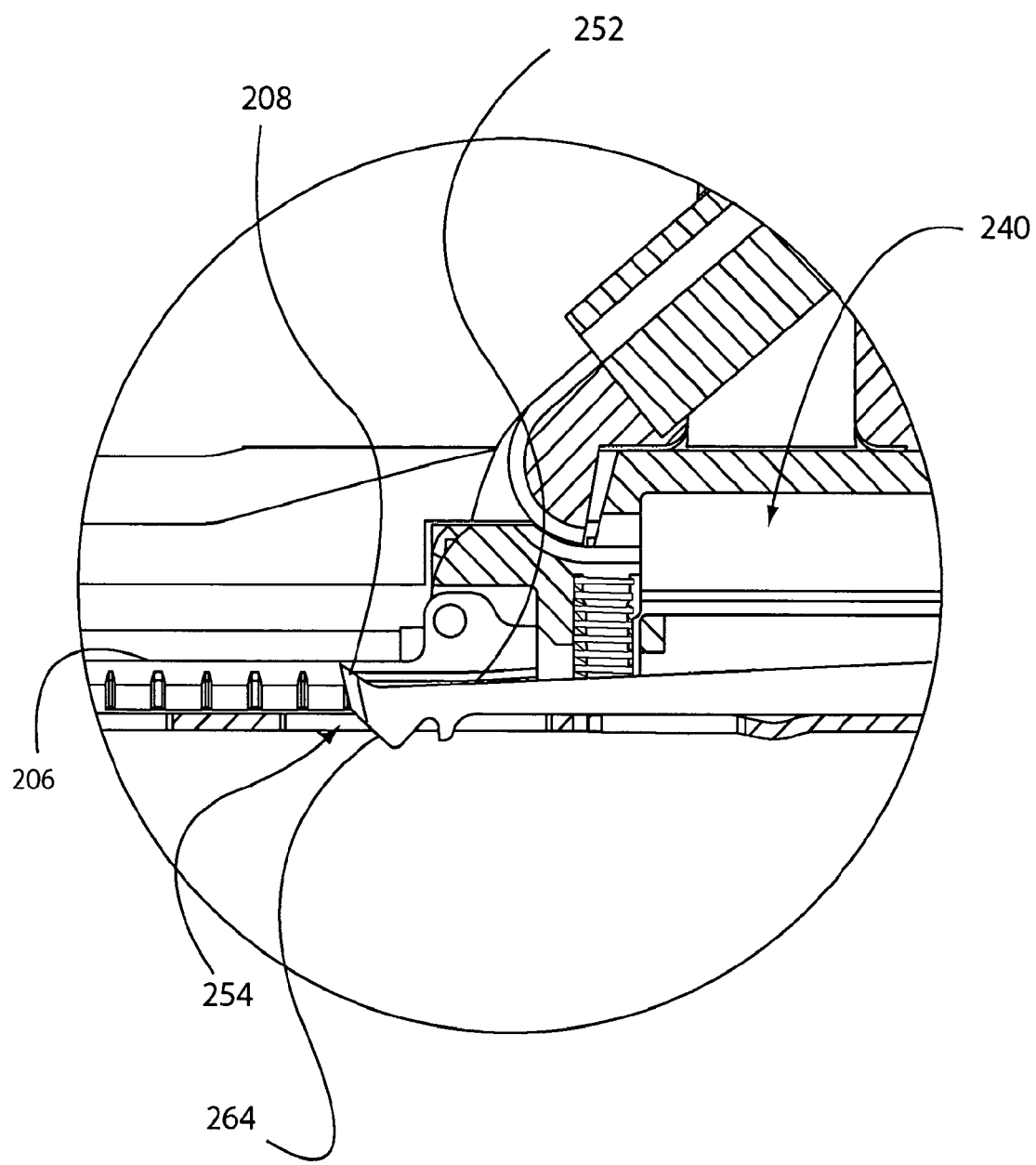
FIG. 45 is a side cutaway view of the anvil and staple holder of FIG. 34, where the cutter is in a second position.

Referring also to FIGS. 45, 58 and 68, the cutter 200 has been freed for translation. The cutter 200 is urged distally by the receiver 218, which engages the engagement feature 216 of the cutter 200. The receiver 218 may be defined in the sled 482, as described above. As the sled 482 is pulled distally by the second cable 490, the receiver 218 moves distally, thereby urging the engagement feature 216 of the cutter 200 distally. Alternately, the receiver 218 is not defined in the sled 482. Instead, the receiver 218 is a separate structure that may be connected to the sled 482, and that is configured to travel along a guide structure 241. The guide structure 241 is a rail or other structure along which the receiver 218 slide, and the receiver 218 interfaces with and translates along the rail. Thus, the guide structure 241 guides the translation of the receiver 218. A cavity 240 is provided in the staple holder 38 adjacent to the guide structure 241 to allow for motion of the receiver 218 along the guide structure 241. The cavity 240 is sized to allow the receiver 218 to translate freely. Alternately, the guide structure 241 is a hollow channel defined within the staple holder 38, such that the walls of the channel guide the translation of the receiver 218. Alternately, the guide structure 241 may be any other structure or mechanism capable of guiding the translation of the receiver 218. The guide structure 241 is substantially aligned with the anvil arm 14. That is, the longitudinal centerline of the guide structure 241 is substantially parallel to the longitudinal centerline of the anvil arm 14. Thus, motion of the receiver 218 along the guide structure 241 causes translation of the engagement feature 216 and therefore translation of the cutter 200 substantially parallel to the centerline of the anvil arm 14. The receiver 218 may be actuated to translate along the guide structure 241 by the second cable 490, which transmits force from the handle 302. Alternately, the actuator may convert stored energy to force that is applied to the cutter. Such stored energy may be provided by a spring, battery, source of compressed gas, or other source. Alternately, any mechanism, structure or method, using stored energy or not, may be used to translate the receiver 218 along the guide structure 241. The particular mechanism, structure or method used to cause translation of the cutter 200 is not critical to the invention.

The upper surface 252 of the cutter 200 is substantially planar proximal to the projection 208. The biasing element 260 contacts the upper surface 252 of the cutter 200 and biases the cutter 200 downward. The cutter 200 includes a keel 264 that extends downward. The keel 264 may be formed into the cutter 200, or may be a separate component connected to the cutter 200. The keel 264 is substantially as wide as the adjacent portion of the cutter 200. However, the keel 264 may be wider or narrower than the adjacent portion of the cutter 200. The keel 264 is positioned at or near the distal end of the cutter 200. Alternately, the keel 264 may be positioned at a different location on the cutter 200.

Figure 43A:
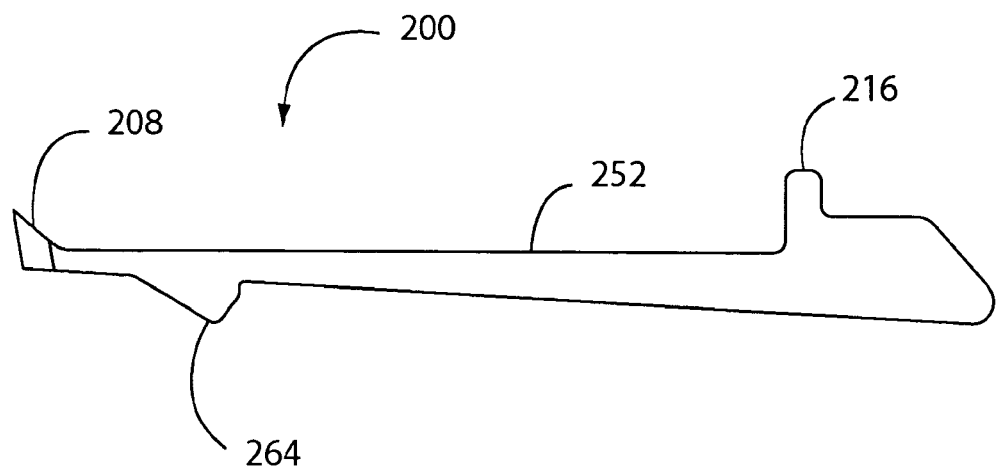
FIG. 43A is a side view of another embodiment of a cutter.

Referring to FIG. 43A, another embodiment of a cutter 200 is shown. As described above, the cutter 200 includes at least one projection 208 extending substantially upward from a position at or near its distal end, and an engagement feature 216 extending upward from the upper surface 252 of the cutter 200. In this embodiment, the keel 264 of the cutter 200 is spaced apart from the projection 208, differing from the embodiment of FIG. 37-38 in which the keel 264 is adjacent to the projection 208. By spacing the keel 264 apart from the projection 208, the keel 264 can project a smaller distance downward while moving the projection 208 substantially the same amount upward and downward. Consequently, the keel 264 as a whole can be made smaller.

Figure 43B:
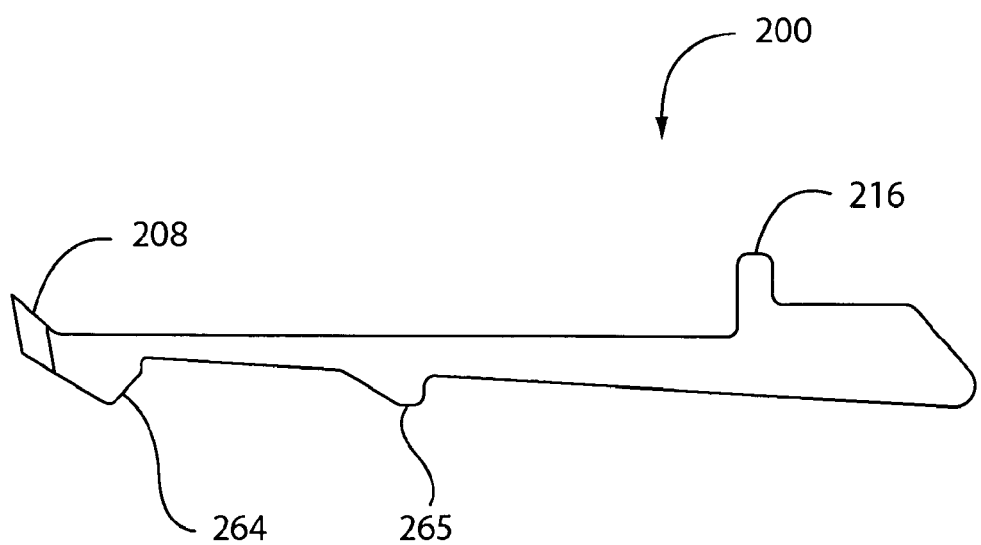
FIG. 43B is a side view of another embodiment of a cutter.

Referring to FIG. 43B, another embodiment of a cutter 200 is shown. As described above, the cutter 200 includes at least one projection 208 extending substantially upward from a position at or near its distal end, and an engagement feature 216 extending upward from the upper surface 252 of the cutter 200. In this embodiment, the cutter 200 includes a first keel 264 and a second keel 265. The first keel 264 may be configured similarly to the keel 264 of FIG. 43, and the second keel 265 may be configured similarly to the keel 265 of FIG. 43A. The first keel 264 extends further below the body of the cutter 200 than the second keel 265. A third lower opening (not shown) is defined through a lower surface 256 of the anvil 10, in addition to the first lower opening 254 and the second lower opening 268. The third lower opening is spaced apart from the second lower opening 268, and is positioned distal to the second lower opening 268. The first keel 264 initially extends into the second lower opening 268, and the second keel 265 initially extends into the first lower opening 254.

As shown in FIG. 45, the keel 264 initially extends into the first lower opening 254, which is defined through a lower surface 256 of the anvil 10. The keel 264 may extend completely through the first lower opening 254, such that its lowest point extends outside the anvil 10. The keel 264 is biased downward into the first lower opening 254 as a result of the downward force exerted on the cutter 200 by the biasing element 260. While the keel 264 is biased into the first lower opening 254, the projection 208 remains below the contact surface 206 of the anvil arm 14. In this way, the projection 208 does not extend out of the anvil arm 14 while the anvil arm 14 is inserted into the wall of a target vessel. Where the cutter 200 of FIG. 43A is used, the keel 264 need not extend into or through the first lower opening 254 as far as the keel 264 of the cutter 200 of FIGS. 37-38. As a result, less clearance for the motion of the keel 264 need be provided, and the tissue effector 400 may be made more compact. The first lower opening 254 extends along a fixed length of the lower surface 256 of the anvil 10. As the cutter 200 translates distally, the keel 264 continues to remain at least partially within the first lower opening 254, such that the projection 208 continues to remain below the contact surface 206 of the anvil arm 14. Initially, the keel 264 may be positioned proximal to the distal end of the first lower opening 254. The length of the first lower opening 254 is selected to cause the projection 208 to remain below the contact surface 206 of the anvil arm 14 across that distance. That is, this distance is selected such that the projection 208 on the cutter 200 does not engage the wall of the target vessel until the projection 208 is positioned within the circumference of the graft vessel. That is, the connection between the graft vessel and the target vessel substantially defines a closed area, and the projection 208 is configured to engage the wall of the target vessel within that closed area. In this way, the projection 208 makes an incision completely within the connection between the graft vessel and the target vessel, completing the anastomosis between the two vessels and minimizing or eliminating leakage at the anastomosis site. While the projection 208 on the cutter 200 remains below the upper surface of the anvil arm 14, it neither engages nor cuts the wall of the target vessel.

Figure 46:
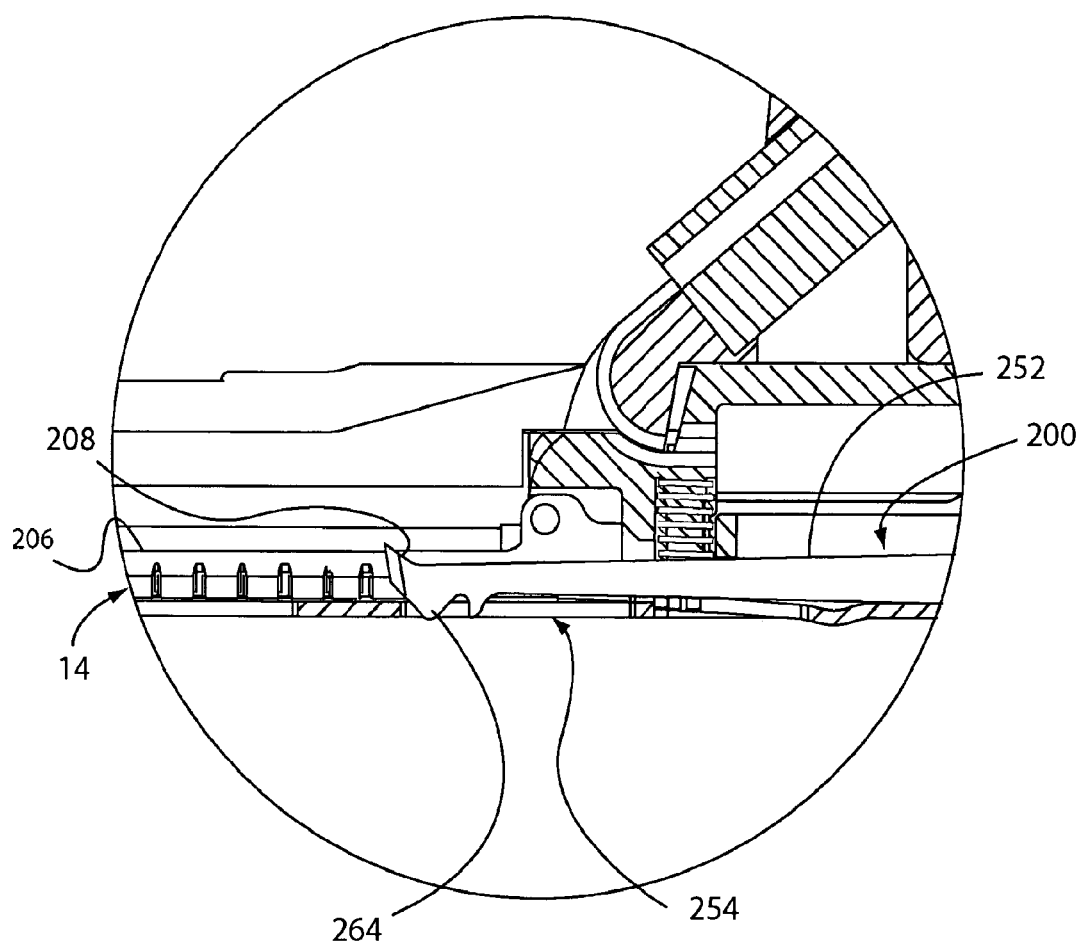
FIG. 46 is a side cutaway view of the anvil and staple holder of FIG. 34, where the cutter is in a third position.

Referring also to FIG. 46, the cutter 200 continues to advance distally as the receiver 218 continues to urge the engagement feature 216 distally. As described above, at least the distal end of the cutter 200 is biased downward. As the cutter 200 advances distally, the keel 264 encounters the distal end of the first lower opening 254. This encounter, and the continued proximal translation of the cutter 200, causes the keel 264 to move upward relative to the anvil arm 14. The keel 264 and/or the distal end of the first lower opening 254 may be constructed to provide a smooth, gradual upward motion of the keel 264, such as by providing a gradual slope on the keel 264 and/or the distal end of the first lower opening 254. Alternately, the keel 264 and/or the distal end of the first lower opening 254 may be constructed to allow or cause the keel 264 to move upward abruptly upon encountering the distal end of the first lower opening 254. The upward motion of the keel 264 causes the distal end of the cutter 200 and the projection 208 to move upward. Thus, the size and position of the first lower opening 254, including the position of the distal end of the first lower opening 254, control the motion of the cutter 200 and the projection 208 in the vertical direction.

Where the cutter 200 of FIG. 43A is used, the keel 264 contacts the distal end of the first lower opening 254 in the same manner as the cutter of FIGS. 37-38. By spacing the keel 264 apart from the projection 208, the projection 208 may be protected from inadvertent contact with the distal end of the first lower opening 254. The initial position of the cutter 200 relative to the remainder of the tissue effector 400 may be different than that of the cutter 200 of FIGS. 37-38, to ensure that the projection 208 enters the wall of the target vessel at a selected point relative to the tissue effector 400. Where the cutter 200 of FIG. 43B is used, as the cutter 200 is urged distally, the second keel 265 and the first lower opening 254 are configured such that the second keel 265 contacts the distal end of the first lower opening 254 before the first keel 264 can contact the distal end of the second lower opening 268. In this way, the distal end of the cutter 200 is prevented from contacting the distal end of the second lower opening 268.

As the distal end of the cutter 200 moves upward, the projection 208 moves upward through the upper opening 248 in the anvil arm 14. The contact surface 206 of the anvil arm 14 is substantially adjacent to the inner surface of the wall of the target vessel. Thus, upward motion of the projection 208 through the upper opening 248 and above the contact surface 206 of the anvil arm 14 causes the projection 208 to enter the wall of the target vessel. The cutter 200 continues to move distally, such that the keel 264 moves out of the first lower opening 254 completely and contacts the bottom surface 266 of the channel 246 of the anvil arm 14. The projection 208 is sized such that the projection 208 completely penetrates the wall of the target vessel when the keel 264 has moved proximally to the first lower opening 254 and is in contact with the bottom surface 266 of the channel 246. That is, at least a portion of the projection 208 passes through the wall of the target vessel and enters the lumen of the target vessel. This initial penetration of the wall of the target vessel defines the starting point of an arteriotomy performed on the target vessel by the projection 208. The starting point of the arteriotomy is spaced apart from the location on the target vessel at which the anvil arm 14 is inserted, because the cutter 200 and the projection 208 have moved proximally a selected distance before penetrating or incising the wall of the target vessel. The insertion point of the anvil arm 14 into the target vessel may be referred to as the anvil entry hole 584 or the anvil insertion point. The portion of the wall of the target vessel between the arteriotomy and the insertion point of the anvil arm 14 may be referred to as a tissue bridge. The incision is referred to as an arteriotomy for convenience, and this terminology does not limit the type of anastomosis that may be performed. For example, anastomosis may be performed between two tissue structures that are not blood vessels, such as bile ducts. The anvil entry hole 584 may be upstream from the arteriotomy, meaning that the anvil entry hole 584 is spaced apart from the arteriotomy in the direction opposite to the direction of fluid flow within the target vessel 580. Alternately, the anvil entry hole 584 may be downstream from the arteriotomy, meaning that the anvil entry hole 584 is spaced apart from the arteriotomy in the same direction as the direction of fluid flow within the target vessel 580.

Figure 115:
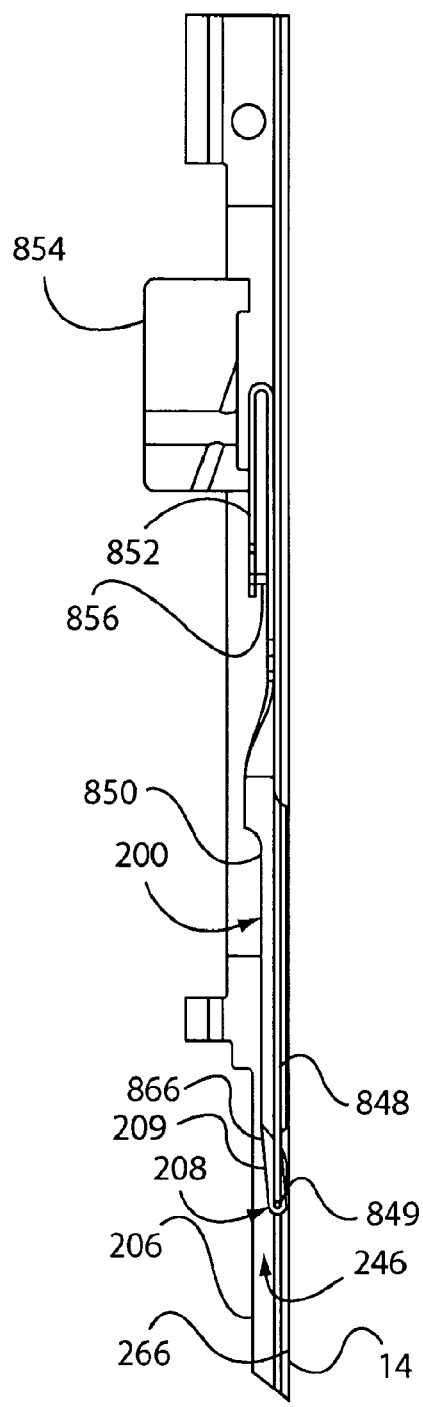

The projection 208 of the cutter 200 enters the wall of the target vessel at a location between the arms 402 of the staple holder 38. Each arm 402 holds at least a portion of a flap 408 of the graft vessel 404 against the wall of the target vessel, such that the projection 208 enters the wall of the target vessel at a location between the flaps 408. The length of the cutter 200, the position of the projection 208 on the cutter 200, and the placement of the first lower opening 254 may be selected such that the projection 208 enters the wall of the target vessel after at least one staple 446 is deployed into one of the flaps 408 and the wall of the target vessel. Alternately, the projection 208 enters the wall of the target vessel before any of the staples 446 have been deployed, or after all of the staples 446 have been deployed. Further, the length of the cutter 200, the position of the projection 208 on the cutter 200, and the placement of the first lower opening 254 may be selected such that the projection enters the wall of the target vessel at substantially the same time that one or more vein knives 432 begin to incise the corresponding flaps 408.

Where the cutter 200 of FIGS. 115-118 is used, the cutter 200 initially is in the stowed position, in which it is substantially restrained from translation. Referring to FIG. 115, the spring 852 presses the pusher 850 against the bottom surface 266 of the channel 246 in the anvil arm 14, substantially restraining the pusher 850 and the remainder of the cutter 200 from translation. The button 854 is positioned relative to the spring 852 such that it compresses the spring 852 when the cutter 200 is in the stowed position. Alternately, any other suitable structure, mechanism or method may be used to restrain the cutter 200.

Figure 116:
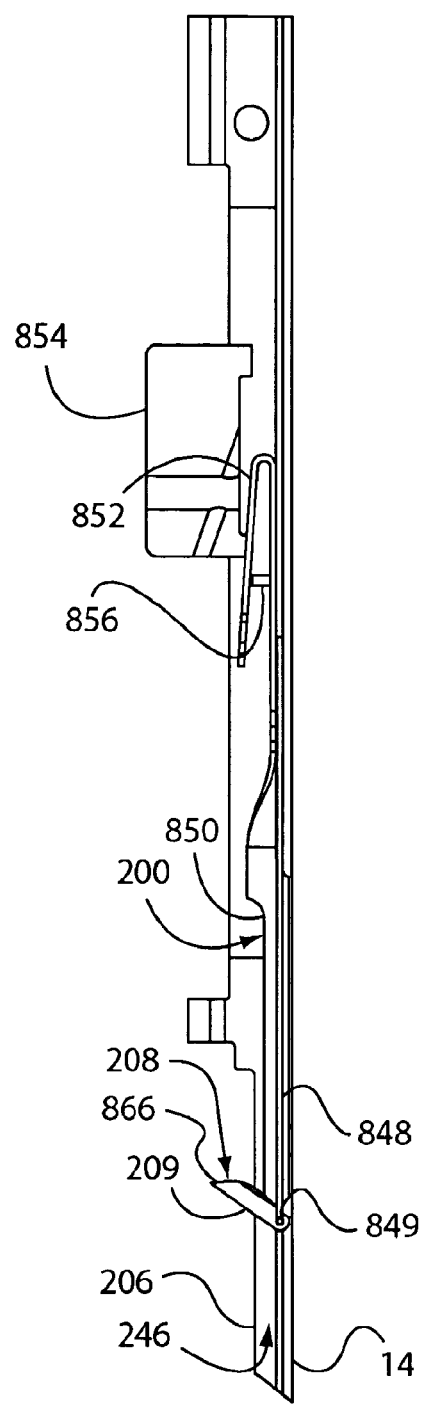

Referring also to FIG. 116, the pusher 850 remains substantially restrained against translation, and the member 848 is moved proximally. This motion of the member 848 exerts a force in the proximal direction on the projection 208, causing the projection 208 to move in the proximal direction. As the projection 208 moves, it encounters the substantially stationary pusher 850. The distal end of the pusher 850 may be beveled or otherwise shaped such that at least the upper portion of that distal end is angled or curved proximally, as described above. The end 866 of the projection 208 initially faces at least partially proximally, and is initially against or in proximity to the distal end of the pusher 850. The angle or curvature of the distal end of the pusher 850 allows the end 866 of the projection 208 to slide onto that distal end of the pusher 850, moving upward as it does so. Because the member 848 is connected to the projection 208 at a location beneath the longitudinal centerline of the pusher 850, such motion of the end 866 of the projection 208 is facilitated. As the end 866 of the projection 208 moves upward, it moves above the contact surface 206 of the anvil arm 14, and continues to move upward into the wall of the target vessel 580. Initially, the edge 209 of the projection 208 is oriented substantially upward. The edge 209 extends substantially to the end 866 of the projection 208, which is the part of the projection 208 that encounters the tissue of the target vessel 580. Alternately, the edge 209 is positioned or configured differently. As the end 866 of the projection 208 moves upward, the edge 209 incises the wall of the target vessel 580, causing the projection 208 to cut through the target vessel wall 580. The cutter 200 is now in the active position, with the projection 208 extending through the wall of the target vessel 580 and the edge 209 of the projection 208 oriented in the direction in which the projection 208 is to be moved, which as shown is the distal direction. The button 854 is moved distally such that it no longer compresses the spring 852. The pusher 850 is thus no longer compressed against the bottom surface 266 of the channel 246 and is therefore free to translate within the channel 246, and the cutter 200 is thereby freed.

Figure 117:
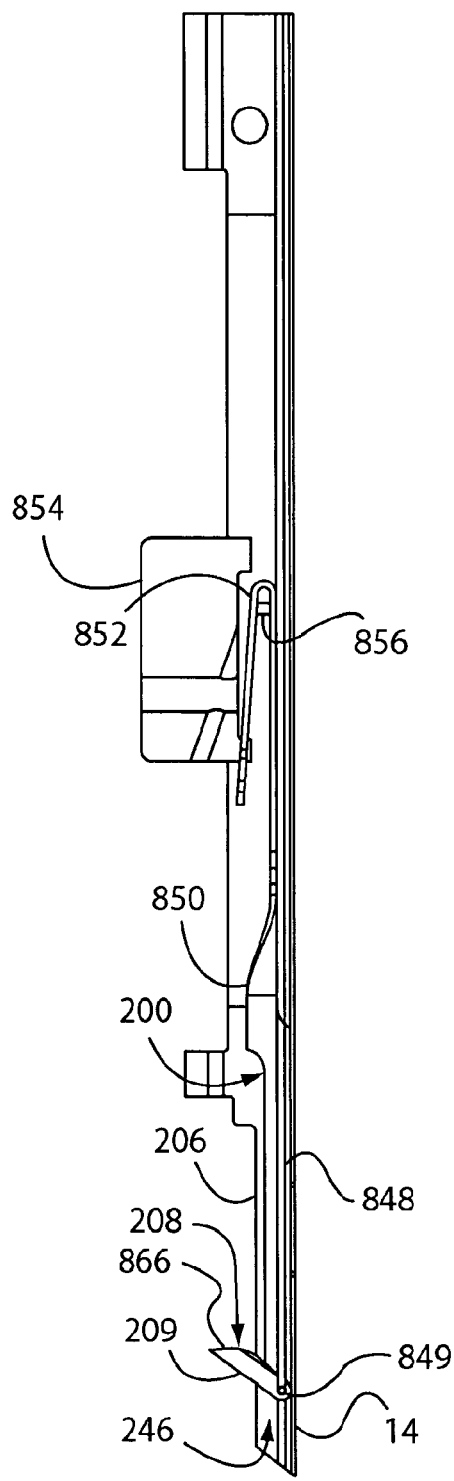

Referring also to FIG. 117, the pusher 850 is then urged distally in any appropriate manner. For example, the pusher 850 may be connected to the sled 482 directly or indirectly, such that the translation of the sled 482 also causes translation of the pusher 850. As another example, the pusher 850 may be connected directly or indirectly to the second cable 490, such that the second cable 490 pulls the pusher 850 distally. As the pusher 850 translates distally within the channel 246, the distal end of the pusher 850 contacts the projection 208 and urges the projection 208 distally. The member 848 connected to the projection 208 moves at substantially the same rate as the pusher 850. The projection 208 is held substantially in the active position by this motion of the member 848 and by contact with the distal end of the translating pusher 850. As the projection 208 translates distally, the edge 209 of the projection moves through the tissue of the wall of the target vessel 580 in a direction substantially parallel to the longitudinal centerline of the anvil arm 14, incising the tissue of the wall of the target vessel to create an arteriotomy. Because the projection 208 is translated by the pusher 850, which is located in the anvil arm 14 that is in turn located within the target vessel 580, the arteriotomy is performed from within the target vessel 580.

Figure 118:
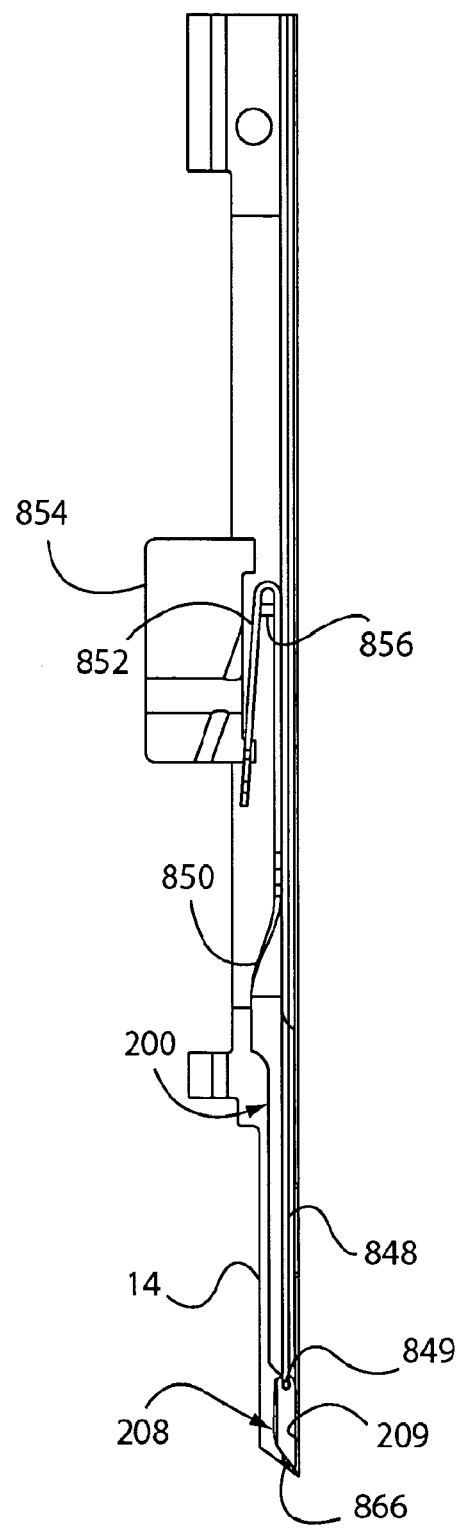

The length of that arteriotomy is related to the distance across which the projection 208 is translated. Thus, the pusher 850 translates distally across a distance substantially equal to the length of the arteriotomy, urging the edge 209 of the projection 208 through tissue across that distance. Referring also to FIG. 117, when the arteriotomy is complete, the projection 208 has reached a final location distal to its starting point, and is moved no further in the distal direction. The motion of the member 848 is controlled such that the final location of the projection 208 is substantially predictable. This control may be accomplished in any appropriate manner with any appropriate structure or mechanism. As one example, the spring 852, member 848 and/or pusher 850 contact the stop 856 in the course of proximal motion, and such contact substantially halts the forward motion of the projection 208. When the projection 208 is in the active position, it is substantially sharp on at least a portion of its distal edge, which is the edge 209, and substantially blunt along its proximal edge. The projection 208 remains in the final location in the active position until the anvil arm 14 is withdrawn from the anvil entry hole 584. Referring also to FIG. 118, as the anvil arm 14 is withdrawn from the anvil entry hole 584, the blunt proximal edge of the projection 208 encounters target vessel tissue adjacent to the anvil entry hole 584. Because that proximal edge of the projection 208 is blunt, that contact causes the projection 208 to rotate substantially about the axis of the aperture 849, into which the member 848 extends. This rotation causes the projection 208 to reenter the channel 246 in the anvil arm 14 and come to rest in a withdrawal position. In the withdrawal position, the projection 208 substantially does not extend out of the anvil arm 14 in any direction, allowing for a minimal cross-section of material to be removed from the lumen of the target vessel 580 through the anvil entry hole 584.

Alternately, the projection 208 is oriented in the opposite direction, and the pusher 850 is configured to pull the projection 208 proximally rather than push it distally. In such a configuration, when the projection 208 is in the active position, the edge 209 is oriented proximally. The projection 208 is configured to be placed in a withdrawal position in a manner other than by contact with the wall of the target vessel 580, as contact between the edge 209 of the projection and the wall of the target vessel 580 during withdrawal of the anvil arm 14 may cause the anvil entry hole 584 to be enlarged.

Figure 119:
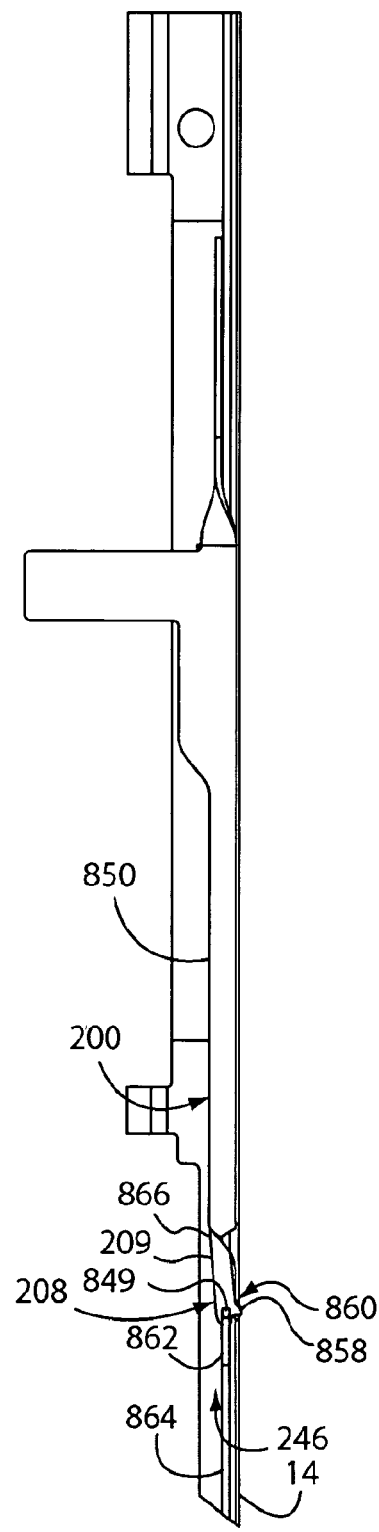

The cutter 200 of FIGS. 119-122 is configured and operates similarly to the cutter 200 of FIGS. 115-118. Referring to FIG. 119, the projection 208 is initially in the stowed position, and is substantially restrained from translation in that stowed position. The pusher 850 may be restrained substantially as described above, or in a different manner. The projection 208 includes a lobe 858 that is initially positioned at least partially in a slot 860 in the bottom surface 266 of the channel 246. The lobe 858 is located closer to the aperture 849 than is the end 866 of the projection 208. The slot 860 may be defined in or completely through the bottom surface 266 of the channel 246.

Figure 120:
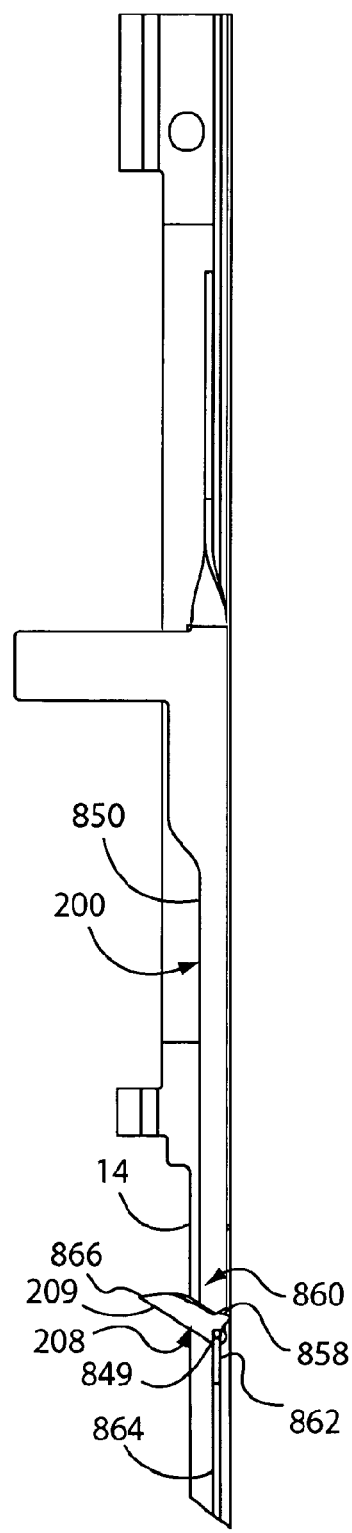

Referring also to FIG. 120, the pusher 850 is advanced distally substantially as described above. The end 866 of the projection 208 initially faces at least partially proximally, and is initially against or in proximity to the distal end of the pusher 850. The motion of the pusher 850 exerts a force in the distal direction against the projection 208, and contact between the pusher 850 and the projection 208 causes the end 866 of the projection 208 opposite from the aperture 849 to move upward. The angle or curvature of the distal end of the pusher 850 allows the end 866 of the projection 208 to slide onto that distal end of the pusher 850, moving upward as it does so. The lobe 858 of the projection 208 is initially in the slot 860, and contact between the lobe 858 and the distal edge of the slot 860 substantially prevents the projection 208 from moving distally as the end 866 moves upward. That is, as the projection 208 rotates upward, at least part of the lobe 858 remains in the slot 860 during that rotation until the projection 208 reaches the active position. As the projection 208 moves upward, it moves above the contact surface 206 of the anvil arm 14. The edge 209 of the projection 208 is oriented substantially upward, and extends substantially to the end 866 of the projection 208, which is the part of the projection 208 that encounters the tissue of the target vessel 580. That edge 209 incises the wall of the target vessel 580, causing the projection 208 to cut through the target vessel wall 580. The cutter 200 is now in the active position, with the projection 208 extending through the wall of the target vessel 580 and the edge 209 of the projection 208 oriented in the direction in which the projection 208 is to be moved, which as shown is the distal direction.

Figures 121, 122:
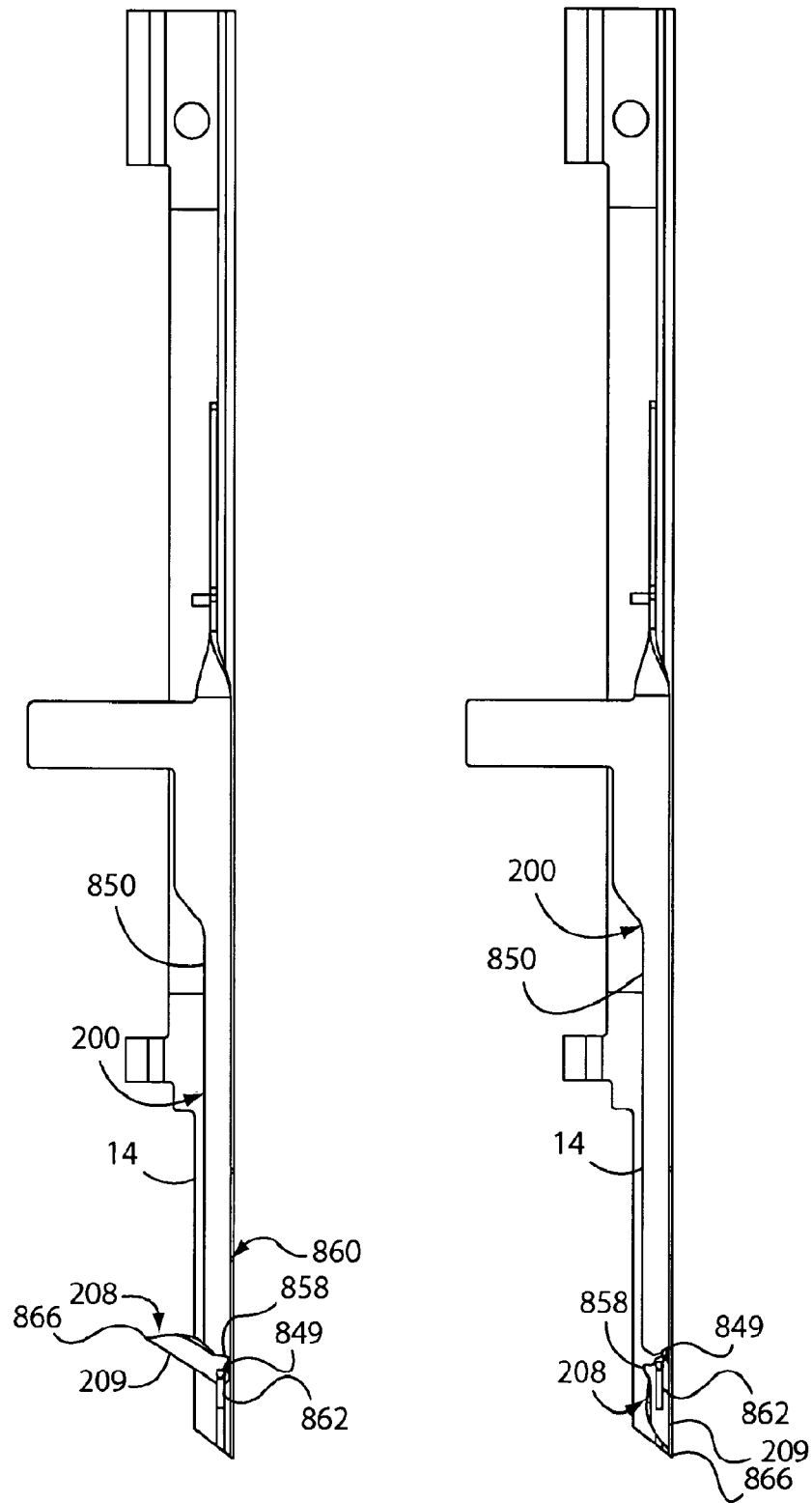

As the projection 208 pivots about the axis of the aperture 849, the lobe 858 of the projection 208 moves upward and out of the slot 860, freeing the projection 208 for translation. Referring also to FIG. 121, the pusher 850 is then urged distally in any suitable manner. For example, the pusher 850 may be connected to the sled 482 directly or indirectly, such that the pusher 850 and the sled 482 translate together. As another example, the pusher 850 may be connected directly or indirectly to the second cable 490, such that the second cable 490 pulls the pusher 850 distally. As the pusher 850 translates distally within the channel 246, the distal end of the pusher 850 contacts the projection 208 and urges the projection 208 distally. As another example, referring also to FIG. 154, the pusher 850 may be connected to the cutter pull 1096.

A clip 862 is connected to the projection 208, such as through the aperture 849. The clip 862 is configured to be held by and to slide along tracks 864 in the interior surfaces 202 of the channel 246 in the anvil arm 14. In this way, the clip 862 is coupled to the anvil arm 14. The projection 208 is held in the active position substantially by contact with the distal end of the pusher 850, and is stabilized as it moves by contact between the clip 862 and the tracks 864. As the projection 208 translates distally, the edge 209 of the projection moves through the tissue of the wall of the target vessel 580 in a direction substantially parallel to the longitudinal centerline of the anvil arm 14, and incises the tissue of the wall of the target vessel to create an arteriotomy. Because the projection 208 is moved by the pusher 850, which is located in the anvil arm 14 that is in turn located within the target vessel 580, the arteriotomy is performed from within the target vessel 580.

The length of the arteriotomy is related to the distance across which the projection 208 is translated. Thus, the pusher 850 translates distally across a distance substantially equal to the length of the arteriotomy, urging the edge 209 of the projection 208 through tissue across that distance. Referring to FIG. 121, when the arteriotomy is complete, the projection 208 has reached a final location distal to its starting point, and is moved no further in the distal direction. When the projection 208 is in the active position, it is substantially sharp on at least a portion of its distal edge, which is the edge 209, and substantially blunt along its proximal edge. The projection 208 remains in that final location, in the active position, until the anvil arm 14 is withdrawn from the anvil entry hole 584. Referring also to FIG. 122, as the anvil arm 14 is withdrawn from the anvil entry hole 584, the blunt proximal edge of the projection 208 encounters target vessel tissue adjacent to the anvil entry hole 584. Because that proximal edge of the projection 208 is blunt, that contact causes the projection 208 to rotate about the axis of the aperture 849, through which the clip 862 extends. This rotation causes the projection 208 to reenter the channel 246 in the anvil arm 14 and come to rest in the withdrawal position. In the withdrawal position, the projection 208 substantially does not extend out of the anvil arm 14 in any direction, allowing for a minimal cross-section of material to be removed from the lumen of the target vessel 580 through the anvil entry hole 584.

Alternately, the projection 208 is oriented in the opposite direction, and the pusher 850 is configured to move the projection 208 proximally rather than push it distally. In such a configuration, when the projection 208 is in the active position, the edge 209 is oriented proximally. The projection 208 is configured to be placed in a withdrawal position in a manner other than contact with the wall of the target vessel 580, as contact between the edge 209 of the projection and the wall of the target vessel 580 during withdrawal of the anvil arm 14 may cause the anvil entry hole 584 to be enlarged.

Where the cutter 200 of FIGS. 125-128 is used, the cutter 200 initially is in the stowed position, in which it is substantially restrained from translation. At least part of the lobe 858 is positioned at least partially within the receiving space 876. The first cam surface 878 is located proximal to the lobe 858, and the structure of the centerpiece 868 is located distal to the lobe 858, holding the lobe 858 is place within the receiving space 876 and thereby holding the projection 208 in the stowed position. The projection 208 is substantially completely within the channel 246 in the anvil arm 14.

Figure 126:
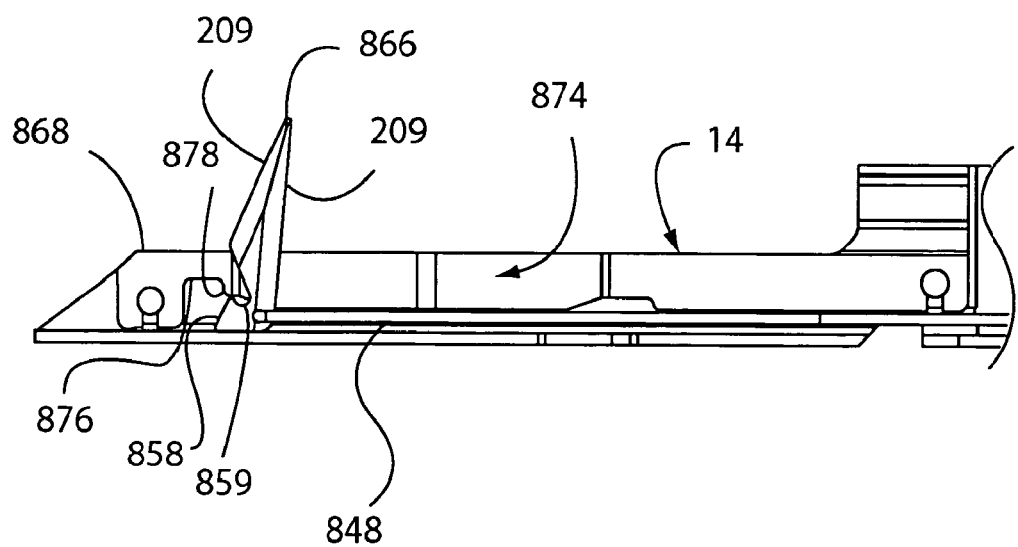

Referring also to FIG. 126, the member 848 is moved proximally. The lobe 858 does not simply translate proximally due to the presence of the first cam surface 878. The aperture 849 in the projection 208 is located below the first cam surface 878. As a result, proximal motion of the member 848 creates a moment, causing the lobe 858 to rotate out of the receiving space 876. The notch 859 in the projection 208 is shaped and sized to allow such rotation around the first cam surface 878. Contact between the first cam surface 878 and the lobe 858, as well as the shape of the first cam surface 878 and the lobe 858 and the moment applied to the projection 208, cause the projection 208 to rotate about the aperture 849 as the member 848 translates the aperture 849 proximally. As the lobe 858 rotates out of the receiving space 876, the free end 866 at the other end of the projection 208 moves upward through the free space 874 in the centerpiece 868 and above the contact surface 206 of the anvil arm 14 into the wall of the target vessel 580. As the end 866 of the projection 208 moves upward, an edge 209 of the projection 208 incises the wall of the target vessel 580, causing the projection 208 to cut through the target vessel wall 580. The cutter 200 is now in the active position, with the projection 208 extending through the wall of the target vessel 580 and an edge 209 of the projection 208 oriented in the direction in which the projection 208 is to be moved, which as shown is the proximal direction.

Referring also to FIG. 143, the member 848 continues to move proximally. This motion may be accomplished in any suitable manner. For example, the member 848 may be connected to the sled 482 directly or indirectly, such that the member 848 and the sled 482 translate proximally together. As the member 848 moves proximally within the channel 246, it causes the projection 208 to move proximally as well. Optionally, a groove 964 is defined in the bottom surface 266 of the channel 246. The groove 964 is slightly wider than the lobe 858 of the projection 208. As the projection 208 rotates to the active position, as described above, at least part of the lobe 858 enters the groove 964. Where the groove 964 is provided, contact between the lobe 858 of the projection 208 and the groove 964 as the projection 208 is moved proximally keeps the projection 208 in the desired orientation and keeps the projection 208 from moving out of contact with the wall of the target vessel 580. That is, the groove 964 provides lateral stability for the lobe 858, substantially preventing the lobe 858 from moving laterally during proximal motion of the projection 208. The free space 874 within the centerpiece 868 in the channel 246 of the anvil arm 14 may have a width selected such that it stabilizes the projection 208 as it translates. That is, the free space 874 may be slightly wider than the thickness of the projection 208, thereby limiting the distance that the projection 208 can move laterally as it translates.

The length of the arteriotomy is related to the distance across which the projection 208 is translated. This distance is controlled by the translation of the member 848 as well as the length of the free space 874 in the centerpiece 868. Referring to FIG. 127, when the arteriotomy is complete, the projection 208 has reached a final location proximal to its starting point due to its contact with the proximal edge of the free space 874 in the centerpiece 868. The member 848 continues to move proximally. The projection 208 cannot translate further proximally due to contact with the proximal edge of the free space 874, but can rotate about the axis of the aperture 849. The second cam surface 880 is spaced apart from the bottom surface 266 of the channel 246 in the anvil arm 14. The aperture 849 in the projection 208 is located below the second cam surface 880. As a result, proximal motion of the member 848 creates a moment, causing the projection 208 to rotate about the axis of the aperture 849 as the member 848 moves proximally, and causing the free end 866 of the projection 208 to rotate into the channel 246 in the anvil arm 14. At least a portion of the lobe 858 rotates into a second receiving space 882. The second receiving space 882 is formed into the centerpiece 868 or a different structure or mechanism associated with the anvil arm 14. As the lobe 858 rotates, at least a portion of the lobe 858 is free to rotate into or through the slot 860. The slot 860 provides clearance for the motion of the lobe 858. Referring also to FIG. 128, motion of the projection 208 is then complete, with the projection 208 in the withdrawal position. In the withdrawal position, the edges 209 of the projection 208 are within the channel 246 in the anvil arm 14, such that they do not incise tissue during removal of the anvil arm 14 through the anvil entry hole 584. However, at least part of the lobe 858 may extend through the slot 860 in the withdrawal position. If so, the lobe 858 is blunt such that motion of the lobe 858 against tissue does not substantially disturb it.

The cutter 200 and the sled 482 may be configured to move proximally rather than distally, regardless of the particular configuration of the cutter 200 or the sled 482. If so, the actuation of the cutter 200 and the sled 482 proceeds substantially as described above, but in the reverse direction.

Where the cutter slide 1092 is used, a cutter pull 1096 may extend distally from the cutter slide 1092 to the cutter 200 or projection 208, as described above. The cutter slide 1092 may be utilized whether the cutter 200 is actuated to move proximally or distally. Where the cutter slide 1092 moves proximally, the cutter pull 1096 may be rigid, such as a wire, or flexible, such as a cable. Where the cutter slide 1092 moves distally, the cutter pull 1096 is advantageously substantially rigid in order to push the cutter 200 and/or the projection 208 distally. After the engagement member 216 and the receiver 218 engage one another, and the second cable 490 causes the receiver 218 to move, the engagement member 216 moves as well. This motion of the engagement member 216 in turn causes the cutter slide 1092 to move, which in turn moves the cutter pull 1096. Motion of the cutter pull 1096 moves the cutter 200 and/or projection 208, substantially as described above. In this way, the cutter 200 and/or projection 208 can be moved without the first cable 480 and the second cable 490 being directly connected to them.

Referring also to FIG. 95, regardless of the particular configuration of cutter 200 or projection 208 utilized, the shield 290 may be used to protect the tissue of the graft vessel 404 from the projection 208. The projection 208 of the cutter 200 may move upward out of the channel 246 at a longitudinal position under the raised element 293 or the first ramp element 294. The raised element 293 of the shield 290 holds the tissue of the graft vessel 404 away from the path of motion of the projection 208 to minimize or eliminate contact between the projection 208 and the graft vessel 404. Where the shield 290 includes an aperture 296, the aperture 296 is substantially aligned with the motion of the projection 208. As the projection 208 begins to move upward above the contact surface 206 of the anvil arm 14, its upper tip may enter the aperture 296. The shield 290 is shaped, and has a particular thickness, such that the upper tip of the projection 208 does not move substantially upward out of the aperture 296 to a position above the upper surface of the shield 290. In this way, the shield 290 protects the tissue of the graft vessel 404 from the projection 208. Alternately, the shield 290 does not include an aperture 296 therein. If so, the shield 290 is shaped, and extends far enough above the contact surface 206 of the anvil arm 14, such that the projection 208 substantially does not contact the shield 290 as it emerges from the channel 246 in the anvil arm 14 or at other locations during its travel.

Figure 47:
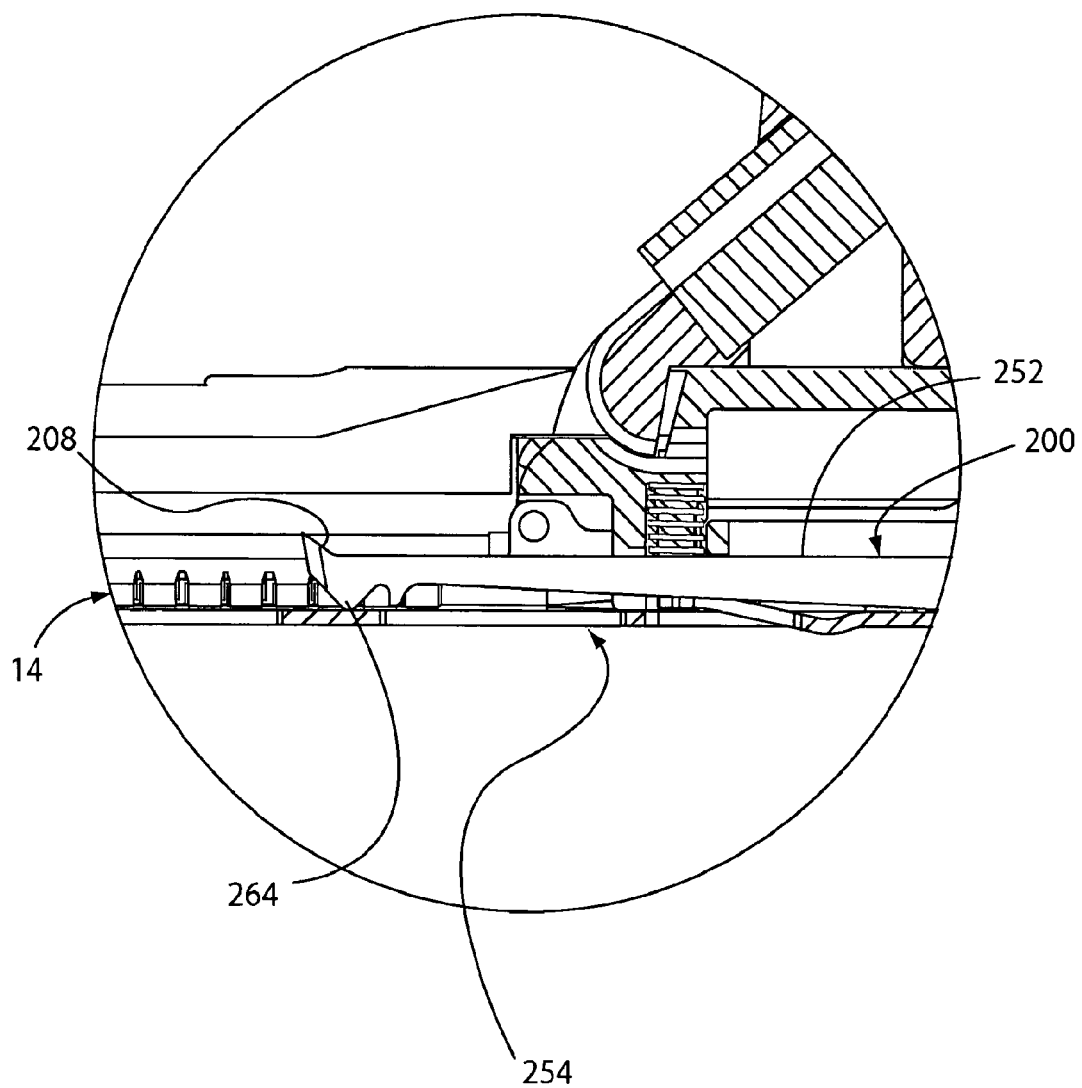
FIG. 47 is a side cutaway view of the anvil and staple holder of FIG. 34, where the cutter is in a fourth position.

As the sled 482 continues to advance distally, the distal end 474 of each ramp element 476 actuates each connector deployer 452 in turn, causing the connector deployers 452 to sequentially deploy the corresponding staples 446 as described above. Additionally, the vein knives 432 continue to move distally as the sled 482 advances distally, lengthening the incision in the root 405 of each flap 408. Further, referring also to FIG. 47, the cutter 200 continues to advance distally as the receiver 218 continues to urge the engagement feature 216 distally. The cutter 200 incises the wall of the target vessel at a given longitudinal position at substantially the same time as each vein knife 432 incises the corresponding flap 408 at the that longitudinal position. Alternately, the timing of the cutting action of the cutter 200 and the vein knives 432 is different, such that the cutter 200 incises the wall of the target vessel at a given longitudinal position either before or after each vein knife 432 incises the corresponding flap 408 at that longitudinal position.

The lower surface of the keel 264 contacts the bottom surface 266 of the channel 246 during this translation. The contact between the keel 264 and the bottom surface 266 of the channel 246 counteracts the downward bias of the distal end of the cutter 200. In this way, the projection 208 is maintained above the contact surface 206 of the anvil arm 14. As the cutter 200 continues to translate distally, the projection 208 moves through the tissue of the wall of the target vessel in a direction substantially parallel to the longitudinal centerline of the anvil arm 14, and incises the tissue of the wall of the target vessel to create an arteriotomy. Because the projection 208 is connected to and translated by the cutter 200, which is within the target vessel, the arteriotomy is performed from within the target vessel. The tip of the projection 208 may maintain substantially the same height relative to the contact surface 206 of the anvil arm 14 during translation of the cutter 200, or may change its height relative to the contact surface 206 of the anvil arm, as long as the projection 208 continues to incise completely through the wall of the target vessel.

Where the cutter of FIG. 43B is used, the lower surface of the second keel 265 and the lower surface of the first keel 264 both contact the bottom surface 266 of the channel 246. Alternately, the lower surface of the first keel 264 extends downward enough that the lower surface of the second keel 265 does not contact the bottom surface 266 of the channel 246.

Figure 48:
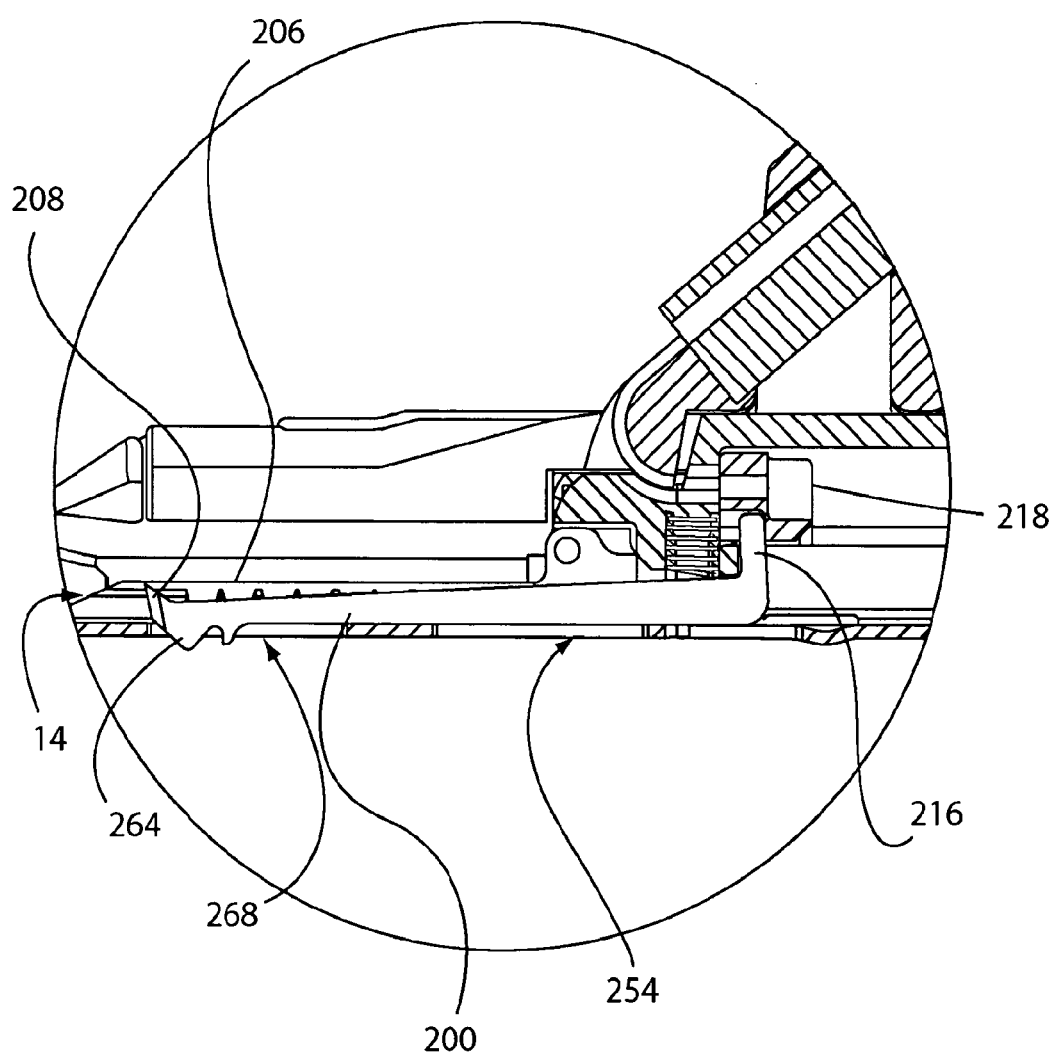
FIG. 48 is a side cutaway view of the anvil and staple holder of FIG. 34, where the cutter is in a fifth position.

Referring also to FIG. 48, a second lower opening 268 is defined through the lower surface 256 of the anvil arm 14. The second lower opening 268 is distal to and substantially aligned with the first lower opening 254. The cutter 200 continues to advance distally as the receiver 218 continues to impel the engagement feature 216 distally. As a result of this translation, the keel 264 encounters the proximal end of the second lower opening 268. Because the distal end of the cutter 200 is biased downward, the keel 264 moves downward at least partially into the second lower opening 268. The downward motion of the keel 264 causes the distal end of the cutter 200 and the projection 208 to move downward. The keel 264 and/or the proximal end of the second lower opening 268 may be constructed to provide a smooth, gradual downward motion of the keel 264, such as by providing a gradual slope on the keel 264 and/or the proximal end of the second lower opening 268. Alternately, the keel 264 and/or the proximal end of the second lower opening 268 may be constructed to allow or cause the keel 264 to move downward abruptly upon encountering the proximal end of the second lower opening 268. Alternately, where the cutter 200 of FIG. 43B is used, the first keel 264 moves as least partially into the third lower opening 269, and the second keel 264 moves at least partially into the second lower opening 268. The downward motion of the distal end of the cutter 200 causes the projection 208 to retract into or completely through the upper opening 248, such that the projection 208 no longer encounters the tissue of the wall of the target vessel. The projection 208 may be urged downward completely into the channel 246, depending on the depth of the channel 246 and the height of the projection 208. As the projection 208 moves relative to the anvil arm 14 and incises the wall of the target vessel 580, the upper tip of the projection 208 travels along a path that may be affected by several characteristics of the cutter 200 and the anvil arm 14, such as the size and shape of the keel 264 and the spacing between the lower openings 254, 268 in the anvil arm 14. Where the shield 290 is utilized, that path is related to the configuration of the shield 290. If the shield 290 includes an aperture 296 therein, the shield 290 is shaped, and has a particular thickness at each longitudinal point, such that the upper tip of the projection 208 does not move substantially upward out of the aperture 296 to a position above the upper surface of the shield 290. In this way, the shield 290 protects the tissue of the graft vessel 404 from the projection 208 during motion of the projection 208. The tip element 297 of the shield 290 protects the graft vessel 404 in the event that the projection 208 contacts the shield 290 near the end of the stroke of the cutter 200. If the shield 290 does not include an aperture 296 therein, the shield 290 is shaped, and extends far enough above the contact surface 206 of the anvil arm 14, such that the projection 208 substantially does not contact the shield 290 as it moves. As a result, the shield 290 without the aperture 296 therein may extend further above the contact surface 206 of the anvil arm 14 than would the shield 290 with the aperture 296 therein.

Alternately, the upper tip of the projection 208 may remain within the upper opening 248. The cutter 200 may stop its distal translation at substantially the same time that the projection 208 retracts completely into the upper opening 248, or may continue to translate distally within the channel 246 before coming to a stop. Alternately, the second lower opening 268 is not provided, and only the first lower opening 254 extends through the lower surface 156 of the anvil arm 14 into the channel 246. In such a configuration, the cutter 200 is refracted in the proximal direction after the arteriotomy is formed, until the keel 264 moves downward into the first lower opening 254 and the projection 208 consequently retracts completely into the upper opening 248.

Operation of Anastomosis Tool—Completion of Anastomosis

Figure 76:
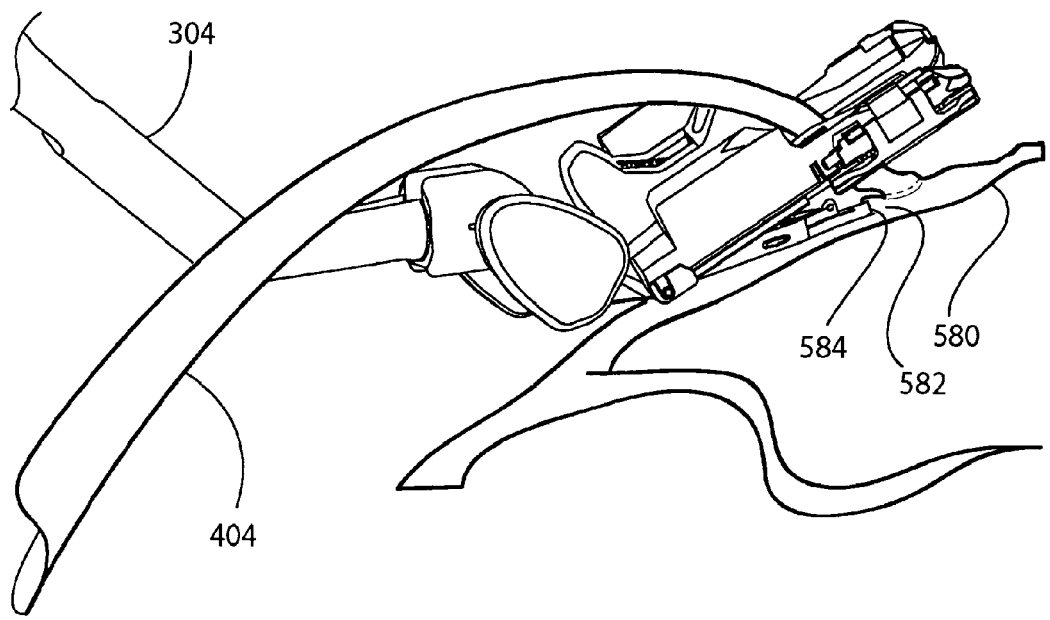
FIG. 76 is a perspective view of the tissue effector of FIG. 74, after the graft vessel has been connected to the target vessel and before the anvil of the tissue effector has been removed from the lumen of the target vessel.

The sled 482 continues to move distally, such that the distal end 474 of the ramp element 446 actuates the most distal connector deployer 452 and deploys the corresponding staple 446. Referring also to FIG. 76, the connection between the end of the graft vessel 404 and the target vessel 580 is then complete. The sled 482 continues to translate, such that each vein knife 432 then moves completely through the corresponding flap 408. A portion of each flap 408 continues to be held between each graft clip 412 and corresponding flap receiving surface 406. Thus, when the root 405 of each flap 408 has been completely incised through by the corresponding vein knife 432, the staple holder 38 no longer holds the graft vessel 404, and is freed from the anastomosis site.

Referring to FIG. 72, the rocker 508 completes its travel when the distal end 520 of the distal arm 516 contacts one or more of the ribs 556 in the handle 302. This contact prevents further downward motion of the distal arm 518, and thereby causes the rocker 508 to cease its motion. Alternately, at least a portion of the distal arm 516 and/or the proximal arm 514 contact a stop or other structure in the handle 302 which obstructs further motion of the rocker 508. Alternately, the motion of the rocker 508 is stopped in a different way, such as by a braking or clutch mechanism. Thus, the corresponding travel of the second cable 490 and the connected sled 482 cease as well. After the rocker 508 has completed its travel, the upper portion 532 of the contact feature 528 of the proximal slider 522 contacts the proximal end 516 of the proximal arm 514. The spring 546 biases the proximal slider 522 distally. Thus, the upper portion 532 of the contact feature 528 is pressed against the proximal end 516 of the proximal arm 514, holding the proximal arm 514 and the rocker 508 in place and substantially preventing rotation of the rocker 508 in a direction opposite to its previous motion. Alternately, the proximal slider 522 does not contact the rocker 508 after the travel of the rocker 508 is complete. At substantially the same time as the motion of the rocker 508 stops, the lower guide 552 of the distal slider 534 contacts a stop 553 defined in or connected to the handle 302. The stop 553 may be integrated with at least one of the ribs 556. The stop 553 is positioned to interfere with further proximal motion of the distal slider 534, such that contact between the lower guide 552 and the stop 553 causes the distal slider 534 to cease moving proximally. Alternately, the stop 553 is not used, and the distal slider 534 is allowed to continue to move proximally after deployment of the staples 446. Referring also to FIG. 77, this is time t=4, at which the distal slider 534 has moved proximally from its position at time t=3, and the proximal slider has moved slightly distally from its position at time t=3.

As described above, the distal slider 534 may include a verification stub 560 that extends substantially upward from the upper end of the distal slider 534 through a slot 562 in the handle 302. Initially, when the distal slider 534 is in its most distal position, the verification stub 560 is also in its most distal position. As the distal slider 534 translates proximally during actuation of the anastomosis tool 300, the verification stub 560 also translates proximally. Thus, after the anastomosis tool 300 has been actuated and the distal slider 534 has moved to its most proximal position, the verification stub 560 has moved to its most proximal position as well. By visually inspecting the position of the verification stub 560, the user can confirm whether the anastomosis tool 300 has been completely actuated. In addition, the distal end 474 of at least one ramp element 446 may be visible after actuation of the anastomosis tool 300 if the distal end 442 of the passage 440 is open, providing another visual indication that the anastomosis tool 300 has been completely actuated. The distal end of the first lower opening 254 and the proximal end of the second lower opening 268 control the motion of the projection 208 and thereby control the penetration of the wall of the target vessel. That is, the distance between the distal end of the first lower opening 254 and the proximal end of the second lower opening 268 determines the length of the arteriotomy.

Alternately, where the snap arm 606 is used instead of the cam lock to hold a corresponding graft clip 412 in the closed position, the distal end 474 of the corresponding ramp element 446 extends out of the distal end 442 of the passage 440 to disengage the catch 608 of the snap arm 606. That is, the lobe 610 of the snap arm 606 is positioned relative to the distal end 442 of the passage 440 such that the distal end 474 of the corresponding ramp element 446 encounters the lobe 610 near the end of the travel of the ramp element, pushing the lobe 610 out of engagement of the arm 402 and thus disengaging the catch 608 from the arm 402. The corresponding graft clip 412 is thereby free to move out of the closed position, freeing the flap 408 held by that graft clip 412. In such an embodiment, the vein knives 432 may be omitted, because the flaps 408 are freed in their entirety. Further, the spikes 410 are omitted, such that the flaps 408 are not held in place on the flap receiving surface 406 after the snap arm 606 is disengaged from the arm 402. Alternately, at least one vein knife 432 may be omitted, and at least one graft clip 412 is simply moved from the closed position to the open position after the anastomosis is complete, thereby freeing each associated flap 408. Such motion may be performed by hand, or by the anastomosis tool 300 itself by any suitable mechanism. Force exerted on the graft clip or clips 412 to move them from the closed position to the open position is sufficient to unsnap the graft clip or clips 412 from the arms 402, overcome the cam lock between the graft clip or clips 412 and the arm, or otherwise overcome the force or forces holding the graft clip or clips 412 in the closed position.

After performing the arteriotomy, the cutter 200 is in a distally-extended position. The cutter 200 remains in that position as the anvil arm 14 is removed from the target vessel 580, where the tissue bridge 582 separates the anastomosis site from the anvil entry hole 584 in the wall of the target vessel 580. Thus, the projection 208 does not extend out of the upper opening 248 during removal of the anvil arm 14 from the target vessel 580. Alternately, after performing the arteriotomy, the cutter 200 may be moved proximally within the channel 246 in the anvil arm 14 before removing the anvil arm 14 from the target vessel 580.

The tissue effector 400 is then returned to the open position from the closed position, to allow the anvil arm 14 to be withdrawn from the target vessel 580. Where the graft affixer 910 is used, the graft affixer 910 moves out of the wall of the target vessel 580 as the tissue effector 400 moves to the open position. Preferably, the diameter of the graft affixer 910 is small enough that substantially no leakage occurs from the target vessel 580 after its removal from the wall thereof. Where the graft affixer 910 is a heel clip 910, the closed heel clip 910 separates from the staple holder 38 and remains in tissue, as described above. After the trigger 308 has been depressed to deploy one or more connectors 464, the distal arm 518 of the rocker 508 has deflected at least a portion of the holder 594. As a result, the deflected holder 594 exerts an opposing bias against the distal arm 518 of the rocker 508. When the user releases the trigger 308, the biased holder 594 then acts against the distal arm 518, pushing it upward and causing the rocker 508 to rotate about the rocker axle 510. As a result, the proximal arm 514 of the rocker 508 moves downward toward its original position. Thus, the proximal end 516 of the proximal arm 514 moves downward against the upper portion 532 of the contact feature 528 of the proximal slider 522, and continues to move downward past the intersection between the two portions 530, 532 of the contact feature 528. As the proximal end 516 of the proximal arm 514 moves past that intersection to contact the lower portion 530 of the contact feature 528, the proximal slider 522 is freed to move distally a small amount due to the bias of the spring 546. This proximal motion relaxes the tension on the first cable 480. As a result, the biasing element 475 pushes the staple holder 38 away from the anvil 10, returning the tissue effector 400 to the open position. The tissue effector 400 thus no longer clamps the wall of the target vessel 580, and the anvil arm 14 can be removed from the lumen of the target vessel 580. The spacing between the staple holder 38 and the anvil 10 in the open position is selected to ensure adequate clearance for separation of the tissue effector 400 from the target vessel 580. For example, the staple holder 38 is moved far enough from the anvil 10 such that the spikes 410 are fully removed from the flaps 408 before the anvil arm 14 is removed from the target vessel 580. Alternately, the tissue effector 400 is returned to the open position in another manner. When the projection 208 is retracted out of the tissue of the wall of the target vessel, the distal end of the arteriotomy is defined, and the arteriotomy is complete. Thus, referring also to FIG. 73, the anastomosis between the graft vessel 404 and the target vessel 580 is complete as well. The spacing between the connectors 464 is such that there is substantially no leakage at the anastomosis. For example, the spacing between the connectors 464 may be comparable to the spacing between sutures in a conventional hand-sewn anastomosis. When the anvil arm 14 is withdrawn from the anvil entry hole 584 in the target vessel 580, the shield 290 (if utilized) slides out of the heel 587 of the anastomosis. The shield 290 may do so whether it is connected to the anvil 10 or to the staple holder 38. The shield 290 is sized and shaped such that it can exit through the heel 587 without substantially disturbing the anastomosis. For example, the shield 290 may be thin and narrow, and flexibly connected to the anvil arm 14, such that it can slip out of the heel 587 substantially without affecting the tissue of the graft vessel 404 or the target vessel 580 and substantially without resulting in leakage at the heel 587. Further, the shield 290 may be composed of a flexible material such as polyethylene that facilitates the flexing and removal of the shield 290 from the anastomosis.

Alternately, referring also to FIGS. 144-145, the shield 290 may be removed through the toe 585 of the anastomosis. As the tissue effector 400 moves back to the open position, the distal end of the staple holder 38 moves away from the anastomosis, such as by rotating away from it. As the distal end of the staple holder 38 moves, contact between the shield 290 and the graft vessel 404 causes the shield 290 to rotate about the hinge 966. Further, as the distal end of the staple holder 38 moves away from the anastomosis, it moves the hinge 966 away from the anastomosis. The combination of the motion of the shield 290 about the hinge 966 and the motion of the hinge 966 itself away from the anastomosis causes the shield 290 to slide smoothly out of the toe 585 of the anastomosis. The shield 290 is shaped to facilitate its smooth withdrawal in this manner, such that the shape of the shield 290 works in conjunction with the path of motion of the shield 290 as it is withdrawn. Alternately, where the hinge 966 is not used, the shield 290 is flexible enough to allow it to flex adequately to be removed from the toe 585 of the anastomosis. This flexibility also minimizes or prevents any disturbance to the toe 585 of the anastomosis during withdrawal of the shield 290 from it.

Where the most proximal connector bay 448 and/or the most distal connector bay 448 in an arm 402 is offset toward the longitudinal centerline of the anvil arm 14 relative to one or more other connector bays 448, the corresponding connectors 464 at the heel 587 and/or toe 585 of the anastomosis are closer to one another than are connectors 464 on opposite sides of the anastomosis that were deployed from the other connector bays 448. By placing the connectors 464 at the heel 587 and/or toe 585 of the anastomosis closer to one another, sealing of the anastomosis may be enhanced. Similarly, where the longitudinal centerline of each connector bay 448 forms a large angle relative to the local horizontal, such an angle may hold the lateral sides of the anastomosis closer together and thus may enhance sealing. Such an angle may be used in addition to offsetting at least one connector bay 448 to provide enhanced sealing.

Referring also to FIG. 135, where the graft affixer 910 is used and the graft vessel 404 has a single flap 408 at one end, the resulting anastomosis may include a tissue overhang 926 at the toe 585, extending beyond the connectors 464 deployed into the graft vessel 404 and the target vessel 580 to create the anastomosis. The tissue overhang 926 is at least partially in contact with the outer surface of the target vessel 580, and may contribute to sealing or minimizing any minor leakage that may be present at the toe 585 of the anastomosis. Optionally, the overhang 926 may be trimmed from the graft vessel 404, at the discretion of the surgeon. The overhang 926 is oriented substantially longitudinally relative to the target vessel 580. For example, the overhang 926 extends away from the toe 585 of the anastomosis in a direction substantially parallel to the longitudinal dimension of the target vessel 580. Alternately, the overhang 926 is oriented differently relative to the target vessel 580.

Alternately, the graft affixer 910 is configured substantially as described above, but is positioned on the staple holder 38 such that it affixes a location on the graft vessel 404 corresponding to the toe of the anastomosis to the staple holder 38. Thus, the graft affixer 910 is positioned on the staple holder 38 in a location distal to the location it would occupy if it were to affix the heel of the graft vessel 404 to the staple holder 38. The anastomosis then may be performed in a reverse direction as compared to the anastomosis where the graft affixer 910 engages the heel of the graft vessel 404. That is, the anvil arm 14 is oriented in the opposite direction relative to the target vessel 580, and the anvil entry hole 584 may be located downstream from the arteriotomy, rather than upstream from it, depending on the direction of flow of fluid through the target vessel 580. As a result, the tissue overhang 926 covers the anvil entry hole 584. Thus, the tissue overhang 926 contributes to the elimination or reduction of minor leakage from the anvil entry hole 584 after removal of the anvil arm 14 therefrom. Optionally, a composition such as an adhesive is used to hold the tissue overhang 926 onto the target vessel 580 and enhance its ability to eliminate or reduce leakage. A sealer 780 as described below may be utilized to substantially seal the anvil entry hole 584, as well.

Optionally, the staple holder 38 includes a deployment indicator 968. Referring to FIGS. 146-147, the deployment indicator 968 may include a window 970 in the upper surface of the staple holder 38. The window 970 may be simply an opening in the upper surface of the staple holder 38. Alternately, clear plastic or other suitable transparent or translucent material may be placed over, under or in the opening. The deployment indicator 968 may also include an indicia 972 associated with the sled 482. The indicia 972 may be a hole or opening in the sled 482, a symbol on the sled 482, a region of color on the sled 482, or any other suitable indicia. The indicia 972 is placed at a location on the sled 482 that is positioned under the window 970 after the sled 482 has completed its motion and deployed the connectors 464. In this way, the indicia 972 is visible to the operator after the sled 482 has completed its motion. Visibility of the indicia 972 through the window 970 confirms that the connectors 464 have all been deployed.

Operation of Anastomosis Tool—Fluid-Driven Actuator

An anastomosis tool 300 that utilizes a fluid-driven actuator 1000 may be operated in a similar manner as that described above. For brevity, only the significant differences between the operation of an anastomosis tool 300 that utilizes a fluid-driven actuator 1000 and the operation of an anastomosis tool 300 that utilizes a different source of energy for its operation are described below.

Initially, a source of pressurized gas is made available to the fluid-driven actuator 1000. As one example, referring to FIGS. 152-153, a gas cylinder 1046 is held within the handle 302 of the anastomosis tool 300. In order to make the gas in the gas cylinder 1046 available, and begin the operation of the anastomosis tool 300, a user turns the knob 1048. The spindle 1049 advances distally as the knob 1048 is turned. As the spindle 1049 advances, it pushes the gas cylinder 1046 distally. As the spindle 1049 continues to advance, it pushes the neck end 1047 of the gas cylinder 1046 against the spike 1064. Continuing advancement of the spindle 1049 exerts greater force against the gas cylinder 1046, and thereby between the neck end 1047 of the gas cylinder 1046 and the spike 1064. The increase in force causes the spike 1064 to puncture and enter the neck end 1047 of the gas cylinder 1046. The aperture 1066 in the spike 1064 also enters the gas cylinder 1046. In this way, gas flows from the gas cylinder 1046 into the aperture 1066, and thereby into the gas inlet 1036 of the fluid-driven actuator 1000. The force exerted on the gas cylinder 1046 by the spindle 1049 holds the gas cylinder 1046 substantially fixed onto the spike 1064, and substantially prevents leakage between the gas cylinder 1046 and the spike 1064.

Where the knob 1048 includes an indicator 1080, such as a substantially planar tab extending from the proximal end of the knob 1048, the position of that indicator 1080 in a particular position provides positive confirmation that the gas cylinder 1046 has been punctured. For example, where the indicator is a substantially planar tab, its orientation relative to the handle 302 and/or a marker on the handle 302 confirms that the knob 1048 is in the activation position and that the gas cylinder 1046 has been punctured by the spike 1064. Further, the second notch 1062 in the spindle 1049 may engage the stop 1054 after the knob 1048 has been moved to the activation position. Contact between the second notch 1062 and the stop 1054 stops the motion of the spindle 1049 when the knob 1048 has been moved to the activation position. In this way, the knob 1048 can be rotated far enough to release gas from the gas cylinder 1046, but not so far as to damage the gas cylinder 1046 and/or the handle 302 of the anastomosis tool 300. Alternately, any other suitable structure, mechanism or method may be used to make pressurized gas available to the fluid-driven actuator 1000. For example, where an external gas source is utilized, that external gas source may be connected directly or indirectly to the gas inlet 1036 in order to make pressurized gas available.

The fluid-driven actuator 1000 is configured to transition among at least two states. Referring to FIG. 149, the fluid-driven actuator 1000 is in a first state, which also may be referred to as the neutral state or the initial state. In this first state, the sealing elements 1006 along the control member 1002, in conjunction with the gas inlet orifice 1038 in the first chamber 1004, define a first gas path associated with the first state of the fluid-driven actuator 1000. When gas is received into the first chamber 1004 through the gas inlet orifice 1038, that gas travels along the first gas path.

In the initial state of the fluid-driven actuator 1000, sealing elements A, B associated with the control member 1002 are positioned on opposite sides of the gas inlet orifice 1038. The sealing element A is positioned proximal to the gas inlet orifice 1038, and the sealing element B is positioned distal to the gas inlet orifice 1038. No other orifices are located in the first chamber 1004 between the sealing elements A, B when the fluid-driven actuator 1000 is in the initial state. Thus, the pressurized gas from the gas inlet orifice 1038 is trapped between the sealing elements A, B. This is the first gas path, which is lightly shaded in FIG. 149. The diameter of the first chamber 1004 is substantially constant between the sealing elements A, B, and each of the sealing elements A, B extends into contact with the wall of the first chamber 1004. Thus, the pressurized gas trapped between the sealing elements A, B exerts substantially the same amount of force on each of those sealing elements A, B. However, that force is exerted proximally on sealing element A and distally on sealing element B, such that the two forces cancel out one another, and the control member 1002 does not substantially move in response to the entry of pressurized gas to the space defined between the sealing elements A, B. Thus, in the neutral state, the pressurized gas entering the first chamber 1004 via the gas inlet orifice 1038 does not move the control member 1002 substantially, and thus the fluid-driven actuator 1000 does not move substantially as a whole.

The operator inserts the anvil arm 14 of the tissue effector 400 into the lumen of the target vessel 580 at a desired location, substantially as described above. Next, referring also to FIG. 152, the operator depresses the trigger 308. The trigger 308 rotates about the projections 1034 relative to the handle 302. Alternately, the trigger 308 moves differently relative to the handle 302. As the trigger 308 rotates about the projections 1034 or otherwise moves relative to the handle 302, the transverse member 1032 of the trigger 308 moves proximally. The transverse member 1032 engages the slot 1017 of the control member 1002, such that the proximal motion of the transverse member 1032 moves the control member 1002 proximally. Referring also to FIG. 148, the proximal motion of the transverse member 1032 is halted by contact between the tab or tabs 1014 extending from the control member 1002 and the surface 1016 of the body 1018 in which the first chamber 1004 is defined. Alternately, proximal motion of the transverse member 1032 is halted in a different manner.

When the tab or tabs 1014 of the control member 1002 stop the proximal motion of the control member 1002, the fluid-driven actuator 1000 is in the second position, which also may be referred to as the clamping position. Referring to FIG. 150, in the clamping position, the sealing element B of the control member 1002 is proximal to the gas inlet orifice 1038. Also in the clamping position, a sealing element C of the control member 1002 is distal to both the sealing element B and to the gas inlet orifice 1036. Thus, the sealing elements B, C seal the pressurized gas entering the first chamber 1004 between them. The ribs 1008 adjacent to the sealing elements B, C do not extend all the way to the wall of the first chamber 1004, at least along the entire circumference of each rib 1008. Thus, compressed gas entering the first chamber 1004 from the gas inlet orifice 1038 moves distally past the rib 1008 distal to and in proximity to the sealing element B.

The gas path within the fluid-driven actuator 1000 in the clamping position is lightly shaded in FIG. 150. Further, for clarity, arrowheads indicate the direction of gas flow through the passages of the fluid-driven actuator 1000 along that gas path. As compressed gas moves from the gas inlet orifice 1038 distally past the rib 1008 distal to and in proximity to the sealing element B, it is prevented from moving further distally in the first chamber 1004 than the sealing element C. Passages P1 and P2 extend from the first chamber 1004 to the second chamber 1012. An orifice O1 exists in the wall of the first chamber 1004 at the intersection between the passage P1 and the first chamber 1004. An orifice O2 exists in the wall of the first chamber 1004 at the intersection between the passage P2 and the first chamber 1004. When the control member 1002 is in the clamping position, the orifices O1 and O2 are between the sealing elements B and C. Thus, in the clamping position, compressed gas flows out of the volume of the first chamber 1004 between the sealing elements B, C and into the orifices O1, O2, then through the passages P1, P2 into the second chamber 1012.

An orifice O3 exists in the wall of the second chamber 1012 at the intersection between the passage P1 and the second chamber 1010. An orifice O4 exists in the wall of the second chamber 1012 at the intersection between the passage P2 and the second chamber 1012. Sealing elements D, E are positioned relative to the clamping member 1010 such that, in the clamping position, the orifices O3 and O4 are located between the sealing elements D, E. The sealing element D is located proximal to the sealing element E. The second chamber 1012 may be configured to have a first cross-sectional area at a more-distal location, and a second, larger cross-sectional area at a more-proximal location. As a result, the sealing element D, which is positioned within the portion of the second chamber 1012 having a larger cross-sectional area, has a larger surface area than the sealing element E, which is positioned within the portion of the second chamber 1012 having a smaller cross-sectional area. Consequently, the pressurized gas entering the second chamber 1012 through the orifices O3, O4 exerts more force on the larger sealing element D than on the smaller sealing element E, because the scalar value of force is equal to pressure multiplied by the area acted on by that pressure. Thus, more force is exerted on the sealing element D than on the sealing element E. The greater force exerted on the sealing element D is substantially in the proximal direction, and the lesser force exerted on the sealing element E is substantially in the distal direction, such that the net force on the clamping member 1010 is exerted in the proximal direction. As a result, the clamping member 1010 moves proximally. Alternately, the force differential on the clamping member 1010 that causes the clamping member 1010 to move proximally is generated in a different manner. Proximal motion of the clamping member 1010 continues until the proximal end of the clamping member 1010 encounters the proximal end of the second chamber 1012. Alternately, the proximal motion of the clamping member 1010 is limited or controlled in a different or additional manner.

The first cable 480 is connected to the clamping member 1010 as described above, such as by the hook 1020 at the distal end of the clamping member 1010. Thus, as the clamping member 1010 moves proximally, the clamping member 1010 pulls the first cable 480 proximally. This motion of the first cable 480 moves the tissue effector 400 to the closed position, as described above. As an example, referring to the exemplary embodiment of FIG. 154, as the first cable 480 moves proximally, it pulls the staple holder 38 downward toward the anvil arm 14, which remains substantially stationary. Motion of the first cable 480 is translated into downward force on the staple holder 38 by the axle 1082.

If the operator decides to move the tissue effector 400 relative to the target vessel 580, he or she may simply release the trigger 308. Upon doing so, the control member 1002 moves back to the position it occupies in the neutral position. As a result, the first cable 480 relaxes, and the tissue effector 400 moves back to the open position. The control member 1002 may be biased to the position it occupies in the neutral position, such as by a spring 1003 or other biasing member. Such biasing exerts a force on the trigger 308, tending to move it back to its original position. For example, distal motion of the control member 1002 results in distal motion of the slot 1017 therein, which in turn moves the transverse member 1032 of the trigger 308 distally, returning the trigger 308 to its initial position. A passage P3 may be connected to the second chamber 1012 and to the first chamber 1004. An orifice O5 exists at the interface between the passage P3 and the second chamber 1012, and an orifice O6 exists at the interface between the passage P3 and the first chamber 1004. The orifice O5 is proximal to the orifice O3, and the orifice O6 is proximal to the orifice O1. Referring also to FIG. 149, when the control member 1002 moves back to the position it occupies in the neutral position, the most-proximal sealing element 1006 on the control member 1002 is distal to the orifice O5, allowing pressurized gas in the second chamber 1012 to vent through the passage P3 into the proximal end of the first chamber 1004, and then through the outlet orifice 1042 and then the gas outlet 1040. A return spring (not shown) is positioned in the proximal portion of the second chamber 1012, and exerts a force in the distal direction on the clamping member 1010. As an example, the return spring is a compression spring that coils around the proximal end of the clamping member 1010, with one end that presses against the most proximal rib 1008 of the clamping member 1010, and an opposite end that presses against the proximal end of the second chamber 1012. By exerting a distal force on the clamping member 1010, the return spring returns the clamping member 1010 to its original position after the pressurized gas has been vented. Similarly, a return spring (not shown) is positioned in the proximal portion of the third chamber 1028, and exerts a force in the distal direction on the firing member 1026. As an example, the return spring is a compression spring that coils around the proximal end of the firing member 1026, with one end that presses against the most proximal rib 1008 of the firing member 1026, and an opposite end that presses against the proximal end of the third chamber 1028. By exerting a distal force on the firing member 1026, the return spring returns the firing member 1026 to its original position after the pressurized gas has been vented. Upon moving the tissue effector 400 to a new position, the user may actuate the trigger 308 again, thereby moving the tissue effector 400 back to the closed position. Thus, the fluid-driven actuator 1000 may be configured to move the tissue effector 400 to and from the open and closed positions, until the operator is satisfied with the position of the tissue effector 400 relative to the target vessel 580.

After the operator has moved the tissue effector 400 to the closed position in a suitable location of the target vessel 580, referring also to FIG. 152, the operator further depresses the trigger 308. The trigger 308 rotates about the projections 1034 relative to the handle 302. Alternately, the trigger 308 moves differently relative to the handle 302. As the trigger 308 rotates about the projections 1034 or otherwise moves relative to the handle 302, the transverse member 1032 of the trigger 308 moves proximally. The transverse member 1032 engages the slot 1017 of the control member 1002, such that the proximal motion of the transverse member 1032 moves the control member 1002 proximally. Referring also to FIG. 148, the application of greater force to the trigger 308 causes the ramp surfaces 1015 of the tabs 1014 to be pressed inward toward the longitudinal axis of the control member 1002 as a result of contact between the ramp surfaces 1015 and the end of the first chamber 1004. After the tabs 1014 have moved inward a sufficient amount, the tabs 1014 are able to move into, and the control member 1002 is able to move along, the first chamber 1004 until the end of the control member 1002 opposite the tabs 1014 contacts the corresponding end of the first chamber 1004. This contact stops the motion of the control member 1002 at a defined third position. Alternately, the control member 1002 is stopped at a defined third position in another manner. In this way, the trigger 308 provides two-stage actuation. That is, a small amount of force applied to the trigger 308 is sufficient to move the fluid-driven actuator 1000 from the initial position to the clamping position, but a larger amount of force is required to move the fluid-driven actuator 1000 from the clamping position to the firing position. In this way, the operator can actuate the trigger 308 and close the tissue effector 400 without inadvertently deploying the connectors 464 at the same time. Alternately, the fluid-driven actuator 1000 only has two states, in which case actuation of the trigger 308 with a single amount of force both closes the tissue effector 400 and deploys the connectors 464. Alternately, the tabs 1014 are not movable into the first chamber 1004.

Referring also to FIG. 151, when the control member 1002 contacts the end of the first chamber 1004 and such contact stops the proximal motion of the control member 1002, the fluid-driven actuator 1000 is in the third position, which also may be referred to as the firing position. The gas path within the fluid-driven actuator 1000 in the clamping position is lightly shaded in FIG. 151. Further, for clarity, arrowheads indicate the direction of gas flow through the passages of the fluid-driven actuator 1000 along that gas path. In the firing position, the sealing element B of the control member 1002 is proximal to the gas inlet orifice 1038 and the orifice O1, and the sealing element C of the control member 1002 is distal to the gas inlet orifice 1038 and the orifice O1, and proximal to the orifice O2. Thus, in the firing position, compressed gas flows into the volume of the first chamber 1004 between the sealing elements B, C, then through the orifice O1 and the passage P1 into the second chamber 1012 through the orifice O3.

The pressurized gas enters the second chamber 1012 through the orifice O3, between the sealing elements D, E. As described above with regard to the clamping position, the pressure of the gas between the sealing elements D, E creates a net proximal force on the clamping member 1010, moving it to a proximal position and thereby actuating the first cable 480 to move the tissue effector 400 to the closed position. In the firing position, the sealing element A of the control member 1002 is located between the gas outlet orifice 1042 and the orifice O6 that exists at the interface between the passage P3 and the first chamber 1004, and the sealing element B of the control member 1002 is located between the orifice O6 and the gas inlet orifice 1038. In this way, pressurized gas that escapes the second chamber 1012 through the orifice O5 and the passage P3 enters the portion of the first chamber 1004 between the sealing elements A, B, and is trapped therebetween while exerting substantially no net force on the control member 1002.

In the firing position, the sealing element C of the control member 1002 is located proximal to the orifice O2 and distal to the orifice O1 in the first chamber 1004, and the sealing element E of the clamping member 1010 is located distal to the orifice O4 in the second chamber 1012. Thus, pressurized gas flows out of the second chamber 1012 through the orifice O4 and the passage P2, and into the first chamber 1004 through the orifice O2. The control member 1002 includes a sealing element G located distal to the sealing element C. When the control member 1002 is in the firing position, the sealing element G is located distal to an orifice O7 that exists at the interface between a passage P4 and the first chamber 1004. The passage P4 connects the first chamber 1002 and the second chamber 1012. An orifice O8 exists at the interface between the passage P4 and the second chamber 1012. Pressurized gas received into the first chamber 1004 through the orifice O2 thus travels out of the orifice O7, through the passage P4, and into the second chamber 1012 through the orifice O8.

In the firing position, the sealing element E of the clamping member 1010 is positioned proximal to the orifice O8, and the sealing element F of the clamping member 1010 is positioned distal to the orifice O9. The pressurized gas entering the second chamber 1012 through the orifice O8 exerts substantially the same amount of force on each of the sealing elements E, F, but in opposite directions, such that the pressurized gas between the sealing elements E, F exerts substantially no net force on the clamping member 1010. An orifice O9 exists in the second chamber 1012 at the interface between a passage P5 and the second chamber 1012. In the firing position, the sealing element F of the clamping member 1010 is located distal to the orifice O9. The passage P5 connects the second chamber 1012 to the third chamber 1028. An orifice O10 exists at the interface between the passage P5 and the third chamber 1028. Thus, in the firing position, pressurized gas travels from the second chamber 1012 between the sealing elements E, F out of the orifice O9, through the passage P5, and into the third chamber 1028 through the orifice O10.

Advantageously, the placement of the orifices and of the sealing elements 1006 ensures that the clamping member 1010 is positioned to hold the tissue effector 400 in the closed position before pressurized gas is allowed into the third chamber 1028. That is, gas cannot flow into the third chamber 1028 until the clamping member 1010 has been moved to a position that actuates the tissue effector 400 to the closed position. The firing member 1026 includes a sealing element I that is positioned distal to the orifice O10 and a sealing element H that is positioned proximal to the sealing element I. The third chamber 1028 may be configured to have a first cross-sectional area at a more-distal location, and a second, larger cross-sectional area at a more-proximal location. As a result, the sealing element H, which is positioned within the portion of the third chamber 1028 having a larger cross-sectional area, has a larger surface area than the sealing element I, which is positioned within the portion of the third chamber 1028 having a smaller cross-sectional area. Consequently, the pressurized gas entering the third chamber 1028 through the orifice O10 exerts more force on the larger sealing element H than on the smaller sealing element I, because the scalar value of force is equal to pressure multiplied by the area acted on by that pressure. Thus, more force is exerted on the sealing element H than on the sealing element I. The greater force exerted on the sealing element H is substantially in the proximal direction, and the lesser force exerted on the sealing element I is substantially in the distal direction, such that the net force on the firing member 1026 is exerted in the proximal direction. As a result, the firing member 1026 moves proximally. Alternately, the force differential on the firing member 1026 that causes the firing member 1026 to move proximally is generated in a different manner.

The second cable 490 is connected to the firing member 1026 as described above, such as by the hook 1020 at the distal end of the firing member 1026. Thus, as the firing member 1026 moves proximally, the firing member 1026 pulls the second cable 490 proximally. This motion of the second cable 490 actuates the sled 482 to deploy the connectors 464 and create an arteriotomy with the cutter 200 and/or projection 208, as described in greater detail elsewhere in this document. Proximal motion of the firing member 1026 continues until the proximal end of the firing member 1026 encounters the proximal end of the third chamber 1028. Alternately, the proximal motion of the firing member 1026 is limited or controlled in a different or additional manner.

An orifice O12 exists at the interface between a passage P6 and the third chamber 1028. The orifice O12 is located proximal to the orifice O10. An orifice O13 exists at the interface between the passage P6 and the first chamber 1004. The orifice O13 is located proximal to the orifice O6. In the firing position, pressurized gas travels through the orifice O12 in the third chamber 1028 into the passage P6 and out of the orifice O13. The sealing element A is positioned distal to the orifice O13, and a sealing element J connected to the control member 1002 is positioned proximal to the orifice O13. The pressurized gas is thus trapped, and pressure is maintained within the fluid-driven actuator 1000.

After the connectors 464 have been deployed, the trigger 308 is released. The fluid-driven actuator 1000 thus moves back from the firing position to the clamping position and then to the neutral position. When the fluid-driven actuator 1000 moves back to the clamping position, the sealing element J of the control member 1002 is positioned distal to the orifice O13, as shown in FIG. 150. Thus, pressurized gas is vented through the passage P6 and the orifice O13 to the gas outlet orifice 1042 and then out of the gas outlet 1040. As the fluid-driven actuator 1000 returns to the neutral position, additional gas may be vented through the passage P3 and the orifice O6 to the gas outlet orifice 1042 and then out of the gas outlet 1040, as described above.

The topology of the fluid-driven actuator 1000 described above may be implemented in any appropriate manner with regard to route, shape, configuration and other properties of the passages, orifices and other elements thereof. Further, other topologies of the fluid-driven actuator 1000 may be utilized in order to move the tissue effector 400 from the open to the closed position and then to deploy a plurality of connectors 464 to connect the graft vessel 404 to the target vessel 580. As a result of the use of the fluid-driven actuator 1000, a user may experience little or no recoil during actuation of the anastomosis tool 300.

Optionally, the pressure regulation assembly 1070 regulates the pressure of the gas released by the gas cylinder 1046. Initially, the pressure regulation assembly 1070 is positioned as shown in FIG. 163. The pressure control member 1072 is biased to an initial position by the biasing element 1074. For example, the proximal end of the pressure control member 1072 may be biased into contact with the proximal end of the regulator space 1078 by the biasing element 1074. The sealing elements K, L are located proximal to the orifice O15 in the wall of the regulator space 1078, and the sealing element M is located distal to the orifice O15.

After the spike 1064 has punctured the neck end 1047 of the gas cylinder 1046, gas enters the regulator space 1078. The regulator space 1078 may be configured to have a first cross-sectional area at a more-distal location, and a second, smaller cross-sectional area at a more-proximal location. As a result, the sealing element M, which is positioned within the portion of the regulator space 1078 having a larger cross-sectional area, has a larger surface area than the sealing element L, which is positioned within the portion of the regulator space 1078 having a smaller cross-sectional area. Consequently, the pressurized gas entering the regulator space 1078 through the orifice O15 exerts more force on the larger sealing element M than on the smaller sealing element L. The greater force exerted on the sealing element M is substantially in the distal direction, and the lesser force exerted on the sealing element L is substantially in the proximal direction, such that the net force on the pressure control member 1072 is exerted in the distal direction. As a result, the pressure control member 1072 moves distally, against the force exerted in the proximal direction by the biasing element 1074. Alternately, the force differential on the pressure control member 1072 that causes the pressure control member 1072 to move distally is generated in a different manner.

Distal motion of the pressure control member 1072 continues until the sealing element L moves to a location at which that sealing element L blocks the orifice O15, as shown in FIG. 164. Alternately, the proximal motion of the pressure control member 1072 is limited or controlled in a different or additional manner. Pressurized gas that is located in the regulator space 1078 between the sealing elements L, M escapes the regulator space 1078 through the orifice O14 into the gas inlet 1036. Referring also to FIG. 165, the stop 1076 may provide a hard stop that limits distal travel of the pressure control member 1072. The stop 1076 may be positioned such that it stops the pressure control member 1072 at a position in which the orifice O15 is located between the sealing elements K, L, blocking the influx of pressurized gas into the regulator space 1078. In such a position, the pressure control member still allows pressurized gas that is located in the regulator space 1078 between the sealing elements L, M to escape through the orifice O14.

As pressurized gas continues to escape through the orifice O14, the pressure in the regulator space 1078 between the sealing elements L, M decreases, because the blockage of the orifice O15 by the sealing element L prevents additional gas from entering the regulator space 1078. As a result of the pressure decrease, the force exerted distally on the sealing element M decreases to a value less than the force exerted proximally on the pressure control member 1072 by the biasing element 1074. As a result, the pressure control member 1072 moves proximally, such as to the position shown in FIG. 164, so that the sealing element L no longer blocks the orifice O15. Pressurized gas can then enter the regulator space 1078 through the orifice O15, repeating the actions described above. In this way, the pressure control member 1072 oscillates, thereby controlling the pressure that is delivered to the gas inlet 1036 through the orifice O14. The gas pressure passing into the aperture may vary substantially sinusoidally or otherwise within an upper limit and a lower limit, as the pressure control member 1072 moves back and forth. Alternately, the pressure of the gas released from the gas cylinder 1046 may be regulated by a different and/or additional structure or mechanism, by a structure and/or mechanism outside the anastomosis tool 300, or by a different method.

After the anastomosis is complete, the tissue effector 400 then may be removed from the anastomosis site, and optionally the anvil entry hole 584 may be sealed as described below. Referring also to FIG. 146, where a deployment indicator is used, the deployment indicator 968 confirms that the sled 482 has completed its motion, and that the connectors 464 have all been deployed. For example, where an indicia 972 is associated with the sled 482, motion of the sled 482 as a result of motion of the second cable 490 moves the indicia 972 under the window 970, such that the operator can view the indicia 972 and confirm that the sled 482 has completed its motion. However, any other suitable deployment indicator, and/or other information associated with completed motion of the sled 482 and/or deployment of the connectors 464, may be utilized to confirm deployment of the connectors 464.

Sealer

After the anastomosis is complete and the anvil arm 14 has been removed from the lumen of the target vessel 580, the anvil entry hole 584 that remains in the wall of the target vessel 580 is small enough to prevent significant bleeding therethrough. To that end, the anvil entry hole 584 may be less than substantially 2 mm wide, and advantageously less than 1 mm wide. Alternately, the anvil entry hole 584 is closed by hand suturing. Alternately, the anvil entry hole 584 is closed with a biocompatible glue, adhesive or the like. Alternately, the anvil entry hole 584 is closed with a clip, clamp, or other implantable device that remains on the target vessel. Such a device may be positioned on the outer surface and/or inner surface of the target vessel, and may extend into the anvil entry hole 584. A sealer for closing the anvil entry hole 584 may be constructed from nitinol or other superelastic or pseudoelastic material, or from stainless steel or other material, where that device moves between a first configuration and a second configuration during deployment, and where the second configuration holds the anvil entry hole 584 closed.

Figure 96:
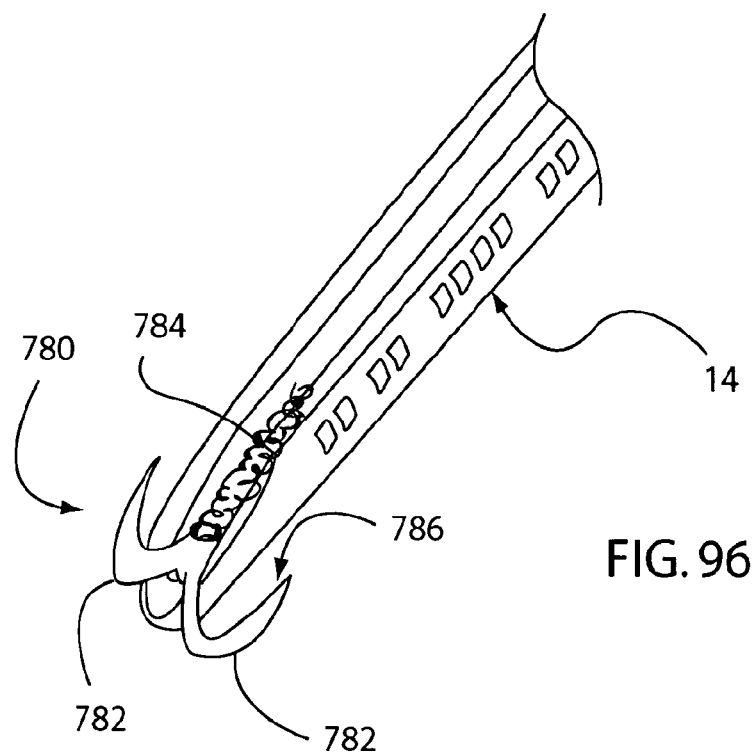
FIG. 96 is a perspective view of a sealer that is detachably connected to the anvil.
Figure 97:
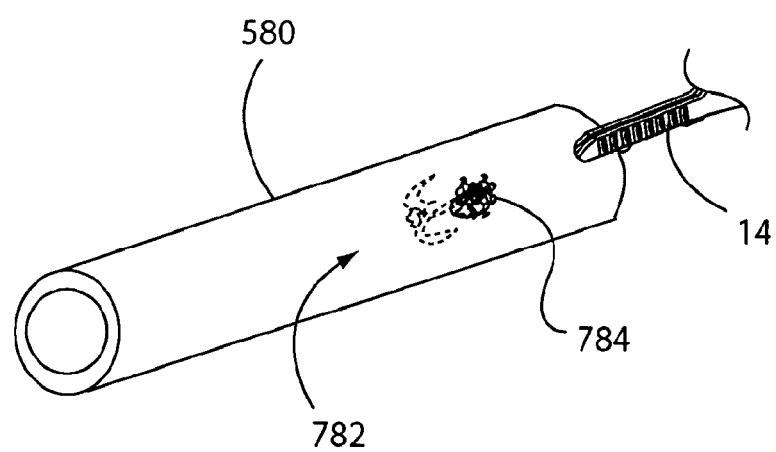
FIG. 97 is a schematic view of the deployment of the sealer of FIG. 96.

Referring to FIGS. 96-97, a sealer 780 includes at least one securing element 782 and at least one plug element 784. The sealer 780 may be detachably connected to the anvil arm 14 at its distal end or at a different location thereof, in such a way that the presence of the sealer 780 does not substantially interfere with the motion of the cutter 200. Alternately, the sealer 780 may be detachably connected to the staple holder 38. Alternately, the sealer 780 is applied to the anvil entry hole 584 with a tool separate from the tissue effector 400. The securing element or elements 782 may be any structure and/or mechanism that can engage the tissue of the target vessel 580. As one example, at least one securing element 782 may be a hook 782. Each hook 782 is oriented such that its free end 786 extends at least partially in the proximal direction, and such that it is substantially blunt in the distal direction. The free end 786 of at least one hook 782 may include a barb. Each hook 782 may be smoothly curved, angled, or shaped in any other appropriate manner. Each hook 782 is connected to a plug element 784, which may be proximal to the hook or hooks 782. Where multiple hooks 782 are used, they may be spaced substantially evenly and/or symmetrically about a plug element 784, or may be spaced unevenly and/or asymmetrically about the central element 784. The plug element 784 may be substantially cylindrical, substantially linear, convoluted, straight, curved, or shaped in any other appropriate manner. Similarly, the plug element 784 may be formed from any appropriate material or combination of materials, such as polytetrafluoroethylene. As one example, the plug element 784 includes an assemblage of one or more flexible elements tightly or loosely coiled or otherwise bunched or tangled into a fibrous mass. The flexible elements may be absorbent, expandable, coated with a coagulant, coated with an adhesive such as fibrin glue and/or have one or more other useful properties. The flexible elements may be fibers, filaments or other structures. The flexible elements may form the plug element 784, or may be a portion of a complete plug element 784. As another example, the plug element 784 includes a solid element, such as a shaft or cylinder, instead of or in addition to one or more flexible elements. The solid element may be composed of any biocompatible material, such as stainless steel or nitinol. One or more flexible elements such as described above may be connected to the solid element. The plug element 784 is detachably connected to the anvil arm 14. Alternately, one or more securing elements 782 are detachably connected to the anvil arm 14 instead of or in addition to the plug element 784. Optionally, at least a portion of the sealer 780 is formed from a resorbable material.

In operation, the anvil arm 14 is inserted into the lumen of the target vessel through the anvil entry hole 584 substantially as described above. The sealer 780 is connected to the anvil arm 14, such as at its distal end. Each hook 782 of the sealer 780 is curved such that its free end 786 is oriented proximally, and the portion of the hook 782 that is oriented distally is substantially blunt. In this way, the sealer 780 does not substantially engage the tissue of the target vessel 580, or substantially enlarge the anvil entry hole 584, as the anvil arm 14 enters the anvil entry hole 584. The connectors 464 are deployed to perform anastomosis substantially as described above. After the anastomosis is complete, the anvil arm 14 is moved proximally. As the distal end of the anvil arm 14 (which is in the lumen of the target vessel 580) approaches the anvil entry hole 584, the free end 786 of each hook 782 encounters the inner surface of the target vessel 580. As the anvil arm 14 continues to move proximally and exit the anvil entry hole 584, the free end 786 of each hook 782 engages the tissue of the target vessel 580. This engagement between one or more hooks 782 and the wall of the target vessel 580 causes the sealer 780 to resist further proximal motion. This resistance, coupled with the continued proximal motion of the anvil arm 14, causes the sealer 780 to detach from the anvil arm 14. The anvil arm 14 then exits the anvil entry hole 584 and moves away from the anastomosis site. The sealer 780 is left behind and held substantially in place by engagement between the hooks 782 and the target vessel 580. The plug element 784 of the sealer 780 thus extends at least partially into the anvil entry hole 584. The presence of the plug element 784 at least partially within the anvil entry hole 584 acts to minimize or eliminate temporary leakage through the anvil entry hole 584. Depending on the material utilized to form the plug element 784, the plug element 784 may expand within the anvil entry hole 584 to facilitate sealing. For example, where the plug element 784 includes a bundle of flexible elements such as fibers, those flexible elements may expand. Further, the plug element 784 may include an adhesive or coagulant, and/or may deliver a therapeutic agent to the tissue in proximity to the anvil entry hole 584, that assists in sealing the anvil entry hole 584.

Referring to FIGS. 98-99, another example of a sealer 780 includes a plug element 784 that is a stopper 784. The stopper 784 is composed of a biocompatible material such as silicone. The cross-section of the stopper 784 is sized and shaped to substantially match the size and shape of the anvil entry hole 584. For example, where the anvil entry hole 584 is substantially circular, the stopper 784 is substantially cylindrical, with a diameter substantially the same as the diameter of the anvil entry hole 584. The stopper 784 may be sized to be slightly larger than the anvil entry hole 584, in order to fit within the anvil entry hole 584 snugly. The stopper 784 may be delivered to the anvil entry hole 584 in any appropriate manner. As one example, the stopper 784 includes an aperture 792 therethrough, through which a line 794 extends. The line 794 may be a strand of polytetrafluoroethylene, suture or any other appropriate material. The line 794 may be connected to at least one securing element 798, such as described above with regard to FIGS. 96-97, where that securing element 798 engages the target vessel 580. The stopper 784 then is urged distally along the line 794 until the stopper 784 moves into the anvil entry hole 584 and/or into substantial contact with the tissue of the target vessel 580 in proximity to the anvil entry hole 584. As described above with reference to FIGS. 96-97, at least part of the surface of the stopper 784 may be treated with a coagulant and/or other therapeutic substance. After the stopper 784 has engaged the tissue of the target vessel 580, optionally at least part of the line 794 extending out of the stopper 784 may be cut off and removed. Alternately, the line 794 is not secured to the target vessel 580 and is removable therefrom. If so, the securing element or elements 798 may be omitted, and the stopper 784 is held in place in the anvil entry hole 784 by contact with the tissue surrounding the anvil entry hole 784. In such an embodiment, the stopper 784 itself constitutes the entire sealer 780.

Figure 102:
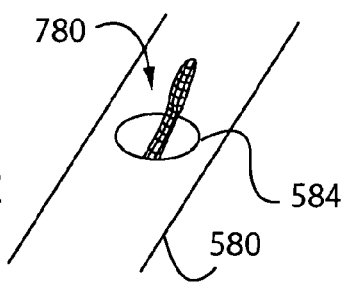
FIG. 102 is a schematic view of another embodiment of a sealer prior to its deployment.

Referring to FIGS. 100-101, another example of a sealer 780 includes a plug element 784 that is a balloon 784. The balloon 784 is made of a biocompatible material such as silicone or latex. The balloon 784 includes an open end (not shown), which may be positioned inside the lumen of the target vessel 580 or outside the lumen of the target vessel 580. The open end of the balloon 784 may be secured to the inner surface of the target vessel 580 with at least one securing element 798 attached thereto, such as described above with regard to FIGS. 96-97. Alternately, the balloon 784 may engage the target vessel 580 differently. Referring to FIG. 102, the balloon 784 initially is in a deflated state, and at least part of the balloon 784 extends through the anvil entry hole 584. The open end of the balloon 784 is positioned in the lumen of the target vessel 580, but is blocked or otherwise closed by the anvil arm 14 (not shown). The anvil arm 14 is then removed from the lumen of the target vessel 580 through the anvil entry hole 584. Blood is then free to flow into the open end of the balloon 784, expanding it to reduce or eliminate leakage through the anvil entry hole 584. As described above with reference to FIGS. 96-97, at least part of the surface of the balloon 784 may be treated with a coagulant and/or other therapeutic substance. Alternately, the open end of the balloon 784 is located outside the target vessel 580. The balloon 784 is filled with fluid, and its open end closed, after the anvil arm 14 is removed from the target vessel 580. The securing element or elements 798 may be omitted, such that the balloon 784 is held in place in the anvil entry hole 784 by contact with the tissue surrounding the anvil entry hole 784. In such an embodiment, the balloon 784 itself constitutes the entire sealer 780.

Figure 103:
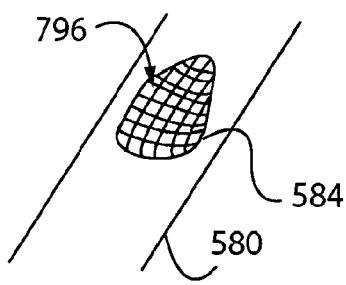
FIG. 103 is a schematic view of the sealer of FIG. 102 after deployment.

Referring to FIGS. 102-103, another example of a sealer 780 includes a plug element 784 that is an expandable structure. Such a sealer 780 includes an expandable frame (not shown) covered at least in part by fabric 796, such as DACRON® brand polyester from DuPont Corporation. The fabric 796 may be substantially impermeable to blood. The frame may be composed at least in part of nickel-titanium alloy or other superelastic alloy. Alternately, the frame is composed at least in part of a different expandable substance, where that substance may be elastically deformable or plastically deformable. Alternately, a material other than fabric 796 covers at least part of the frame, and/or the fabric 796 is omitted altogether. Such a sealer 780 may be detachably connected to the anvil arm 14 at any appropriate location. The plug element 784 may be connected to at least one securing element 798, such as described above with regard to FIGS. 96-97. Alternately, the securing element or elements 798 may be omitted, such that the plug element 784 is held in place in the anvil entry hole 784 by contact with the tissue surrounding the anvil entry hole 784. In such an embodiment, the plug element 784 itself constitutes the entire sealer 780. Initially, as shown in FIG. 102, the plug element 784 is in an undeployed state. When the anvil arm 14 is removed from the anvil entry hole 584, the plug element 784 remains in place within or adjacent to the anvil entry hole 584. The plug element 784 is configured to expand from the undeployed state to a deployed state after removal of the anvil arm 14, as shown in FIG. 103. The frame expands to a circumference at least substantially equal to the circumference of the anvil entry hole 584, causing the fabric 796 to expand and substantially seal the anvil entry hole 584.

Figure 104:
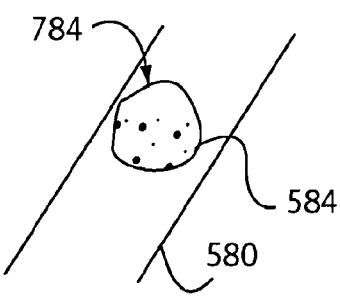
FIG. 104 is a schematic view of another embodiment of a sealer after deployment.

Referring to FIG. 104, another example of a sealer 780 includes a plug element 784 that is composed of super-absorbent material such as polyacrylate. This plug element 784 may be shaped and sized in any appropriate manner for placement at least partially within or in proximity to the anvil entry hole 584. For example, the plug element 784 may be initially small compared to the size of the anvil entry hole 584, but then expand upon absorbing blood to minimize or prevent leakage through the anvil entry hole 584. The plug element 784 may be connected to at least one securing element 798, such as described above with regard to FIGS. 96-97. Alternately, the securing element or elements 798 may be omitted, such that the plug element 784 is held in place in the anvil entry hole 784 by contact with the tissue surrounding the anvil entry hole 784. In such an embodiment, the plug element 784 itself constitutes the entire sealer 780. The plug element 784 may begin expanding when the anvil arm 14 enters the anvil entry hole 584. Thus, when the anvil arm 14 is removed from the anvil entry hole 584, it leaves a space between the plug element 784 and a segment of the anvil entry hole 584. However, due to the superabsorbency of the material from which it is formed, the plug element 784 expands further to fill that space. Thus, the sealer minimizes or stops leakage through the anvil entry hole 584.

Figure 105:
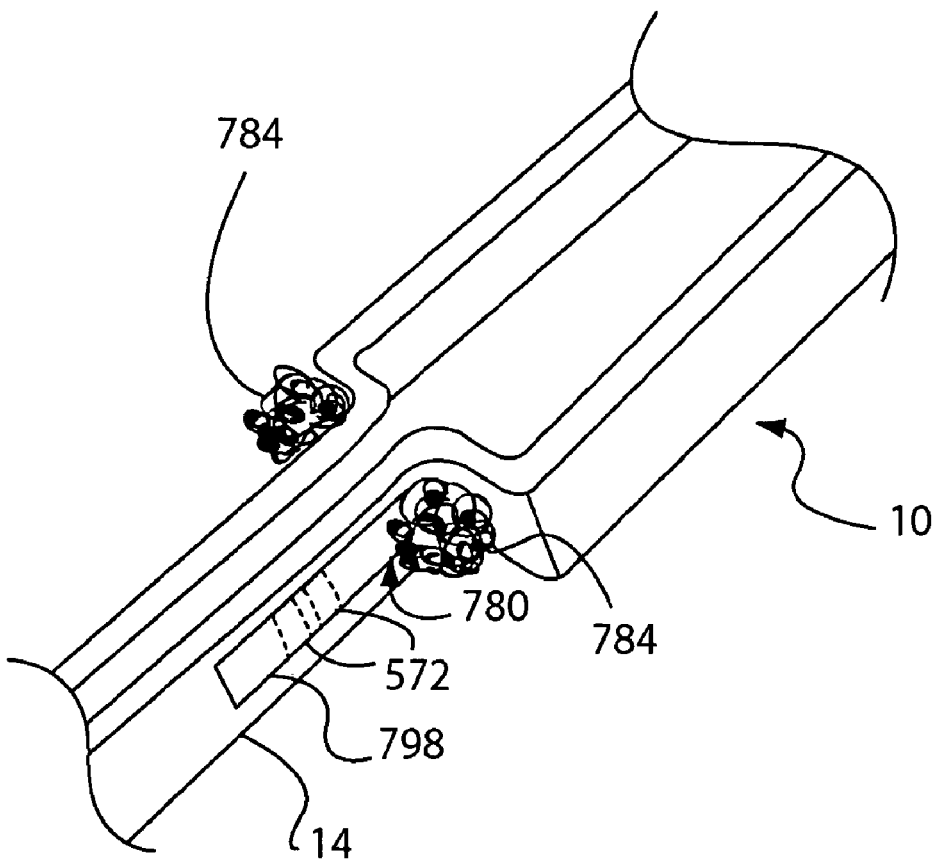
FIG. 105 is a schematic view of another embodiment of a sealer prior to its deployment.

Referring to FIG. 105, another embodiment of a sealer 780 is shown. At least one sealer 780 is used, where each sealer 780 includes an securing element 798 connected to a plug element 784. Advantageously, two sealers 780 are used; however, a single sealer 780 or more than two sealers 780 may be used if desired. Each securing element 798 is a strand, line, sheet, strip, or other configuration of material. Each securing element 798 may be detachably connected to the anvil arm 14, such as by adhesive. Alternately, at least one securing element 798 is simply held against or in proximity to the anvil arm 14 without being detachably connected to it. Each securing element 798 may be placed on a different surface of the anvil arm 14, such that each securing element 798 covers at least one staple bending feature 572 of the anvil arm 14 at least in part. At least one plug element 784 includes an assemblage of one or more flexible elements tightly or loosely coiled or otherwise bunched or tangled into a fibrous mass. The flexible elements may be absorbent, expandable, coated with a coagulant, coated with an adhesive such as fibrin glue and/or have one or more other useful properties. As one example, such flexible elements may be fabricated from polytetrafluoroethylene. The flexible elements may be fibers, filaments or other structures. Each plug element 784 is positioned at the proximal end of the corresponding securing element 798. Alternately, at least one plug element 784 is positioned at a different location relative to the corresponding securing element 798. Each plug element 784 and corresponding securing element 798 may be composed of the same material, or of different materials. Further, each plug element 784 and corresponding securing element 798 may be manufactured as a single unitary structure, or may be made from two or more separate pieces connected together. As one example, each plug element 784 and corresponding securing element 798 are made of a single piece of polytetrafluoroethylene. Other biocompatible materials may be used if desired. Alternately, the plug element 784 of at least one sealer 780 of FIG. 105 may be configured in any other suitable manner, such as described above with regard to FIGS. 98-104.

Referring also to FIG. 34, each plug element 784 may be positioned at or near the proximal end of the anvil arm 14, such as in proximity to the tissue stop 220. The plug elements 784 may extend away from the anvil arm 14, such that they do not substantially enter the lumen of the target vessel 580 through the anvil entry hole 584. Alternately, at least a portion of at least one plug element 784 enters the lumen of the target vessel 580. Optionally, the tissue stop 220 may be omitted, if at least one of the plug elements 784 extends away from the anvil arm 14 such that contact between those plug elements 784 and the outer surface of the target vessel 580 stops the motion of the anvil arm 14 during insertion in the same manner as the tissue stop 220.

The anvil arm 14 is inserted into the target vessel 580 as described above. When the connectors 464 are deployed, at least one connector 464 engages a securing element 798 of a sealer 780 as that connector 464 moves toward its corresponding staple bending feature 572. At least one connector 464 may penetrate the securing element 798, grab the securing element 798, or otherwise engage the securing element 798 as it deploys. In this way, at least one connector 464 engages a securing element 798 as well as the target vessel 580, thereby securing the sealer 780 to the target vessel 580. Advantageously, two or more connectors 464 may engage each securing element 798. The anvil arm 14 is then withdrawn through the anvil entry hole 584 as described above; the sealer 780, being restrained against proximal motion by its engagement with the target vessel 580, detaches from the anvil arm 14. At least a portion of each securing element 798 remains in the lumen of the target vessel 580, held by one or more connectors 464 to the target vessel 580. That is, one or more connectors 464 secure a corresponding securing element 798 to tissue, such that each plug element 784 remains in position adjacent to and/or at least partially in the anvil entry hole 584. Thus, each securing element 798 holds the corresponding plug element 784 in place in proximity to the anvil entry hole 584. The plug element or elements 784 minimize or eliminate temporary leakage through the anvil entry hole 584, and/or promote coagulation at the anvil entry hole 584. At least one plug element 784 may be treated with a coagulant and/or other therapeutic substance, as described above with regard to FIGS. 96-97.

Sealer—Clip

Referring to FIG. 106, the sealer 780 may be at least one clip 800. Each clip 800 may be detachably connected to the anvil arm 14 in any suitable manner. For example, the clip 800 may be pressure-fit to the anvil 10, or may be connected to the anvil 10 by a frangible link or other structure or mechanism. The clip or clips 800 are connected to the anvil arm 14 distal to the tissue stop 220. Alternately, the clip 800 may be located adjacent to or in contact with the tissue stop 220. If desired, at least one clip 800 may replace the tissue stop 220. Alternately, at least one clip 800 is detachably connected to the staple holder 38 in any suitable manner. Each clip 800 may be shaped in any manner that facilitates sealing of the anvil entry hole 584. The clip 800 may be formed from a single wire or other structure, or may be fabricated from two or more different parts assembled together to form the clip 800.

Referring also to FIG. 129, the clip 800 may include at least one penetrating element 884. The penetrating element or elements 884 are sized to penetrate only partially into the target vessel 580. Alternately, at least one penetrating element may be configured to penetrate completely through the wall of the target vessel. Alternately, the penetrating element or elements 884 do not penetrate the target vessel 580 at all, and instead grip the outer surface of the target vessel 580. The clip 800 is substantially bilaterally symmetrical, but may be formed in an asymmetrical manner if desired. The distal end of the clip 800 is open, and two penetrating elements 884 are positioned at that distal end, spaced apart from and facing one another. Alternately, the penetrating element or elements 884 are positioned differently. The penetrating element or elements 884 are oriented at least partially in the proximal direction to facilitate engaging tissue, as described in greater detail below. Extending proximally from each penetrating element 884 is a clip arm 886. Alternately, at least one clip arm 886 includes two or more penetrating elements 884. The clip arms 886 are spaced apart from one another. Moving proximally, the clip arms 886 are bent, curved or otherwise shaped such that they are spaced apart from one another by a lesser distance. This region of the clip arms 886 may be described as the anvil engagement region 888. Moving proximally, each clip arm 86 is connected to a spring 890. Each spring 890 is configured to bias the corresponding clip arm 886 inward toward the longitudinal centerline of the clip 800. The springs 890 are connected to one another by a crossbar 892.

Advantageously, all of the components of the clip 800 are part of a unitary structure, such as a wire that is formed into the configuration of the clip 800. However, the clip 800 may be composed of two or more separate components that are connected together. The clip 800 may be formed from nickel-titanium alloy, stainless steel or any other appropriate material. The clip 800 may be superelastic, elastic, plastically deformable, or it may have other properties and/or a combination of these properties under stress or in deformation.

Referring also to FIG. 106, in an exemplary embodiment, the clip 800 may be connected to the anvil 10 by a pressure fit. That is, the anvil engagement regions 888 of the clip 800 are biased toward one another by the springs 890, and a portion of the anvil 10 is located between the anvil engagement regions 888 that are biased together. As one example, the anvil 10 may include an indentation 894 on either side thereof that is configured to be held by the anvil engagement regions 888 of the clip 800. Each indentation 894 is open at its distal end and closed at its proximal end. That is, each anvil engagement region 888 is allowed to translate out of the distal end of the corresponding indentation 894, but is not allowed to translate substantially proximally out of the indentation 894. Further, a ledge 896 may extend substantially longitudinally along the bottom of at least one indentation, where that ledge 896 prevents the clip 800 from moving downward out of the indentation. The clip 800 is positioned on the anvil 10 such that the penetrating elements 884 are positioned longitudinally at approximately the same location as the tissue stop 220, and on laterally opposed sides of the tissue stop 220. Advantageously, the penetrating elements 884 may be located a short distance distal from the tissue stop 220.

The anastomosis is performed as described above, and the anvil arm 14 is then moved proximally to begin its exit from the lumen of the target vessel 580 through the anvil entry hole 584. As the anvil arm 14 moves proximally, the penetrating element or elements 884 engage the tissue of the target vessel 580. Alternately, at least one penetrating element 884 engages the tissue of the target vessel 580 prior to motion of the anvil arm 14. For example, the anvil arm 14 may be substantially stationary, and the clip 800 may detach from the anvil arm 14 as the clip arms 886 move toward one another. Because the penetrating element or elements 884 are oriented distally, this engagement causes the clip 800 to begin to resist proximal motion. Due to the relative locations of the penetrating elements 884 and the tissue stop 220, the penetrating elements 884 engage the target vessel 580 substantially on opposite sides of the anvil entry hole 584. As the anvil 10 continues to move proximally, such resistance generates a force on the clip 800. When that force exceeds the frictional force between the anvil engagement regions 888 of the clip 800 and the anvil 10, the anvil 10 begins to move proximally relative to the clip 800. The indentation 894 is open at its distal end, allowing the clip 800 to slide out distally. As the anvil 10 continues to move proximally, the anvil engagement regions 888 move out of the indentation 894 altogether. At that time, the springs 890 urge the anvil engagement regions 888 and the clip arms 886 toward one another. This motion of the clip arms 886 toward one another on opposite sides of the anvil entry hole 584 substantially seals the anvil entry hole 584. Alternately, the clip 800 or other sealer 780 may be placed onto the target vessel 580 to substantially seal the anvil entry hole 584 in another manner. For example, the clip 800 or other sealer 780 may be detachably connected to the staple holder 38 rather than the anvil 10. As another example, a separate tool may be utilized to place one or more clips 800 and/or other sealers 780 onto the target vessel 580 to substantially seal the anvil entry hole 584.

Figure 107:
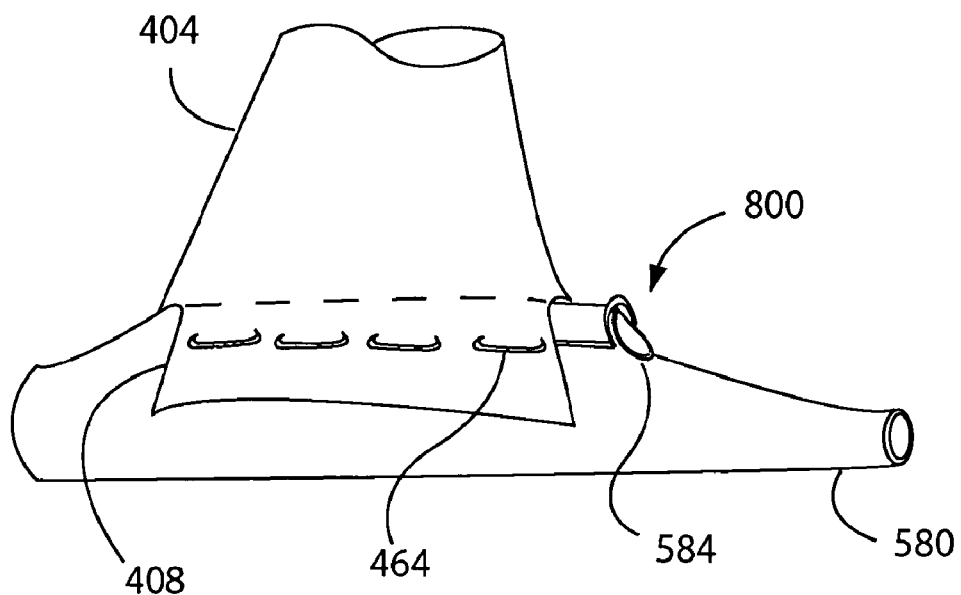
FIG. 107 is a side view of an exemplary clip used to seal the anvil entry hole adjacent to the anastomosis site, where that clip is secured to tissue.
Figure 108:
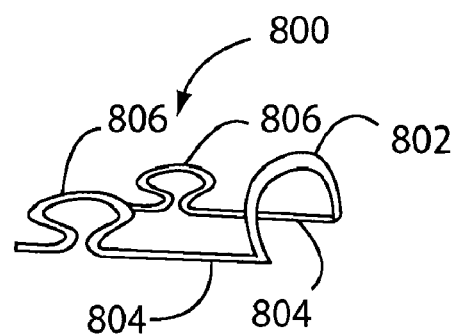
FIG. 108 is a perspective view of the clip of FIG. 107.

Referring to FIGS. 107-108, another exemplary clip 800 is open-ended, with a bridge 802 at its proximal end connecting two spaced-apart outriggers 804. The bridge 802 extends above and between the outriggers 804, accommodating the anvil arm 14. That is, the bridge 802 extends along at least part of the perimeter of the anvil entry hole 584, and allows the anvil arm 14 to slide out of the lumen of the target vessel 580 relative to it. At least one outrigger 804 may include an engagement region 806 configured to be engaged by a corresponding connector 464 when the connectors 464 are deployed. The engagement region 806 may be shaped or configured in any appropriate manner. As one example, the engagement region 806 is a curved or convoluted portion of the outrigger 804, extending above a remainder of the outrigger 804. However, the engagement region 806 may be shaped differently if desired.

Figure 109:
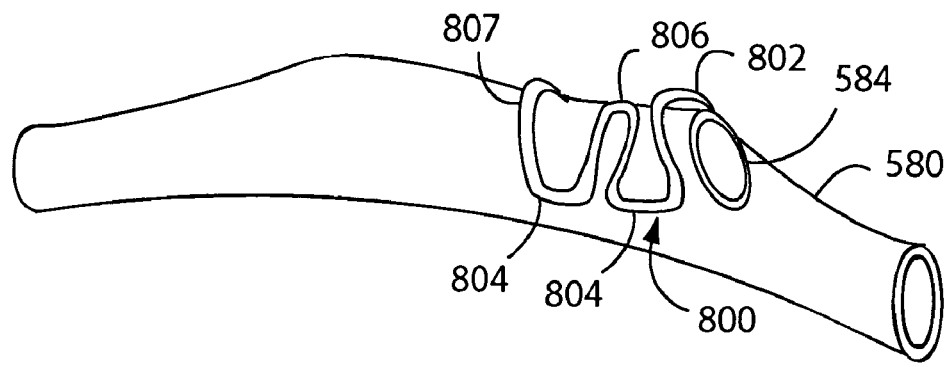
FIG. 109 is a perspective view of another embodiment of a clip, prior to its release. The anvil and staple holder are not shown for clarity.
Figure 110:
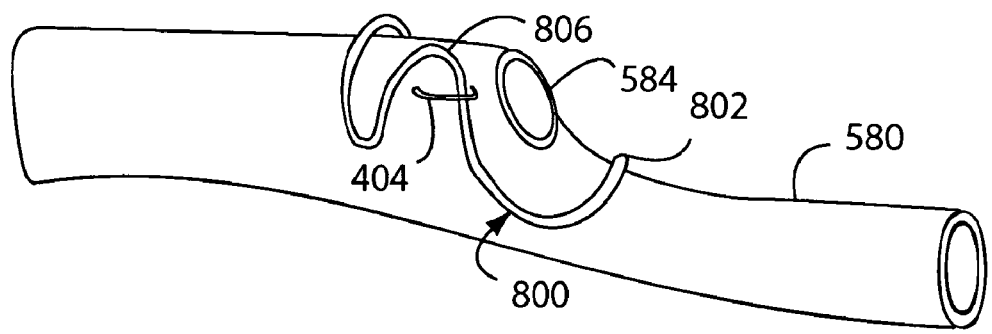
FIG. 110 is a perspective view of the clip of FIG. 109 after its release.

Referring also to FIGS. 109-110, another exemplary clip 800 has a closed perimeter. A bridge 802 is located at the proximal end of the clip 800, and may be configured to accommodate the anvil arm 14 as described above. Moving distally, at least one engagement region 806 is defined in or attached to the clip 800. Each engagement region 806 may be configured substantially as described above. A second bridge 807 connects the outriggers 804 at or near their distal ends, closing the perimeter of the clip 800. The second bridge 807 is configured similarly to the bridge 802 to accommodate the anvil arm 14 in the same manner as the bridge 802. Initially, the clip 800 may be in a first position. The clip 800 may be held in that first position by contact with the anvil arm 14. The bridge 802 may rotate or move downward from that first position, as shown in FIG. 110, to a second position to substantially seal the anvil entry hole 584. Alternately, the bridge 800 and/or other portion of the clip 800 may be configured to seal the anvil entry hole 584 in a different manner.

The clip 800 may be composed of superelastic material such as nickel-titanium alloy, or of elastic material. If so, the clip 800 is configured such that it self-deforms to compress the tissue in proximity to the anvil entry hole 584 when it is detached from the anvil arm 14 or other portion of the tissue effector 400. The clip 800 may be configured to self-deform from a first stable configuration while it is attached to the anvil 10 or other portion of the tissue effector 400 to a second stable configuration after it has been detached. However, the clip 800 need not transition between stable configurations in order to seal the anvil entry hole 584. Alternately, the clip 800 may be composed of plastically deformable material such as stainless steel. If so, the clip 800 is deformed in some manner to seal the anvil entry hole 584, such as by motion of one or more connectors 464, one or more structures or mechanisms connected to or formed into the anvil 10, and/or one or more structures or mechanisms connected to a different portion of the tissue effector 400.

Referring to FIGS. 64 and 106-110, the clip 800 is positioned on or relative to the anvil arm 14 or other portion of the tissue effector 400 such that at least one connector 464 is deployed from the staple holder 38 to engage a corresponding engagement region 806 of the clip 800. As one example, the clip 800 is positioned on or relative to the anvil arm 14 such that when the tissue effector 400 is in the closed position, at least one engagement region 806 of the clip 800 is aligned with a corresponding connector bay 448 defined in an arm 402 of the staple holder 38. That is, at least one engagement region 806 is positioned so that at least a portion thereof is located between a corresponding connector bay 448 and the anvil arm 14, such that deployment of a connector 464 from the connector bay 448 causes that connector 464 to engage the engagement region 806 of the clip 800. Advantageously, the clip 800 is positioned such that at least one engagement region 806 is aligned with the most-proximal connector bay 448 in an arm 402 of the staple holder 38. However, the clip 800 may be aligned with one or more different connector bays 448. The clip 800 advantageously includes at least two engagement regions 806, where at least one engagement region 806 is aligned with a connector bay 448 in one arm 402 of the staple holder 38 and at least one other engagement region 806 is aligned with a connector bay 446 in the other arm 402 of the staple holder 38, such that the clip 800 can be engaged by at least one connector 464 on each side of the anastomosis.

Where a clip 800 is used to seal the anvil entry hole 584, the anastomosis is performed substantially as described above. Referring to FIGS. 64 and 106-110, as the anvil arm 14 is inserted into the lumen of the target vessel 580 through the anvil entry hole 584, the tissue stop 220 contacts the target vessel 580 to stop distal motion of the anvil 10. Alternately, the clip 800 may be utilized instead of the tissue stop 220 to contact the surface of the target vessel and cause distal motion of the anvil arm 14 to stop. If so, the tissue stop 220 may be omitted from the anvil 10. Alternately, the clip 800 is positioned on the anvil 10 proximal to the tissue stop 220, and the tissue stop 220 is utilized as described above.

The sealer 780 may be any other appropriate structure or mechanism, and need not be connected to the anvil 10. For example, the sealer 780 may be an adhesive patch placed onto the target vessel 580 over the anvil entry hole 584. As another example, the anastomosis tool 300 may include a mechanism configured to spray or otherwise deliver a substance to the anvil entry hole 584 to substantially seal it. Such a substance may be an adhesive such as cyanoacrylate or fibrin, a coagulant, or any other suitable substance. Such substance may be held in a reservoir or other container in the anastomosis tool 300 until it is delivered to the anvil entry hole 584. As another example, energy such as thermal energy or radio frequency (RF) energy may be applied to the anvil entry hole 584 to seal it substantially. For example, RF energy may be applied to the anvil arm 14 as it is removed from the anvil entry hole 584, substantially sealing it. As another example, RF energy may be applied to the anvil entry hole 584 by one or more structures or mechanisms other than the anvil arm 14 that are part of or connected to the anastomosis tool 300, wherein those energy-applying structures or mechanisms are placed on the target vessel 580 on or in proximity to the anvil entry hole 584. As another example, the sealer 780 may be a one-piece device having spaced-apart arms, or a multi-piece device having independent, separate arms, at least one of which is magnetized or has a magnet included therein. As the anvil arm 14 is withdrawn, the arms catch on the wall of and become connected to the target vessel 580 in proximity to the anvil entry hole 584. Magnetic force draws the arms together to substantially seal the anvil entry hole 584. Any combination of features described above may be utilized in a particular sealer 780, as appropriate.

The connectors 464 are deployed as described above. At least one connector 464 engages an engagement region 806 of the clip 800 as it is deployed. As one example, where at least one connector 464 is a staple, the engagement region 806 is a wire, strut, thin region, or other structure that is narrower than the staple and at an angle relative to the body of the staple. The staple is deployed such that the body contacts the engagement region 806 and the legs straddle the engagement region 806, such that when the legs are deformed by contact with the anvil arm 14 the staple securely holds the clip 800 relative to the target vessel 580. Advantageously, at least one staple on each side of the anastomosis engages an engagement region 806 of the clip 800, and such staples are in the most proximal location or locations of the anastomosis. Alternately, additional and/or different staples engage the clip 800.

The anastomosis is completed as described above, and the anvil arm 14 is then moved proximally to begin its exit from the lumen of the target vessel 580 through the anvil entry hole 584. The clip 800 is secured in place relative to the anvil entry hole 584 by its engagement with at least one connector 464 that has connected the tissue of the graft vessel 404 to the tissue of the target vessel 580. Thus, as the anvil arm 14 moves proximally, at least one connector 464 holds the clip 800 against that motion. As a result, a force is exerted on the clip 800 that causes the clip 800 to detach from the anvil 10. The clip 800 is detachably connected to the anvil 10 in such a manner that the force required to detach the clip 800 from the anvil 10 is low enough that the tissue effector 40 does not damage tissue as the anvil arm 14 is moved out of the lumen of the target vessel 580, but large enough such that the clip 800 does not become disconnected from the anvil 10 before the anastomosis is complete and the anvil arm 14 is moved out of the lumen of the target vessel 580. The clip 800 is thereby left in place on the target vessel 580. The clip 580 self-deforms or is deformed to from the first position to the second position, such that it substantially seals the anvil entry hole 584. At least a portion of the clip 800 may extend across the perimeter of the anastomosis, if desired.

Sealer—Separate Applier

Referring to FIGS. 136-138, at least one sealer 780 may be held and deployed by an applier 930 separate from the anastomosis tool 300. The sealer 780 utilized with the applier may be a clip 800, or any other suitable sealer 780 such as described above. The applier 930 may be sized and configured to be held in a surgeon's hand, by a surgical instrument such as forceps or needle holders, or any other suitable tool. An exemplary applier 930 includes two arms 932 connected at or near their proximal ends and biased apart from one another at their distal ends. The applier 930 may be fabricated as a unitary mechanism, or may be assembled from two or more separate pieces.

Each arm 932 may include a latch 934 extending toward the opposite arm 932. The latches 934 may be positioned in proximity to the distal ends of the arms 932, or at different positions relative to each arm 932. Each latch 934 includes a stop 936 at or near the portion of the latch 934 furthest from the arm 932 to which is it connected. The stops 936 prevent the arms 932 from spreading apart from one another as far as they would absent the presence of the stops 936, such as by overlapping one another. That is, each stop 936 is further from its associated arm 932 than the stop 936 associated with the opposite arm 932, and extends in a direction toward the other stop 936; as a result, the stops 936 contact one another as the arms 932 move apart. Such contact prevents further motion of the arms 932 away from one another. Because the arms 932 are biased apart from one another, the neutral position of the applier 930 is that in which the stops 936 are in contact with one another.

Optionally, at least one alignment guide 938 extends from each arm 932 toward the opposite arm 932. The alignment guides 938 may extend far enough to be at least partially adjacent to one another. This adjacent positioning of the alignment guides 938 prevents or minimizes lateral motion of the arms 932 relative to one another as the applier is actuated. That is, any lateral motion of one alignment guide 938 toward the other is prevented or minimized by contact between the alignment guides 938.

Optionally, a bump 940 is provided on at least one latch 934 between the stop 936 on that latch 934 and the arm 932 to which the latch is connected. The bump 940 is spaced apart from the stop 936 far enough such that an edge of the other stop 936 is held between the bump 940 and the stop 936. As a result, interference prevents or restricts motion of one stop 936 from moving beyond the bump 940 or the other stop 936. The bump 940 and/or the stop 936 restrained by it are shaped such that a preselected force can overcome the interference between them and allow the applier 930 to close. For example, the edge of the stop 936 may be angled, and/or the bump 940 may be rounded. By preventing or restricting movement of the arms 932 together, the applier 930 is in a known initial configuration when it is first taken in hand by the surgeon.

A holder 942 is located at the distal end of each arm 932. Alternately, at least one holder 942 is located in a different position relative to the corresponding arm 932. At least one holder 942 is configured to engage a sealer 780. In FIG. 136, the sealer is a clip 800 such as shown in FIGS. 137-138, and the applier 930 and its use are described with reference to the clip 800. However, a different clip 800, or a sealer 780 other than a clip could be used, if desired. The holder or holders 942 may engage the clip 800 in any suitable manner. As one example, each holder 942 may include a channel 944 defined therein, where that channel 944 is sized to hold at least part of the clip 800. At least one channel 944 may be sized to provide a pressure fit with the clip 800. The clip 800 may be held in place by force exerted by the holders 942 toward one another. That is, where the bump 940 is utilized to hold the applier 930 in an initial configuration, that initial configuration may be selected such that the distance between the holders 942 is slightly less than the width of the clip 800 held therebetween. In this way, the holders 942 exert force on the clip 800 and hold it securely in place prior to use by the surgeon. Optionally, the holders 942 and/or the clip 800 may include a roughened or otherwise frictionally-enhanced surface at one or more points of contact therebetween, in order to hold the clip 800 in place more securely. Alternately, the clip 800 may flex during assembly, then spring back against the holders 942.

The clip 800 may be shaped and sized in any suitable manner. As one example, the clip 800 may have two prongs 946 connected at their proximal ends. The proximal portions of the prongs 946 may form a V-shape. Moving distally, at least one prong 946 may bend to form an L-shape at its distal end, such that the distal end 948 of at least one prong 946 may be oriented toward the other prong 946. The distal end of each prong 946 may be pointed or sharpened. The distal ends of the prongs 946 may be asymmetrical. That is, the distal end of one prong 946 may be pointed, and while oriented toward the other prong 946, may be closer to the proximal end of the clip 800 than the distal end of the other prong 946. This asymmetry may facilitate closure of the clip 800, as described in greater detail below.

Referring also to FIG. 139, to operate the applier 930, the surgeon grasps it by hand or with a tool such as a forceps 950, and places its distal end in proximity to the anvil entry hole 584. Advantageously, the applier 930 is positioned such that the distal ends 948 of the prongs 946 of the clip 800 are on substantially opposite sites of the anvil entry hole 584. Further, where the distal ends of the prongs 946 of the clip 800 are substantially L-shaped, the applier 930 can place the clip 800 in contact with the target vessel 580 without puncturing the target vessel 580.

When the surgeon is satisfied with the placement of the distal end of the applier 930, compressive force is applied to the arms 932. Where the bump 940 is used, this compressive force overcomes the interference between the bump 940 on one latch 934 and the stop 936 on the other latch 934, causing the distal ends of the arms 932 to move toward one another. As the distal ends of the arms 932 move closer together, the holders 942 move closer together, thereby applying compressive force to the clip 800. As the holders 942 continue to compress the clip 800, the distal ends 948 of the prongs 946 move closer together, until the clip 800 is closed, such as shown in FIG. 138. Where the distal ends 948 of the prongs 946 are asymmetrical, the distal ends 948 may substantially engage one another, rather than passing by one another. In this way, the clip 800 may form a substantially continuous closed path along its perimeter in the closed position, which may be advantageous for closure of the anvil entry hole 584. Alternately, the clip 800 may have a different configuration in the closed position. After the clip 800 is closed, the surgeon releases the applier 930. Because the arms 932 are biased apart from one another, the arms 932 move apart from one another, the holders 942 release the now-closed clip 800, and the anvil entry hole 584 is closed.

As another example, referring to FIG. 157, the clip 800 may be shaped differently. Such a clip 800 is asymmetrical. The clip 800 may include a needle segment 1100 at one end thereof, where that needle segment 1100 has a free end 1102. The free end 1102 of the needle segment 1100 is also one end of the clip 800. The free end 1102 may be sharpened to facilitate penetration of tissue. Moving along the clip 800 away from the free end 1102, a central segment 1104 of the clip 800 is connected to the needle segment 1100. The central segment 1104 may be angled relative to the needle segment 1100 at any suitable angle. For example, the central segment 1104 may be oriented at substantially a right angle to the needle segment 1100.

Optionally, a first tab 1106 may extend inward from the central segment 1104 of the clip 800. Alternately, the first tab 1106 may extend inward from the needle segment 1100 or a different segment of the clip 800. Alternately, the first tab 1106 may be omitted altogether. Optionally, a second tab 1108 may extend outward from the central segment 1104 of the clip 800. Alternately, the second tab 1108 may extend outward from the needle segment 1100 or a different segment of the clip 800. Alternately, the second tab 1108 may be omitted altogether.

Moving along the central segment 1104 away from the free end 1102, the central segment 1104 may angle or curve further. Optionally, at least one indentation 1110 may be defined in the central segment 1104 and/or another segment of the clip 800 in order to define a preferred bending direction and/or increase the amount of bending of which the clip 800 is capable. Optionally, a third tab 1112 may extend outward from the central segment 1104. The third tab 1112 may be positioned on the other side of the tabs 1106, 1108 from the needle segment 1110. Alternately, the third tab 1112 may be positioned differently. Alternately, the third tab 1112 may extend from a different segment of the clip 800. The clip 800 may be restrained between the holders 942 by contact between the second tab 1108 and the notch 1120 of one holder 942, and contact between the third tab 1112 and a surface 1122 on the other holder 942 adjacent to an end of the channel 944 defined therein.

Moving along the clip 800 away from the free end 1102, a third segment 1114 of the clip 800 is connected to the central segment 1104. The third segment 1114 may be angled relative to the central segment 1104 at any suitable angle. For example, the third segment 1114 may angle back toward the central segment 1104 to define an acute angle therewith. Alternately, the third segment 1114 may be oriented differently relative to the central segment 1104. A tip 1116 may be formed at the intersection between the third segment 1114 and the central segment 1104. The tip 1116 may be substantially sharp or substantially blunt. The free end 1118 of the third segment 1114 may be blunt and/or curved. Alternately, the free end 1118 of the third segment 1114 may be sharp. The clip 800 may be fabricated from a single unit of material, such that the segments 1100, 1104, 1114 thereof are simply portions of an integral clip 800. Alternately, at least one of the segments 1100, 1104, 1114 is fabricated separately and connected to one of the others in any suitable manner, such as by welding.

Optionally, referring also to FIG. 158, the applier 930 may be configured differently to hold and deploy the clip 800 of FIG. 157. As one example, one of the holders 942 may include a notch 1120 configured to receive the second tab 1108. As another example, the channel 944 in one of the holders 942 may be oriented such that the third tab 1112 encounters a surface 1122 on the holder 942 adjacent to the channel 944. A portion of the central segment 1104 of the clip 800 between the third tab 1112 and the third segment 1114 may reside within the channel 944.

To deploy the clip 800 of FIG. 157, the applier 930 of FIG. 158 is operated substantially as described above. For brevity, only the significant differences in operation are described here. The surgeon inserts the free end 1102 of the needle segment 1100 into the tissue of the target vessel 580 on one side of the anvil entry hole 584. Then, the surgeon moves the needle segment 1100 through the lumen of the target vessel 580 across the width of the anvil entry hole 584, poking the free end 1102 of the needle segment 1100 back out of the wall of the target vessel 580 on the other side of the anvil entry hole 584. This motion mimics the motion that the surgeon would use to close the anvil entry hole 584 with a needle and suture. The needle segment 1100 can be removed from the target vessel 580 and repositioned if the surgeon is not satisfied with its placement.

When the surgeon is satisfied with the placement of the distal end of the applier 930, compressive force is applied to the arms 932, causing the distal ends of the arms 932 to move toward one another. As the distal ends of the arms 932 move closer together, the holders 942 move closer together and exert a compressive force on the clip 800. The notch 1120 in one holder 942 holds at least part of the second tab 1108 of the clip 800, and the third tab 1112 contacts the surface 1122 on the other holder 942 adjacent to an end of the channel 944 defined therein, thereby substantially preventing the clip 800 from sliding out from between or rotating relative to the holders 942 as they move closer together. The clip 800 may bend about the indentation 1110 in the preferred bending direction established by the indentation 1110. As the holders 942 continue to move closer together, the notch 1120 still holds at least part of the second tab 1108 of the clip 800. However, as the clip 800 bends about the indentation 1110 or other location, and the arms 932 of the applier 930 move about the location of their connection to one another, the relative position of the third tab 1112 and the surface 1122 changes. The third tab 1112 slides along the surface 1122 and into the channel 944. The channel 944 in combination with the notch 1120 still hold the clip 800 between the holders 942; however, the central member 1104 is now free to slide within the channel 944.

Referring to FIG. 159, after the clip 800 has been bent to a closed position, the surgeon releases pressure on the arms 932 of the applier 930. The holders 942 then move apart from one another. The second tab 1108 of the clip 800 moves out of the notch 1120 in one holder, and the central member 1104 of the clip 800 moves out of the channel 944 in the other holder 942. The clip 800 is thus freed. Referring also to FIG. 160, in the closed position in tissue, the clip 800 substantially closes the anvil entry hole 584. As the clip 800 is moved to the closed position, the tip 1116 at the intersection between the third segment 1114 and the central segment 1104 engages the tissue of the target vessel 580 on one side of the anvil entry hole 584 and pulls that tissue toward the other side of the anvil entry hole 584, substantially closing it. The tip 1116 may engage the tissue of the target vessel 580 by penetrating into or completely through the wall of the target vessel 580. When the clip 800 is in the closed position, the first tab 1106 may act to shield the tip 1116 and/or to hold tissue of the target vessel 580 between itself and the tip 1116. When the clip 800 is in the closed position, at least part of the third segment 1114 may act to shield the free end 1102 of the needle segment 1100 and/or to hold tissue of the target vessel 580 between itself and the needle segment 1100.

The clip 800 may be shaped in any other suitable manner or configuration, and may be fabricated from any suitable material in any manner. As one example, the clip 800 may be laser-cut or stamped from a sheet of metal such as stainless steel. As another example, the clip 800 may be a wire segment having any suitable cross section. As another example, one or more cutouts or notches may be provided in the clip 800 to establish a preferred bending direction of some or all of the clip 800. The clip 800 may be configured such that at least one end of the clip 800 encounters a holder 942 or other part of the applier 930 during its deployment, where that encounter deforms at least part of the clip 800.

Operation of Other Exemplary Cutters

As described above, the cutter 200 incises the wall of the target vessel while the staple holder 38 is stapling or otherwise connecting the graft vessel to the target vessel, as described in greater detail below. Alternately, the staple holder 38 may completely staple or otherwise connect the graft vessel to the target vessel before the cutter 200 is urged forward, such that the two vessels are connected before the cutter 200 makes an incision between them. Alternately, the cutter 200 incises the wall of the target vessel before the staple holder 38 has stapled or otherwise connected the graft vessel to the target vessel.

Figure 49:
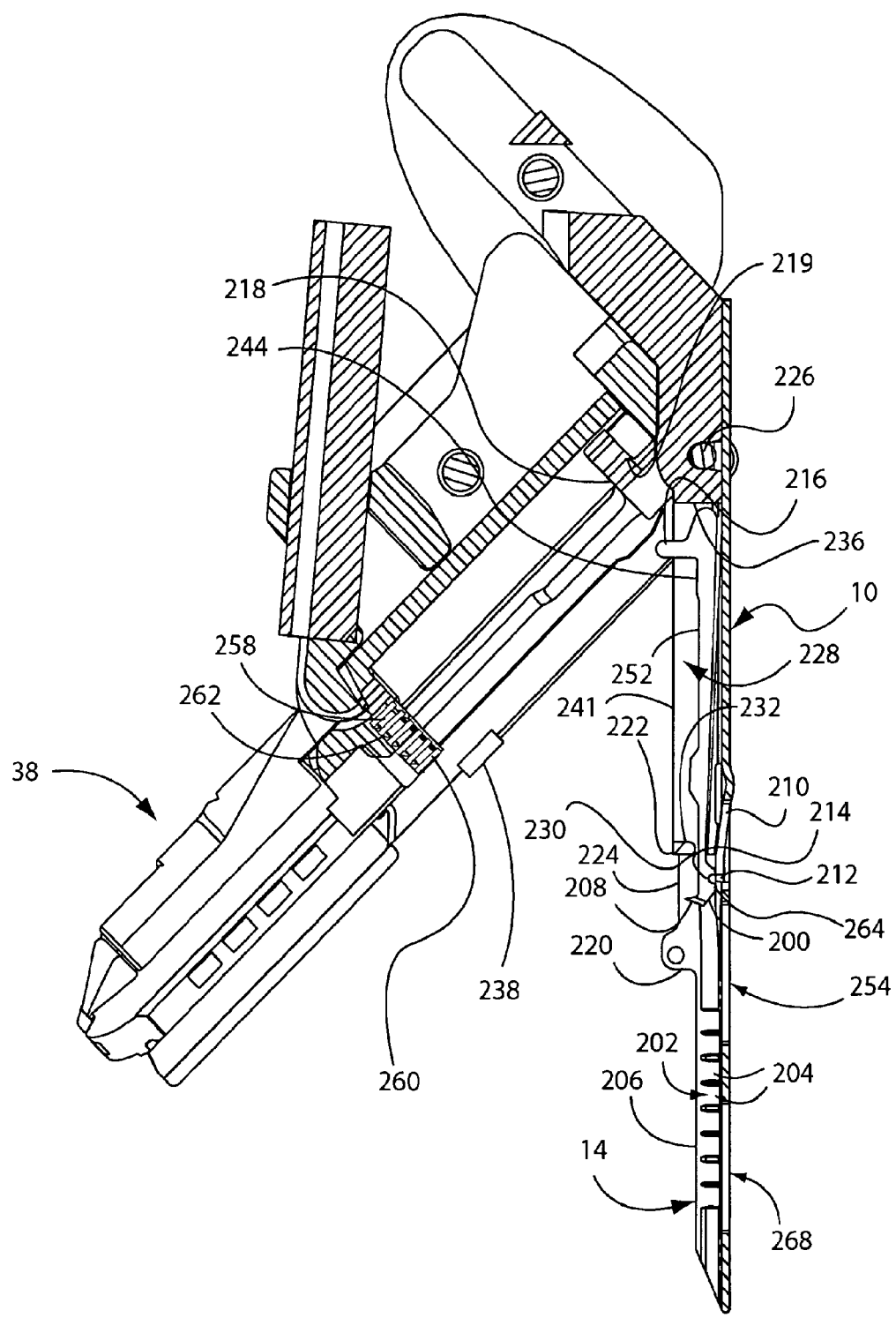
FIG. 49 is a side cutaway view of a second embodiment of an anvil and a staple holder, where the anvil and staple holder are spaced apart from each other.

Referring to FIG. 49, a different embodiment of the anvil 10 also includes a cutter 200 moveable relative to the anvil 10 for making an incision in the wall of a target vessel. The anvil 10, anvil arm 14, staple holder 38, and other components are substantially as described above with regard to FIGS. 34-38 and 44-49. In this embodiment, at least the distal end of the cutter 200 is biased upward. In other regards, the actuation of the anastomosis tool 300, the operation of the mechanisms within the handle 302, and the operation of the tissue effector 400 are substantially as described above. Referring to FIGS. 35 and 49, an anvil insert 222 may be connected to the anvil 10. If so, an aperture 230 is defined through the distal end of the anvil insert 222 into the cavity 228 defined within the anvil insert 222, connecting the channel 246 to the cavity 228. The cutter 200 extends through the aperture 230 in the anvil insert 222, such that the distal end of the cutter 200 is positioned within the channel 246 and the proximal end of the cutter 200 is positioned within the cavity 228. A cam 232 is positioned within the cavity 228 above the aperture 230. Alternately, the cam 232 may be positioned differently relative to the aperture 230. The cam 232 is a structure used in controlling the motion of the cutter 200, as is described in greater detail below.

At least the distal end of the cutter 200 may be biased upward. This biasing may be performed by any appropriate structure or mechanism, such as by one or more springs (not shown). Such a spring or springs may act in compression to push the distal end of the cutter 200 upward, or may act in tension to pull the distal end of the cutter upward. As another example, the cutter 200 may be constructed from an elastic or superelastic material that is formed in such a way as to produce an upward bias. The entire cutter 200 may be biased upward, if desired. At least the distal end of the cutter 200 is biased upward during the translation of the cutter 200 along the anvil arm 14. Alternately, the cutter 200 is not biased, either upward or downward. Instead, the cutter 200 is urged upward and downward at different locations during its translation by the interaction between at least one cam follower on the cutter 200 and at least the cam 232. As described above with regard to the embodiment of the anvil 10 in which the cutter 200 is biased downward, optionally a shield 290 may be connected to the anvil 10. The shield 290 is constructed and is operated substantially as described above.

Figure 50:
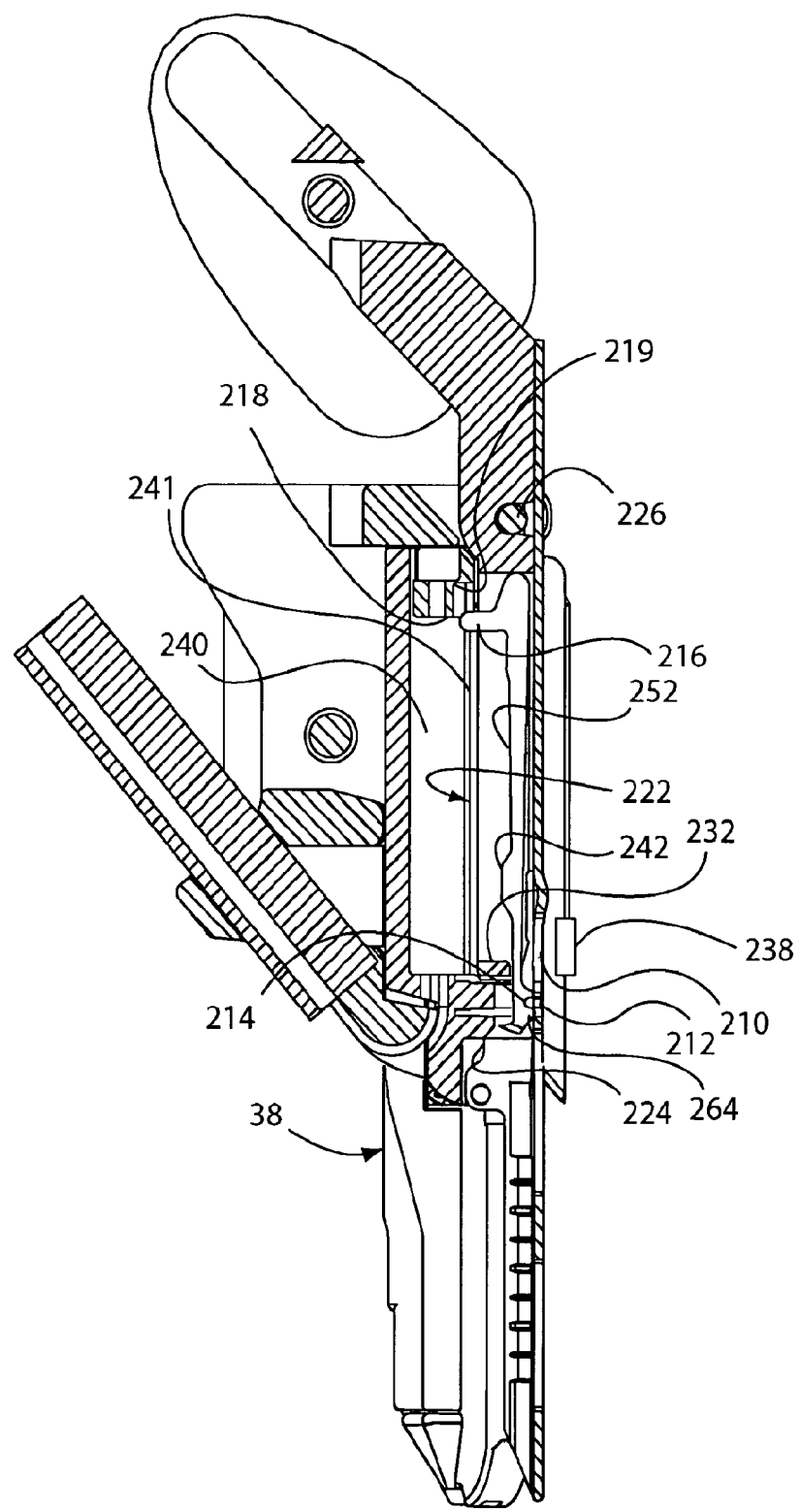
FIG. 50 is a side cutaway view of the anvil and staple holder of FIG. 40, where the cutter is in a first position.

As shown in FIG. 49, the distal end of the anvil arm 14 is spaced apart from the staple holder 38. The anvil arm 14 is inserted through the wall of the target vessel, as described above, such that the contact surface 206 of the anvil arm 14 is in substantial contact with the inner wall of the target vessel. Next, referring to FIG. 50, the staple holder 38 and anvil 10 are moved relative to one another into the standby position, as described above. In the standby position, the cutter 200 is freed for translation along the channel 246, because the tip 212 of the safety feature 210 no longer engages the safety recess 214 of the cutter 200. At least the distal end of the cutter 200 is biased upward, and the cam 232 limits the upward motion of the cutter 200 by contacting at least a portion of the upper surface 252 of the cutter 200. The cam 232 controls the motion of the distal end of the cutter 200 in the vertical direction as the cutter 200 translates within the channel 246. Because the projection 208 is fixed to the cutter 200, the cam 232 also controls the motion of the projection 208 in the vertical direction, and thus controls the location at which the projection 208 encounters the wall of the target vessel.

Figure 51:
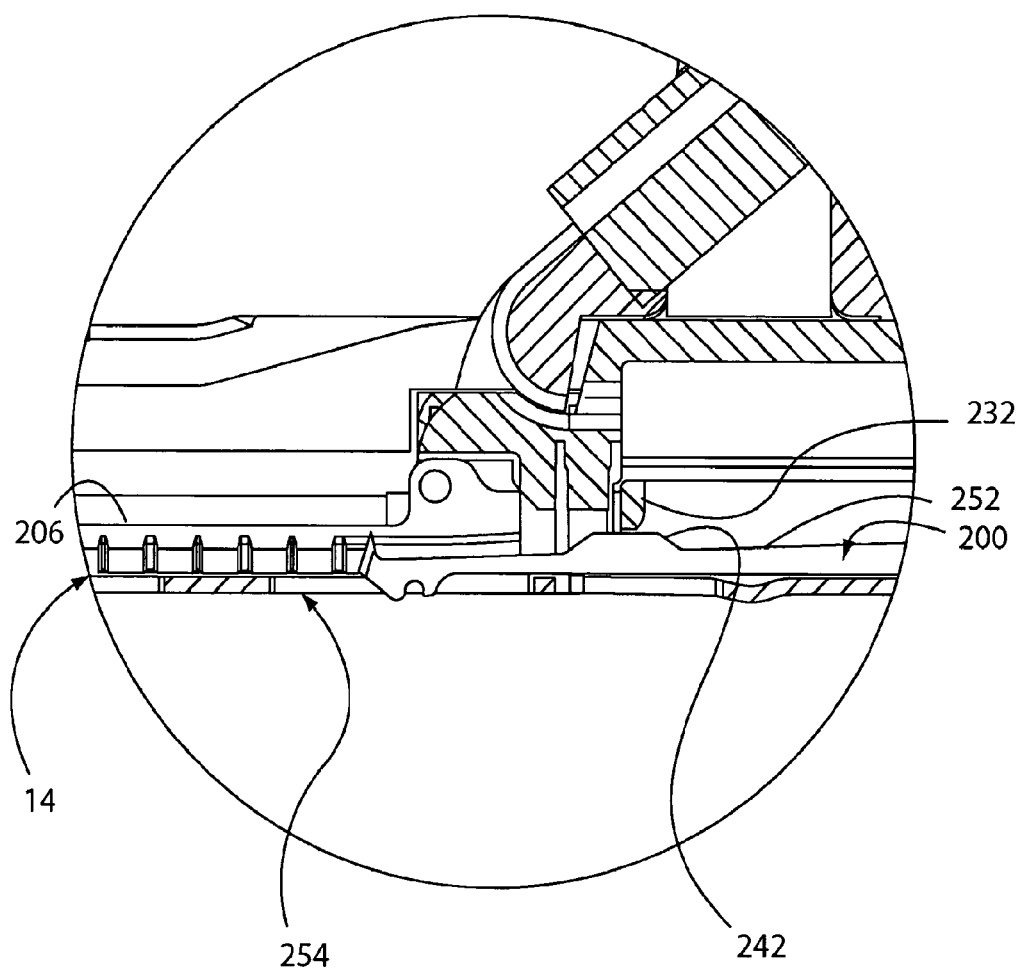
FIG. 51 is a side cutaway view of the anvil and staple holder of FIG. 40, where the cutter is in a second position.

Referring also to FIG. 51, after the cutter 200 has been freed for translation, it is urged distally by the receiver 218 as described above. A first cam follower 242 is defined on the upper surface 252 of the cutter 200. The first cam follower 242 is a raised structure formed into the upper surface 252 of the cutter 200. Alternately, the first cam follower 242 is a separate structure or mechanism constructed separately from the cutter 200 and later connected to the cutter 200. Alternately, the first cam follower 242 may be located on a surface of the cutter 200 in addition to or instead of its upper surface 252, depending on the position and configuration of the cam 232. The first cam follower 242 may be shaped as a trapezoid or similar shape, or may be shaped differently.

The cam 232 is fixed, and the first cam follower 242 is raised relative to the upper surface 252 of the cutter 200. At least the distal end of the cutter 200 is biased upward. Thus, as the cutter 200 translates distally, the cam 232 engages the first cam follower 242 and causes the cutter 200 to move downward. The cam 232 and the first cam follower 242 are shaped to smoothly engage each other. Alternately, the first cam follower 242 is shaped to induce the cutter 200 to abruptly move downward when the first cam follower 242 initially encounters the cam 232. The height of the first cam follower 242 relative to the contact surface 206 of the anvil arm 14 determines the distance that the distal end of the cutter 200 is moved downward. As described above, the cutter 200 may include a keel 264 or similar projection extending downward. As the distal end of the cutter 200 moves downward, the keel 264 or other projection moves into the first lower opening 254. In this embodiment, the first lower opening 254 does not control the motion of the cutter 200; instead, it provides a space for the keel 264 to move downward without interfering with the vertical motion of the distal end of the cutter 200. If the keel 264 is omitted, the first lower opening 254 and the second lower opening 268 may be omitted as well.

The connection between the graft vessel and the target vessel substantially defines a closed area, and the projection 208 is configured to engage the wall of the target vessel within that closed area. That is, the end of the graft vessel has a perimeter that contacts the side of the target vessel, such that the perimeter of the end of the graft vessel defines a closed area on the wall of the target vessel. In this way, the projection 208 makes an incision completely within the connection between the graft vessel and the target vessel, completing the anastomosis between the two vessels and minimizing or eliminating leakage at the anastomosis site. While the projection 208 on the cutter 200 remains below the contact surface 206 of the anvil arm 14, it neither engages nor cuts the wall of the target vessel. Thus, the first cam follower 242 is sized to translate the tip of the projection 208 below the contact surface 206 of the anvil arm 14 for a selected distance such that the projection 208 does not engage the tissue of the target vessel until the projection 208 is positioned to enter the closed area on the wall of the target vessel defined by the perimeter of the end of the graft vessel.

Figure 52:
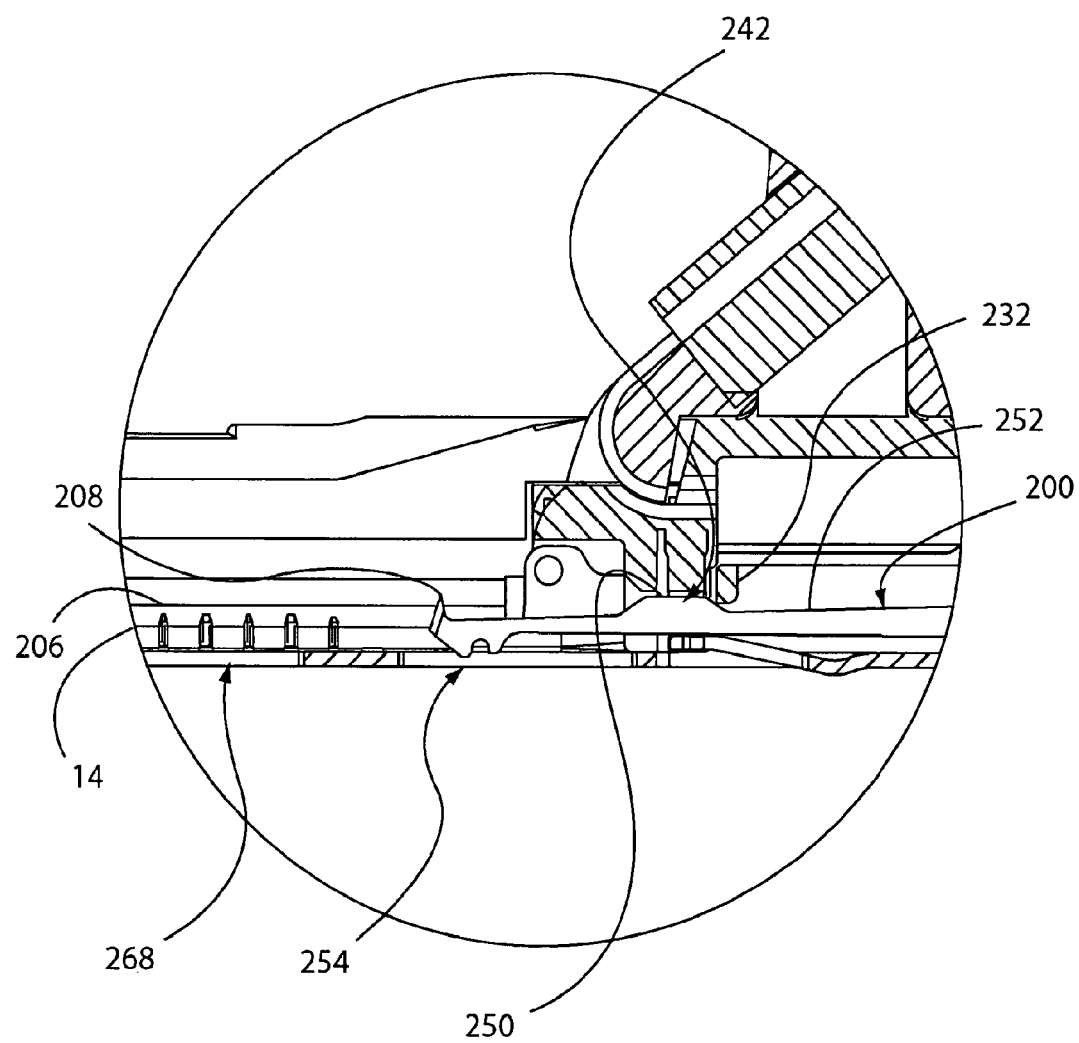
FIG. 52 is a side cutaway view of the anvil and staple holder of FIG. 40, where the cutter is in a third position.

Referring also to FIG. 52, the cutter 200 continues to advance distally as the receiver 218 continues to impel the engagement feature 216 distally. Thus, the first cam follower 242 of the cutter 200 advances distally relative to the cam 232. As described above, at least the distal end of the cutter 200 is biased upward. The first cam follower 242 decreases in height at its proximal end. Thus, as the upwardly-biased first cam follower 242 moves distally relative to the cam 232, the cam 232 and the first cam follower 242 gradually disengage, causing both the distal end of the cutter 200 and the projection 208 to move upward. The first cam follower 242 is constructed to provide a smooth, gradual upward motion of the distal end of the cutter 200 and the projection 208, such as by providing a gradual slope between an upper surface 250 of the first cam follower 242 and an upper surface 252 of the cutter 200. Alternately, the first cam follower 242 may be constructed to allow the distal end of the cutter 200 and the projection 208 to abruptly snap upward as the first cam follower 242 moves distal to the cam 232.

As the distal end of the cutter 200 moves upward, the projection 208 moves upward through the upper opening 248 in the anvil arm 14. The contact surface 206 of the anvil arm 14 is adjacent to the inner surface of the wall of the target vessel. Thus, upward motion of the projection 208 through the upper opening 248 causes the projection 208 to enter the wall of the target vessel. The projection 208 is sized, and the first cam follower 242 and cam 232 are shaped, such that the upward motion of the projection 208 after the first cam follower 242 has moved distal to the cam 232 causes the projection 208 to completely penetrate through the wall of the target vessel. That is, at least a portion of the projection 208 passes through the wall of the target vessel and enters the lumen. This initial penetration of the wall of the target vessel defines the starting point of an arteriotomy performed on the target vessel by the projection 208. The starting point of the arteriotomy is spaced apart from the location on the target vessel at which the anvil arm 14 is inserted, resulting in a tissue bridge therebetween.

Figure 53:
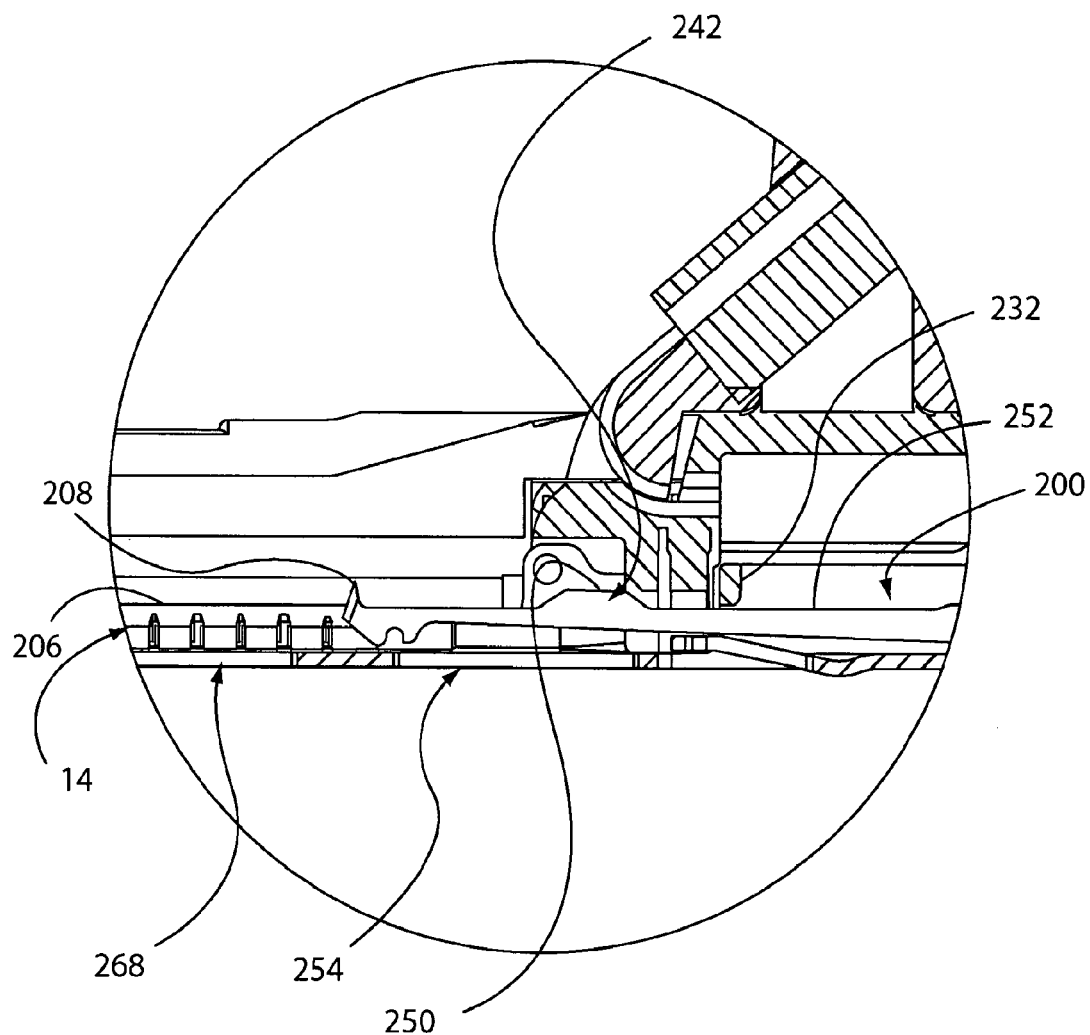
FIG. 53 is a side cutaway view of the anvil and staple holder of FIG. 40, where the cutter is in a fourth position.

Referring also to FIG. 53, the cutter 200 continues to advance distally as the receiver 218 continues to impel the engagement feature 216 distally. The upper surface 252 of the cutter 200 may contact the cam 232 during this motion, because the distal end of the cutter 200 continues to be biased upward. As the cutter 200 translates, the projection 208 moves through the tissue of the wall of the target vessel in a direction substantially parallel to the longitudinal centerline of the anvil arm 14. In this way, the projection 208 incises the tissue of the wall of the target vessel to create an arteriotomy. The tip of the projection 208 may maintain substantially the same height relative to the contact surface 206 of the anvil arm 14 during its distal translation, or may change its height relative to the contact surface 206 of the anvil arm 14, as long as the tip of the projection 208 remains in the lumen of the target vessel during that translation.

Figure 54:
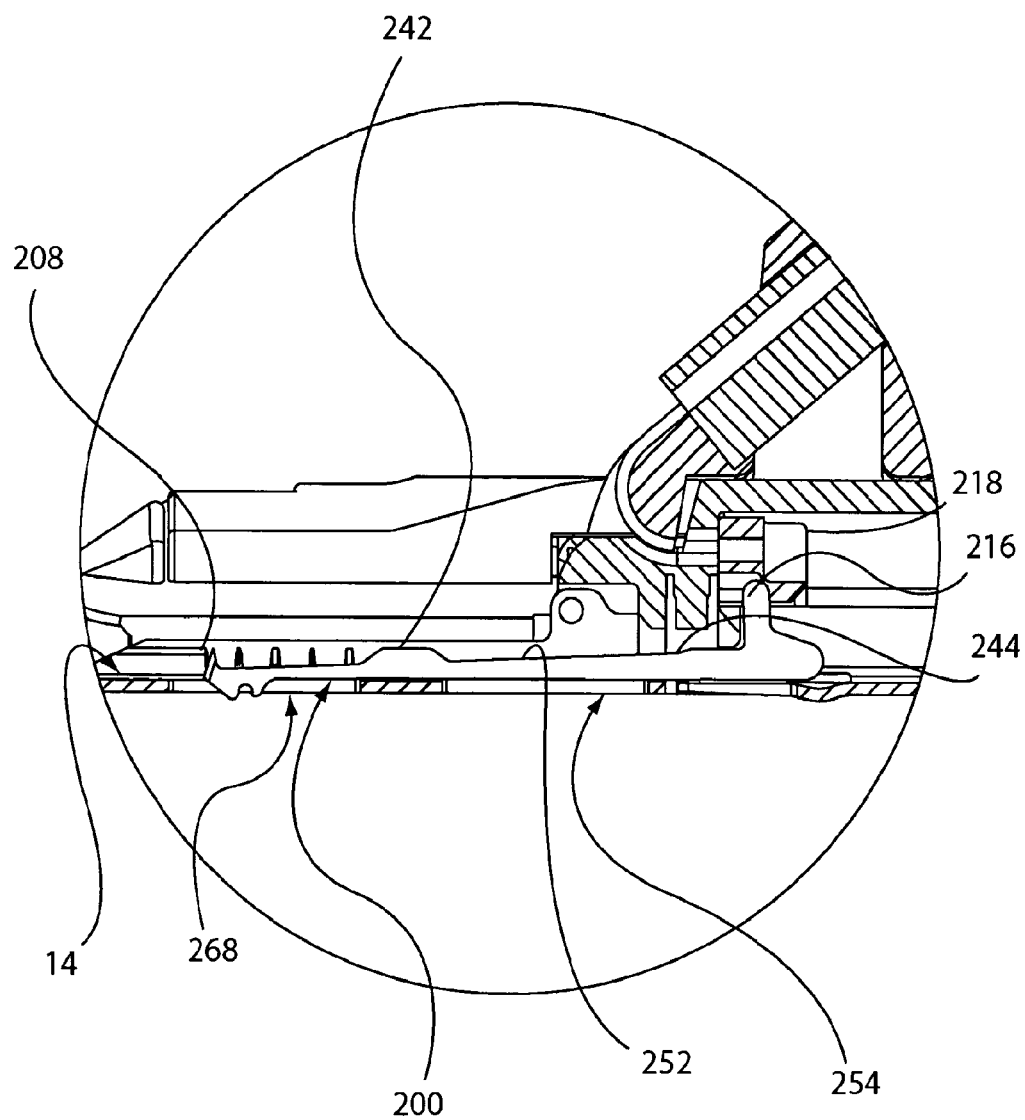
FIG. 54 is a side cutaway view of the anvil and staple holder of FIG. 40, where the cutter is in a fifth position.

Referring also to FIG. 54, a second cam follower 244 is defined on the upper surface 252 of the cutter 200, proximal to and spaced apart from the first cam follower 242. Alternately, a single cam follower is defined on the upper surface 252 of the cutter 200, where that single cam follower includes a feature corresponding to the first cam follower 242, a feature corresponding to the second cam follower 244, and a section of reduced height between them corresponding to the upper surface 252 of the cutter 200. The cutter 200 continues to advance distally as the receiver 218 continues to impel the engagement feature 216 distally. As a result of this motion, the second cam follower 244 contacts the cam 232. Engagement between the second cam follower 244 and the cam 232 pushes the distal end of the cutter 200 downward. The shape and size of the second cam follower 244 and cam 232 are selected such that the distal end of the cutter 200 is pushed downward far enough to cause the projection 208 to retract into the upper opening 248. The projection 208 may be urged downward completely into the channel 246, depending on the depth of the channel 246 and the height of the projection 208. Alternately, the upper tip of the projection 208 may remain within the upper opening 248. The cutter 200 may stop its distal translation at substantially the same time that the projection 208 retracts completely into the upper opening 248, or may continue to translate distally within the channel 246 before coming to a stop.

When the projection 208 is retracted out of the tissue of the wall of the target vessel, the distal end of the arteriotomy is defined, and the arteriotomy is complete. The distance between the first cam follower 242 and the second cam follower 244, and the shape of the cam followers 242, 244, determine the length of the arteriotomy. That is, each cam follower 242, 244 includes a location thereon having a height relative to the upper surface 252 of the cutter 200 sufficient to cause the projection 208 to be pushed out of contact with the wall of the target vessel. The distance between these locations defines the length of the arteriotomy. Thus, the cam followers 242, 244 control the motion of the projection 208 and control the penetration of the wall of the target vessel.

After performing the arteriotomy, the cutter 200 is in a distally-extended position. The cutter 200 remains in that position as the anvil arm 14 is removed from the target vessel. Alternately, after performing the arteriotomy, the cutter 200 may be moved proximally within the channel 246 before removing the anvil arm 14 from the target vessel. The anvil arm 14 is removed from the target vessel after the anastomosis between the graft vessel and the target vessel has been completed. The anvil entry hole 584 and its closure are substantially as described above.

Alternately, the cutter 200 is initially in a distally-extended position, and retracted proximally in order to make an incision in the wall of the target vessel. Similarly, the sled 482 is initially at its most distal location. The structures and mechanisms are substantially as described above, but operated in substantially the reverse order as described above. In this embodiment, the channels 496 in the staple holder 38 are not needed, nor it is necessary to reverse the direction of motion of the second cable 490 as applied to the sled 482; rather, the sled 482 is deployed by pulling it proximally with the second cable 490. Thus, the second cable 490 may be connected to the proximal end or other portion of the sled 482. Alternately, the cutter 200 and the projection 208 may be moved in a different way in order to incise the tissue of the wall of the target vessel. Further, this embodiment is particularly suited for the use of a cutter 200 having a sharp distal end that initially extends out of the distal end of the anvil arm 14 in order to puncture the target vessel, after which the cutter 200 is retracted proximally to move its sharp distal end into the anvil arm 14.

Where multiple projections 208 are provided on the cutter 200 as shown in FIGS. 39-43, the cutter 200 need not be translated as far to make an incision in the wall of the target vessel as it would if only a single projection were used. Because the projections 208 are spaced apart from each other along the direction of translation of the cutter 200, each projection 208 is able to form a portion of the incision during translation of the cutter 200. Thus, by translating each projection 208 across a distance less then the intended length of the entire incision, the complete incision can be formed. The distance that the cutter 200 is translated to form the incision is related to the distance between the projections 208. That is, because each projection 208 forms a portion of the incision, no single projection 208 need be translated along the entire length of the incision.

Alternately, where multiple projections 208 are utilized, the projections 208 may be inserted into the wall of the target vessel, after which energy is applied to the projections 208 via the cutter 200 or directly in order to create an incision in the wall of the target vessel. In such an embodiment, an energy source (not shown) is connected to the cutter 200. For example, an ultrasound generator (not shown) may be connected to the cutter 200 and to the energy source. The ultrasound generator may be a piezoelectric crystal, as is standard, or a different structure or mechanism. Electrical energy may be applied to the ultrasound generator from the energy source, thereby causing the ultrasound generator to vibrate the projections 208. Thus, energy may be applied from the energy source to the ultrasound generator after the projections 208 have been inserted into the wall of the target vessel, causing the projections 208 to move and thereby create an incision. Advantageously, a plurality of projections 208 spaced relatively close to one another are utilized. Other methods may be used to vibrate, move or oscillate the projections 208. Alternately, energy may be applied to the cutter 200 to form an opening in the wall of the target vessel 580 even if the cutter 200 has no projections 208 at all.

Adjustable Staple Line and Target Vessel Opening Size

Alternately, the length of the arteriotomy created by and the number of connectors 464 deployed by the tissue effector 400 are adjustable. By controlling these parameters, graft vessels of different diameters can be attached to a target vessel within a small range of angles relative to the graft vessel. The cross-sectional area of the connection between the graft vessel and the target vessel thus can be controlled across a range of two or more sizes while providing for a substantially fixed angle between the target vessel and the graft vessel.

Figure 111:
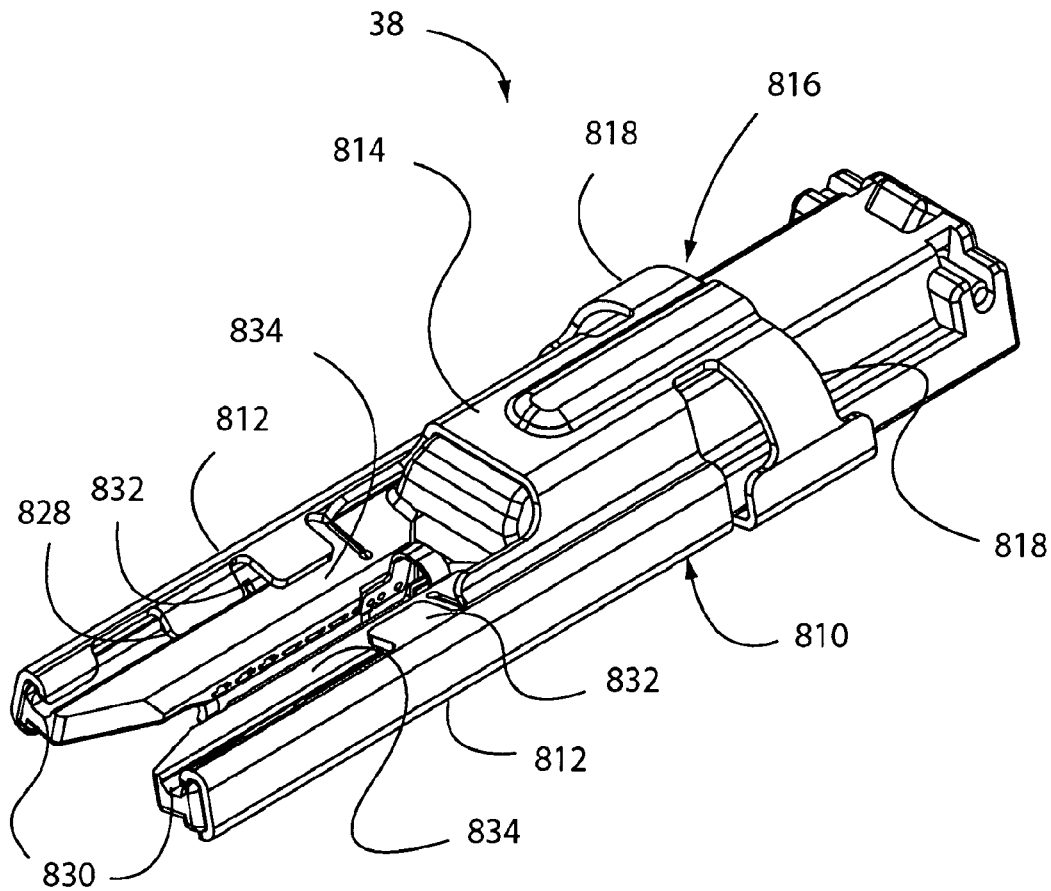
FIG. 111 is a perspective view of a tissue effector configured to deploy user-selectable number of connectors.
Figure 112:
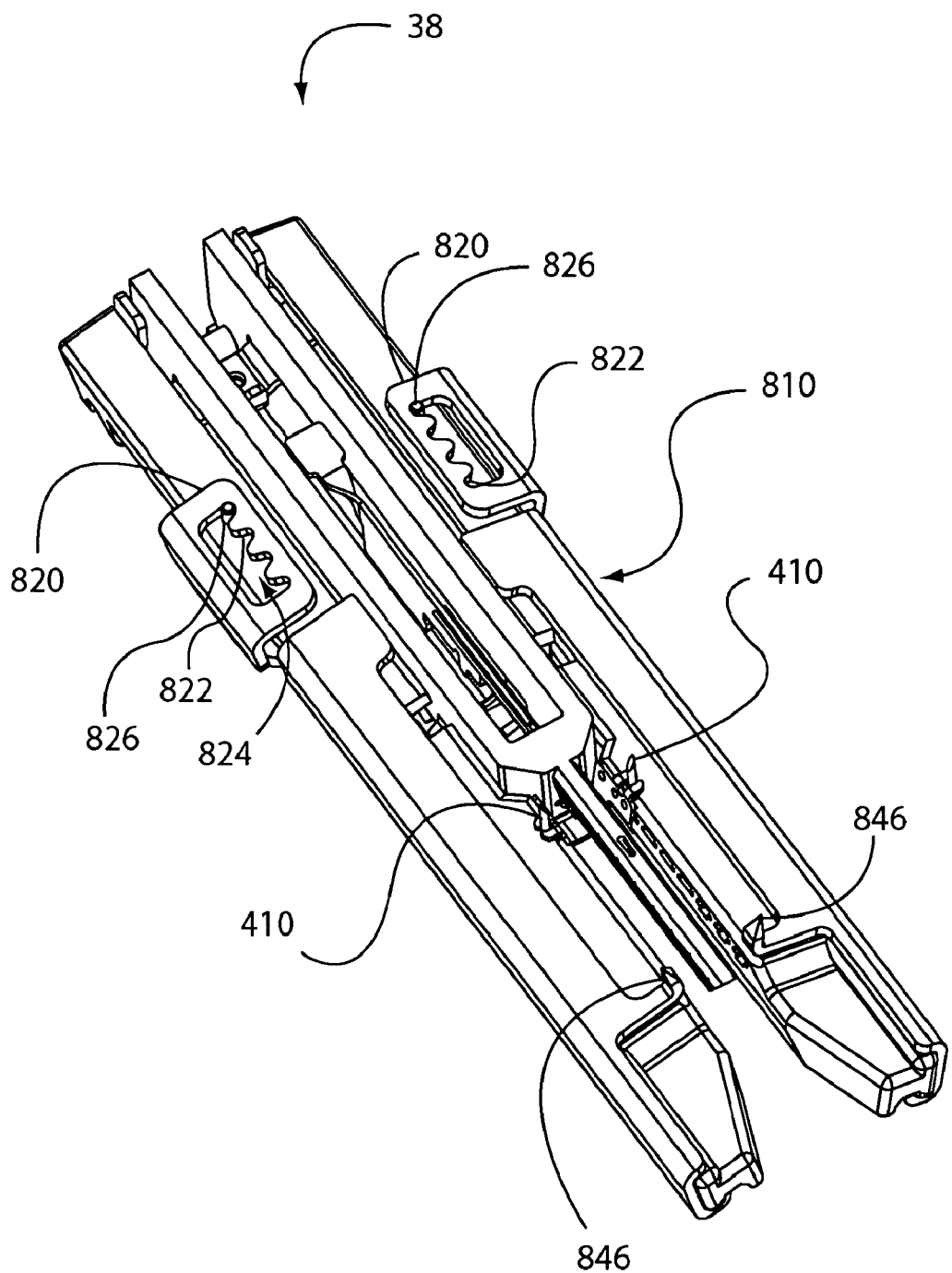
FIG. 112 is a perspective view of the underside of the tissue effector of FIG. 111.
Figure 113:
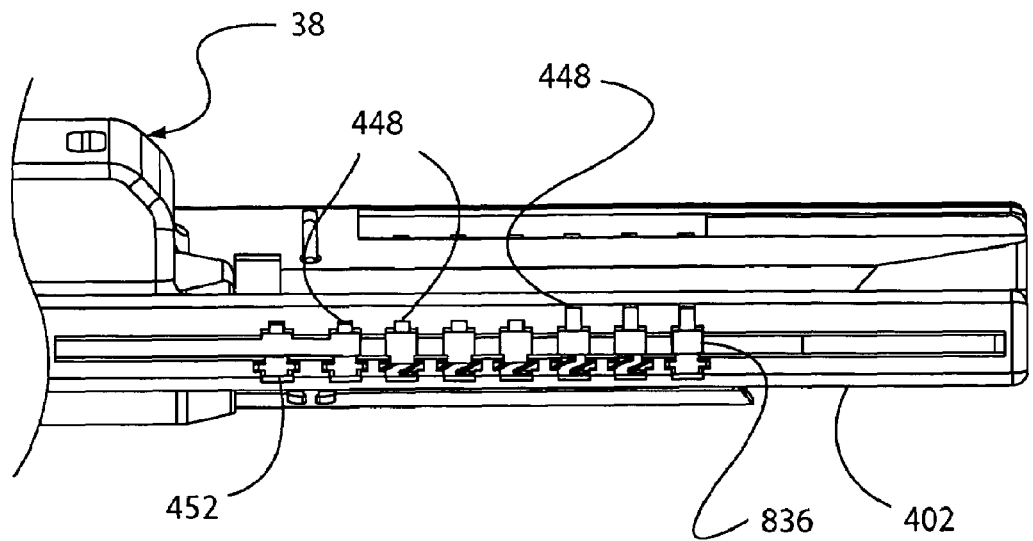
FIG. 113 is a side cross-section view of the tissue effector of FIG. 111.

The number of connectors 464 deployed by the tissue effector 400 can be controlled in any appropriate manner. Referring also to FIGS. 111-113, an example of a staple holder 38 configured to deploy a selectable number of connectors 464 is shown. This staple holder 38 is similar to the embodiments described above, such as with regard to FIGS. 56-58 and 64; for clarity and conciseness, only the significant differences are described here. The staple holder 38 includes a cap 810 movable relative to at least one arm 402 of the staple holder 38. For example, the cap 810 may be slidable relative to at least one arm 402 of the staple holder 38. For compactness, the cap 810 may be, at least in part, thin and substantially conformal to the exterior shape of the remainder of the staple holder. However, the cap 810 may be shaped in any appropriate manner. As one example, the cap 810 includes two members 812 each extending distally from a body 814. At least one member 812 may have a C-shaped or U-shaped cross-section at least in part, such that at least one member 812 is configured to slide along an outer lateral surface of a corresponding arm 402 of the staple holder 38. The C-shaped or U-shaped cross section of at least one member 812 may restrict or substantially prevent lateral motion of the cap 810 relative to the staple holder 38 to guide the motion of the cap 810 longitudinally. Alternately, at least one member 812 may have a different cross section. Similarly, the body 814 may have a C-shaped or U-shaped cross section that facilitates the sliding of the cap 810 relative to the staple holder 38, and assists in holding the cap 180 on the staple holder 38. Alternately, the body 814 may have a different cross-section.

The cap 810 includes at least one control element 816 that is connected to the body 814 or that is part of the body 814. Alternately, the control element or elements 816 may be connected to at least one member 812. The control element 816 provides positive control over the longitudinal position of the cap 810 relative to the staple holder 38. As one example of a control element 816, two legs 818 extend laterally and downward from a proximal part of the upper portion of the body 814, and are compressible toward one another. Lateral force exerted on a portion of the legs 818 in proximity to the lower portion of the staple holder 38 thus may cause lateral motion of the legs 818. Each leg 818 may wrap around a side of the staple holder 38 to the underside of the staple holder 38, substantially conforming to the shape of the staple holder 38. Advantageously, the legs 818 are not connected to each other on the underside of the staple holder 38. The portion of each leg 818 located in contact with or in proximity to the underside of the staple holder 38 may be characterized as the foot 820 of that leg 818.

Each foot 820 includes at least one registration feature 822. As one example, at least one foot 820 may include an aperture 824 therethrough or therein, where an edge of that aperture 824 includes at least one registration feature 822 such as an indentation. At least one post 826 or other structure or mechanism may extend from the underside of the staple holder 38 into the aperture 824. Each post 826 is substantially fixed to the staple holder 38. Each post 826 is configured to engage a selected one of the registration features 822, which are spaced apart from one another by a distance substantially equal to the spacing between the connectors bays 448. The registration features 822 of each foot 820 may be positioned on the edge of the aperture 824 closest to the longitudinal centerline of the staple holder 38. Correspondingly, each post 826 may be positioned relative to the corresponding foot 820 such that each post 826 engages a registration feature 822 when the legs 818 are not compressed together, and such that the registration features 822 are moved out of engagement with the posts 826 when the legs are compressed together. The cap 810 is thus movable to a selected one of a number of positions relative to the staple holder 38, where the number of positions is equal to the number of registration features 822. Each discrete position corresponds to the release of a particular number of connectors 464, as described in greater detail below.

At least one member 812 of the cap 810 includes a first tab 828 extending at least partially inwardly therefrom. At least one arm 402 of the staple holder 38 includes a trough 830 or similar structure along which the first tab 828 is configured to translate substantially longitudinally. Optionally, at least one member 812 also includes a second tab 832 extending at least partially inwardly therefrom. The second tab 832 may be positioned proximal to and near the first tab 828. However, the second tab 832 may be positioned differently relative to the first tab 828. The second tab 832 is configured to travel along a surface 834 of the staple holder 38 that is located above the trough 830. The second tab 832 may assist in guiding the motion of the first tab 828 along the trough 830.

Figure 114:
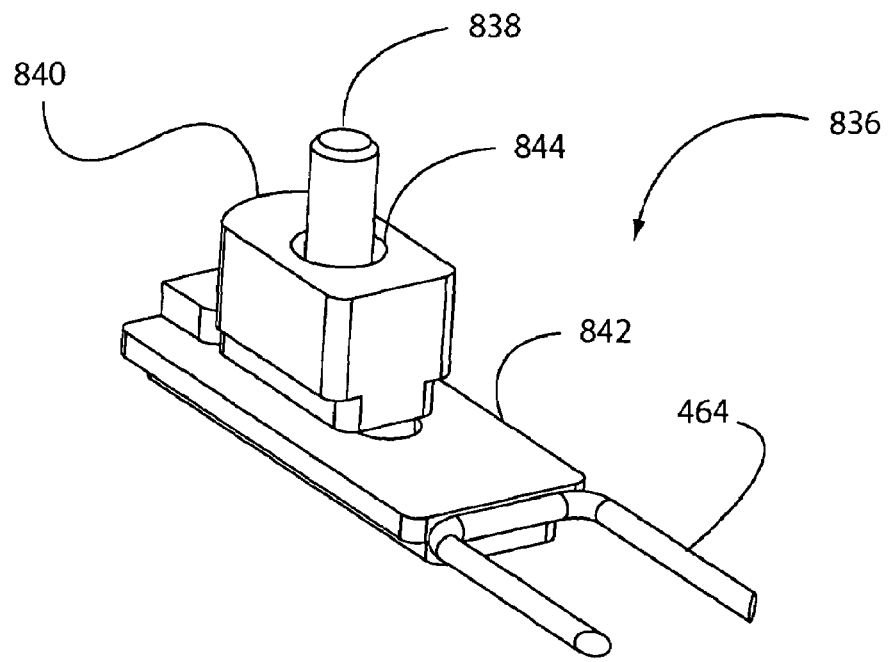
FIG. 114 is a perspective view of a split deployer used in the tissue effector of FIG. 111.

Referring also to FIGS. 113-114, the staple holder 38 includes a number of connector bays 448 defined in each arm 402 of the staple holder 38, as described above. At least one of the connector bays 448 in each arm 402 of the staple holder 38 holds a split deployer 836. Each split deployer 836 is switchable between a state in which it can deploy a corresponding connector 464 and a state in which it cannot deploy a corresponding connector 464. At least one additional connector bay 448 in at least one arm 402 of the staple holder 38 may hold a connector deployer 452 configured as described above. Connector deployers 452 may be used along a length of the arm 402 that corresponds to the smallest anastomosis to be performed with the tissue effector 400, which corresponds to the smallest size of the graft vessel 404 to be used. The split deployers 836 may be used along a length of the arm 402 that corresponds to larger sizes of graft vessel 404.

The split deployer 836 includes a pin 838 that connects a first driver element 840 to a second driver element 842. The first driver element 840 is located above the second driver element 842; however, they may be positioned differently relative to one another. The pin 838 extends through an aperture 844 in the first driver element 840 and through an aperture (not shown) in the second driver element 842. Alternately, the second driver element 842 includes a recess defined therein, rather than an aperture defined completely therethrough. Advantageously, the pin 838 is oriented in a direction substantially perpendicular to the direction of travel of the split deployer 836. However, the pin 838 may be oriented in a different direction if desired. The pin 838 is used to transmit force between the first driver element 840 and the second driver element 842. Alternately, a structure or mechanism other than the pin 838 is used to transmit force between the elements 840, 842.

The pin 838 is movable relative to both the first driver element 840 and the second driver element 842, in a direction substantially along its axis. The pin 838 is movable between a first position in which no portion thereof is located within the second driver element 842, and a second position in which a portion thereof is located within both the first driver element 840 and the second driver element 842. Referring also to FIG. 69, as described above, the distal end 474 of the ramp element 446 is configured to engage the connector deployers 452 as it moves, causing those connector deployers 452 in turn to translate or otherwise move relative to their respective connector bays 448. The split deployers 836 and/or the connector bays 448 that hold them are configured such that the distal end 474 of the ramp element 446 contacts only the first driver element 840 and not the second driver element 842. Further, only the second driver element 842 contacts the connector 464. Thus, in order for motion of the ramp element 446 to cause deployment of a connector 464 from a split deployer 836, the driver elements 840, 842 are first connected such that force can be transmitted therebetween. When the pin 838 is located in the first position, the first driver element 840 moves when the distal end 474 of the ramp element 446 engages it, but the second driver element 842 does not move, because the pin 838 is not located in the aperture or recess in the second driver element 842 and thus cannot transmit force to the second driver element 842. As a result, the second driver element 842 does not move and the corresponding connector 464 is not deployed. When the pin 838 is in the second position, the first driver element 840 moves when the distal end 474 of the ramp element 446 engages it. The pin 838 extends through the aperture 844 in the first driver element 840 and into the aperture or recess of the second driver element 842. As a result, the pin 838 couples the elements 840, 842, thereby causing the second driver element 842 to move along with the motion of the first driver element 840. As a result, the second driver element 842 deploys the corresponding connector.

Prior to the motion of the ramp element, the pin 838 may be in the first position. The pin 838 may be held in or biased to the first position in any appropriate manner. As one example, the pin 838 has a diameter substantially equal to the diameter of the aperture 844 in the first driver element 840. Thus, the surface of the pin 838 is substantially in contact with the walls of the aperture 844, and that contact results in a frictional force. That frictional force is chosen, such as by the selection of materials and the manufacturing tolerances utilized, such that the pin 838 is held securely in the first position prior to its motion to the second position. Such motion is caused by a force having a magnitude selected such that it overcomes the frictional force between the pin 838 and the walls of the aperture 844. As another example, a barrier (not shown) is located at the bottom end of the aperture 844. This barrier may include one or more frangible members, a membrane, a plug of material, or any other appropriate structure or mechanism. The barrier is strong enough to hold the pin 838 in the first position prior to motion of the pin 838 to the second position. Such motion is caused by a force having a magnitude selected such that it breaks, penetrates, shears or otherwise passes through or around the barrier. As another example, the pin 838 is biased to the first position, such as by a spring (not shown) within the aperture 844 of the first driver element 840.

One or more attachment elements, such as the spikes 410 described above, extend from the underside of the staple holder 38 and are substantially fixed relative to the staple holder 38. Advantageously, two spikes 410 are provided, each on a different arm 402 at or near its proximal end. Alternately, more than two spikes 410 are utilized. Alternately, one or more attachment elements other than spikes 410 may be utilized, such as clips. In addition, one or more movable attachment elements 846 are connected to or formed into at least one member 812 of the cap 810, such as on the lower surface of that member 812. Each movable attachment element 846 may be fixed to the corresponding member 812 of the cap 810 and thereby movable relative to the staple holder 38. The movable attachment elements 846 may be located distal to the spikes 410 fixed to the staple holder 38. Alternately, the movable attachment elements 836 and the spikes 410 are positioned differently relative to one another. Each movable attachment element 846 may be a spike, clip or any other appropriate structure or mechanism.

Other than controlling the number of connectors 464 deployed, the tissue effector 400 operates substantially as described above. In the interest of clarity and conciseness, only the significant differences are described here. Each flap 408 in the graft vessel 404 is initially placed onto and poked down on at least one corresponding spike 410, where each spike 410 is substantially fixed relative to the staple holder 38. Where the spike or spikes 410 are located closer to the proximal end of each member 812, a proximal portion of a corresponding flap 408 is engaged. Where the spike or spikes 410 are located closer to the distal end of each member 812, a distal portion of a corresponding flap 408 is engaged. In this way, an end of each flap 408 is connected to the staple holder 38 at a fixed location. Each flap 408 is not yet connected to at least one corresponding movable attachment element 846.

The cap 810 is then moved relative to the staple holder 38, such as by translation. As shown, the cap 810 is positioned initially at a proximal location, and is movable distally. The fixed spikes 410 are positioned proximal to the cap 810, and thus proximal to the movable attachment elements 846 on the cap 810. As the cap 810 is moved distally, the movable attachment elements 846 move distally as well, increasing the spacing between each spike 410 and the corresponding movable attachment element 846. The user continues to move the cap 810 distally until the movable attachment elements 846 are close to the distal ends of the flaps 408. The motion of the cap 810 is then stopped by the user, and the flaps 408 are pressed or otherwise brought into engagement with the movable attachment elements 846. In this way, the final position of the cap 810 is related to the width of the graft vessel 404, and may be said to measure the width of the graft vessel 404. If the graft vessel 404 has a width such that the movable attachment elements 846 are close to the distal ends of the flaps 408 when the cap 810 is in its initial position, then the cap 810 is not moved, and the initial position and the final position of the cap 810 are the same. Alternately, the cap 810 may be positioned initially at a distal location, and be movable proximally, where the spikes 410 fixed to the staple holder 38 are initially located distal to the movable attachment elements 846. Where the cap 810 is utilized, the transfer clamp assembly 670 may be omitted. If so, the wings 760 of the staple holder 38 may be omitted, reducing its height as compared to other embodiments of the staple holder 38. Such a staple holder 38 may be characterized as having a low profile. A low-profile staple holder 38 may facilitate access to more locations on the heart, and may be better suited for closed-chest coronary artery bypass graft surgery, such as via an intercostal or sub-xyphoid incision, or other port in the patient's thoracic cavity.

In order to move the cap 810, the user manipulates its control section 816. As one example, the legs 818 of the control section 816 are compressed together. This compression moves at least one registration feature 822 in each foot 820 of the control section 816 out of engagement with the corresponding post 826 connected to the staple holder 38, freeing the cap 810. The cap 810 then is slid relative to the staple holder 38. The post 826 remains within the aperture 824 in the foot 820 as the cap 810 slides. Where two flaps 408 are utilized and each flap 408 is penetrated near its proximal edge by at least one spike 410, the cap 810 is slid along the staple holder 38 until each movable attachment element 846 is positioned close to the distal edge of the corresponding flap 408. When each movable attachment element 846 is positioned close to the distal edge of the corresponding flap 408, the legs 818 are released, and at least one engagement feature 822 engages the corresponding post 826 on the staple holder 38. This engagement holds the cap 810 substantially motionless in its new position. At least one movable attachment element 846 is then connected to each flap 408.

As the cap 810 is slid relative to the staple holder 38 to engage the flaps 408 with the movable attachment elements 846, each first tab 828 slides along the corresponding trough 830. The upper end of each pin 838 of each split deployer 836 extends upward into the corresponding trough 830 when that pin 838 is in the first position. The upper end of each pin 838, and/or the distal edge of each first tab 828, is shaped such that contact between a first tab 828 and a pin 838 urges the pin 838 downward into engagement with the corresponding second driver element 842. For example, the upper end of at least one pin 838 may be rounded, curved, angled, beveled or otherwise shaped such that the corresponding first tab 828 can smoothly engage it and press it downward as it moves along the trough 830. As another example, the distal edge of at least one first tab 828 may be beveled such that it can smoothly engage one pin 838 or a number of pins 838 in succession.

Each pin 838 is initially in the first position. When the first tab 828 encounters a pin 838 and presses it downward, that pin 838 is moved to the second position, in which a portion of the pin 838 is located within the first driver element 840 and a portion of the pin 838 is located within the second driver element 842. In the second position, the driver elements 840, 842 are coupled, as described above, and the split deployer 836 is said to be activated. The clearance between the first tab 828 and the trough 830, and the length of the pin 838, are selected to ensure that contact between the first tab 828 and the pin 838 urges the pin 838 into the second position. Alternately, one or more split deployers 836 may be actuated in a different manner.

The first tab 828 is sized such that it can cover or otherwise engage a number of pins 838 up to the number of split deployers 836. In this way, motion of the first tab 828 relative to the pins 838 determines the number of pins 838 depressed, and thus the number of split deployers 836 activated. In the embodiment shown, three split deployers 836 are utilized, and are located distal to the connector deployers 452. The cap 810 is initially located in a proximal position, and is slid distally as part of the measurement process. The first tab 828 is sized to engage up to three pins 838. In this way, motion of the cap 810 causes the first tab 828 to activate up to all of the split deployers 836. Alternately, more or fewer than three split deployers 836 may be provided, and the first tab 828 is then sized accordingly.

A number of connector deployers 452 are provided, corresponding to a minimum size of the graft vessel 404. That is, where the graft vessel 404 has a width such that the cap 810 is not moved before the flaps 408 are connected to the spikes 410 and the movable attachment elements 846, the connector deployers 452 are positioned relative to the cap 810 and the flaps 408 such that the flaps 408 are connected to the target vessel 580 solely by deployment of connectors 464 by the connector deployers 452; none of the split deployers 836 are actuated. The process of moving the cap 810 automatically matches the number of split deployers 836 actuated to the size of the flaps 408 of the graft vessel 404, and thus matches the number of connectors 464 deployed to the size of those flaps 408, eliminating the need to take a separate measurement. Further, by controlling the number of connectors 464 deployed to connect graft vessels 404 of different sizes to a target vessel 580, the angle between the graft vessel 404 and the target vessel 580 can be substantially the same for different widths of graft vessel 404. The number of connectors 464 deployed, and not the angle of the graft vessel 404 relative to the target vessel 580, is controlled in order to accommodate graft vessels 404 of different sizes.

The registration features 822 provide positive control over the position of the cap 810 relative to the staple holder 38, and thus over the position of the first tab 828 relative to the pins 838 of the split deployers 836. The registration features 822 are longitudinally spaced from one another, and that spacing corresponds to discrete longitudinal positions of the cap 810 relative to the staple holder 38. Therefore, the longitudinal position of the cap 810 is controlled by selecting the particular registration feature 822 to engage the corresponding post 826. The first tab 828 is positioned on the cap 810 such that when the cap 810 is in the initial, proximal-most position and the post 826 engages the most-distal registration feature 822, the first tab 828 engages none of the pins 838 and thus actuates none of the split deployers 836. This position is utilized for the smallest diameter graft vessels 404. When the cap 810 is moved proximally such that the post 826 engages the next most proximal registration feature 822, the first tab 828 is in position to urge the pin 838 of the most proximal split deployer 836 downward and activate that split deployer 836. The number of registration features 822 may correspond to the number of split deployers 836, such that the most-distal position of the cap 810 that corresponds to the engagement of the post 826 with the most-proximal registration feature 822 places the first tab 828 in a position to engage all of the pins 838 and thus actuate all of the split deployers 836. The registration features 822 ensure that the first tab 828 is positioned accurately relative to the appropriate pin or pins 838. In this way, the registration features 822 provide positive control over the number of split deployers 836 to be activated.

The tissue effector 400 is moved to the closed position, the anastomosis tool 300 is actuated, and the sled 482 moves distally, substantially as described above. The deployment of connectors 464 by connector deployers 452 also proceeds substantially as described above. Referring also to FIG. 64, as the ramp element 446 moves distally and sequentially contacts the connector deployers 452, each connector deployer 452 is urged in turn into the corresponding connector bay 448, thereby urging the associated connector 464 out of the connector 448 and deploying that connector 464 into tissue to connect a flap 408 of the graft vessel 404 to the wall of the target vessel 580.

As the sled 482 continues to move distally, each ramp element 446 continues to move distally. For clarity of description, the motion and action of one ramp element 446 is described; the other ramp element 446 is understood to move and act in substantially the same manner. The first driver element 840 of each split deployer 836 is initially positioned such that a portion thereof extends into the passage 440, as described above with regard to the initial position of the connector deployers 452. As the ramp element 446 moves distally, it sequentially contacts each first driver element 840 and urges it along the corresponding connector bay 448. If a split deployer 836 is activated, such that the pin 838 extends between the driver elements 840, 842 or the driver elements 840, 842 are otherwise connected, motion of the first driver element 840 under the influence of the ramp element 446 is transmitted to the corresponding second driver element 842. As the second driver element 842 moves along the connector bay 448, it deploys the associated connector 464 in substantially the same manner as described above with regard to the connector deployers 452. If a split deployer 836 is not activated, such that the pin 838 does not extend into the second driver element 842 or otherwise connect the driver elements 840, 842, that motion of the first driver element 840 is not transmitted to the corresponding second driver element 842. The second driver element 842 substantially does not move, and thus does not deploy the corresponding connector 464.

By arranging the split deployers 836 relative to the connector deployers 452, graft vessels of different widths may be accommodated by deploying different numbers of connectors 464. One or more split deployers 836 are grouped together and provided on an arm 410 of the staple holder 38, and placed either proximal or distal to one or more connector deployers 452 which are also grouped together. Either the split deployers 836 or the connector deployers 452 may be deployed first; the deployment order is determined by the direction in which the sled 482 translates and the positional relationship between the split deployers 836 and the connector deployers 452. As described above, the sled 482 may begin in a more-proximal location and translate distally to actuate the deployers 452, 836, or the sled 482 may begin in a more-distal location and translate proximally to actuate the deployers 452, 836.

As with regard to the embodiment of the anastomosis tool 300 without split deployers 836, the sled 482 translates through a substantially complete stroke regardless of the number of split deployers 836 that were actuated and the corresponding number of connectors 464 deployed by those split deployers 836. That is, the number of connectors 464 deployed is not related to the distance across which the sled 482 translates, but rather to the actuation state of the split deployers 836. Because the sled 482 translates through a substantially complete stroke regardless of the number of split deployers 836 that are actuated, the cutter 200 may be configured to make an arteriotomy of a standard size that corresponds to the smallest graft vessel. In this way, the length of the arteriotomy does not vary with the width of the graft vessel 404.

However, the number of connectors 464 deployed and/or the length of the arteriotomy may be controlled by varying the length of stroke of the sled 482. If so, the split deployers 836 optionally may be omitted, and the connector deployers 452 instead may be used in all of the connector bays 448. As an example, by varying the stroke of the sled 482 and therefore the length along each passage 440 that is traversed by the corresponding ramp element 446 of the sled 482, the number of connectors 464 deployed as a result of motion of the sled 482 can be controlled. The variable length of stroke of the sled 482 can be used to control the motion of the cutter 200 and thus vary the length of the arteriotomy to correspond to the width of the graft vessel 404. Control of the stroke of the sled 482 may be accomplished in any appropriate manner. For example, a control (not shown) connected to the handle 302 may allow the selection of a particular number of connectors 464 for deployment. Such a control may interact with the second cable 490 and/or other components of or connected to the handle 302, in order to restrict the length that the second cable 490 moves upon actuation. By restricting the motion of the second cable 490, the stroke of the sled 482 is controlled, and hence the number of connectors 464 deployed is controlled. As another example, a set of controllable stops (not shown) may be provided within the tissue effector 400. Each stop is positioned in proximity to a connector bay 448, and is moveable between a first position that is out of the passage 440 adjacent to the connector bay 448 and a second position that is at least partially into the passage 440. In the second position, the stop contacts and prevents further distal motion of the corresponding ramp element 446 of the sled 482. The control interacts with the stops, such that when the control is used to select a particular number of connectors 464 for deployment, at least one stop is moved to its second position into a passage 440 of the tissue effector 400. Each stop that is moved to its second position corresponds to the connector bay 448 from which the last of the selected number of connectors 464 is to be deployed. Other mechanisms, structures or methods may be used to control the number of connectors 464 that are deployed.

Similarly, the length of the arteriotomy is controlled to correspond to the length of tissue that is connected by the selected number of connectors 464. The length of the arteriotomy can be controlled by controlling the motion of the cutter 200. The motion of the cutter 200 can be controlled in several ways. As one example, the openings 254, 268 in the anvil arm 14 can be changed both in length and position, to ensure that the arteriotomy is made to the correct length in the correct position. The openings 254, 268 can be changed in length and position in any appropriate manner. As one example, one or more pins or other structures (not shown) are extendable laterally across the openings 254, 268, such that the presence of those pins or other structures across the openings 254, 268 effectively changes their length and position. Other mechanisms, structures or methods may be used to control the length and position of the openings 254, 268 and/or the motion of the cutter 200.

Additional Exemplary Tissue Effectors

Figure 17:
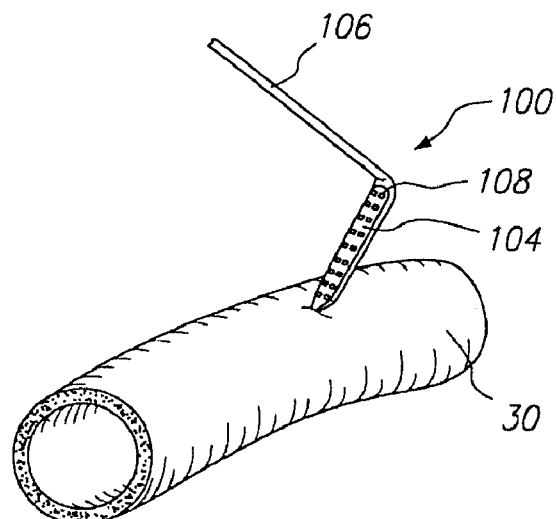
FIG. 17 is a perspective view of an anvil according to a second aspect of the invention being inserted into a target vessel.
Figure 18:
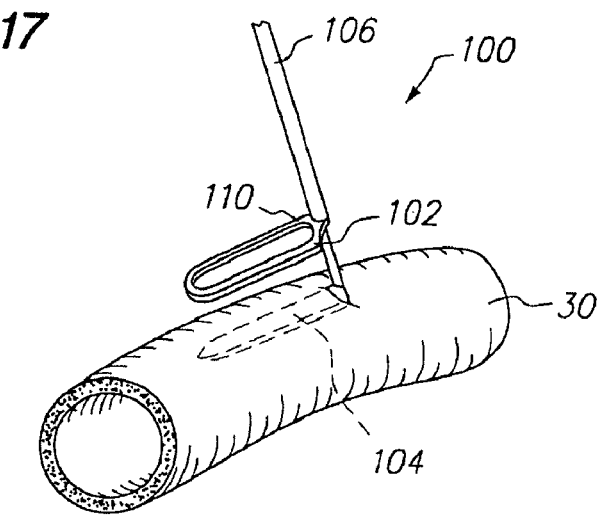
FIG. 18 is a perspective view of the anvil of FIG. 17 positioning inside a target vessel and a clamp being advanced to clamp the wall of the target vessel between the anvil and the clamp.

FIGS. 17-23 illustrate an alternate anvil 100 that is used with a clamp 102 for controlling an incision site during an anastomosis procedure. As shown in FIGS. 17 and 18, the anvil 100 includes an anvil arm 104 and a handle 106. The clamp 102 is slidable on the handle 106 to clamp the tissue of the target vessel 30 between the clamp 102 and the anvil arm 104. As with the anvil arm 104 described above, the anvil arm 104 includes two rows of staple bending features 108 in the form of recesses positioned in two parallel rows along a top surface of the anvil arm 104. The clamp 102 has a central opening 110. Once the tissue of the target vessel wall has been trapped between the clamp 102 and the anvil arm 104, an incision may be made through the target vessel wall and the edges of the incision are controlled by the combination of the anvil arm 104 and the clamp 102.

Figure 19:
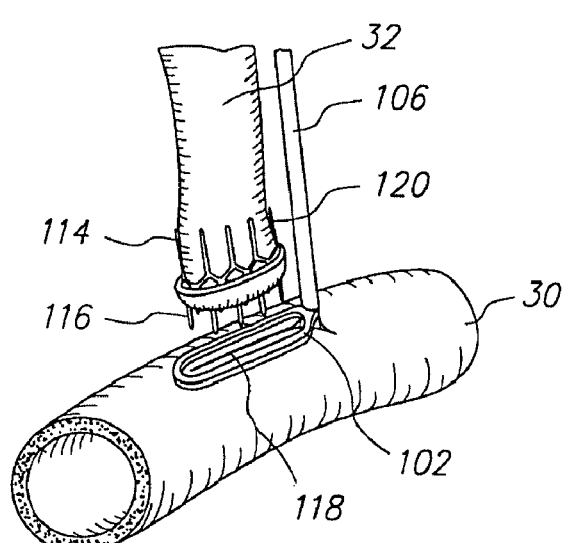
FIG. 19 is a perspective view of a graft vessel being advanced to the target vessel with a continuous anastomosis staple while the anastomosis site on the target vessel is controlled by the anvil and clamp.

As shown in FIG. 19, a continuous anastomosis staple device 114 may be used to connect the graft vessel 32 to the target vessel 30 at the anastomosis site. The staple device 114 as shown in FIG. 19 includes a plurality of linkages forming a tubular configuration and a plurality of staple ends extending from the linkages. FIGS. 20-22 illustrate how the staple ends 116 of the staple device 114 are positioned in the end of the graft vessel 32 and are inserted through the incision 118 in the target vessel and bent over by contact with the staple bending features 108 of the anvil. As shown in FIG. 22, the opposite ends 120 of the staple device 114 are folded over to complete the anastomosis. FIG. 23 illustrates a completed anastomosis performed according to the steps illustrated in FIGS. 19-22.

Figure 26:
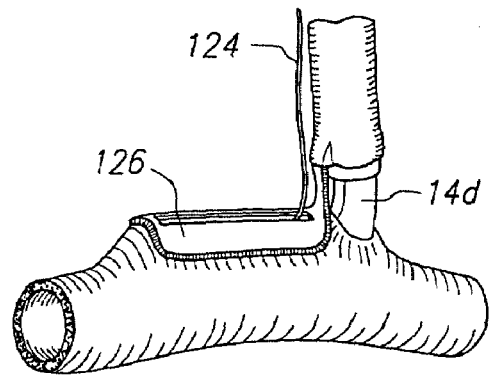
Figure 27:
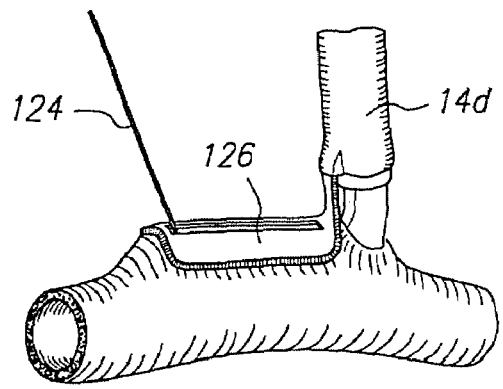

FIGS. 24-27 illustrate an alternate example of an anvil arm 14*d* having a cutting wire 124 for forming the incision in the wall of the target vessel 30. The cutting wire 124 may be used to form an incision before, during or after performing an end-to-side anastomosis procedure. Referring particularly to FIGS. 26-27, for forming the incision after the anastomosis procedure, a clamp 126 is used to trap the tissue at the anastomosis site between the clamp 126 and the anvil arm 14*d* prior to performing the incision. The incision is spaced apart from the entry point of the anvil arm 14*d* into the target vessel, creating a tissue bridge between the incision made in the wall of the target vessel and the entry point of the anvil arm 14*d* into the target vessel. A portion of the contact between the anastomosed graft vessel and target vessel extends across the tissue bridge, such that the incision is located within the closed area defined by the contact between the perimeter of the end of the graft vessel and the wall of the target vessel.

Figure 28:
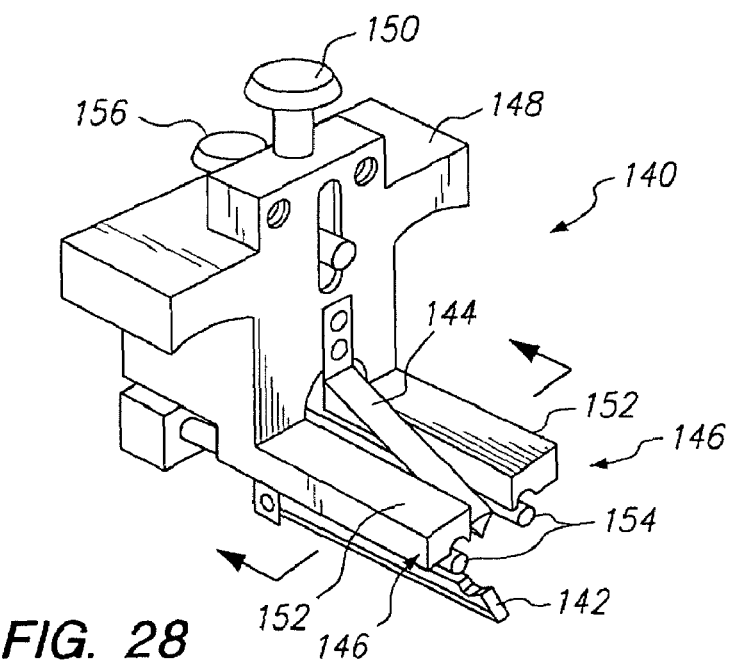
FIG. 28 is a perspective view of a system for controlling a tissue site and performing anastomosis according to the present invention.

FIG. 28 shows a system 140 for controlling a tissue site and performing anastomosis. For purposes of clarity, the staple holder and staples have been omitted from FIG. 28. The system 140 includes an anvil arm 142, a cutter 144, and a graft vessel holder 146 all mounted on a handle 148. The anvil arm 142 is mounted on the handle 148 and connected to a first actuator 150 that allows the anvil to be moved downward against the bias of a spring inside the handle. The cutter 144 may be biased or fixed and is positioned on the handle 148 directly above the anvil arm 142. The graft vessel holder 146 includes two fixed arms 152 and two movable arms 154. The two movable arms 154 are connected to a second actuator 156 on the handle 148. Depression of the second actuator 156 against the bias of a spring within the handle causes the movable arms 154 to be moved downward away from the fixed arms to receive portions of a graft vessel between the movable and fixed arms.

The operation of the system 140 of FIG. 28 is shown in the cross sectional views of FIGS. 29-31. As shown in FIG. 29, an end of a graft vessel 32 is split so that each half of the graft vessel 32 can be held between a fixed arm 152 and a movable arm 154. In order to load the graft vessel 32 into the system 140, the first actuator 150 and the second actuator 156 are depressed to move the anvil arm 142 and the movable arms 154 downward. The split graft vessel 32 is then inserted between the fixed and movable arms 152, 154 and the second actuator 156 is released to trap the ends of the graft vessel 32, as shown in FIG. 30. The anvil arm 142 is then inserted into the target vessel 30 in the same or similar manner as described above.

Once the anvil has been inserted in the target vessel 30 as shown in FIG. 30, the first actuator 150 is released to allow the anvil to move upward to tent the wall of the target vessel. FIG. 31 illustrates the tented target vessel 30 positioned adjacent the split and trapped graft vessel 32 in a position for performing anastomosis. The staple holders 38 are then advanced in the direction of the arrows D toward opposite sides of the anvil to staple the graft vessel and target vessel together. The staple holders 38 may hold a staple strip with an expandable backbone as shown in FIGS. 10A and 10B, or may instead or additionally hold different types of staples not connected to a backbone. The staple holders 38 may be provided with movable pins which allow the spacing between the staples to be adjusted depending on a size of the graft vessel used. Once the staples have been placed, the anvil arm 142 is removed and the cutter 144 makes an incision in the target vessel before or during removal of the anvil.

As described above, staple bending features are provided on the anvil and staples are provided at an exterior of the tissue. Alternately, the staples and/or staple holding strips may be positioned on the anvil and an exterior member with staple bending features may be moved toward the anvil to bend the ends of the staples and secure the graft and target vessels together.

Figure 32:
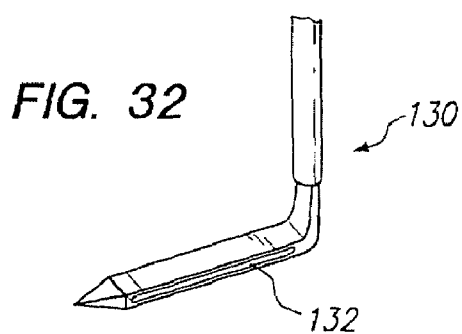
FIG. 32 is a perspective view of an anvil according to another aspect of the present invention for use with sutures.
Figure 33:
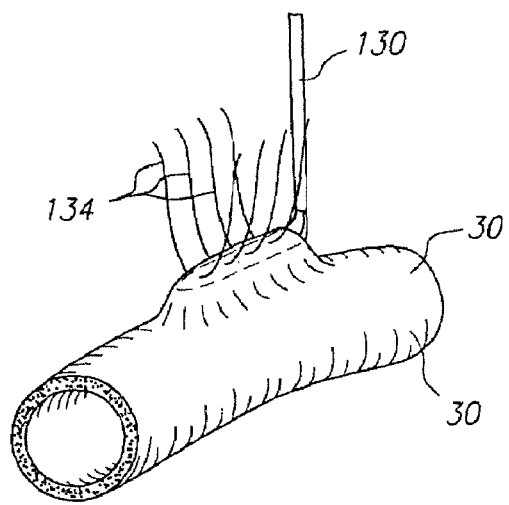
FIG. 33 is a perspective view of the anvil of FIG. 32 positioned within a target vessel and used to locate a plurality of suture at an anastomosis site.

FIGS. 32-33 illustrate the use of an alternate anvil 130 for controlling the tissue at an anastomosis site. The anvil 130 includes a longitudinal opening 132 extending through the anvil 130 for application of a plurality of conventional sutures at the anastomosis site. According to this method, the anvil 130 is inserted into the target vessel 30 and pulled against the interior wall of the target vessel 30, tenting the target vessel as shown in FIG. 33. Sutures 134 are then passed through the opening 132 in the anvil 130 and through the tissue of the target vessel wall on opposite sides of the anvil 130. Once the sutures 134 are placed as shown in FIG. 33, an incision is made in the target vessel along a center of the anvil 130. A center portion of each of the sutures 34 is then pulled out through the incision in the target vessel and cut so that an even row of sutures is provided along each of the sides of the incision. This system eliminates the tedious procedure of placing each individual suture very close to the edge of the incision in the very thin and flexible target vessel wall. Each of the sutures 134 is connected to a graft vessel in a conventional manner completing the anastomosis. The anvil as shown in FIGS. 32-33 allows quick and easy placement of a plurality of sutures in a very even manner close to the edge of the incision. For example, the sutures of a conventional anastomosis are generally within about one millimeter of the edge of the incision and are advantageously within 0.5 millimeters of the edge of the incision.

In an alternate embodiment, the cutter 200 does not include one or more projections 208. Instead, the cutter 200 includes or is connected directly or indirectly to an energy source (not shown), which is used to create an opening in the wall of the target vessel. For example, an emitter of laser or RF energy, or another type of energy, may be connected to the cutter 200 and to the energy source. As the cutter 200 translates along the anvil arm 14, it translates the emitter of laser or RF energy relative to the wall of the target vessel. The emitter of laser or RF energy is selectively actuated to transmit energy into the wall of the target vessel during translation of the cutter 200, thereby creating an opening therein. The energy source may transmit a first type of energy to the emitter or other mechanism, which is converted by the emitter into a second type of energy delivered into the wall of the target vessel. Alternately, the cutter 200 may include a projection 208 and additionally be connected to an energy source that is selectively actuated in order to assist in creating an opening in the wall of the target vessel. As another example, example, the cutter 200 may be a bipolar cutter or cautery tool that is movable relative to, or substantially fixed relative to, the anvil 10. Where the cutter 200 is substantially fixed relative to the anvil 10, the structures and mechanisms described above for moving other exemplary cutters 200 may be omitted. Alternately, the cutter 200 may be separate from the tissue effector 400, and may be a separate tool placed at the anastomosis site through the lumen of the graft vessel 404 or through the lumen of the target vessel 580.

In an alternate embodiment, the cutter 200 does not translate through the anvil arm 14. Instead, the cutter 200 is spatially removed from the anvil arm 14, and creates an opening in the wall of the target vessel before or after the anvil arm 14 is inserted into the target vessel. In one example of such an embodiment, the anvil arm 14 is inserted into a hole in the wall of the target vessel and the staple holder 38 deploys staples or other connectors to connect the graft vessel to the target vessel, as described above. The anvil arm 14 is removed, and an independent cutter 200 is then introduced through the hole in the wall of the target vessel. The cutter 200 may be configured as described above, including a projection 208 extending therefrom, or may be configured differently. The cutter 200 is manipulated relative to the connection between the target vessel and the graft vessel to create an opening at the junction therebetween. That is, registration is maintained between the cutter 200 and the junction between the end of the graft vessel and the wall of the target vessel. In order to position and manipulate the cutter 200 to create an opening at the location of the junction between the target vessel and the graft vessel, an imaging device (not shown) or other device may be connected to the cutter 200 or utilized in conjunction with the cutter 200. For example, a standard intravascular ultrasound unit may be connected to or used in conjunction with the cutter 200. The intravascular ultrasound unit is connected to a display device (not shown) visible to the operator. The operator controls the intravascular ultrasound unit to visualize the interior of the target vessel and the surrounding area, thereby locating the junction between the target vessel and the graft vessel and allowing the cutter 200 to be controlled to incise an opening in the wall of the target vessel within the closed area on the wall of the target vessel defined by the perimeter of the end of the graft vessel, thereby allowing blood to flow through the opening into the target vessel. A different visualization device or devices may be inserted into or positioned outside of the target vessel to locate the junction with the graft vessel. The cutter 200 and any visualization device present in the lumen of the target vessel are then removed from the lumen of the target vessel and/or the graft vessel, and the opening in the wall of the target vessel through which they were removed (if any) is sealed.

In another example of such an embodiment, the anvil arm 14 is inserted into a hole in the wall of the target vessel and the staple holder 38 deploys staples or other connectors to connect the graft vessel to the target vessel, as described above. The anvil arm 14 is removed, and the hole in the wall of the target vessel is removed. A cannula (not shown) is inserted into the lumen of the graft vessel through the free end of the graft vessel, and a stylet (not shown) is inserted through the lumen of the cannula. The cannula and the stylet are surgical instruments that are well known in the art. The stylet has a distal end configured to penetrate the wall of the target vessel. Thus, a sharp point, blade, or other penetrating member may be formed into or connected to the distal end of the stylet. The cannula may be inserted into the lumen of the graft vessel such that its distal end contacts the outer wall of the target vessel. After the stylet has been inserted into the cannula, a force is exerted on the stylet to cause its distal end to penetrate the wall of the target vessel. Consequently, an opening is created between the graft vessel and the target vessel within the circumference of the end of the graft vessel. The cannula and stylet are then removed from the lumen of the graft vessel through its free end.

In another example of such an embodiment, the anvil arm 14 is inserted into a hole in the wall of the target vessel and the staple holder 38 deploys staples or other connectors to connect the graft vessel to the target vessel, as described above. The anvil arm 14 is removed, and the hole in the wall of the target vessel is closed. An independent cutter 200 is then introduced through the wall of the graft vessel. The cutter 200 itself may create an opening in the wall of the graft vessel through which it can enter, or a separate implement may be used to create an opening in the wall of the graft vessel. The cutter 200 may be configured as described above, including a projection 208 extending therefrom, or may be configured differently. For example, the cutter 200 may be J-shaped or L-shaped to facilitate creation of the opening between the graft vessel and the target vessel through the wall of the graft vessel. The cutter 200 is manipulated relative to the connection between the target vessel and the graft vessel to create an opening in the wall of the target vessel at the junction therebetween. That is, registration is maintained between the cutter 200 and the junction between the end of the graft vessel and the wall of the target vessel. The cutter 200 is then removed through the wall of the graft vessel, and the opening in the wall of the graft vessel is sealed.

In an alternate embodiment, at least the anvil arm 14 portion of the anvil 10 is expandable from a first, narrower configuration to a second, wider configuration. Consequently, the anvil arm 14 can be inserted into the lumen of the target vessel 580 through the anvil entry hole 584 in the first configuration, expanded to the second configuration, and then collapsed back to the first configuration for removal through the anvil entry hole 584. In this way, the size of the anvil entry hole 584 may be minimized. As a result, the sealer 780 may be smaller, or omitted altogether. The anvil arm 14 and/or anvil 10 may be fabricated in any suitable manner to allow for its transition between first and second configurations. As one example, the anvil arm 14 may be inflatable from the first configuration to the second configuration. The anvil arm 14 may be made from, coated with, attached to or otherwise associated with a material strong enough to allow gas to inflate it to a substantially rigid state, and/or to allow the connectors 464 to be deflected upon contact with the surface of the inflatable anvil arm 14. For example, the anvil arm 14 may be made from, or coated with, KEVLAR® brand fiber. As another example, metallic strips, panels or other elements may be attached to the anvil arm 14 at locations where the connectors 464 contact the anvil arm 14, such that those metallic elements engage the tines 466 of the connectors. The anvil arm 14 may be otherwise fabricated to move between first and second configurations. For example, the anvil arm 14 may be a truss, linkage or other mechanism that is movable from a first, narrower configuration to a second, wider configuration.

In an alternate embodiment, more than one anvil arm 14, or an anvil arm 14 having two or more components, is utilized.

As one example, the anvil arm 14 may be bifurcated. In such an embodiment, the cutter 200 slides between the bifurcations of the anvil arm 14. The cutter 200 need not be connected to the anvil arm 14, and may be slid out of the heel 587 of the anastomosis after the arteriotomy has been completed. As another example, two or more separate anvil arms 14 are inserted into the lumen of the target vessel 580 via the anvil entry hole 584, at the same time as one another or at different times. As another example, at least one anvil arm 14 is inserted into the lumen of the target vessel 580 via the anvil entry hole 584, and at least one anvil arm 14 is positioned outside the target vessel 580. The anvil arms 14 may be moved toward one another to clamp the tissue of the wall of the target vessel 580 between them. Optionally, the cutter 200 may be associated with the anvil arm 14 outside the target vessel 580, rather than the anvil arm 14 inside the target vessel 580. After completing the anastomosis, the anvil arm 14 outside the target vessel 580 may be removed from the anastomosis site via the heel 587.

In an alternate embodiment, the anvil 10 is not part of the anastomosis tool 300. Instead, an external anvil (not shown) is positioned at or in proximity to the exit of each connector bay 448. Each external anvil may be a tab or other structure or mechanism. As each connector 464 is urged out of the corresponding connector bay 448, that connector 464 encounters the corresponding external anvil 448. Contact between the connector 464 and the external anvil causes the connector 464 to deform. This deformation deflects the tines 466 of the connectors 464, such that the connectors 464 deform to a position in which they hold the corresponding flap 408 to the target vessel 580. The staple holder 38 is later pulled away from the anastomosis, and each external anvil slides out from underneath the base 468 of the corresponding connector 464.

In an alternate embodiment, the anvil 10 is not part of the anastomosis tool 300. The connectors 464 are composed of superelastic material, or are otherwise fabricated and/or configured, such that they are deployable without the use of an anvil 10 or an external anvil or anvils. For example, where the connectors 464 are superelastic, they may be held in a first position under a restraining force. To deploy the connectors 464, they may be placed against the corresponding flap 408, after which the restraining force on the connectors 464 is released. The superelastic connectors 464 then self-deform to connect the flap or flaps 408, without the need for an anvil 10. As another example, the connectors 464 are deployed so quickly that a backing such as the anvil 10 is not needed. The connectors 464 are advanced into the wall of the target vessel 580 fast enough such that the blood or other fluid in the target vessel 580 acts as a solid and supports the wall of the target vessel 580 against the advance of the connectors 464. That is, the connectors 464 advance into the wall of the target vessel 580 fast enough that the fluid within substantially does not have time to move in response to the motion of the connectors 464, such that the fluid acts as if it were a solid. To accomplish this effect, the connectors 464 may advance at a rate of substantially 0.8-1.4 m/sec. Thus, the connectors 464 may be deployed without the use of the anvil 10. Where the anvil 10 is not used, the anastomosis tool 300 may be configured more simply. As one example, the staple holder 38 is pressed against a flap 408 of the graft vessel 404 after the flap 408 has been placed on the target vessel 580. The staple holder 38 is then actuated. The staple holder 38 may include a single arm 402, in which case a different single-use staple holder 38 may be utilized for each flap 408, or the same reusable staple holder 38 may be reloaded and then utilized for more than one flap 408.

In an alternate embodiment, the staple holder 38 includes a single arm 402. The single arm 402 is movable from one side of the anastomosis site to the other to perform part of the anastomosis at a time. For example, where two flaps 408 are formed at the end of the graft vessel 404, the single arm 402 may deploy at least one connector 464 to connect one flap 408 to the target vessel 580, then move to the other side of the graft vessel 404 to deploy at least one connector 464 to connect the other flap 408 to the target vessel 580. The anvil arm 14 may be left in place while the single arm 402 sequentially deploys the connectors 464 at different locations. The cutter 200 and/or projection 208 may be actuated to create an opening in the wall of the target vessel 580 at any suitable time. For example, the cutter 200 and/or projection 208 may be actuated after the single arm 402 has deployed all of the connectors 464 needed to complete the anastomosis. The sled 482 may be configured and/or actuated to sequentially deploy one or more connectors 464 at different times and locations. Alternately, any other suitable mechanism may be utilized to deploy one or more connectors 464 at different times and locations.

In an alternate embodiment, the connectors 464 may be deployed from the staple holder 38 using ultrasonic or piezoelectric energy. The connectors 464 may be held in the connector bays 448 as described above, or may be held in a different manner by the arms 402. Optionally, the connector deployer 452 may be omitted from at least one connector bay 448. Where ultrasonic deployment is used, ultrasonic energy is applied to the connectors 464 in any suitable manner. For example, at least one ultrasonic transmitter may be located in the staple holder 38 adjacent to or in proximity to each connector 464. Application of ultrasonic energy to the connectors 464 causes each connector 464 to move out of the staple holder 38, through the corresponding flap 408, then into the wall of the target vessel 580. The frequency of the ultrasonic energy applied to the connectors 464 causes the connectors 464 to vibrate as they advance through tissue, facilitating their deployment. Where piezoelectric deployment is used, one or more piezoelectric emitters may be located in the staple holder 38 adjacent to or in proximity to each connector 464. Actuation of the piezoelectric emitter or emitters causes each connector 464 to vibrate and move out of the staple holder 38, through the corresponding flap 408, then into the wall of the target vessel 580. The vibration of the connectors 464 as they advance through tissue facilitates their deployment. Alternately, the connector deployers 452 are utilized, and actuation of an ultrasonic transmitter or piezoelectric emitter causes the connector deployers 452 to urge the connectors 464 out of the connector bays 448. If so, the sled 482 or the ramp elements 446 of the sled 482 may be omitted.

In an alternate embodiment, the tissue effector 400 may be used to perform a side-to-side anastomosis. At least part of the staple holder 38 is sized to fit into the lumen of the graft vessel 404 through an end thereof. Where the tissue effector 400 is used to perform a side-to-side anastomosis, the staple holder 38 is not detachable from the remainder of the tissue effector 400 or from any other part of the anastomosis tool 300; that is, the staple holder 38 is not a cartridge. After at least part of the staple holder 38 is placed into the lumen of the graft vessel 404 through an end thereof, the anastomosis procedure continues substantially as described above. The cutter 200 and/or projection 208 is sized and/or shaped to cut through both the wall of the target vessel 580 and the wall of the graft vessel 404, to allow fluid to flow therebetween. After the anastomosis is complete, the staple holder 38 is removed from the lumen of the graft vessel 404 through the end thereof. That end of the graft vessel 404 is then closed in any suitable manner, such as by suturing, stapling or clipping.

In an alternate embodiment, the graft vessel 404 is connected to the cutter 200, rather than the staple holder 38. Advantageously, the graft vessel 404 is connected to a proximal portion of the cutter 200, such as by a spike, clip and/or other structure or mechanism. However, the graft vessel 404 may be attached, directly or indirectly, to any other part of the cutter 200. As the cutter 200 creates the arteriotomy in the target vessel 580, it pulls the end of the graft vessel 404 over the arteriotomy. The connectors 464 are then deployed to connect the end of the graft vessel 404 to the target vessel 580. That is, the arteriotomy is created before the connectors 464 are deployed.

While the invention has been described in detail, it will be apparent to one skilled in the art that various changes and modifications can be made and equivalents employed, without departing from the present invention. It is to be understood that the invention is not limited to the details of construction, the arrangements of components, and/or the process of performing anastomosis set forth in the above description or illustrated in the drawings. Further, the invention is not limited to the performance of anastomosis in the context of a CABG procedure, nor it is limited to the anastomosis of two bodily vessels. Other tissue structures than vessels may be connected together within the body utilizing the present invention. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A method of performing anastomosis between a graft vessel and a target vessel, each having a circumferential wall and a lumen therethrough, the method comprising:
   providing an anastomosis tool including a tissue effector and a fluid-driven actuator operationally connected to said tissue effector, wherein said tissue effector includes an anvil connected to a connector holder, and wherein said connector holder includes two arms spaced apart along at least part of their length;
   connecting said fluid-driven actuator to an energy source;
   sliding at least part of said anvil through an anvil entry hole in the wall of the target vessel;
   creating at least one flap in an end of the graft vessel;
   placing the end of the graft vessel in proximity to the wall of the target vessel;
   actuating said fluid-driven actuator to connect the end of the graft vessel to the wall of the target vessel;
   removing said anvil outward through the anvil entry hole in the wall of the target vessel; and
   closing the anvil entry hole by deploying a sealer in proximity to the anvil entry hole.

2. The method of claim 1, wherein said energy source is a gas cylinder connected to said anastomosis tool.

3. The method of claim 1, wherein said energy source is an external utility.

4. The method of claim 1, wherein said placing comprises moving said at least one flap onto an outer surface of the wall of the target vessel.

5. The method of claim 1, further comprising creating an aperture in the wall of the target vessel at a site of the connection between the end of the graft vessel and the wall of the target vessel.

6. The method of claim 1, wherein said actuating moves the end of the graft vessel into contact with the wall of the target vessel.

7. The method of claim 1, wherein said connecting includes deploying at least one connector.

8. The method of claim 1, wherein said anastomosis tool includes at least one force transmission member connected to said tissue effector and said fluid-driven actuator, and wherein said actuating moves said at least one force transmission member.

9. The method of claim 1, further comprising providing an applier separate from said anastomosis tool, wherein said deploying said sealer is performed by said applier.

10. The method of claim 1, wherein said anastomosis tool includes a sealer detachably connected to said anvil; and wherein the method further comprises engaging the wall of the target vessel with said sealer during said removing, and wherein closing the anvil entry hole comprises closing the hole with said sealer after said removing is complete.

11. The method of claim 1, further comprising holding the graft vessel between said arms of said connector holder before said actuating.

12. The method of claim 1, wherein said anastomosis tool further comprises a shaft connected to said tissue effector, said shaft having an articulation, and wherein the method further comprises moving said tissue effector about said articulation before said actuating.

13. The method of claim 12, further comprising substantially locking said tissue effector relative to said articulation before said actuating.

14. The method of claim 1, wherein said anastomosis tool further comprises:
   a handle connected to said tissue effector, wherein said fluid-driven actuator is located in said handle; and
   at least one cable connected to said tissue effector and said fluid-driven actuator, wherein said actuating pulls said at least one cable proximally toward said handle.

15. The method of claim 1, wherein said actuating comprises first clamping said tissue effector, then deploying a plurality of staples from said tissue effector.

* * * * *